US011535864B2

(12) United States Patent
Joshi et al.

(10) Patent No.: US 11,535,864 B2
(45) Date of Patent: Dec. 27, 2022

(54) DNA MOLECULES PRODUCING CUSTOM DESIGNED REPLICATING AND NON-REPLICATING NEGATIVE STRANDED RNA VIRUSES AND USES THERE OF

(71) Applicant: Vishwas Dattatraya Joshi, Maharashtra (IN)

(72) Inventors: Vishwas Dattatraya Joshi, Maharashtra (IN); U. M. Sreenivasa Murthy, Hyderabad (IN); Shailendra Devicharan Rane, Maharashtra (IN); Manasi Sanjay Nade, Maharashtra (IN)

(73) Assignee: Vishwas Dattatraya Joshi, Maharashtra (IN)

( * ) Notice: Subject to any disclaimer, the term of this patent is extended or adjusted under 35 U.S.C. 154(b) by 157 days.

(21) Appl. No.: 15/541,691

(22) PCT Filed: Jan. 4, 2016

(86) PCT No.: PCT/IN2016/000004
§ 371 (c)(1),
(2) Date: Jul. 5, 2017

(87) PCT Pub. No.: WO2016/110869
PCT Pub. Date: Jul. 14, 2016

(65) Prior Publication Data

US 2019/0211355 A1 Jul. 11, 2019

(30) Foreign Application Priority Data

Jan. 5, 2015 (IN) ............................ 39/MUM/2015

(51) Int. Cl.
*C12N 15/86* (2006.01)
*A61P 37/04* (2006.01)
*A61P 35/00* (2006.01)

(52) U.S. Cl.
CPC .............. *C12N 15/86* (2013.01); *A61P 35/00* (2018.01); *A61P 37/04* (2018.01); *C12N 2760/18421* (2013.01); *C12N 2760/18432* (2013.01); *C12N 2760/18433* (2013.01); *C12N 2760/18443* (2013.01); *C12N 2770/24123* (2013.01); *C12N 2770/24134* (2013.01); *C12N 2840/20* (2013.01)

(58) Field of Classification Search
None
See application file for complete search history.

(56) References Cited

U.S. PATENT DOCUMENTS

| | | | | |
|---|---|---|---|---|
| 6,896,881 | B1 | 5/2005 | Russel et al. | |
| 7,118,740 | B1 | 10/2006 | Russel et al. | |
| 7,393,527 | B2 | 7/2008 | Russel et al. | |
| 7,670,598 | B2 | 3/2010 | Russell et al. | |
| 8,586,364 | B2 | 11/2013 | Tangy et al. | |
| 2014/0212922 | A1* | 7/2014 | Joshi ..................... | C12N 15/85 435/69.1 |

FOREIGN PATENT DOCUMENTS

| | | | |
|---|---|---|---|
| WO | WO 1996010400 | A1 | 4/1996 |
| WO | WO 199706270 | A1 | 2/1997 |
| WO | WO 2008118369 | A2 | 10/2008 |
| WO | WO 2012022495 | A1 | 2/2012 |
| WO | WO 2013046216 | A2 | 4/2013 |

OTHER PUBLICATIONS

International Search Report, dated Jul. 28, 2016 for corresponding International Application No. PCT/IN2016/000004.
Written Opinion of ISA, dated Jul. 28, 2016 for corresponding International Application No. PCT/ IN2016/000004.
Bluming, A.Z. and J.L. Ziegler, Regression of Burkitt's lymphoma in association with measles infection. Lancet, 1971. 2(7715): p. 105-6.
Gross, S., Measles and leukaemia. Lancet, 1971. 1(7695): p. 397-8.
Pasquinucci, G., Possible effect of measles on leukaemia. Lancet, 1971. 1(7690): p. 136.
Zygiert, Z., Hodgkin's disease: remissions after measles. Lancet, 1971. 1(7699): p. 593.
McDonald, C.J., et al., A measles virus vaccine strain derivative as a novel oncolytic agent against breast cancer. Breast Cancer Res Treat, 2006. 99(2): p. 177-84.
Heinzerling, L., et al., Oncolytic measles virus in cutaneous T-cell lymphomas mounts antitumor immune responses in vivo and targets interferon-resistant tumor cells. Blood, 2005. 106(7): p. 2287-94.
Kunzi, V., et al., Recombinant measles virus induces cytolysis of cutaneous T-cell lymphoma in vitro and in vivo. J Invest Dermatol, 2006. 126(11): p. 2525-32.
Lin, E.H., et al., Fusogenic membrane glycoproteins induce syncytia formation and death in vitro and in vivo: a potential therapy agent for lung cancer. Cancer Gene Ther, 2010. 17(4): p. 256-65.
Peng, K.W., et al., Systemic therapy of myeloma xenografts by an attenuated measles virus. Blood, 2001. 98(7): p. 2002-7.

(Continued)

*Primary Examiner* — Benjamin P Blumel
(74) *Attorney, Agent, or Firm* — Intellectual Property Law Group LLP

(57) ABSTRACT

This invention comprises: compositions comprising a derivative, plasmids, a reagent kit and methods of making these compositions a derivative, vaccine- and non-vaccine-compositions of above for causing death of cancer cells that form part of a tunoour and virus infected Denguue, Measles and other diseased cells; the derivative comprising replicating as well as non-replicating dervivaties of an attenuated negative stranded RNA virus belonging to family paramyxoviridae, including Measles Virus, comprising a single additional transcriptional unit carrying either only one or two or more non-viral genes, and the non-replicating derivatives being free from contaminating replicating Measles Virus (b) a Measles Virus packaging cell line for making above compositions, expressing the M, F and H proteins of MV stably. And (c) a reagent kit for producing the Measles Virus derivatives describved above.

6 Claims, 15 Drawing Sheets

Figure 1:
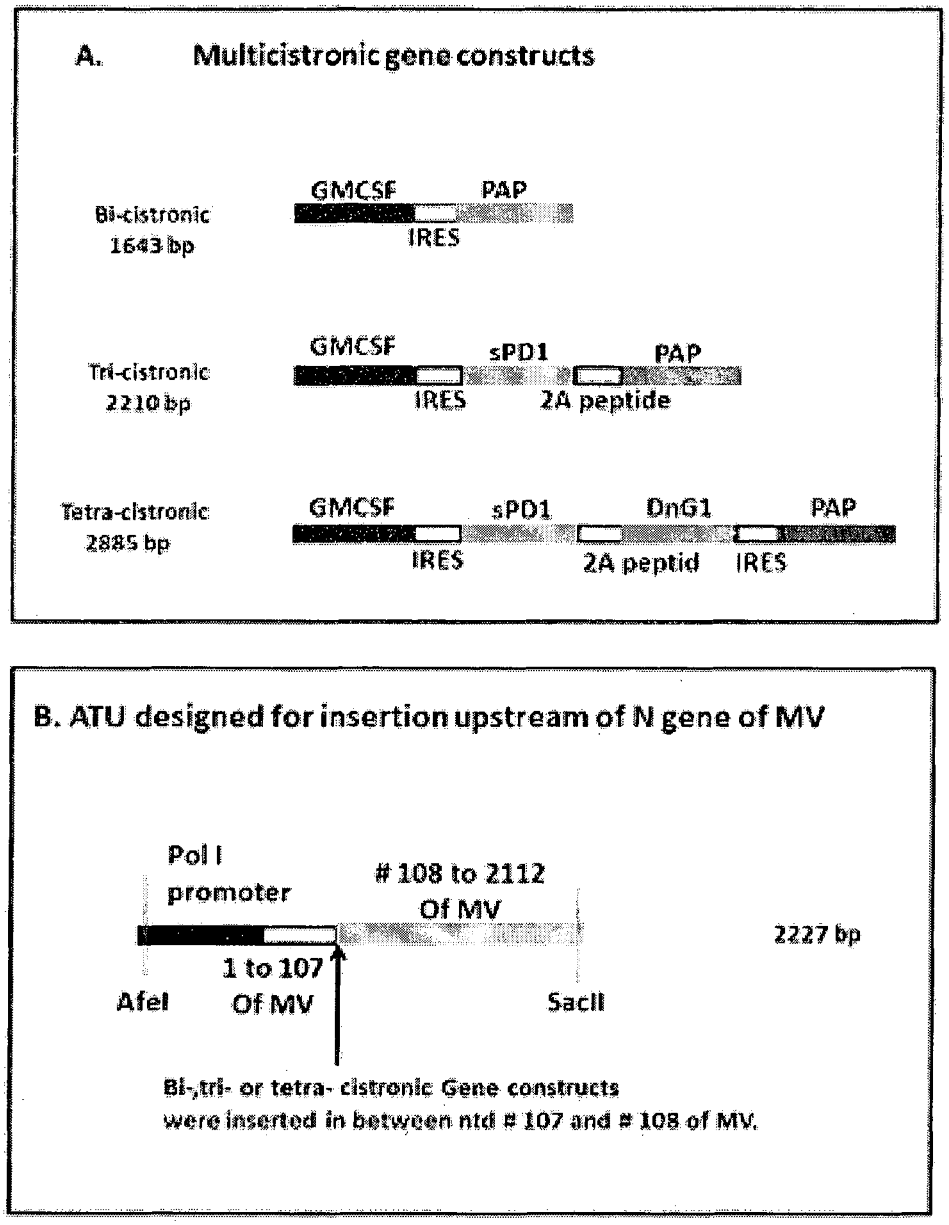

Specification includes a Sequence Listing.

(56) References Cited

OTHER PUBLICATIONS

Galanis, E., et al., Phase I trial of intraperitoneal administration of an oncolytic measles virus strain engineered to express carcinoembryonic antigen for recurrent ovarian cancer. Cancer Res, 2010. 70(3): p. 875-82.
Msaouel, P., A. Dispenzieri, and E. Galanis, Clinical testing of engineered oncolytic measles virus strains in the treatment of cancer: an overview. Curr Opin Mol Ther, 2009. 11(1): p. 43-53.
Russell, S.J., et al., Remission of disseminated cancer after systemic oncolytic virotherapy. Mayo Clin Proc, 2014. 89(7): p. 926-33.
Blechacz, B. and S.J. Russell, Measles virus as an oncolytic vector platform. Curr Gene Ther, 2008. 8(3): p. 162-75.
Radecke, F., et al., Rescue of measles viruses from cloned DNA. EMBO J, 1995. 14(23): p. 5773-84.
Parks, C.L., et al., Comparison of predicted amino acid sequences of measles virus strains in the Edmonston vaccine lineage. J Virol, 2001. 75(2): p. 910-20.
Parks, C.L., et al., Analysis of the noncoding regions of measles virus strains in the Edmonston vaccine lineage. J Virol, 2001. 75(2): p. 921-33.
Dorig, R.E., et al., The human CD46 molecule is a receptor for measles virus (Edmonston strain). Cell, 1993. 75(2): p. 295-305.
Hsu, E.C., et al., CDw150(SLAM) is a receptor for a lymphotropic strain of measles virus and may account for the immunosuppressive properties of this virus. Virology, 2001. 279(1): p. 9-21.
Anderson, B.D., et al., High CD46 receptor density determines preferential killing of tumor cells by oncolytic measles virus. Cancer Res, 2004. 64(14): p. 4919-26.
Rama, A., et al., On advances in cancer suicide genes therapy. SOJ Genet Sc, 2014. 1(1): p. 1-6.
Liu, T.J., et al., Growth suppression of human head and neck cancer cells by the introduction of a wild-type p53 gene via a recombinant adenovirus. Cancer Res, 1994. 54(14): p. 3662-7.
Gibson, S.A., et al., Induction of apoptosis in oral cancer cells by an anti-bcl-2 ribozyme delivered by an adenovirus vector. Clin Cancer Res, 2000. 6(1): p. 213-22.
Martin, L.A. and M. Dowsett, BCL-2: a new therapeutic target in estrogen receptor-positive breast cancer? Cancer Cell, 2013. 24(1): p. 7-9.
Wong, R.J., et al., Oncolytic herpesvirus effectively treats murine squamous cell carcinoma and spreads by natural lymphatics to treat sites of lymphatic metastases. Hum Gene Ther, 2002. 13(10): p. 1213-23.
Dingli, D., et al., Image-guided radiovirotherapy for multiple myeloma using a recombinant measles virus expressing the thyroidal sodium iodide symporter. Blood, 2004. 103(5): p. 1641-6.
Bossow, S., et al., Armed and targeted measles virus for chemovirotherapy of pancreatic cancer. Cancer Gene Ther, 2011. 18(8): p. 598-608.
Hartkopf, A.D., et al., Enhanced killing of ovarian carcinoma using oncolytic measles vaccine virus armed with a yeast cytosine deaminase and uracil phosphoribosyltransferase. Gynecol Oncol, 2013. 130(2): p. 362-8.
Kaufmann, J.K., et al., Chemovirotherapy of malignant melanoma with a targeted and armed oncolytic measles virus. J Invest Dermatol, 2013. 133(4): p. 1034-42.
Grossardt, C., et al., Granulocyte-macrophage colony-stimulating factor-armed oncolytic measles virus is an effective therapeutic cancer vaccine. Hum Gene Ther, 2013. 24(7): p. 644-54.
Engeland, C.E., et al., CTLA-4 and PD-L1 checkpoint blockade enhances oncolytic measles virus therapy. Mol Ther, 2014. 22(11): p. 1949-59.
Rushmere, N.K., et al., Analysis of the level of mRNA expression of the membrane regulators of complement, CD59, CD55 and CD46, in breast cancer. Int J Cancer, 2004. 108(6): p. 930-6.
Iankov, I.D., et al., Infected cell carriers: a new strategy for systemic delivery of oncolytic measles viruses in cancer virotherapy. Mol Ther, 2007. 15(1): p. 114-22.
Miest, T.S., et al., Envelope-chimeric entry-targeted measles virus escapes neutralization and achieves oncolysis. Mol Ther, 2011. 19(10): p. 1813-20.
Bateman, A., et al., Fusogenic membrane glycoproteins as a novel class of genes for the local and immune-mediated control of tumor growth. Cancer Res, 2000. 60(6): p. 1492-7.
Higuchi, H., et al., Viral fusogenic membrane glycoprotein expression causes syncytia formation with bioenergetic cell death: implications for gene therapy. Cancer Res, 2000. 60(22): p. 6396-402.
Liniger, M., et al., Recombinant measles viruses expressing single or multiple antigens of human immunodeficiency virus (HIV-1) induce cellular and humoral immune responses. Vaccine, 2009. 27(25-26): p. 3299-305.
Liniger, M., et al., Induction of neutralising antibodies and cellular immune responses against SARS coronavirus by recombinant measles viruses. Vaccine, 2008. 26(17): p. 2164-74.
Wang, Z., et al., Recombinant measles viruses expressing heterologous antigens of mumps and simian immunodeficiency viruses. Vaccine, 2001. 19(17-19): p. 2329-36.
Brandler, S., et al., Measles vaccine expressing the secreted form of West Nile virus envelope glycoprotein induces protective immunity in squirrel monkeys, a new model of West Nile virus infection. J Infect Dis, 2012. 206(2): p. 212-9.
Brandler, S., et al., A recombinant measles vaccine expressing chikungunya virus-like particles is strongly immunogenic and protects mice from lethal challenge with chikungunya virus. Vaccine, 2013. 31(36): p. 3718-25.
Brandler, S., et al., Pediatric measles vaccine expressing a dengue antigen induces durable serotype-specific neutralizing antibodies to dengue virus. PLoS Negl Trop Dis, 2007. 1(3): p. e96.
Billeter, M.A., H.Y. Naim, and S.A. Udem, Reverse genetics of measles virus and resulting multivalent recombinant vaccines: applications of recombinant measles viruses. Curr Top Microbiol Immunol, 2009. 329: p. 129-62.
Wang, P.G., et al., Efficient assembly and secretion of recombinant subviral particles of the four dengue serotypes using native prM and E proteins. PLoS One, 2009. 4(12): p. e8325.
Erbs, P., et al., In vivo cancer gene therapy by adenovirus-mediated transfer of a bifunctional yeast cytosine deaminase/uracil phosphoribosyltransferase fusion gene. Cancer Res, 2000. 60(14): p. 3813-22.
Gordon, E.M., et al., Inhibition of metastatic tumor growth in nude mice by portal vein infusions of matrix-targeted retroviral vectors bearing a cytocidal cyclin G1 construct. Cancer Res, 2000. 60(13): p. 3343-7.
Chappell, S.A., G.M. Edelman, and V.P. Mauro, A 9-nt segment of a cellular mRNA can function as an internal ribosome entry site (IRES) and when present in linked multiple copies greatly enhances IRES activity. Proc Natl Acad Sci U S A, 2000. 97(4): p. 1536-41.
Szymczak, A.L., et al., Correction of multi-gene deficiency in vivo using a single 'self-cleaving' 2A peptide-based retroviral vector. Nat Biotechnol, 2004. 22(5): p. 589-94.
Liu, Y., et al., Tetravalent recombinant dengue virus-like particles as potential vaccine candidates: immunological properties. BMC Microbiol, 2014. 14(1): p. 233.
Grote, D., R. Cattaneo, and A.K. Fielding, Neutrophils contribute to the measles virus-induced antitumor effect: enhancement by granulocyte macrophage colony-stimulating factor expression. Cancer Res, 2003. 63(19): p. 6463-8.

* cited by examiner

Helper Plasmid
pINPL
15775 bp

The serum from Mice immunized with Dengue Virosomes (AS) and standard anti-DenV E protein antibodies (Ab) recognize the same protein.

A: Uninfected Vero cells
B: Vero cells infected with MVAC (Serum Instt)
C: Vero cells infected with MVAC + anti-Virosome serum

SEQUENCE LISTING

```
<160> NUMBER OF SEQ ID NOS: 28

<210> SEQ ID NO 1
<211> LENGTH: 4908
<212> TYPE: DNA
<213> ORGANISM: Artificial Sequence
<220> FEATURE:
<223> OTHER INFORMATION: Artificial DNA containing selected elements
      from MV sequence - plasmid pMTX-P1T

<400> SEQUENCE: 1

aagcttggct agcacatcct cttggtccta tcacggttat gaggtcgacc agttgttgct      60

ttgatgttcg gttctctcgt tgattgggac aatatttggg gcacttcgcc ggtcccgact     120

tccagaattt ccgtgtggtc tgtgaattta tcaccgctac actgtcatca tattccagtt     180

ttgcaatctg ctctctttgt acctgcagat aggtaccaaa caaagttggg taaggatagt     240

tcaatcaatg atcatttttct agtgcactta ggattcaaga tcctattatc agggacaaga     300

gcaggattaa ggatatccga gtcgcgacgc gtacatgtag cgctcgcacc ggtccgcggg     360

gcgcgccctc gaggtgcgag aggccgagga ccagaacaac atccgcctac cctccatcat     420

tgttataaaa aacttaggaa ccaggtccac acagccgcca gcccatcaac catccactcc     480

cacgattgga gccgcacgtg tctagagggc ccgtttaaac cctgcaggtt aattaagtga     540

attcttggtt gaactccgga accctaatcc tgccctaggt ggttaggcat tatttgcaat     600

agattaaaga aaactttgaa aatacgaagt ttctattccc agctttgtct ggttttttttc     660

ccccccaact tcggaggtcg accagtactc cgggcgacac tttgtttttt ttttttcccc     720

cgatgctgga ggtcgaccag atgtccgaaa gtgtcccccc cccccccccc cccccccgg      780

cgcggagcgg cggggccacc ccggacccct tttttttttt tttttttttt tttaaattcc     840

tggaaccttt aggtcgacca gttgtccgtc ttttactcct tcatataggt cgaccagtac     900

tccgggtggt actttgtctt tttctgaaaa tcccagaggt cgaccagata tccgcggccg     960

ccgagctcgt taacaacaac aattgcattc attttatgtt tcaggttcag ggggagatgt    1020

gggaggtttt ttaaagcaag taaaacctct acaaatgtgg taaaatccga taaggatcga    1080

tccgggctgg cgtaatagcg aagaggcccg caccgatcgc ccttcccaac agttgcgcag    1140

cctgaatggc gaatggacgc gccctgtagc ggcgcattaa gcgcggcggg tgtggtggtt    1200

acgcgcagcg tgaccgctac acttgccagc gccctagcgc ccgctccttt cgctttcttc    1260

ccttcctttc tcgccacgtt cgccggcttt ccccgtcaag ctctaaatcg ggggctccct    1320

ttagggttcc gatttagagc tttacggcac ctcgaccgca aaaaacttga tttgggtgat    1380

ggttcacgta gtgggccatc gccctgatag acggtttttc gccctttgac gttggagtcc    1440

acgttcttta atagtggact cttgttccaa actggaacaa cactcaaccc tatctcggtc    1500
```

```
tattcttttg atttataagg gattttgccg atttcggcct attggttaaa aaatgagctg   1560
atttaacaaa tatttaacgc gaattttaac aaaatattaa cgtttacaat ttcgcctgat   1620
gcggtatttt ctccttacgc atctgtgcgg tatttcacac cgcatacgcg gatctgcgca   1680
gcaccatggc ctgaaataac ctctgaaaga ggaacttggt taggtacctt ctgaggcgga   1740
aagaaccagc tgtggaatgt gtgtcagtta gggtgtggaa agtccccagg ctccccagca   1800
ggcagaagta tgcaaagcat gcatctcaat tagtcagcaa ccaggtgtgg aaagtcccca   1860
ggctccccag caggcagaag tatgcaaagc atgcatctca attagtcagc aaccatagtc   1920
ccgcccctaa ctccgcccat cccgccccta actccgccca gttccgccca ttctccgccc   1980
catggctgac taattttttt tatttatgca gaggccgagg ccgcctcggc ctctgagcta   2040
ttccagaagt agtgaggagg cttttttgga ggcctaggct tttgcaaaaa gcttgattct   2100
tctgacacaa cagtctcgaa cttaaggcta gagccaccat ggttcgacca ttgaactgca   2160
tcgtcgccgt gtcccaaaat atggggattg gcaagaacgg agacctaccc tggcctccgc   2220
tcaggaacga gttcaagtac ttccaaagaa tgaccacaac ctcttcagtg gaaggtaaac   2280
agaatctggt gattatgggt aggaaaacct ggttctccat tcctgagaag aatcgacctt   2340
taaaggacag aattaatata gttctcagta gagaactcaa agaaccacca cgaggagctc   2400
attttcttgc caaaagtttg gatgatgcct taagacttat tgaacaaccg gaattggcaa   2460
gtaaagtaga catggtttgg atagtcggag gcagttctgt ttaccaggaa gccatgaatc   2520
aaccaggcca cctcagactc tttgtgacaa ggatcatgca ggaatttgaa agtgacacgt   2580
ttttcccaga aattgatttg gggaaatata aacttctccc agaataccca ggcgtcctct   2640
ctgaggtcca ggaggaaaaa ggcatcaagt ataagtttga agtctacgag aagaaagact   2700
aagcgggact ctggggttcg aaatgaccga ccaagcgacg cccaacctgc catcacgatg   2760
gccgcaataa aatatcttta ttttcattac atctgtgtgt tggttttttg tgtgaatcga   2820
tagcgataag gatccgcgta tggtgcactc tcagtacaat ctgctctgat gccgcatagt   2880
taagccagcc ccgacacccg ccaacacccg ctgacgcgcc ctgacgggct tgtctgctcc   2940
cggcatccgc ttacagacaa gctgtgaccg tctccgggag ctgcatgtgt cagaggtttt   3000
caccgtcatc accgaaacgc gcgagacgaa agggcctcgt gatacgccta tttttatagg   3060
ttaatgtcat gataataatg gtttcttaga cgtcaggtgg cacttttcgg ggaaatgtgc   3120
gcggaacccc tatttgttta tttttctaaa tacattcaaa tatgtatccg ctcatgagac   3180
aataaccctg ataaatgctt caataatatt gaaaaaggaa gagtatgagt attcaacatt   3240
tccgtgtcgc ccttattccc ttttttgcgg cattttgcct tcctgttttt gctcacccag   3300
aaacgctggt gaaagtaaaa gatgctgaag atcagttggg tgcacgagtg ggttacatcg   3360
aactggatct caacagcggt aagatccttg agagttttcg ccccgaagaa cgttttccaa   3420
tgatgagcac ttttaaagtt ctgctatgtg gcgcggtatt atcccgtatt gacgccgggc   3480
aagagcaact cggtcgccgc atacactatt ctcagaatga cttggttgag tactcaccag   3540
tcacagaaaa gcatcttacg gatggcatga cagtaagaga attatgcagt gctgccataa   3600
ccatgagtga taacactgcg gccaacttac ttctgacaac gatcggagga ccgaaggagc   3660
taaccgcttt tttgcacaac atgggggatc atgtaactcg ccttgatcgt tgggaaccgg   3720
agctgaatga agccatacca aacgacgagc gtgacaccac gatgcctgta gcaatggcaa   3780
caacgttgcg caaactatta actggcgaac tacttactct agcttcccgg caacaattaa   3840
```

-continued

```
tagactggat ggaggcggat aaagttgcag gaccacttct gcgctcggcc cttccggctg   3900

gctggtttat tgctgataaa tctggagccg gtgagcgtgg gtctcgcggt atcattgcag   3960

cactggggcc agatggtaag ccctcccgta tcgtagttat ctacacgacg gggagtcagg   4020

caactatgga tgaacgaaat agacagatcg ctgagatagg tgcctcactg attaagcatt   4080

ggtaactgtc agaccaagtt tactcatata tactttagat tgatttaaaa cttcattttt   4140

aatttaaaag gatctaggtg aagatccttt ttgataatct catgaccaaa atcccttaac   4200

gtgagttttc gttccactga gcgtcagacc ccgtagaaaa gatcaaagga tcttcttgag   4260

atcctttttt tctgcgcgta atctgctgct tgcaaacaaa aaaaccaccg ctaccagcgg   4320

tggtttgttt gccggatcaa gagctaccaa ctctttttcc gaaggtaact ggcttcagca   4380

gagcgcagat accaaatact gtccttctag tgtagccgta gttaggccac cacttcaaga   4440

actctgtagc accgcctaca tacctcgctc tgctaatcct gttaccagtg gctgctgcca   4500

gtggcgataa gtcgtgtctt accgggttgg actcaagacg atagttaccg gataaggcgc   4560

agcggtcggg ctgaacgggg ggttcgtgca cacagcccag cttggagcga acgacctaca   4620

ccgaactgag atacctacag cgtgagctat gagaaagcgc cacgcttccc gaagggagaa   4680

aggcggacag gtatccggta agcggcaggg tcggaacagg agagcgcacg agggagcttc   4740

caggggggaaa cgcctggtat ctttatagtc ctgtcgggtt tcgccacctc tgacttgagc   4800

gtcgattttt gtgatgctcg tcaggggggc ggagcctatg gaaaaacgcc agcaacgcgg   4860

cctttttacg gttcctggcc ttttgctggc cttttgctca ggctcgac                4908
```

<210> SEQ ID NO 2
<211> LENGTH: 490
<212> TYPE: DNA
<213> ORGANISM: Artificial Sequence
<220> FEATURE:
<223> OTHER INFORMATION: Artificial DNA containing selected elements from MV sequence - Modified PstI region

<400> SEQUENCE: 2

```
ctgcagatag gtaccaaaca aagttgggta aggatagttc aatcaatgat cattttctag     60

tgcacttagg attcaagatc ctattatcag ggacaagagc aggattaagg atatccgaga    120

tggccacact tttaaggagc ttagcattgt tcaaaagaaa caaggacaaa ccacccatta    180

catcaggatc cggtggagcc atcagaggaa tcaaacacat tattatagta ccaatccctg    240

gagattcctc aattaccact cgatccagac ttctggaccg gttcgcgacg cgtacatgta    300

gcgctcgcac cggtccgcgg ggcgcgccct cgaggtgcga gaggccgagg accagaacaa    360

catccgccta ccctccatca ttgttataaa aaacttagga accaggtcca cacagccgcc    420

agcccatcaa ccatccactc ccacgattgg ccgcacgtgt ctagagggcc cgtttaaacc    480

ctgcaggtta                                                           490
```

<210> SEQ ID NO 3
<211> LENGTH: 3209
<212> TYPE: DNA
<213> ORGANISM: Artificial Sequence
<220> FEATURE:
<223> OTHER INFORMATION: Fragment from MV sequence - Age_MV upto Spe_Age fragment

<400> SEQUENCE: 3

```
ggaccggttg gtcaggttaa ttggaaaccc ggatgtgagc gggcccaaac taacaggggc     60

actaataggt atattatcct tatttgtgga gtctccaggt caattgattc agaggatcac    120
```

-continued

```
cgatgaccct gacgttagca taaggctgtt agaggttgtc cagagtgacc agtcacaatc    180
tggccttacc ttcgcatcaa gaggtaccaa catggaggat gaggcggacc aatacttttc    240
acatgatgat ccaattagta gtgatcaatc caggttcgga tggttcgaga acaaggaaat    300
ctcagatatt gaagtgcaag accctgaggg attcaacatg attctgggta ccatcctagc    360
tcaaatttgg gtcttgctcg caaaggcggt tacggcccca gacacggcag ctgattcgga    420
gctaagaagg tggataaagt acacccaaca aagaagggta gttggtgaat ttagattgga    480
gagaaaatgg ttggatgtgg tgaggaacag gattgccgag gacctctcct tacgccgatt    540
catggtcgct ctaatcctgg atatcaagag aacacccgga aacaaaccca ggattgctga    600
aatgatatgt gacattgata catatatcgt agaggcagga ttagccagtt ttatcctgac    660
tattaagttt gggatagaaa ctatgtatcc tgctcttgga ctgcatgaat ttgctggtga    720
gttatccaca cttgagtcct tgatgaacct ttaccagcaa atgggggaaa ctgcacccta    780
catggtaatc ctggagaact caattcagaa caagttcagt gcaggatcat accctctgct    840
ctggagctat gccatgggag taggagtgga acttgaaaac tccatgggag gtttgaactt    900
tggccgatct tactttgatc cagcatattt tagattaggg caagagatgg taaggaggtc    960
agctggaaag gtcagttcca cattggcatc tgaactcggt atcactgccg aggatgcaag   1020
gcttgtttca gagattgcaa tgcatactac tgaggacaag atcagtagag cggttggacc   1080
cagacaagcc caagtatcat ttctacacgg tgatcaaagt gagaatgagc taccgagatt   1140
ggggggcaag gaagatagga gggtcaaaca gagtcgagga gaagccaggg agagctacag   1200
agaaaccggg cccagcagag caagtgatgc gagagctgcc catcttccaa ccggcacacc   1260
cctagacatt gacactgcat cggagtccag ccaagatccg caggacagtc gaaggtcagc   1320
tgacgccctg cttaggctgc aagccatggc aggaatctcg gaagaacaag gctcagacac   1380
ggacacccct atagtgtaca atgacagaaa tcttctagac taggtgcgag aggccgagga   1440
ccagaacaac atccgcctac cctccatcat tgttataaaa aacttaggaa ccaggtccac   1500
acagccgcca gcccatcaac catccactcc cacgattgga gccgatggca gaagagcagg   1560
cacgccatgt caaaaacgga ctggaatgca tccgggctct caaggccgag cccatcggct   1620
cactggccat cgaggaagct atggcagcat ggtcagaaat atcagacaac ccaggacagg   1680
agcgagccac ctgcagggaa gagaaggcag gcagttcggg tctcagcaaa ccatgcctct   1740
cagcaattgg atcaactgaa ggcggtgcac ctcgcatccg cggtcaggga cctggagaga   1800
gcgatgacga cgctgaaact ttgggaatcc ccccaagaaa tctccaggca tcaagcactg   1860
ggttacagtg ttattatgtt tatgatcaca gcggtgaagc ggttaaggga atccaagatg   1920
ctgactctat catggttcaa tcaggccttg atggtgatag caccctctca ggaggagaca   1980
atgaatctga aaacagcgat gtggatattg gcgaacctga taccgaggga tatgctatca   2040
ctgaccgggg atctgctccc atctctatgg ggttcagggc ttctgatgtt gaaactgcag   2100
aaggagggga gatccacgag ctcctgagac tccaatccag aggcaacaac tttccgaagc   2160
ttgggaaaac tctcaatgtt cctccgcctc cggaccccgg tagggccagc acttccggga   2220
cacccattaa aaagggcaca gacgcgagat tagcctcatt tggaacggag atcgcgtctt   2280
tattgacagg tggtgcaacc caatgtgctc gaaagtcacc ctcggaacca tcagggccag   2340
gtgcacctgc ggggaatgtc cccgagtgtg tgagcaatgc cgcactgata caggagtgga   2400
cacccgaatc tggtaccaca atctccccga gatcccagaa taatgaagaa gggggagact   2460
```

```
attatgatga tgagctgttc tctgatgtcc aagatattaa aacagccttg gccaaaatac   2520

acgaggataa tcagaagata atctccaagc tagaatcact gctgttattg aagggagaag   2580

ttgagtcaat taagaagcag atcaacaggc aaaatatcag catatccacc ctggaaggac   2640

acctctcaag catcatgatc gccattcctg gacttgggaa ggatcccaac gaccccactg   2700

cagatgtcga aatcaatccc gacttgaaac ccatcatagg cagagattca ggccgagcac   2760

tggccgaagt tctcaagaaa cccgttgcca gccgacaact ccaaggaatg acaaatggac   2820

ggaccagttc cagaggacag ctgctgaagg aatttcagct aaagccgatc gggaaaaaga   2880

tgagctcagc cgtcgggttt gttcctgaca ccggccctgc atcacgcagt gtaatccgct   2940

ccattataaa atccagccgg ctagaggagg atcggaagcg ttacctgatg actctccttg   3000

atgatatcaa aggagccaat gatcttgcca agttccacca gatgctgatg aagataataa   3060

tgaagtagct acagctcaac ttacctgcca accccatgcc agtcgaccca actagtacaa   3120

cctaaatcca ttataaaaaa cttaggagca aagtgattgc ctcccaagtt ccacatcgcg   3180

acgcgtacat gtagcgctcg caccggtcc                                     3209
```

<210> SEQ ID NO 4
<211> LENGTH: 8241
<212> TYPE: DNA
<213> ORGANISM: Artificial Sequence
<220> FEATURE:
<223> OTHER INFORMATION: Artificial DNA containing selected elements from MV sequence - pMTX-P1T-Intermediate

<400> SEQUENCE: 4

```
ccggtccgcg gggcgcgccc tcgaggtgcg agaggccgag gaccagaaca acatccgcct     60

accctccatc attgttataa aaaacttagg aaccaggtcc acacagccgc cagcccatca    120

accatccact cccacgattg gagccgcacg tgtctagagg gcccgtttaa accctgcagg    180

ttaattaagt gaattcttgg ttgaactccg gaaccctaat cctgccctag gtggttaggc    240

attatttgca atagattaaa gaaaactttg aaaatacgaa gtttctattc ccagctttgt    300

ctggtttttt tcccccccaa cttcggaggt cgaccagtac tccgggcgac actttgtttt    360

ttttttttcc cccgatgctg gaggtcgacc agatgtccga aagtgtcccc cccccccccc    420

cccccccccc ggcgcggagc ggcggggcca ccccggaccc cttttttttt tttttttttt    480

tttttaaatt cctggaacct ttaggtcgac cagttgtccg tcttttactc cttcatatag    540

gtcgaccagt actccgggtg gtactttgtc tttttctgaa aatcccagag gtcgaccaga    600

tatccgcggc cgccgagctc gttaacaaca acaattgcat tcattttatg tttcaggttc    660

agggggagat gtgggaggtt ttttaaagca agtaaaacct ctacaaatgt ggtaaaatcc    720

gataaggatc gatccgggct ggcgtaatag cgaagaggcc cgcaccgatc gcccttccca    780

acagttgcgc agcctgaatg gcgaatggac gcgccctgta gcggcgcatt aagcgcggcg    840

ggtgtggtgg ttacgcgcag cgtgaccgct acacttgcca gcgccctagc gcccgctcct    900

ttcgctttct tcccttcctt tctcgccacg ttcgccggct ttccccgtca agctctaaat    960

cgggggctcc ctttagggtt ccgatttaga gctttacggc acctcgaccg caaaaaactt   1020

gatttgggtg atggttcacg tagtgggcca tcgccctgat agacggtttt tcgccctttg   1080

acgttggagt ccacgttctt taatagtgga ctcttgttcc aaactggaac aacactcaac   1140

cctatctcgg tctattcttt tgatttataa gggattttgc cgatttcggc ctattggtta   1200

aaaaatgagc tgatttaaca aatatttaac gcgaatttta acaaaatatt aacgtttaca   1260
```

-continued atttcgcctg atgcggtatt ttctccttac gcatctgtgc ggtatttcac accgcatacg 1320
cggatctgcg cagcaccatg gcctgaaata acctctgaaa gaggaacttg gttaggtacc 1380
ttctgaggcg gaaagaacca gctgtggaat gtgtgtcagt tagggtgtgg aaagtcccca 1440
ggctccccag caggcagaag tatgcaaagc atgcatctca attagtcagc aaccaggtgt 1500
ggaaagtccc caggctcccc agcaggcaga agtatgcaaa gcatgcatct caattagtca 1560
gcaaccatag tcccgcccct aactccgccc atcccgcccc taactccgcc cagttccgcc 1620
cattctccgc cccatggctg actaattttt tttatttatg cagaggccga ggccgcctcg 1680
gcctctgagc tattccagaa gtagtgagga ggcttttttg gaggcctagg cttttgcaaa 1740
aagcttgatt cttctgacac aacagtctcg aacttaaggc tagagccacc atggttcgac 1800
cattgaactg catcgtcgcc gtgtcccaaa atatggggat tggcaagaac ggagacctac 1860
cctggcctcc gctcaggaac gagttcaagt acttccaaag aatgaccaca acctcttcag 1920
tggaaggtaa acagaatctg gtgattatgg gtaggaaaac ctggttctcc attcctgaga 1980
agaatcgacc tttaaaggac agaattaata tagttctcag tagagaactc aaagaaccac 2040
cacgaggagc tcattttctt gccaaaagtt tggatgatgc cttaagactt attgaacaac 2100
cggaattggc aagtaaagta gacatggttt ggatagtcgg aggcagttct gtttaccagg 2160
aagccatgaa tcaaccaggc cacctcagac tctttgtgac aaggatcatg caggaatttg 2220
aaagtgacac gtttttccca gaaattgatt tggggaaata taaacttctc ccagaatacc 2280
caggcgtcct ctctgaggtc caggaggaaa aaggcatcaa gtataagttt gaagtctacg 2340
agaagaaaga ctaagcggga ctctggggtt cgaaatgacc gaccaagcga cgcccaacct 2400
gccatcacga tggccgcaat aaaatatctt tattttcatt acatctgtgt gttggttttt 2460
tgtgtgaatc gatagcgata aggatccgcg tatggtgcac tctcagtaca atctgctctg 2520
atgccgcata gttaagccag ccccgacacc cgccaacacc cgctgacgcg ccctgacggg 2580
cttgtctgct cccggcatcc gcttacagac aagctgtgac cgtctccggg agctgcatgt 2640
gtcagaggtt ttcaccgtca tcaccgaaac gcgcgagacg aaagggcctc gtgatacgcc 2700
tatttttata ggttaatgtc atgataataa tggtttctta gacgtcaggt ggcacttttc 2760
ggggaaatgt gcgcggaacc cctatttgtt tatttttcta aatacattca aatatgtatc 2820
cgctcatgag acaataaccc tgataaatgc ttcaataata ttgaaaaagg aagagtatga 2880
gtattcaaca tttccgtgtc gcccttattc ccttttttgc ggcattttgc cttcctgttt 2940
ttgctcaccc agaaacgctg gtgaaagtaa aagatgctga agatcagttg ggtgcacgag 3000
tgggttacat cgaactggat ctcaacagcg gtaagatcct tgagagtttt cgccccgaag 3060
aacgttttcc aatgatgagc acttttaaag ttctgctatg tggcgcggta ttatcccgta 3120
ttgacgccgg gcaagagcaa ctcggtcgcc gcatacacta ttctcagaat gacttggttg 3180
agtactcacc agtcacagaa aagcatctta cggatggcat gacagtaaga gaattatgca 3240
gtgctgccat aaccatgagt gataacactg cggccaactt acttctgaca acgatcggag 3300
gaccgaagga gctaaccgct tttttgcaca acatggggga tcatgtaact cgccttgatc 3360
gttgggaacc ggagctgaat gaagccatac caaacgacga gcgtgacacc acgatgcctg 3420
tagcaatggc aacaacgttg cgcaaactat taactggcga actacttact ctagcttccc 3480
ggcaacaatt aatagactgg atggaggcgg ataaagttgc aggaccactt ctgcgctcgg 3540
cccttccggc tggctggttt attgctgata aatctggagc cggtgagcgt gggtctcgcg 3600
gtatcattgc agcactgggg ccagatggta agccctcccg tatcgtagtt atctacacga 3660
cggggagtca ggcaactatg gatgaacgaa atagacagat cgctgagata ggtgcctcac 3720
tgattaagca ttggtaactg tcagaccaag tttactcata tatactttag attgatttaa 3780
aacttcattt ttaatttaaa aggatctagg tgaagatcct ttttgataat ctcatgacca 3840
aaatccctta acgtgagttt tcgttccact gagcgtcaga ccccgtagaa aagatcaaag 3900
gatcttcttg agatcctttt tttctgcgcg taatctgctg cttgcaaaca aaaaaaccac 3960
cgctaccagc ggtggtttgt ttgccggatc aagagctacc aactcttttt ccgaaggtaa 4020
ctggcttcag cagagcgcag ataccaaata ctgtccttct agtgtagccg tagttaggcc 4080
accacttcaa gaactctgta gcaccgccta catacctcgc tctgctaatc ctgttaccag 4140
tggctgctgc cagtggcgat aagtcgtgtc ttaccgggtt ggactcaaga cgatagttac 4200
cggataaggc gcagcggtcg ggctgaacgg ggggttcgtg cacacagccc agcttggagc 4260
gaacgaccta caccgaactg agatacctac agcgtgagct atgagaaagc gccacgcttc 4320
ccgaagggag aaaggcggac aggtatccgg taagcggcag ggtcggaaca ggagagcgca 4380
cgagggagct tccaggggga aacgcctggt atctttatag tcctgtcggg tttcgccacc 4440
tctgacttga gcgtcgattt ttgtgatgct cgtcaggggg gcggagccta tggaaaaacg 4500
ccagcaacgc ggccttttta cggttcctgg ccttttgctg gccttttgct cacatggctc 4560
gacaagcttg gctagcacat cctcttggtc ctatcacggt tatgaggtcg accagttgtt 4620
gctttgatgt tcggttctct cgttgattgg gacaatattt ggggcacttc gccggtcccg 4680
acttccagaa tttccgtgtg gtctgtgaat ttatcaccgc tacactgtca tcatattcca 4740
gttttgcaat ctgctctctt tgtacctgca gataggtacc aaacaaagtt gggtaaggat 4800
agttcaatca atgatcattt tctagtgcac ttaggattca agatcctatt atcagggaca 4860
agagcaggat taaggatatc cgagatggcc acacttttaa ggagcttagc attgttcaaa 4920
agaaacaagg acaaaccacc cattacatca ggatccggtg gagccatcag aggaatcaaa 4980
cacattatta tagtaccaat ccctggagat tcctcaatta ccactcgatc cagacttctg 5040
gaccggttgg tcaggttaat tggaaacccg gatgtgagcg ggcccaaact aacaggggca 5100
ctaataggta tattatcctt atttgtggag tctccaggtc aattgattca gaggatcacc 5160
gatgaccctg acgttagcat aaggctgtta gaggttgtcc agagtgacca gtcacaatct 5220
ggccttacct tcgcatcaag aggtaccaac atggaggatg aggcggacca atacttttca 5280
catgatgatc caattagtag tgatcaatcc aggttcggat ggttcgagaa caaggaaatc 5340
tcagatattg aagtgcaaga ccctgaggga ttcaacatga ttctgggtac catcctagct 5400
caaatttggg tcttgctcgc aaaggcggtt acggccccag acacggcagc tgattcggag 5460
ctaagaaggt ggataaagta cacccaacaa agaagggtag ttggtgaatt tagattggag 5520
agaaaatggt tggatgtggt gaggaacagg attgccgagg acctctcctt acgccgattc 5580
atggtcgctc taatcctgga tatcaagaga acacccggaa acaaacccag gattgctgaa 5640
atgatatgtg acattgatac atatatcgta gaggcaggat tagccagttt tatcctgact 5700
attaagtttg ggatagaaac tatgtatcct gctcttggac tgcatgaatt tgctggtgag 5760
ttatccacac ttgagtcctt gatgaacctt taccagcaaa tgggggaaac tgcaccctac 5820
atggtaatcc tggagaactc aattcagaac aagttcagtg caggatcata ccctctgctc 5880
tggagctatg ccatgggagt aggagtggaa cttgaaaact ccatgggagg tttgaacttt 5940
ggccgatctt actttgatcc agcatatttt agattagggc aagagatggt aaggaggtca 6000

-continued

```
gctggaaagg tcagttccac attggcatct gaactcggta tcactgccga ggatgcaagg   6060
cttgtttcag agattgcaat gcatactact gaggacaaga tcagtagagc ggttggaccc   6120
agacaagccc aagtatcatt tctacacggt gatcaaagtg agaatgagct accgagattg   6180
gggggcaagg aagataggag ggtcaaacag agtcgaggag aagccaggga gagctacaga   6240
gaaaccgggc ccagcagagc aagtgatgcg agagctgccc atcttccaac cggcacaccc   6300
ctagacattg acactgcatc ggagtccagc caagatccgc aggacagtcg aaggtcagct   6360
gacgccctgc ttaggctgca agccatggca ggaatctcgg aagaacaagg ctcagacacg   6420
gacaccccta tagtgtacaa tgacagaaat cttctagact aggtgcgaga ggccgaggac   6480
cagaacaaca tccgcctacc ctccatcatt gttataaaaa acttaggaac caggtccaca   6540
cagccgccag cccatcaacc atccactccc acgattggag ccgatggcag aagagcaggc   6600
acgccatgtc aaaaacggac tggaatgcat ccgggctctc aaggccgagc ccatcggctc   6660
actggccatc gaggaagcta tggcagcatg gtcagaaata tcagacaacc caggacagga   6720
gcgagccacc tgcagggaag agaaggcagg cagttcgggt ctcagcaaac catgcctctc   6780
agcaattgga tcaactgaag gcggtgcacc tcgcatccgc ggtcagggac ctggagagag   6840
cgatgacgac gctgaaactt tgggaatccc cccaagaaat ctccaggcat caagcactgg   6900
gttacagtgt tattatgttt atgatcacag cggtgaagcg gttaagggaa tccaagatgc   6960
tgactctatc atggttcaat caggccttga tggtgatagc accctctcag gaggagacaa   7020
tgaatctgaa aacagcgatg tggatattgg cgaacctgat accgagggat atgctatcac   7080
tgaccgggga tctgctccca tctctatggg gttcagggct tctgatgttg aaactgcaga   7140
aggaggggag atccacgagc tcctgagact ccaatccaga ggcaacaact ttccgaagct   7200
tgggaaaact ctcaatgttc ctccgcctcc ggaccccggt agggccagca cttccgggac   7260
acccattaaa aagggcacag acgcgagatt agcctcattt ggaacggaga tcgcgtcttt   7320
attgacaggt ggtgcaaccc aatgtgctcg aaagtcaccc tcggaaccat cagggccagg   7380
tgcacctgcg gggaatgtcc ccgagtgtgt gagcaatgcc gcactgatac aggagtggac   7440
acccgaatct ggtaccacaa tctccccgag atcccagaat aatgaagaag gggagacta    7500
ttatgatgat gagctgttct ctgatgtcca agatattaaa acagccttgg ccaaaataca   7560
cgaggataat cagaagataa tctccaagct agaatcactg ctgttattga agggagaagt   7620
tgagtcaatt aagaagcaga tcaacaggca aaatatcagc atatccaccc tggaaggaca   7680
cctctcaagc atcatgatcg ccattcctgg acttgggaag gatcccaacg accccactgc   7740
agatgtcgaa atcaatcccg acttgaaacc catcataggc agagattcag gccgagcact   7800
ggccgaagtt ctcaagaaac ccgttgccag ccgacaactc caaggaatga caaatggacg   7860
gaccagttcc agaggacagc tgctgaagga atttcagcta aagccgatcg ggaaaaagat   7920
gagctcagcc gtcgggtttg ttcctgacac cggccctgca tcacgcagtg taatccgctc   7980
cattataaaa tccagccggc tagaggagga tcggaagcgt tacctgatga ctctccttga   8040
tgatatcaaa ggagccaatg atcttgccaa gttccaccag atgctgatga agataataat   8100
gaagtagcta cagctcaact tacctgccaa ccccatgcca gtcgacccaa ctagtacaac   8160
ctaaatccat tataaaaaac ttaggagcaa agtgattgcc tcccaagttc cacatcgcga   8220
cgcgtacatg tagcgctcgc a                                             8241
```

<210> SEQ ID NO 5
<211> LENGTH: 998

-continued

<212> TYPE: DNA
<213> ORGANISM: Artificial Sequence
<220> FEATURE:
<223> OTHER INFORMATION: Fragment from MV sequence - PmlI-L2-EcoRI fragment

<400> SEQUENCE: 5

```
tcacgtgggt aggcagtgta gattgcttca atttcatagt tagtaatatc cctacctcta     60
gtgtggggtt tatccattca gatatagaga ccttgcctaa caaagatact atagagaagc    120
tagaggaatt ggcagccatc ttatcgatgg ctctgctcct gggcaaaata ggatcaatac    180
tggtgattaa gcttatgcct ttcagcgggg attttgttca gggatttata agttatgtag    240
ggtcccatta tagagaagtg aaccttgtat accctagata cagcaacttc atatctactg    300
aatcttattt ggttatgaca gatctcaagg ctaaccggct aatgaatcct gaaaagatta    360
agcagcagat aattgaatca tctgtgagga cttcacctgg acttataggt cacatcctat    420
ccattaagca actaagctgc atacaagcaa ttgtgggaga cgcagttagt agaggtgata    480
tcaatcctac tctgaaaaaa cttacaccta tagagcaggt gctgatcaat tgcgggttgg    540
caattaacgg acctaagctg tgcaaagaat tgatccacca tgatgttgcc tcagggcaag    600
atggattgct taattctata ctcatcctct acagggagtt ggcaagattc aaagacaacc    660
aaagaagtca acaagggatg ttccacgctt accccgtatt ggtaagtagc aggcaacgag    720
aacttatatc taggatcacc cgcaaatttt gggggcacat tcttctttac tccgggaaca    780
gaaagttgat aaataagttt atccagaatc tcaagtccgg ctatctgata ctagacttac    840
accagaatat cttcgttaag aatctatcca agtcagagaa acagattatt atgacggggg    900
gtttgaaacg tgagtgggtt tttaaggtaa cagtcaagga gaccaaagaa tggtataagt    960
tagtcggata cagtgccctg attaaggact aagaattc                            998
```

<210> SEQ ID NO 6
<211> LENGTH: 5746
<212> TYPE: DNA
<213> ORGANISM: Artificial Sequence
<220> FEATURE:
<223> OTHER INFORMATION: Fragment from MV sequence - PmlI-L1-PmlI fragment

<400> SEQUENCE: 6

```
cacgtgtggg atggtgggca tgggagtcag ctgcacagtc acccgggaag atggaaccaa     60
tcgcagatag ggctgctagt gaaccaatct catgatgtca cccagacatc aggcataccc    120
actagtgtga aatagacatc agaattaaga aaaacgtagg gtccaagtgg ttccccgtta    180
tggactcgct atctgtcaac cagatcttat accctgaagt tcacctagat agcccgatag    240
ttaccaataa gatagtagcc atcctggagt atgctcgagt ccctcacgct tacagcctgg    300
aggaccctac actgtgtcag aacatcaagc accgcctaaa aaacggattt tccaaccaaa    360
tgattataaa caatgtggaa gttgggaatg tcatcaagtc caagcttagg agttatccgg    420
cccactctca tattccatat ccaaattgta atcaggattt atttaacata gaagacaaag    480
agtcaacgag gaagatccgt gaactcctca aaaaggggaa ttcgctgtac tccaaagtca    540
gtgataaggt tttccaatgc ttaaggacca ctaactcacg gcttggccta ggctccgaat    600
tgagggagga catcaaggag aaagttatta acttgggagt ttacatgcac agctcccagt    660
ggtttgagcc ctttctgttt tggtttacag tcaagactga gatgaggtca gtgattaaat    720
cacaaaccca tacttgccat aggaggagac acacacctgt attcttcact ggtagttcag    780
```

-continued

```
ttgagttgct aatctctcgt gaccttgttg ctataatcag taaagagtct caacatgtat    840
attacctgac atttgaactg gttttgatgt attgtgatgt catagagggg aggttaatga    900
cagagaccgc tatgactatt gatgctaggt atacagagct tctaggaaga gtcagataca    960
tgtggaaact gatagatggt ttcttccctg cactcgggaa tccaacttat caaattgtag   1020
ccatgctgga gcctctttca cttgcttacc tgcagctgag ggatataaca gtagaactca   1080
gaggtgcttt ccttaaccac tgctttactg aaatacatga tgttcttgac caaaacgggt   1140
tttctgatga aggtacttat catgagttaa ttgaagctct agattacatt ttcataactg   1200
atgacataca tctgacaggg gagattttct catttttcag aagtttcggc caccccagac   1260
ttgaagcagt aacggctgct gaaaatgtta ggaaatacat gaatcagcct aaagtcattg   1320
tgtatgagac tctgatgaaa ggtcatgcca tattttgtgg aatcataatc aacggctatc   1380
gtgacaggca cggaggcagt tggccaccgc tgaccctccc cctgcatgct gcagacacaa   1440
tccggaatgc tcaagcttca ggtgaagggt taacacatga gcagtgcgtt gataactgga   1500
gatcttttgc tggagtgaaa tttggctgct ttatgcctct tagcctggat agtgatctga   1560
caatgtacct aaaggacaag gcacttgctg ctctccaaag ggaatgggat tcagtttacc   1620
cgaaagagtt cctgcgttac gaccctccca agggaaccgg gtcacggagg cttgtagatg   1680
ttttccttaa tgattcgagc tttgacccat atgatgtgat aatgtatgtt gtaagtggag   1740
cttacctcca tgaccctgag ttcaacctgt cttacagcct gaaagaaaag gagatcaagg   1800
aaacaggtag actttttgct aaaatgactt acaaaatgag ggcatgccaa gtgattgctg   1860
aaaatctaat ctcaaacggg attggcaaat attttaagga caatgggatg gccaaggatg   1920
agcacgattt gactaaggca ctccacactc tagctgtctc aggagtcccc aaagatctca   1980
aagaaagtca caggggggggg ccagtcttaa aaacctactc ccgaagccca gtccacacaa   2040
gtaccaggaa cgtgagagca gcaaaagggt ttatagggtt ccctcaagta attcggcagg   2100
accaagacac tgatcatccg gagaatatgg aagcttacga gacagtcagt gcatttatca   2160
cgactgatct caagaagtac tgccttaatt ggagatatga gaccatcagc ttgtttgcac   2220
agaggctaaa tgagatttac ggattgccct catttttcca gtggctgcat aagaggcttg   2280
agacctctgt cctgtatgta agtgaccctc attgcccccc cgaccttgac gcccatatcc   2340
cgttatataa agtccccaat gatcaaatct tcattaagta ccctatggga ggtatagaag   2400
ggtattgtca gaagctgtgg accatcagca ccattcccta tctatacctg gctgcttatg   2460
agagcggagt aaggattgct tcgttagtgc aaggggacaa tcagaccata gccgtaacaa   2520
aaagggtacc cagcacatgg ccctacaacc ttaagaaacg ggaagctgct agagtaacta   2580
gagattactt tgtaattctt aggcaaaggc tacatgatat tggccatcac ctcaaggcaa   2640
atgagacaat tgtttcatca catttttttg tctattcaaa aggaatatat tatgatgggc   2700
tacttgtgtc ccaatcactc aagagcatcg caagatgtgt attctggtca gagactatag   2760
ttgatgaaac aagggcagca tgcagtaata ttgctacaac aatggctaaa agcatcgaga   2820
gaggttatga ccgttacctt gcatattccc tgaacgtcct aaaagtgata cagcaaattc   2880
tgatctctct tggcttcaca atcaattcaa ccatgacccg ggatgtagtc ataccccctcc  2940
tcacgaacaa cgacctctta ataaggatgg cactgttgcc cgctcctatt ggggggatga   3000
attatctgaa tatgagcagg ctgtttgtca gaaacatcgg tgatccagta acatcatcaa   3060
ttgctgatct caagagaatg attctcgcct cactaatgcc tgaagagacc ctccatcaag   3120
taatgacaca acaaccgggg gactcttcat tcctagactg ggctagcgac ccttactcag   3180
```

-continued

```
caaatcttgt atgtgtccag agcatcacta gactcctcaa gaacataact gcaaggtttg   3240
tcctgatcca tagtccaaac ccaatgttaa aaggattatt ccatgatgac agtaaagaag   3300
aggacgaggg actggcggca ttcctcatgg acaggcatat tatagtacct agggcagctc   3360
atgaaatcct ggatcatagt gtcacagggg caagagagtc tattgcaggc atgctggata   3420
ccacaaaagg cctgattcga gccagcatga ggaagggggg gttaacctct cgagtgataa   3480
ccagattgtc caattatgac tatgaacaat tcagagcagg gatggtgcta ttgacaggaa   3540
gaaagagaaa tgtcctcatt gacaaagagt catgttcagt gcagctggcg agagctctaa   3600
gaagccatat gtgggcgagg ctagctcgag gacggcctat ttacggcctt gaggtccctg   3660
atgtactaga atctatgcga ggccacctta ttcggcgtca tgagacatgt gtcatctgcg   3720
agtgtggatc agtcaactac ggatggtttt ttgtcccctc gggttgccaa ctggatgata   3780
ttgacaagga aacatcatcc ttgagagtcc catatattgg ttctaccact gatgagagaa   3840
cagacatgaa gcttgccttc gtaagagccc caagtcgatc cttgcgatct gctgttagaa   3900
tagcaacagt gtactcatgg gcttacggtg atgatgatag ctcttggaac gaagcctggt   3960
tgttggctag gcaaagggcc aatgtgagcc tggaggagct aagggtgatc actcccatct   4020
caacttcgac taatttagcg cataggttga gggatcgtag cactcaagtg aaatactcag   4080
gtacatccct tgtccgagtg gcgaggtata ccacaatctc caacgacaat ctctcatttg   4140
tcatatcaga taagaaggtt gatactaact ttatatacca acaaggaatg cttctagggt   4200
tgggtgtttt agaaacattg tttcgactcg agaaagatac cggatcatct aacacggtat   4260
tacatcttca cgtcgaaaca gattgttgcg tgatcccgat gatagatcat cccaggatac   4320
ccagctcccg caagctagag ctgagggcag agctatgtac caacccattg atatatgata   4380
atgcaccttt aattgacaga gatacaacaa ggctatacac ccagagccat aggaggcacc   4440
ttgtggaatt tgttacatgg tccacacccc aactatatca cattttagct aagtccacag   4500
cactatctat gattgacctg gtaacaaaat ttgagaagga ccatatgaat gaaatttcag   4560
ctctcatagg ggatgacgat atcaatagtt tcataactga gtttctgctc atagagccaa   4620
gattattcac tatctacttg ggccagtgtg cggccatcaa ttgggcattt gatgtacatt   4680
atcatagacc atcagggaaa tatcagatgg gtgagctgtt gtcatcgttc ctttctagaa   4740
tgagcaaagg agtgtttaag gtgcttgtca atgctctaag ccacccaaag atctacaaga   4800
aattctggca ttgtggtatt atagagccta tccatggtcc ttcacttgat gctcaaaact   4860
tgcacacaac tgtgtgcaac atggtttaca catgctatat gacctacctc gacctgttgt   4920
tgaatgaaga gttagaagag ttcacatttc tcttgtgtga aagcgacgag gatgtagtac   4980
cggacagatt cgacaacatc caggcaaaac acttatgtgt tctggcagat ttgtactgtc   5040
aaccagggac ctgcccacca attcgaggtc taagaccggt agagaaatgt gcagttctaa   5100
ccgaccatat caaggcagag gctaggttat ctccagcagg atcttcgtgg aacataaatc   5160
caattattgt agaccattac tcatgctctc tgacttatct ccggcgagga tcgatcaaac   5220
agataagatt gagagttgat ccaggattca ttttcgacgc cctcgctgag gtaaatgtca   5280
gtcagccaaa gatcggcagc aacaacatct caaatatgag catcaaggct ttcagacccc   5340
cacacgatga tgttgcaaaa ttgctcaaag atatcaacac aagcaagcac aatcttccca   5400
tttcaggggg caatctcgcc aattatgaaa tccatgcttt ccgcagaatc gggttgaact   5460
catctgcttg ctacaaagct gttgagatat caacattaat taggagatgc cttgagccag   5520
```

```
gggaggacgg cttgttcttg ggtgagggat cgggttccat gttgatcact tataaggaga   5580

tacttaaact aaacaagtgc ttctataata gtggggtttc cgccaattct agatctggtc   5640

aaagggaatt agcaccctat ccctccgaag ttggccttgt cgaacacaga atgggagtag   5700

gtaatattgt caaagtgctc tttaacggga ggcccgaagt cacgtg                  5746


<210> SEQ ID NO 7
<211> LENGTH: 14922
<212> TYPE: DNA
<213> ORGANISM: Artificial Sequence
<220> FEATURE:
<223> OTHER INFORMATION: Artificial DNA containing selected elements
      from MV sequence - pMTX-P1T-High

<400> SEQUENCE: 7

gtgggtaggc agtgtagatt gcttcaattt catagttagt aatatcccta cctctagtgt     60

ggggtttatc cattcagata tagagacctt gcctaacaaa gatactatag agaagctaga    120

ggaattggca gccatcttat cgatggctct gctcctgggc aaaataggat caatactggt    180

gattaagctt atgcctttca gcggggattt tgttcaggga tttataagtt atgtagggtc    240

ccattataga gaagtgaacc ttgtataccc tagatacagc aacttcatat ctactgaatc    300

ttatttggtt atgacagatc tcaaggctaa ccggctaatg aatcctgaaa agattaagca    360

gcagataatt gaatcatctg tgaggacttc acctggactt ataggtcaca tcctatccat    420

taagcaacta agctgcatac aagcaattgt gggagacgca gttagtagag gtgatatcaa    480

tcctactctg aaaaaactta cacctataga gcaggtgctg atcaattgcg ggttggcaat    540

taacggacct aagctgtgca aagaattgat ccaccatgat gttgcctcag ggcaagatgg    600

attgcttaat tctatactca tcctctacag ggagttggca agattcaaag acaaccaaag    660

aagtcaacaa gggatgttcc acgcttaccc cgtattggta agtagcaggc aacgagaact    720

tatatctagg atcacccgca aattttgggg gcacattctt ctttactccg ggaacagaaa    780

gttgataaat aagtttatcc agaatctcaa gtccggctat ctgatactag acttacacca    840

gaatatcttc gttaagaatc tatccaagtc agagaaacag attattatga cggggggttt    900

gaaacgtgag tgggttttta aggtaacagt caaggagacc aaagaatggt ataagttagt    960

cggatacagt gccctgatta aggactaatt ggttgaactc cggaacccta atcctgccct   1020

aggtggttag gcattatttg caatagatta aagaaaactt tgaaaatacg aagtttctat   1080

tcccagcttt gtctggtttt tttccccccc aacttcggag gtcgaccagt actccgggcg   1140

acactttgtt tttttttttt cccccgatgc tggaggtcga ccagatgtcc gaaagtgtcc   1200

cccccccccc cccccccccc ccggcgcgga gcggcggggc caccccggac cccttttttt   1260

tttttttttt tttttttaaa ttcctggaac ctttaggtcg accagttgtc cgtcttttac   1320

tccttcatat aggtcgacca gtactccggg tggtactttg tctttttctg aaaatcccag   1380

aggtcgacca gatatccgcg gccgccgagc tcgttaacaa caacaattgc attcatttta   1440

tgtttcaggt tcagggggag atgtgggagg ttttttaaag caagtaaaac ctctacaaat   1500

gtggtaaaat ccgataagga tcgatccggg ctggcgtaat agcgaagagg cccgcaccga   1560

tcgcccttcc caacagttgc gcagcctgaa tggcgaatgg acgcgccctg tagcggcgca   1620

ttaagcgcgg cgggtgtggt ggttacgcgc agcgtgaccg ctacacttgc cagcgcccta   1680

gcgcccgctc ctttcgcttt cttcccttcc tttctcgcca cgttcgccgg ctttccccgt   1740

caagctctaa atcgggggct ccctttaggg ttccgattta gagctttacg gcacctcgac   1800
```

-continued

```
cgcaaaaaac ttgatttggg tgatggttca cgtagtgggc catcgccctg atagacggtt   1860
tttcgccctt tgacgttgga gtccacgttc tttaatagtg gactcttgtt ccaaactgga   1920
acaacactca accctatctc ggtctattct tttgatttat aagggatttt gccgatttcg   1980
gcctattggt taaaaaatga gctgatttaa caaatattta acgcgaattt taacaaaata   2040
ttaacgttta caatttcgcc tgatgcggta ttttctcctt acgcatctgt gcggtatttc   2100
acaccgcata cgcggatctg cgcagcacca tggcctgaaa taacctctga aagaggaact   2160
tggttaggta ccttctgagg cggaaagaac cagctgtgga atgtgtgtca gttagggtgt   2220
ggaaagtccc caggctcccc agcaggcaga agtatgcaaa gcatgcatct caattagtca   2280
gcaaccaggt gtggaaagtc cccaggctcc ccagcaggca gaagtatgca aagcatgcat   2340
ctcaattagt cagcaaccat agtcccgccc ctaactccgc ccatcccgcc cctaactccg   2400
cccagttccg cccattctcc gccccatggc tgactaattt ttttatttta tgcagaggcc   2460
gaggccgcct cggcctctga gctattccag aagtagtgag gaggcttttt tggaggccta   2520
ggcttttgca aaaagcttga ttcttctgac acaacagtct cgaacttaag gctagagcca   2580
ccatggttcg accattgaac tgcatcgtcg ccgtgtccca aaatatgggg attggcaaga   2640
acggagacct accctggcct ccgctcagga acgagttcaa gtacttccaa agaatgacca   2700
caacctcttc agtggaaggt aaacagaatc tggtgattat gggtaggaaa acctggttct   2760
ccattcctga gaagaatcga cctttaaagg acagaattaa tatagttctc agtagagaac   2820
tcaaagaacc accacgagga gctcattttc ttgccaaaag tttggatgat gccttaagac   2880
ttattgaaca accggaattg gcaagtaaag tagacatggt ttggatagtc ggaggcagtt   2940
ctgtttacca ggaagccatg aatcaaccag gccacctcag actctttgtg acaaggatca   3000
tgcaggaatt tgaaagtgac acgtttttcc cagaaattga tttggggaaa tataaacttc   3060
tcccagaata cccaggcgtc ctctctgagg tccaggagga aaaaggcatc aagtataagt   3120
ttgaagtcta cgagaagaaa gactaagcgg gactctgggg ttcgaaatga ccgaccaagc   3180
gacgcccaac ctgccatcac gatggccgca ataaaatatc tttattttca ttacatctgt   3240
gtgttggttt tttgtgtgaa tcgatagcga taaggatccg cgtatggtgc actctcagta   3300
caatctgctc tgatgccgca tagttaagcc agccccgaca cccgccaaca cccgctgacg   3360
cgccctgacg ggcttgtctg ctcccggcat ccgcttacag acaagctgtg accgtctccg   3420
ggagctgcat gtgtcagagg ttttcaccgt catcaccgaa acgcgcgaga cgaaagggcc   3480
tcgtgatacg cctattttta taggttaatg tcatgataat aatggtttct tagacgtcag   3540
gtggcacttt tcggggaaat gtgcgcggaa cccctatttg tttatttttc taaatacatt   3600
caaatatgta tccgctcatg agacaataac cctgataaat gcttcaataa tattgaaaaa   3660
ggaagagtat gagtattcaa catttccgtg tcgcccttat tccctttttt gcggcatttt   3720
gccttcctgt ttttgctcac ccagaaacgc tggtgaaagt aaaagatgct gaagatcagt   3780
tgggtgcacg agtgggttac atcgaactgg atctcaacag cggtaagatc cttgagagtt   3840
ttcgccccga agaacgtttt ccaatgatga gcacttttaa agttctgcta tgtggcgcgg   3900
tattatcccg tattgacgcc gggcaagagc aactcggtcg ccgcatacac tattctcaga   3960
atgacttggt tgagtactca ccagtcacag aaaagcatct tacggatggc atgacagtaa   4020
gagaattatg cagtgctgcc ataaccatga gtgataacac tgcggccaac ttacttctga   4080
caacgatcgg aggaccgaag gagctaaccg cttttttgca caacatgggg gatcatgtaa   4140
ctcgccttga tcgttgggaa ccggagctga atgaagccat accaaacgac gagcgtgaca   4200
```

ccacgatgcc tgtagcaatg gcaacaacgt tgcgcaaact attaactggc gaactactta 4260
ctctagcttc ccggcaacaa ttaatagact ggatggaggc ggataaagtt gcaggaccac 4320
ttctgcgctc ggcccttccg gctggctggt ttattgctga taaatctgga gccggtgagc 4380
gtgggtctcg cggtatcatt gcagcactgg ggccagatgg taagccctcc cgtatcgtag 4440
ttatctacac gacggggagt caggcaacta tggatgaacg aaatagacag atcgctgaga 4500
taggtgcctc actgattaag cattggtaac tgtcagacca agtttactca tatatacttt 4560
agattgattt aaaacttcat ttttaattta aaaggatcta ggtgaagatc ctttttgata 4620
atctcatgac caaaatccct taacgtgagt tttcgttcca ctgagcgtca gaccccgtag 4680
aaaagatcaa aggatcttct tgagatcctt tttttctgcg cgtaatctgc tgcttgcaaa 4740
caaaaaaacc accgctacca gcggtggttt gtttgccgga tcaagagcta ccaactcttt 4800
ttccgaaggt aactggcttc agcagagcgc agataccaaa tactgtcctt ctagtgtagc 4860
cgtagttagg ccaccacttc aagaactctg tagcaccgcc tacatacctc gctctgctaa 4920
tcctgttacc agtggctgct gccagtggcg ataagtcgtg tcttaccggg ttggactcaa 4980
gacgatagtt accggataag gcgcagcggt cgggctgaac ggggggttcg tgcacacagc 5040
ccagcttgga gcgaacgacc tacaccgaac tgagatacct acagcgtgag ctatgagaaa 5100
gcgccacgct tcccgaaggg agaaaggcgg acaggtatcc ggtaagcggc agggtcggaa 5160
caggagagcg cacgagggag cttccagggg gaaacgcctg gtatctttat agtcctgtcg 5220
ggtttcgcca cctctgactt gagcgtcgat ttttgtgatg ctcgtcaggg gggcggagcc 5280
tatggaaaaa cgccagcaac gcggcctttt tacggttcct ggccttttgc tggccttttg 5340
ctcacatggc tcgacaagct tggctagcac atcctcttgg tcctatcacg gttatgaggt 5400
cgaccagttg ttgctttgat gttcggttct ctcgttgatt gggacaatat ttggggcact 5460
tcgccggtcc cgacttccag aatttccgtg tggtctgtga atttatcacc gctacactgt 5520
catcatattc cagttttgca atctgctctc tttgtacctg cagataggta ccaaacaaag 5580
ttgggtaagg atagttcaat caatgatcat tttctagtgc acttaggatt caagatccta 5640
ttatcaggga caagagcagg attaaggata tccgagatgg ccacactttt aaggagctta 5700
gcattgttca aaagaaacaa ggacaaacca cccattacat caggatccgg tggagccatc 5760
agaggaatca aacacattat tatagtacca atccctggag attcctcaat taccactcga 5820
tccagacttc tggaccggtt ggtcaggtta attggaaacc cggatgtgag cgggcccaaa 5880
ctaacagggg cactaatagg tatattatcc ttatttgtgg agtctccagg tcaattgatt 5940
cagaggatca ccgatgaccc tgacgttagc ataaggctgt tagaggttgt ccagagtgac 6000
cagtcacaat ctggccttac cttcgcatca agaggtacca acatggagga tgaggcggac 6060
caatactttt cacatgatga tccaattagt agtgatcaat ccaggttcgg atggttcgag 6120
aacaaggaaa tctcagatat tgaagtgcaa gaccctgagg gattcaacat gattctgggt 6180
accatcctag ctcaaatttg ggtcttgctc gcaaaggcgg ttacggcccc agacacggca 6240
gctgattcgg agctaagaag gtggataaag tacacccaac aaagaagggt agttggtgaa 6300
tttagattgg agagaaaatg gttggatgtg gtgaggaaca ggattgccga ggacctctcc 6360
ttacgccgat tcatggtcgc tctaatcctg gatatcaaga gaacacccgg aaacaaaccc 6420
aggattgctg aaatgatatg tgacattgat acatatatcg tagaggcagg attagccagt 6480
tttatcctga ctattaagtt tgggatagaa actatgtatc ctgctcttgg actgcatgaa 6540

-continued

```
tttgctggtg agttatccac acttgagtcc ttgatgaacc tttaccagca aatgggggaa   6600
actgcaccct acatggtaat cctggagaac tcaattcaga acaagttcag tgcaggatca   6660
taccctctgc tctggagcta tgccatggga gtaggagtgg aacttgaaaa ctccatggga   6720
ggtttgaact ttggccgatc ttactttgat ccagcatatt ttagattagg gcaagagatg   6780
gtaaggaggt cagctggaaa ggtcagttcc acattggcat ctgaactcgg tatcactgcc   6840
gaggatgcaa ggcttgtttc agagattgca atgcatacta ctgaggacaa gatcagtaga   6900
gcggttggac ccagacaagc ccaagtatca tttctacacg gtgatcaaag tgagaatgag   6960
ctaccgagat tgggggcaa ggaagatagg agggtcaaac agagtcgagg agaagccagg   7020
gagagctaca gagaaaccgg gcccagcaga gcaagtgatg cgagagctgc ccatcttcca   7080
accggcacac ccctagacat tgacactgca tcggagtcca gccaagatcc gcaggacagt   7140
cgaaggtcag ctgacgccct gcttaggctg caagccatgg caggaatctc ggaagaacaa   7200
ggctcagaca cggacacccc tatagtgtac aatgacagaa atcttctaga ctaggtgcga   7260
gaggccgagg accagaacaa catccgccta ccctccatca ttgttataaa aaacttagga   7320
accaggtcca cacagccgcc agcccatcaa ccatccactc ccacgattgg agccgatggc   7380
agaagagcag gcacgccatg tcaaaaacgg actggaatgc atccgggctc tcaaggccga   7440
gcccatcggc tcactggcca tcgaggaagc tatggcagca tggtcagaaa tatcagacaa   7500
cccaggacag gagcgagcca cctgcaggga agagaaggca ggcagttcgg gtctcagcaa   7560
accatgcctc tcagcaattg gatcaactga aggcggtgca cctcgcatcc gcggtcaggg   7620
acctggagag agcgatgacg acgctgaaac tttgggaatc cccccaagaa atctccaggc   7680
atcaagcact gggttacagt gttattatgt ttatgatcac agcggtgaag cggttaaggg   7740
aatccaagat gctgactcta tcatggttca atcaggcctt gatggtgata gcaccctctc   7800
aggaggagac aatgaatctg aaaacagcga tgtggatatt ggcgaacctg ataccgaggg   7860
atatgctatc actgaccggg gatctgctcc catctctatg gggttcaggg cttctgatgt   7920
tgaaactgca gaaggagggg agatccacga gctcctgaga ctccaatcca gaggcaacaa   7980
ctttccgaag cttgggaaaa ctctcaatgt tcctccgcct ccggaccccg gtagggccag   8040
cacttccggg acacccatta aaaagggcac agacgcgaga ttagcctcat ttggaacgga   8100
gatcgcgtct ttattgacag gtggtgcaac ccaatgtgct cgaaagtcac cctcggaacc   8160
atcagggcca ggtgcacctg cggggaatgt ccccgagtgt gtgagcaatg ccgcactgat   8220
acaggagtgg acacccgaat ctggtaccac aatctccccg agatcccaga ataatgaaga   8280
agggggagac tattatgatg atgagctgtt ctctgatgtc caagatatta aaacagcctt   8340
ggccaaaata cacgaggata atcagaagat aatctccaag ctagaatcac tgctgttatt   8400
gaagggagaa gttgagtcaa ttaagaagca gatcaacagg caaaatatca gcatatccac   8460
cctggaagga cacctctcaa gcatcatgat cgccattcct ggacttggga aggatcccaa   8520
cgaccccact gcagatgtcg aaatcaatcc cgacttgaaa cccatcatag gcagagattc   8580
aggccgagca ctggccgaag ttctcaagaa acccgttgcc agccgacaac tccaaggaat   8640
gacaaatgga cggaccagtt ccagaggaca gctgctgaag gaatttcagc taaagccgat   8700
cgggaaaaag atgagctcag ccgtcgggtt tgttcctgac accggccctg catcacgcag   8760
tgtaatccgc tccattataa aatccagccg gctagaggag gatcggaagc gttacctgat   8820
gactctcctt gatgatatca aaggagccaa tgatcttgcc aagttccacc agatgctgat   8880
gaagataata atgaagtagc tacagctcaa cttacctgcc aaccccatgc cagtcgaccc   8940
```

-continued aactagtaca acctaaatcc attataaaaa acttaggagc aaagtgattg cctcccaagt 9000
tccacatcgc gacgcgtaca tgtagcgctc gcaccggtcc gcggggcgcg ccctcgaggt 9060
gcgagaggcc gaggaccaga acaacatccg cctaccctcc atcattgtta taaaaaactt 9120
aggaaccagg tccacacagc cgccagccca tcaaccatcc actcccacga ttggagccgc 9180
acgtgtggga tggtgggcat gggagtcagc tgcacagtca cccgggaaga tggaaccaat 9240
cgcagatagg gctgctagtg aaccaatctc atgatgtcac ccagacatca ggcataccca 9300
ctagtgtgaa atagacatca gaattaagaa aaacgtaggg tccaagtggt tccccgttat 9360
ggactcgcta tctgtcaacc agatcttata ccctgaagtt cacctagata gcccgatagt 9420
taccaataag atagtagcca tcctggagta tgctcgagtc cctcacgctt acagcctgga 9480
ggaccctaca ctgtgtcaga acatcaagca ccgcctaaaa aacggatttt ccaaccaaat 9540
gattataaac aatgtggaag ttgggaatgt catcaagtcc aagcttagga gttatccggc 9600
ccactctcat attccatatc caaattgtaa tcaggattta tttaacatag aagacaaaga 9660
gtcaacgagg aagatccgtg aactcctcaa aaaggggaat tcgctgtact ccaaagtcag 9720
tgataaggtt ttccaatgct taagggacac taactcacgg cttggcctag gctccgaatt 9780
gagggaggac atcaaggaga aagttattaa cttgggagtt tacatgcaca gctcccagtg 9840
gtttgagccc tttctgtttt ggtttacagt caagactgag atgaggtcag tgattaaatc 9900
acaaacccat acttgccata ggaggagaca cacacctgta ttcttcactg gtagttcagt 9960
tgagttgcta atctctcgtg accttgttgc tataatcagt aaagagtctc aacatgtata 10020
ttacctgaca tttgaactgg ttttgatgta ttgtgatgtc atagagggga ggttaatgac 10080
agagaccgct atgactattg atgctaggta tacagagctt ctaggaagag tcagatacat 10140
gtggaaactg atagatggtt tcttccctgc actcgggaat ccaacttatc aaattgtagc 10200
catgctggag cctctttcac ttgcttacct gcagctgagg gatataacag tagaactcag 10260
aggtgctttc cttaaccact gctttactga aatacatgat gttcttgacc aaaacgggtt 10320
ttctgatgaa ggtacttatc atgagttaat tgaagctcta gattacattt tcataactga 10380
tgacatacat ctgacagggg agattttctc atttttcaga agtttcggcc accccagact 10440
tgaagcagta acggctgctg aaaatgttag gaaatacatg aatcagccta aagtcattgt 10500
gtatgagact ctgatgaaag gtcatgccat attttgtgga atcataatca acggctatcg 10560
tgacaggcac ggaggcagtt ggccaccgct gaccctcccc ctgcatgctg cagacacaat 10620
ccggaatgct caagcttcag gtgaagggtt aacacatgag cagtgcgttg ataactggag 10680
atcttttgct ggagtgaaat ttggctgctt tatgcctctt agcctggata gtgatctgac 10740
aatgtaccta aaggacaagg cacttgctgc tctccaaagg gaatgggatt cagtttaccc 10800
gaaagagttc ctgcgttacg accctcccaa gggaaccggg tcacggaggc ttgtagatgt 10860
tttccttaat gattcgagct ttgacccata tgatgtgata atgtatgttg taagtggagc 10920
ttacctccat gaccctgagt tcaacctgtc ttacagcctg aaagaaaagg agatcaagga 10980
aacaggtaga ctttttgcta aaatgactta caaaatgagg gcatgccaag tgattgctga 11040
aaatctaatc tcaaacggga ttggcaaata ttttaaggac aatgggatgg ccaaggatga 11100
gcacgatttg actaaggcac tccacactct agctgtctca ggagtcccca aagatctcaa 11160
agaaagtcac aggggggggc cagtcttaaa aacctactcc cgaagcccag tccacacaag 11220
taccaggaac gtgagagcag caaaagggtt tatagggttc cctcaagtaa ttcggcagga 11280

-continued ccaagacact gatcatccgg agaatatgga agcttacgag acagtcagtg catttatcac 11340
gactgatctc aagaagtact gccttaattg gagatatgag accatcagct tgtttgcaca 11400
gaggctaaat gagatttacg gattgccctc atttttccag tggctgcata agaggcttga 11460
gacctctgtc ctgtatgtaa gtgaccctca ttgccccccc gaccttgacg cccatatccc 11520
gttatataaa gtccccaatg atcaaatctt cattaagtac cctatgggag gtatagaagg 11580
gtattgtcag aagctgtgga ccatcagcac cattccctat ctatacctgg ctgcttatga 11640
gagcggagta aggattgctt cgttagtgca aggggacaat cagaccatag ccgtaacaaa 11700
aagggtaccc agcacatggc cctacaacct taagaaacgg gaagctgcta gagtaactag 11760
agattacttt gtaattctta ggcaaaggct acatgatatt ggccatcacc tcaaggcaaa 11820
tgagacaatt gtttcatcac atttttttgt ctattcaaaa ggaatatatt atgatgggct 11880
acttgtgtcc caatcactca agagcatcgc aagatgtgta ttctggtcag agactatagt 11940
tgatgaaaca agggcagcat gcagtaatat tgctacaaca atggctaaaa gcatcgagag 12000
aggttatgac cgttaccttg catattccct gaacgtccta aaagtgatac agcaaattct 12060
gatctctctt ggcttcacaa tcaattcaac catgacccgg gatgtagtca tacccctcct 12120
cacgaacaac gacctcttaa taaggatggc actgttgccc gctcctattg gggggatgaa 12180
ttatctgaat atgagcaggc tgtttgtcag aaacatcggt gatccagtaa catcatcaat 12240
tgctgatctc aagagaatga ttctcgcctc actaatgcct gaagagaccc tccatcaagt 12300
aatgacacaa caaccggggg actcttcatt cctagactgg gctagcgacc cttactcagc 12360
aaatcttgta tgtgtccaga gcatcactag actcctcaag aacataactg caaggtttgt 12420
cctgatccat agtccaaacc caatgttaaa aggattattc catgatgaca gtaaagaaga 12480
ggacgaggga ctggcggcat tcctcatgga caggcatatt atagtaccta gggcagctca 12540
tgaaatcctg gatcatagtg tcacaggggc aagagagtct attgcaggca tgctggatac 12600
cacaaaaggc ctgattcgag ccagcatgag gaaggggggg ttaacctctc gagtgataac 12660
cagattgtcc aattatgact atgaacaatt cagagcaggg atggtgctat tgacaggaag 12720
aaagagaaat gtcctcattg acaaagagtc atgttcagtg cagctggcga gagctctaag 12780
aagccatatg tgggcgaggc tagctcgagg acggcctatt tacggccttg aggtccctga 12840
tgtactagaa tctatgcgag gccaccttat tcggcgtcat gagacatgtg tcatctgcga 12900
gtgtggatca gtcaactacg gatggttttt tgtcccctcg ggttgccaac tggatgatat 12960
tgacaaggaa acatcatcct tgagagtccc atatattggt tctaccactg atgagagaac 13020
agacatgaag cttgccttcg taagagcccc aagtcgatcc ttgcgatctg ctgttagaat 13080
agcaacagtg tactcatggg cttacggtga tgatgatagc tcttggaacg aagcctggtt 13140
gttggctagg caaagggcca atgtgagcct ggaggagcta agggtgatca ctcccatctc 13200
aacttcgact aatttagcgc ataggttgag ggatcgtagc actcaagtga aatactcagg 13260
tacatccctt gtccgagtgg cgaggtatac cacaatctcc aacgacaatc tctcatttgt 13320
catatcagat aagaaggttg atactaactt tatataccaa caaggaatgc ttctagggtt 13380
gggtgtttta gaaacattgt ttcgactcga gaaagatacc ggatcatcta acacggtatt 13440
acatcttcac gtcgaaacag attgttgcgt gatcccgatg atagatcatc ccaggatacc 13500
cagctcccgc aagctagagc tgagggcaga gctatgtacc aacccattga tatatgataa 13560
tgcaccttta attgacagag atacaacaag gctatacacc cagagccata ggaggcacct 13620
tgtggaattt gttacatggt ccacacccca actatatcac attttagcta agtccacagc 13680

-continued actatctatg attgacctgg taacaaaatt tgagaaggac catatgaatg aaatttcagc 13740
tctcataggg gatgacgata tcaatagttt cataactgag tttctgctca tagagccaag 13800
attattcact atctacttgg gccagtgtgc ggccatcaat tgggcatttg atgtacatta 13860
tcatagacca tcagggaaat atcagatggg tgagctgttg tcatcgttcc tttctagaat 13920
gagcaaagga gtgtttaagg tgcttgtcaa tgctctaagc cacccaaaga tctacaagaa 13980
attctggcat tgtggtatta tagagcctat ccatggtcct tcacttgatg ctcaaaactt 14040
gcacacaact gtgtgcaaca tggtttacac atgctatatg acctacctcg acctgttgtt 14100
gaatgaagag ttagaagagt tcacatttct cttgtgtgaa agcgacgagg atgtagtacc 14160
ggacagattc gacaacatcc aggcaaaaca cttatgtgtt ctggcagatt tgtactgtca 14220
accagggacc tgcccaccaa ttcgaggtct aagaccggta gagaaatgtg cagttctaac 14280
cgaccatatc aaggcagagg ctaggttatc tccagcagga tcttcgtgga acataaatcc 14340
aattattgta gaccattact catgctctct gacttatctc cggcgaggat cgatcaaaca 14400
gataagattg agagttgatc caggattcat tttcgacgcc ctcgctgagg taaatgtcag 14460
tcagccaaag atcggcagca acaacatctc aaatatgagc atcaaggctt tcagaccccc 14520
acacgatgat gttgcaaaat tgctcaaaga tatcaacaca agcaagcaca atcttcccat 14580
ttcagggggc aatctcgcca attatgaaat ccatgctttc cgcagaatcg ggttgaactc 14640
atctgcttgc tacaaagctg ttgagatatc aacattaatt aggagatgcc ttgagccagg 14700
ggaggacggc ttgttcttgg gtgagggatc gggttccatg ttgatcactt ataaggagat 14760
acttaaacta aacaagtgct tctataatag tggggtttcc gccaattcta gatctggtca 14820
aagggaatta gcaccctatc cctccgaagt tggccttgtc gaacacagaa tgggagtagg 14880
taatattgtc aaagtgctct ttaacgggag gcccgaagtc ac 14922

<210> SEQ ID NO 8
<211> LENGTH: 12973
<212> TYPE: DNA
<213> ORGANISM: Artificial Sequence
<220> FEATURE:
<223> OTHER INFORMATION: Artificial DNA containing selected elements
from MV sequence - pMTX-P1T-NP-RE1-FH-RE2-RE3

<400> SEQUENCE: 8
ctctttctag tgtgaaatag acatcagaat taagaaaaac gtagggtcca agtggttccc 60
cgttctcgag cacgtggtgc gagaggccga ggaccagaac aacatccgcc taccctccat 120
cattgttata aaaaacttag gaaccaggtc cacacagccg ccagcccatc aaccatccac 180
tcccacgatt ggagccgatg ggaattctcg cgattggttg aactccggaa ccctaatcct 240
gccctaggtg gttaggcatt atttgcaata gattaaagaa aactttgaaa atacgaagtt 300
tctattccca gctttgtctg gtttttttcc cccccaactt cggaggtcga ccagtactcc 360
gggcgacact ttgttttttt tttttccccc gatgctggag gtcgaccaga tgtccgaaag 420
tgtccccccc cccccccccc cccccccggc gcggagcggc ggggccaccc cggacccctt 480
tttttttttt tttttttttt ttaaattcct ggaaccttta ggtcgaccag ttgtccgtct 540
tttactcctt catataggtc gaccagtact ccgggtggta ctttgtcttt ttctgaaaat 600
cccagaggtc gaccagatat ccgcggccgc cgagctcgtt aacaacaaca attgcattca 660
ttttatgttt caggttcagg gggagatgtg ggaggttttt taaagcaagt aaaacctcta 720
caaatgtggt aaaatccgat aaggatcgat ccgggctggc gtaatagcga agaggcccgc 780

-continued

```
accgatcgcc cttcccaaca gttgcgcagc ctgaatggcg aatggacgcg ccctgtagcg    840
gcgcattaag cgcggcgggt gtggtggtta cgcgcagcgt gaccgctaca cttgccagcg    900
ccctagcgcc cgctcctttc gctttcttcc cttcctttct cgccacgttc gccggctttc    960
cccgtcaagc tctaaatcgg gggctccctt tagggttccg atttagagct ttacggcacc   1020
tcgaccgcaa aaaacttgat ttgggtgatg gttcacgtag tgggccatcg ccctgataga   1080
cggtttttcg ccctttgacg ttggagtcca cgttctttaa tagtggactc ttgttccaaa   1140
ctggaacaac actcaaccct atctcggtct attcttttga tttataaggg attttgccga   1200
tttcggccta ttggttaaaa aatgagctga tttaacaaat atttaacgcg aattttaaca   1260
aaatattaac gtttacaatt tcgcctgatg cggtattttc tccttacgca tctgtgcggt   1320
atttcacacc gcatacgcgg atctgcgcag caccatggcc tgaaataacc tctgaaagag   1380
gaacttggtt aggtaccttc tgaggcggaa agaaccagct gtggaatgtg tgtcagttag   1440
ggtgtggaaa gtccccaggc tccccagcag gcagaagtat gcaaagcatg catctcaatt   1500
agtcagcaac caggtgtgga aagtccccag gctccccagc aggcagaagt atgcaaagca   1560
tgcatctcaa ttagtcagca accatagtcc cgcccctaac tccgcccatc ccgcccctaa   1620
ctccgcccag ttccgcccat tctccgcccc atggctgact aatttttttt atttatgcag   1680
aggccgaggc cgcctcggcc tctgagctat tccagaagta gtgaggaggc ttttttggag   1740
gcctaggctt ttgcaaaaag cttgattctt ctgacacaac agtctcgaac ttaaggctag   1800
agccaccatg gttcgaccat tgaactgcat cgtcgccgtg tcccaaaata tggggattgg   1860
caagaacgga gacctaccct ggcctccgct caggaacgag ttcaagtact tccaaagaat   1920
gaccacaacc tcttcagtgg aaggtaaaca gaatctggtg attatgggta ggaaaacctg   1980
gttctccatt cctgagaaga atcgaccttt aaaggacaga attaatatag ttctcagtag   2040
agaactcaaa gaaccaccac gaggagctca ttttcttgcc aaaagtttgg atgatgcctt   2100
aagacttatt gaacaaccgg aattggcaag taaagtagac atggtttgga tagtcggagg   2160
cagttctgtt taccaggaag ccatgaatca accaggccac ctcagactct ttgtgacaag   2220
gatcatgcag gaatttgaaa gtgacacgtt tttcccagaa attgatttgg ggaaatataa   2280
acttctccca gaatacccag gcgtcctctc tgaggtccag gaggaaaaag gcatcaagta   2340
taagtttgaa gtctacgaga agaaagacta agcgggactc tggggttcga aatgaccgac   2400
caagcgacgc ccaacctgcc atcacgatgg ccgcaataaa atatctttat tttcattaca   2460
tctgtgtgtt ggttttttgt gtgaatcgat agcgataagg atccgcgtat ggtgcactct   2520
cagtacaatc tgctctgatg ccgcatagtt aagccagccc cgacacccgc caacacccgc   2580
tgacgcgccc tgacgggctt gtctgctccc ggcatccgct tacagacaag ctgtgaccgt   2640
ctccgggagc tgcatgtgtc agaggttttc accgtcatca ccgaaacgcg cgagacgaaa   2700
gggcctcgtg atacgcctat ttttataggt taatgtcatg ataataatgg tttcttagac   2760
gtcaggtggc acttttcggg gaaatgtgcg cggaacccct atttgtttat ttttctaaat   2820
acattcaaat atgtatccgc tcatgagaca ataaccctga taaatgcttc aataatattg   2880
aaaaaggaag agtatgagta ttcaacattt ccgtgtcgcc cttattccct tttttgcggc   2940
attttgcctt cctgtttttg ctcacccaga aacgctggtg aaagtaaaag atgctgaaga   3000
tcagttgggt gcacgagtgg gttacatcga actggatctc aacagcggta agatccttga   3060
gagttttcgc cccgaagaac gttttccaat gatgagcact tttaaagttc tgctatgtgg   3120
```

-continued cgcggtatta tcccgtattg acgccgggca agagcaactc ggtcgccgca tacactattc 3180
tcagaatgac ttggttgagt actcaccagt cacagaaaag catcttacgg atggcatgac 3240
agtaagagaa ttatgcagtg ctgccataac catgagtgat aacactgcgg ccaacttact 3300
tctgacaacg atcggaggac cgaaggagct aaccgctttt ttgcacaaca tgggggatca 3360
tgtaactcgc cttgatcgtt gggaaccgga gctgaatgaa gccataccaa acgacgagcg 3420
tgacaccacg atgcctgtag caatggcaac aacgttgcgc aaactattaa ctggcgaact 3480
acttactcta gcttcccggc aacaattaat agactggatg gaggcggata aagttgcagg 3540
accacttctg cgctcggccc ttccggctgg ctggtttatt gctgataaat ctggagccgg 3600
tgagcgtggg tctcgcggta tcattgcagc actggggcca gatggtaagc cctcccgtat 3660
cgtagttatc tacacgacgg ggagtcaggc aactatggat gaacgaaata gacagatcgc 3720
tgagataggt gcctcactga ttaagcattg gtaactgtca gaccaagttt actcatatat 3780
actttagatt gatttaaaac ttcattttta atttaaaagg atctaggtga agatcctttt 3840
tgataatctc atgaccaaaa tcccttaacg tgagttttcg ttccactgag cgtcagaccc 3900
cgtagaaaag atcaaaggat cttcttgaga tccttttttt ctgcgcgtaa tctgctgctt 3960
gcaaacaaaa aaaccaccgc taccagcggt ggtttgtttg ccggatcaag agctaccaac 4020
tctttttccg aaggtaactg gcttcagcag agcgcagata ccaaatactg tccttctagt 4080
gtagccgtag ttaggccacc acttcaagaa ctctgtagca ccgcctacat acctcgctct 4140
gctaatcctg ttaccagtgg ctgctgccag tggcgataag tcgtgtctta ccgggttgga 4200
ctcaagacga tagttaccgg ataaggcgca gcggtcgggc tgaacggggg gttcgtgcac 4260
acagcccagc ttggagcgaa cgacctacac cgaactgaga tacctacagc gtgagctatg 4320
agaaagcgcc acgcttcccg aagggagaaa ggcggacagg tatccggtaa gcggcagggt 4380
cggaacagga gagcgcacga gggagcttcc agggggaaac gcctggtatc tttatagtcc 4440
tgtcgggttt cgccacctct gacttgagcg tcgatttttg tgatgctcgt caggggggcg 4500
gagcctatgg aaaaacgcca gcaacgcggc ctttttacgg ttcctggcct tttgctggcc 4560
ttttgctcac atggctcgac aagcttggct agcacatcct cttggtccta tcacggttat 4620
gaggtcgacc agttgttgct ttgatgttcg gttctctcgt tgattgggac aatatttggg 4680
gcacttcgcc ggtcccgact tccagaattt ccgtgtggtc tgtgaattta tcaccgctac 4740
actgtcatca tattccagtt ttgcaatctg ctctctttgt acctgcagat aggtaccaaa 4800
caaagttggg taaggatagt tcaatcaatg atcattttct agtgcactta ggattcaaga 4860
tcctattatc agggacaaga gcaggattaa ggatatccga gatggccaca cttttaagga 4920
gcttagcatt gttcaaaaga aacaaggaca aaccacccat tacatcagga tccggtggag 4980
ccatcagagg aatcaaacac attattatag taccaatccc tggagattcc tcaattacca 5040
ctcgatccag acttctggac cggttggtca ggttaattgg aaacccggat gtgagcgggc 5100
ccaaactaac aggggcacta ataggtatat tatccttatt tgtggagtct ccaggtcaat 5160
tgattcagag gatcaccgat gaccctgacg ttagcataag gctgttagag gttgtccaga 5220
gtgaccagtc acaatctggc cttaccttcg catcaagagg taccaacatg gaggatgagg 5280
cggaccaata cttttcacat gatgatccaa ttagtagtga tcaatccagg ttcggatggt 5340
tcgagaacaa ggaaatctca gatattgaag tgcaagaccc tgagggattc aacatgattc 5400
tgggtaccat cctagctcaa atttgggtct tgctcgcaaa ggcggttacg gccccagaca 5460
cggcagctga ttcggagcta agaaggtgga taaagtacac ccaacaaaga agggtagttg 5520

```
gtgaatttag attggagaga aaatggttgg atgtggtgag gaacaggatt gccgaggacc   5580
tctccttacg ccgattcatg gtcgctctaa tcctggatat caagagaaca cccggaaaca   5640
aacccaggat tgctgaaatg atatgtgaca ttgatacata tatcgtagag gcaggattag   5700
ccagttttat cctgactatt aagtttggga tagaaactat gtatcctgct cttggactgc   5760
atgaatttgc tggtgagtta tccacacttg agtccttgat gaacctttac cagcaaatgg   5820
gggaaactgc accctacatg gtaatcctgg agaactcaat tcagaacaag ttcagtgcag   5880
gatcataccc tctgctctgg agctatgcca tgggagtagg agtggaactt gaaaactcca   5940
tgggaggttt gaactttggc cgatcttact ttgatccagc atatttttaga ttagggcaag   6000
agatggtaag gaggtcagct ggaaaggtca gttccacatt ggcatctgaa ctcggtatca   6060
ctgccgagga tgcaaggctt gtttcagaga ttgcaatgca tactactgag gacaagatca   6120
gtagagcggt tggacccaga caagcccaag tatcatttct acacggtgat caaagtgaga   6180
atgagctacc gagattgggg ggcaaggaag ataggagggt caaacagagt cgaggagaag   6240
ccagggagag ctacagagaa accgggccca gcagagcaag tgatgcgaga gctgcccatc   6300
ttccaaccgg cacaccccta gacattgaca ctgcatcgga gtccagccaa gatccgcagg   6360
acagtcgaag gtcagctgac gccctgctta ggctgcaagc catggcagga atctcggaag   6420
aacaaggctc agacacggac acccctatag tgtacaatga cagaaatctt ctagactagg   6480
tgcgagaggc cgaggaccag aacaacatcc gcctaccctc catcattgtt ataaaaaact   6540
taggaaccag gtccacacag ccgccagccc atcaaccatc cactcccacg attggagccg   6600
atggcagaag agcaggcacg ccatgtcaaa aacggactgg aatgcatccg ggctctcaag   6660
gccgagccca tcggctcact ggccatcgag gaagctatgg cagcatggtc agaaatatca   6720
gacaacccag gacaggagcg agccacctgc agggaagaga aggcaggcag ttcgggtctc   6780
agcaaaccat gcctctcagc aattggatca actgaaggcg gtgcacctcg catccgcggt   6840
cagggacctg gagagagcga tgacgacgct gaaactttgg gaatcccccc aagaaatctc   6900
caggcatcaa gcactgggtt acagtgttat tatgtttatg atcacagcgg tgaagcggtt   6960
aagggaatcc aagatgctga ctctatcatg gttcaatcag gccttgatgg tgatagcacc   7020
ctctcaggag gagacaatga atctgaaaac agcgatgtgg atattggcga acctgatacc   7080
gagggatatg ctatcactga ccggggatct gctcccatct ctatggggtt cagggcttct   7140
gatgttgaaa ctgcagaagg aggggagatc cacgagctcc tgagactcca atccagaggc   7200
aacaactttc cgaagcttgg gaaaactctc aatgttcctc cgcctccgga ccccggtagg   7260
gccagcactt ccgggacacc cattaaaaag ggcacagacg cgagattagc ctcatttgga   7320
acggagatcg cgtctttatt gacaggtggt gcaacccaat gtgctcgaaa gtcaccctcg   7380
gaaccatcag ggccaggtgc acctgcgggg aatgtccccg agtgtgtgag caatgccgca   7440
ctgatacagg agtggacacc cgaatctggt accacaatct ccccgagatc ccagaataat   7500
gaagaagggg gagactatta tgatgatgag ctgttctctg atgtccaaga tattaaaaca   7560
gccttggcca aaatacacga ggataatcag aagataatct ccaagctaga atcactgctg   7620
ttattgaagg gagaagttga gtcaattaag aagcagatca acaggcaaaa tatcagcata   7680
tccaccctgg aaggacacct ctcaagcatc atgatcgcca ttcctggact tgggaaggat   7740
cccaacgacc ccactgcaga tgtcgaaatc aatcccgact tgaaacccat cataggcaga   7800
gattcaggcc gagcactggc cgaagttctc aagaaacccg ttgccagccg acaactccaa   7860
```

-continued

```
ggaatgacaa atggacggac cagttccaga ggacagctgc tgaaggaatt tcagctaaag   7920
ccgatcggga aaaagatgag ctcagccgtc gggtttgttc ctgacaccgg ccctgcatca   7980
cgcagtgtaa tccgctccat tataaaatcc agccggctag aggaggatcg gaagcgttac   8040
ctgatgactc tccttgatga tatcaaagga gccaatgatc ttgccaagtt ccaccagatg   8100
ctgatgaaga taataatgaa gtagctacag ctcaacttac ctgccaaccc catgccagtc   8160
gacccaacta gtacaaccta aatccattat aaaaaactta ggagcaaagt gattgcctcc   8220
caagttccac aacgcgtagc gctaccgtag tgcccagcaa tgcccgaaaa cgaccccct    8280
cacaatgaca gccagaaggc ccggacaaaa aagcccctc cgaaagactc cacggaccaa    8340
gcgagaggcc agccagcagc cgacggcaag cgcgaacacc aggcggcccc agcacagaac   8400
agccctgata caaggccacc accagccacc ccaatctgca tcctcctcgt gggaccccg    8460
aggaccaacc cccaaggctg cccccgatcc aaaccaccaa ccgcatcccc accaccccg    8520
ggaaagaaac ccccagcaat tggaaggccc ctccccctct tcctcaacac aagaactcca   8580
caaccgaacc gcacaagcga ccgaggtgac ccaaccgcag gcatccgact ccctagacag   8640
atcctctctc cccggcaaac taaacaaaac ttagggccaa ggaacataca cacccaacag   8700
aacccagacc ccggcccacg gcgccgcgcc cccaaccccc gacaaccaga gggagccccc   8760
aaccaatccc gccggctccc ccggtgccca caggcaggga caccaacccc cgaacagacc   8820
cagcacccaa ccatcgacaa tccaagacgg gggggccccc ccaaaaaaag gcccccaggg   8880
gccgacagcc agcaccgcga ggaagcccac ccaccccaca cacgaccacg gcaaccaaac   8940
cagaacccag accaccctgg gccaccagct cccagactcg gccatcaccc cgcagaaagg   9000
aaaggccaca acccgcgcac cccagccccg atccggcggg gagccaccca acccgaacca   9060
gcacccaaga gcgatccccg aaggaccccc gaaccgcaaa ggacatcagt atcccacagc   9120
ctctccaagt cccccggtct cctccccttc tcgaagggac caaaagatca atccaccaca   9180
cccgacgaca ctcaactccc cacccctaaa ggagacaccg ggaatcccag aatcaagact   9240
catccaatgt ccatcatggg tctcaaggtg aacgtctctg ccatattcat ggcagtactg   9300
ttaactctcc aaacacccac cggtcaaatc cattggggca atctctctaa gataggggtg   9360
gtaggaatag gaagtgcaag ctacaaagtt atgactcgtt ccagccatca atcattagtc   9420
ataaaattaa tgcccaatat aactctcctc aataactgca cgagggtaga gattgcagaa   9480
tacaggagac tactgagaac agttttggaa ccaattagag atgcacttaa tgcaatgacc   9540
cagaatataa gaccggttca gagtgtagct tcaagtagga gacacaagag atttgcggga   9600
gtagtcctgg caggtgcggc cctaggcgtt gccacagctg ctcagataac agccggcatt   9660
gcacttcacc agtccatgct gaactctcaa gccatcgaca atctgagagc gagcctggaa   9720
actactaatc aggcaattga ggcaatcaga caagcagggc aggagatgat attggctgtt   9780
cagggtgtcc aagactacat caataatgag ctgataccgt ctatgaacca actatcttgt   9840
gatttaatcg gccagaagct cgggctcaaa ttgctcagat actatacaga aatcctgtca   9900
ttatttggcc ccagcttacg ggaccccata tctgcggaga tatctatcca ggctttgagc   9960
tatgcgcttg gaggagacat caataaggtg ttagaaaagc tcggatacag tggaggtgat  10020
ttactgggca tcttagagag cagaggaata aaggcccgga taactcacgt cgacacagag  10080
tcctacttca ttgtcctcag tatagcctat ccgacgctgt ccgagattaa gggggtgatt  10140
gtccaccggc tagagggggt ctcgtacaac ataggctctc aagagtggta taccactgtg  10200
cccaagtatg ttgcaaccca agggtacctt atctcgaatt ttgatgagtc atcgtgtact  10260
```

-continued

```
ttcatgccag aggggactgt gtgcagccaa aatgccttgt acccgatgag tcctctgctc  10320
caagaatgcc tccgggggtc caccaagtcc tgtgctcgta cactcgtatc cgggtctttt  10380
gggaaccggt tcattttatc acaagggaac ctaatagcca attgtgcatc aatcctttgc  10440
aagtgttaca caacaggaac gatcattaat caagaccctg acaagatcct aacatacatt  10500
gctgccgatc actgcccggt agtcgaggtg aacggcgtga ccatccaagt cgggagcagg  10560
aggtatccag atgctgtgta cttgcacaga attgacctcg gtcctcccat atcattggag  10620
aggttggacg tagggacaaa tctggggaat gcaattgcta agttggagga tgccaaggaa  10680
ttgttggagt catcggacca gatattgagg agtatgaaag gtttatcgag cactagcata  10740
gtctacatcc tgattgcagt gtgtcttgga gggttgatag ggatccccgc tttaatatgt  10800
tgctgcaggg ggcgttgtaa caaaaaggga gaacaagttg gtatgtcaag accaggccta  10860
aagcctgatc ttacgggaac atcaaaatcc tatgtaaggt cgctctgatc ctctacaact  10920
cttgaaacac aaatgtccca caagtctcct cttcgtcatc aagcaaccac cgcacccagc  10980
atcaagccca cctgaaatta tctccggctt ccctctggcc gaacaatatc ggtagttaat  11040
taaaacttag ggtgcaagat catccacaat gtcaccacaa cgagaccgga taaatgcctt  11100
ctacaaagat aacccccatc ccaagggaag taggatagtc attaacagag aacatcttat  11160
gattgataga ccttatgttt tgctggctgt tctgtttgtc atgtttctga gcttgatcgg  11220
gttgctagcc attgcaggca ttagacttca tcgggcagcc atctacaccg cagagatcca  11280
taaaagcctc agcaccaatc tagatgtaac taactcaatc gagcatcagg tcaaggacgt  11340
gctgacacca ctcttcaaaa tcatcggtga tgaagtgggc ctgaggacac ctcagagatt  11400
cactgaccta gtgaaattca tctctgacaa gattaaattc cttaatccgg atagggagta  11460
cgacttcaga gatctcactt ggtgtatcaa cccgccagag agaatcaaat tggattatga  11520
tcaatactgt gcagatgtgg ctgctgaaga gctcatgaat gcattggtga actcaactct  11580
actggagacc agaacaacca atcagttcct agctgtctca aagggaaact gctcagggcc  11640
cactacaatc agaggtcaat tctcaaacat gtcgctgtcc ctgttagact tgtatttagg  11700
tcgaggttac aatgtgtcat ctatagtcac tatgacatcc cagggaatgt atgggggaac  11760
ttacctagtg gaaaagccta atctgagcag caaaaggtca gagttgtcac aactgagcat  11820
gtaccgagtg tttgaagtag gtgttatcag aaatccgggt ttgggggctc cggtgttcca  11880
tatgacaaac tatcttgagc aaccagccag taatgatctc agcaactgta tggtggcttt  11940
gggggagctc aaactcgcag ccctttgtca cggggaagat tctatcacaa ttccctatca  12000
gggatcaggg aaaggtgtca gcttccagct cgtcaagcta ggtgtctgga aatccccaac  12060
cgacatgcaa tcctgggtcc ccttatcaac ggatgatcca gtgatagaca ggctttacct  12120
ctcatctcac agaggtgtta tcgctgacaa tcaagcaaaa tgggctgtcc cgacaacacg  12180
aacagatgac aagttgcgaa tggagacatg cttccaacag gcgtgtaagg gtaaaatcca  12240
agcactctgc gagaatcccg agtgggcacc attgaaggat aacaggattc cttcatacgg  12300
ggtcttgtct gttgatctga gtctgacagt tgagcttaaa atcaaaattg cttcgggatt  12360
cgggccattg atcacacacg gttcagggat ggacctatac aaatccaacc acaacaatgt  12420
gtattggctg actatcccgc caatgaagaa cctagcctta ggtgtaatca acacattgga  12480
gtggataccg agattcaagg ttagtcccta cctcttcaat gtcccaatta aggaagcagg  12540
cgaagactgc catgccccaa catacctacc tgcggaggtg gatggtgatg tcaaactcag  12600
```

-continued ttccaatctg gtgattctac ctggtcaaga tctccaatat gttttggcaa cctacgatac 12660
ttccagggtt gaacatgctg tggtttatta cgtttacagc ccaggccgct cattttctta 12720
cttttatcct tttaggttgc ctataaaggg ggtccccatc gaattacaag tggaatgctt 12780
cacatgggac caaaaactct ggtgccgtca cttctgtgtg cttgcggact cagaatctgg 12840
tggacatatc actcactctg ggatggtggg catgggagtc agctgcacag tcacccggga 12900
agatggaacc aatcgcagat agggctgcta gtgaaccaat ctcatgatgt cacccagaca 12960
tcaggcatac cca 12973

<210> SEQ ID NO 9
<211> LENGTH: 20366
<212> TYPE: DNA
<213> ORGANISM: Artificial Sequence
<220> FEATURE:
<223> OTHER INFORMATION: Artificial DNA containing entire MV sequence - pMV

<400> SEQUENCE: 9
ctagtgtgaa atagacatca gaattaagaa aaacgtaggg tccaagtggt tccccgttat 60
ggactcgcta tctgtcaacc agatcttata ccctgaagtt cacctagata gcccgatagt 120
taccaataag atagtagcca tcctggagta tgctcgagtc cctcacgctt acagcctgga 180
ggaccctaca ctgtgtcaga acatcaagca ccgcctaaaa aacggatttt ccaaccaaat 240
gattataaac aatgtggaag ttgggaatgt catcaagtcc aagcttagga gttatccggc 300
ccactctcat attccatatc caaattgtaa tcaggattta tttaacatag aagacaaaga 360
gtcaacgagg aagatccgtg aactcctcaa aaaggggaat tcgctgtact ccaaagtcag 420
tgataaggtt ttccaatgct taagggacac taactcacgg cttggcctag gctccgaatt 480
gagggaggac atcaaggaga aagttattaa cttgggagtt tacatgcaca gctcccagtg 540
gtttgagccc tttctgtttt ggtttacagt caagactgag atgaggtcag tgattaaatc 600
acaaacccat acttgccata ggaggagaca cacacctgta ttcttcactg gtagttcagt 660
tgagttgcta atctctcgtg accttgttgc tataatcagt aaagagtctc aacatgtata 720
ttacctgaca tttgaactgg ttttgatgta ttgtgatgtc atagagggga ggttaatgac 780
agagaccgct atgactattg atgctaggta tacagagctt ctaggaagag tcagatacat 840
gtggaaactg atagatggtt tcttccctgc actcgggaat ccaacttatc aaattgtagc 900
catgctggag cctctttcac ttgcttacct gcagctgagg gatataacag tagaactcag 960
aggtgctttc cttaaccact gctttactga aatacatgat gttcttgacc aaaacgggtt 1020
ttctgatgaa ggtacttatc atgagttaat tgaagctcta gattacattt tcataactga 1080
tgacatacat ctgacagggg agattttctc atttttcaga agtttcggcc accccagact 1140
tgaagcagta acggctgctg aaaatgttag gaaatacatg aatcagccta aagtcattgt 1200
gtatgagact ctgatgaaag gtcatgccat attttgtgga atcataatca acggctatcg 1260
tgacaggcac ggaggcagtt ggccaccgct gaccctcccc ctgcatgctg cagacacaat 1320
ccggaatgct caagcttcag gtgaagggtt aacacatgag cagtgcgttg ataactggag 1380
atcttttgct ggagtgaaat ttggctgctt tatgcctctt agcctggata gtgatctgac 1440
aatgtaccta aaggacaagg cacttgctgc tctccaaagg gaatgggatt cagtttaccc 1500
gaaagagttc ctgcgttacg accctcccaa gggaaccggg tcacggaggc ttgtagatgt 1560
tttccttaat gattcgagct ttgacccata tgatgtgata atgtatgttg taagtggagc 1620

-continued

```
ttacctccat gaccctgagt tcaacctgtc ttacagcctg aaagaaaagg agatcaagga   1680
aacaggtaga ctttttgcta aaatgactta caaaatgagg gcatgccaag tgattgctga   1740
aaatctaatc tcaaacggga ttggcaaata ttttaaggac aatgggatgg ccaaggatga   1800
gcacgatttg actaaggcac tccacactct agctgtctca ggagtcccca aagatctcaa   1860
agaaagtcac aggggggggc cagtcttaaa aacctactcc cgaagcccag tccacacaag   1920
taccaggaac gtgagagcag caaaagggtt tatagggttc cctcaagtaa ttcggcagga   1980
ccaagacact gatcatccgg agaatatgga agcttacgag acagtcagtg catttatcac   2040
gactgatctc aagaagtact gccttaattg gagatatgag accatcagct tgtttgcaca   2100
gaggctaaat gagatttacg gattgccctc atttttccag tggctgcata agaggcttga   2160
gacctctgtc ctgtatgtaa gtgaccctca ttgccccccc gaccttgacg cccatatccc   2220
gttatataaa gtccccaatg atcaaatctt cattaagtac cctatgggag gtatagaagg   2280
gtattgtcag aagctgtgga ccatcagcac cattccctat ctatacctgg ctgcttatga   2340
gagcggagta aggattgctt cgttagtgca aggggacaat cagaccatag ccgtaacaaa   2400
aagggtaccc agcacatggc cctacaacct taagaaacgg gaagctgcta gagtaactag   2460
agattacttt gtaattctta ggcaaaggct acatgatatt ggccatcacc tcaaggcaaa   2520
tgagacaatt gtttcatcac atttttttgt ctattcaaaa ggaatatatt atgatgggct   2580
acttgtgtcc caatcactca agagcatcgc aagatgtgta ttctggtcag agactatagt   2640
tgatgaaaca agggcagcat gcagtaatat tgctacaaca atggctaaaa gcatcgagag   2700
aggttatgac cgttaccttg catattccct gaacgtccta aaagtgatac agcaaattct   2760
gatctctctt ggcttcacaa tcaattcaac catgacccgg gatgtagtca taccccctcct   2820
cacgaacaac gacctcttaa taaggatggc actgttgccc gctcctattg gggggatgaa   2880
ttatctgaat atgagcaggc tgtttgtcag aaacatcggt gatccagtaa catcatcaat   2940
tgctgatctc aagagaatga ttctcgcctc actaatgcct gaagagaccc tccatcaagt   3000
aatgacacaa caaccggggg actcttcatt cctagactgg gctagcgacc cttactcagc   3060
aaatcttgta tgtgtccaga gcatcactag actcctcaag aacataactg caaggtttgt   3120
cctgatccat agtccaaacc caatgttaaa aggattattc catgatgaca gtaaagaaga   3180
ggacgaggga ctggcggcat tcctcatgga caggcatatt atagtaccta gggcagctca   3240
tgaaatcctg gatcatagtg tcacaggggc aagagagtct attgcaggca tgctggatac   3300
cacaaaaggc ctgattcgag ccagcatgag gaagggggg ttaacctctc gagtgataac   3360
cagattgtcc aattatgact atgaacaatt cagagcaggg atggtgctat tgacaggaag   3420
aaagagaaat gtcctcattg acaaagagtc atgttcagtg cagctggcga gagctctaag   3480
aagccatatg tgggcgaggc tagctcgagg acggcctatt tacggccttg aggtccctga   3540
tgtactagaa tctatgcgag gccaccttat tcggcgtcat gagacatgtg tcatctgcga   3600
gtgtggatca gtcaactacg gatggttttt tgtcccctcg ggttgccaac tggatgatat   3660
tgacaaggaa acatcatcct tgagagtccc atatattggt tctaccactg atgagagaac   3720
agacatgaag cttgccttcg taagagcccc aagtcgatcc ttgcgatctg ctgttagaat   3780
agcaacagtg tactcatggg cttacggtga tgatgatagc tcttggaacg aagcctggtt   3840
gttggctagg caaagggcca atgtgagcct ggaggagcta agggtgatca ctcccatctc   3900
aacttcgact aatttagcgc ataggttgag ggatcgtagc actcaagtga aatactcagg   3960
tacatccctt gtccgagtgg cgaggtatac cacaatctcc aacgacaatc tctcatttgt   4020
```

-continued catatcagat aagaaggttg atactaactt tatataccaa caaggaatgc ttctagggtt 4080
gggtgtttta gaaacattgt ttcgactcga gaaagatacc ggatcatcta acacggtatt 4140
acatcttcac gtcgaaacag attgttgcgt gatcccgatg atagatcatc ccaggatacc 4200
cagctcccgc aagctagagc tgagggcaga gctatgtacc aacccattga tatatgataa 4260
tgcaccttta attgacagag atacaacaag gctatacacc cagagccata ggaggcacct 4320
tgtggaattt gttacatggt ccacacccca actatatcac attttagcta agtccacagc 4380
actatctatg attgacctgg taacaaaatt tgagaaggac catatgaatg aaatttcagc 4440
tctcataggg gatgacgata tcaatagttt cataactgag tttctgctca tagagccaag 4500
attattcact atctacttgg gccagtgtgc ggccatcaat tgggcatttg atgtacatta 4560
tcatagacca tcagggaaat atcagatggg tgagctgttg tcatcgttcc tttctagaat 4620
gagcaaagga gtgtttaagg tgcttgtcaa tgctctaagc cacccaaaga tctacaagaa 4680
attctggcat tgtggtatta tagagcctat ccatggtcct tcacttgatg ctcaaaactt 4740
gcacacaact gtgtgcaaca tggtttacac atgctatatg acctacctcg acctgttgtt 4800
gaatgaagag ttagaagagt tcacatttct cttgtgtgaa agcgacgagg atgtagtacc 4860
ggacagattc gacaacatcc aggcaaaaca cttatgtgtt ctggcagatt tgtactgtca 4920
accagggacc tgcccaccaa ttcgaggtct aagaccggta gagaaatgtg cagttctaac 4980
cgaccatatc aaggcagagg ctaggttatc tccagcagga tcttcgtgga acataaatcc 5040
aattattgta gaccattact catgctctct gacttatctc cggcgaggat cgatcaaaca 5100
gataagattg agagttgatc caggattcat tttcgacgcc ctcgctgagg taaatgtcag 5160
tcagccaaag atcggcagca acaacatctc aaatatgagc atcaaggctt tcagaccccc 5220
acacgatgat gttgcaaaat tgctcaaaga tatcaacaca agcaagcaca atcttcccat 5280
ttcagggggc aatctcgcca attatgaaat ccatgctttc cgcagaatcg ggttgaactc 5340
atctgcttgc tacaaagctg ttgagatatc aacattaatt aggagatgcc ttgagccagg 5400
ggaggacggc ttgttcttgg gtgagggatc gggttccatg ttgatcactt ataaggagat 5460
acttaaacta aacaagtgct tctataatag tggggtttcc gccaattcta gatctggtca 5520
aagggaatta gcaccctatc cctccgaagt tggccttgtc gaacacagaa tgggagtagg 5580
taatattgtc aaagtgctct ttaacgggag gcccgaagtc acgtgggtag gcagtgtaga 5640
ttgcttcaat ttcatagtta gtaatatccc tacctctagt gtggggttta tccattcaga 5700
tatagagacc ttgcctaaca aagatactat agagaagcta gaggaattgg cagccatctt 5760
atcgatggct ctgctcctgg gcaaaatagg atcaatactg gtgattaagc ttatgccttt 5820
cagcggggat tttgttcagg gatttataag ttatgtaggg tcccattata gagaagtgaa 5880
ccttgtatac cctagataca gcaacttcat atctactgaa tcttatttgg ttatgacaga 5940
tctcaaggct aaccggctaa tgaatcctga aaagattaag cagcagataa ttgaatcatc 6000
tgtgaggact tcacctggac ttataggtca catcctatcc attaagcaac taagctgcat 6060
acaagcaatt gtgggagacg cagttagtag aggtgatatc aatcctactc tgaaaaaact 6120
tacacctata gagcaggtgc tgatcaattg cgggttggca attaacggac ctaagctgtg 6180
caaagaattg atccaccatg atgttgcctc agggcaagat ggattgctta attctatact 6240
catcctctac agggagttgg caagattcaa agacaaccaa agaagtcaac aagggatgtt 6300
ccacgcttac cccgtattgg taagtagcag gcaacgagaa cttatatcta ggatcacccg 6360

-continued caaattttgg gggcacattc ttctttactc cgggaacaga aagttgataa ataagtttat 6420
ccagaatctc aagtccggct atctgatact agacttacac cagaatatct tcgttaagaa 6480
tctatccaag tcagagaaac agattattat gacggggggt ttgaaacgtg agtgggtttt 6540
taaggtaaca gtcaaggaga ccaaagaatg gtataagtta gtcggataca gtgccctgat 6600
taaggactaa ttggttgaac tccggaaccc taatcctgcc ctaggtggtt aggcattatt 6660
tgcaatagat taaagaaaac tttgaaaata cgaagtttct attcccagct ttgtctggtt 6720
tttttccccc ccaacttcgg aggtcgacca gtactccggg cgacactttg tttttttttt 6780
ttcccccgat gctggaggtc gaccagatgt ccgaaagtgt cccccccccc cccccccccc 6840
ccccggcgcg gagcggcggg gccaccccgg acccctttttt tttttttttt ttttttttta 6900
aattcctgga acctttaggt cgaccagttg tccgtctttt actccttcat ataggtcgac 6960
cagtactccg ggtggtactt tgtctttttc tgaaaatccc agaggtcgac cagatatccg 7020
cggccgccga gctcgttaac aacaacaatt gcattcattt tatgtttcag gttcaggggg 7080
agatgtggga ggttttttaa agcaagtaaa acctctacaa atgtggtaaa atccgataag 7140
gatcgatccg ggctggcgta atagcgaaga ggcccgcacc gatcgccctt cccaacagtt 7200
gcgcagcctg aatggcgaat ggacgcgccc tgtagcggcg cattaagcgc ggcgggtgtg 7260
gtggttacgc gcagcgtgac cgctacactt gccagcgccc tagcgcccgc tcctttcgct 7320
ttcttccctt cctttctcgc cacgttcgcc ggctttcccc gtcaagctct aaatcggggg 7380
ctccctttag ggttccgatt tagagcttta cggcacctcg accgcaaaaa acttgatttg 7440
ggtgatggtt cacgtagtgg gccatcgccc tgatagacgg tttttcgccc tttgacgttg 7500
gagtccacgt tctttaatag tggactcttg ttccaaactg gaacaacact caaccctatc 7560
tcggtctatt cttttgattt ataagggatt ttgccgattt cggcctattg gttaaaaaat 7620
gagctgattt aacaaatatt taacgcgaat tttaacaaaa tattaacgtt tacaatttcg 7680
cctgatgcgg tattttctcc ttacgcatct gtgcggtatt tcacaccgca tacgcggatc 7740
tgcgcagcac catggcctga aataacctct gaaagaggaa cttggttagg taccttctga 7800
ggcggaaaga accagctgtg gaatgtgtgt cagttagggt gtggaaagtc cccaggctcc 7860
ccagcaggca gaagtatgca aagcatgcat ctcaattagt cagcaaccag gtgtggaaag 7920
tccccaggct ccccagcagg cagaagtatg caaagcatgc atctcaatta gtcagcaacc 7980
atagtcccgc ccctaactcc gcccatcccg cccctaactc cgcccagttc cgcccattct 8040
ccgccccatg gctgactaat tttttttatt tatgcagagg ccgaggccgc ctcggcctct 8100
gagctattcc agaagtagtg aggaggcttt tttggaggcc taggcttttg caaaaagctt 8160
gattcttctg acacaacagt ctcgaactta aggctagagc caccatggtt cgaccattga 8220
actgcatcgt cgccgtgtcc caaaatatgg ggattggcaa gaacggagac ctaccctggc 8280
ctccgctcag gaacgagttc aagtacttcc aaagaatgac cacaacctct tcagtggaag 8340
gtaaacagaa tctggtgatt atgggtagga aaacctggtt ctccattcct gagaagaatc 8400
gacctttaaa ggacagaatt aatatagttc tcagtagaga actcaaagaa ccaccacgag 8460
gagctcattt tcttgccaaa agtttggatg atgccttaag acttattgaa caaccggaat 8520
tggcaagtaa agtagacatg gtttggatag tcggaggcag ttctgtttac caggaagcca 8580
tgaatcaacc aggccacctc agactctttg tgacaaggat catgcaggaa tttgaaagtg 8640
acacgttttt cccagaaatt gatttgggga aatataaact tctcccagaa tacccaggcg 8700
tcctctctga ggtccaggag gaaaaaggca tcaagtataa gtttgaagtc tacgagaaga 8760

-continued

```
aagactaagc gggactctgg ggttcgaaat gaccgaccaa gcgacgccca acctgccatc   8820
acgatggccg caataaaata tctttatttt cattacatct gtgtgttggt tttttgtgtg   8880
aatcgatagc gataaggatc cgcgtatggt gcactctcag tacaatctgc tctgatgccg   8940
catagttaag ccagccccga cacccgccaa cacccgctga cgcgccctga cgggcttgtc   9000
tgctcccggc atccgcttac agacaagctg tgaccgtctc cgggagctgc atgtgtcaga   9060
ggttttcacc gtcatcaccg aaacgcgcga gacgaaaggg cctcgtgata cgcctatttt   9120
tataggttaa tgtcatgata ataatggttt cttagacgtc aggtggcact tttcggggaa   9180
atgtgcgcgg aacccctatt tgtttatttt tctaaataca ttcaaatatg tatccgctca   9240
tgagacaata accctgataa atgcttcaat aatattgaaa aaggaagagt atgagtattc   9300
aacatttccg tgtcgccctt attccctttt ttgcggcatt ttgccttcct gtttttgctc   9360
acccagaaac gctggtgaaa gtaaaagatg ctgaagatca gttgggtgca cgagtgggtt   9420
acatcgaact ggatctcaac agcggtaaga tccttgagag ttttcgcccc gaagaacgtt   9480
ttccaatgat gagcactttt aaagttctgc tatgtggcgc ggtattatcc cgtattgacg   9540
ccgggcaaga gcaactcggt cgccgcatac actattctca gaatgacttg gttgagtact   9600
caccagtcac agaaaagcat cttacggatg gcatgacagt aagagaatta tgcagtgctg   9660
ccataaccat gagtgataac actgcggcca acttacttct gacaacgatc ggaggaccga   9720
aggagctaac cgcttttttg cacaacatgg gggatcatgt aactcgcctt gatcgttggg   9780
aaccggagct gaatgaagcc ataccaaacg acgagcgtga caccacgatg cctgtagcaa   9840
tggcaacaac gttgcgcaaa ctattaactg gcgaactact tactctagct tcccggcaac   9900
aattaataga ctggatggag gcggataaag ttgcaggacc acttctgcgc tcggcccttc   9960
cggctggctg gtttattgct gataaatctg gagccggtga gcgtgggtct cgcggtatca  10020
ttgcagcact ggggccagat ggtaagccct cccgtatcgt agttatctac acgacgggga  10080
gtcaggcaac tatggatgaa cgaaatagac agatcgctga gataggtgcc tcactgatta  10140
agcattggta actgtcagac caagtttact catatatact ttagattgat ttaaaacttc  10200
atttttaatt taaaaggatc taggtgaaga tcctttttga taatctcatg accaaaatcc  10260
cttaacgtga gttttcgttc cactgagcgt cagaccccgt agaaaagatc aaaggatctt  10320
cttgagatcc tttttttctg cgcgtaatct gctgcttgca aacaaaaaaa ccaccgctac  10380
cagcggtggt ttgtttgccg gatcaagagc taccaactct ttttccgaag gtaactggct  10440
tcagcagagc gcagatacca aatactgtcc ttctagtgta gccgtagtta ggccaccact  10500
tcaagaactc tgtagcaccg cctacatacc tcgctctgct aatcctgtta ccagtggctg  10560
ctgccagtgg cgataagtcg tgtcttaccg ggttggactc aagacgatag ttaccggata  10620
aggcgcagcg gtcgggctga acggggggtt cgtgcacaca gcccagcttg gagcgaacga  10680
cctacaccga actgagatac ctacagcgtg agctatgaga aagcgccacg cttcccgaag  10740
ggagaaaggc ggacaggtat ccggtaagcg gcagggtcgg aacaggagag cgcacgaggg  10800
agcttccagg gggaaacgcc tggtatcttt atagtcctgt cgggtttcgc cacctctgac  10860
ttgagcgtcg atttttgtga tgctcgtcag gggggcggag cctatggaaa aacgccagca  10920
acgcggcctt tttacggttc ctggcctttt gctggccttt tgctcacatg gctcgacaag  10980
cttggctagc acatcctctt ggtcctatca cggttatgag gtcgaccagt tgttgcttg  11040
atgttcggtt ctctcgttga ttgggacaat atttggggca cttcgccggt cccgacttcc  11100
```

-continued

```
agaatttccg tgtggtctgt gaatttatca ccgctacact gtcatcatat tccagttttg  11160
caatctgctc tctttgtacc tgcagatagg taccaaacaa agttgggtaa ggatagttca  11220
atcaatgatc attttctagt gcacttagga ttcaagatcc tattatcagg gacaagagca  11280
ggattaagga tatccgagat ggccacactt ttaaggagct tagcattgtt caaaagaaac  11340
aaggacaaac cacccattac atcaggatcc ggtggagcca tcagaggaat caaacacatt  11400
attatagtac caatccctgg agattcctca attaccactc gatccagact tctggaccgg  11460
ttggtcaggt taattggaaa cccggatgtg agcgggccca aactaacagg ggcactaata  11520
ggtatattat ccttatttgt ggagtctcca ggtcaattga ttcagaggat caccgatgac  11580
cctgacgtta gcataaggct gttagaggtt gtccagagtg accagtcaca atctggcctt  11640
accttcgcat caagaggtac caacatggag gatgaggcgg accaatactt ttcacatgat  11700
gatccaatta gtagtgatca atccaggttc ggatggttcg agaacaagga aatctcagat  11760
attgaagtgc aagaccctga gggattcaac atgattctgg gtaccatcct agctcaaatt  11820
tgggtcttgc tcgcaaaggc ggttacggcc ccagacacgg cagctgattc ggagctaaga  11880
aggtggataa agtacaccca acaaagaagg gtagttggtg aatttagatt ggagagaaaa  11940
tggttggatg tggtgaggaa caggattgcc gaggacctct ccttacgccg attcatggtc  12000
gctctaatcc tggatatcaa gagaacaccc ggaaacaaac ccaggattgc tgaaatgata  12060
tgtgacattg atacatatat cgtagaggca ggattagcca gttttatcct gactattaag  12120
tttgggatag aaactatgta tcctgctctt ggactgcatg aatttgctgg tgagttatcc  12180
acacttgagt ccttgatgaa cctttaccag caaatggggg aaactgcacc ctacatggta  12240
atcctggaga actcaattca gaacaagttc agtgcaggat catacccctct gctctggagc  12300
tatgccatgg gagtaggagt ggaacttgaa aactccatgg gaggtttgaa ctttggccga  12360
tcttactttg atccagcata ttttagatta gggcaagaga tggtaaggag gtcagctgga  12420
aaggtcagtt ccacattggc atctgaactc ggtatcactg ccgaggatgc aaggcttgtt  12480
tcagagattg caatgcatac tactgaggac aagatcagta gagcggttgg acccagacaa  12540
gcccaagtat catttctaca cggtgatcaa agtgagaatg agctaccgag attgggggc  12600
aaggaagata ggagggtcaa acagagtcga ggagaagcca gggagagcta cagagaaacc  12660
gggcccagca gagcaagtga tgcgagagct gcccatcttc caaccggcac acccctagac  12720
attgacactg catcggagtc cagccaagat ccgcaggaca gtcgaaggtc agctgacgcc  12780
ctgcttaggc tgcaagccat ggcaggaatc tcggaagaac aaggctcaga cacggacacc  12840
cctatagtgt acaatgacag aaatcttcta gactaggtgc gagaggccga ggaccagaac  12900
aacatccgcc taccctccat cattgttata aaaaacttag gaaccaggtc cacacagccg  12960
ccagcccatc aaccatccac tcccacgatt ggagccgatg gcagaagagc aggcacgcca  13020
tgtcaaaaac ggactggaat gcatccgggc tctcaaggcc gagcccatcg gctcactggc  13080
catcgaggaa gctatggcag catggtcaga aatatcagac aacccaggac aggagcgagc  13140
cacctgcagg gaagagaagg caggcagttc gggtctcagc aaaccatgcc tctcagcaat  13200
tggatcaact gaaggcggtg cacctcgcat ccgcggtcag ggacctggag agagcgatga  13260
cgacgctgaa actttgggaa tccccccaag aaatctccag gcatcaagca ctgggttaca  13320
gtgttattat gtttatgatc acagcggtga agcggttaag ggaatccaag atgctgactc  13380
tatcatggtt caatcaggcc ttgatggtga tagcaccctc tcaggaggag acaatgaatc  13440
tgaaaacagc gatgtggata ttggcgaacc tgataccgag ggatatgcta tcactgaccg  13500
```

-continued gggatctgct cccatctcta tggggttcag ggcttctgat gttgaaactg cagaaggagg 13560
ggagatccac gagctcctga gactccaatc cagaggcaac aactttccga agcttgggaa 13620
aactctcaat gttcctccgc ctccggaccc cggtagggcc agcacttccg ggacacccat 13680
taaaaagggc acagacgcga gattagcctc atttggaacg gagatcgcgt ctttattgac 13740
aggtggtgca acccaatgtg ctcgaaagtc accctcggaa ccatcagggc caggtgcacc 13800
tgcggggaat gtccccgagt gtgtgagcaa tgccgcactg atacaggagt ggacacccga 13860
atctggtacc acaatctccc cgagatccca gaataatgaa gaagggggag actattatga 13920
tgatgagctg ttctctgatg tccaagatat taaaacagcc ttggccaaaa tacacgagga 13980
taatcagaag ataatctcca agctagaatc actgctgtta ttgaagggag aagttgagtc 14040
aattaagaag cagatcaaca ggcaaaatat cagcatatcc accctggaag gacacctctc 14100
aagcatcatg atcgccattc ctggacttgg gaaggatccc aacgacccca ctgcagatgt 14160
cgaaatcaat cccgacttga aacccatcat aggcagagat tcaggccgag cactggccga 14220
agttctcaag aaacccgttg ccagccgaca actccaagga atgacaaatg gacggaccag 14280
ttccagagga cagctgctga aggaatttca gctaaagccg atcgggaaaa agatgagctc 14340
agccgtcggg tttgttcctg acaccggccc tgcatcacgc agtgtaatcc gctccattat 14400
aaaatccagc cggctagagg aggatcggaa gcgttacctg atgactctcc ttgatgatat 14460
caaaggagcc aatgatcttg ccaagttcca ccagatgctg atgaagataa taatgaagta 14520
gctacagctc aacttacctg ccaaccccat gccagtcgac ccaactagta caacctaaat 14580
ccattataaa aaacttagga gcaaagtgat tgcctcccaa gttccacaat gacagagatc 14640
tacgacttcg acaagtcggc atgggacatc aaagggttga tcgctccgat acaacccacc 14700
acctacagtg atggcaggct ggtgccccag gtcagagtca tagatcctgg tctaggcgac 14760
aggaaggatg aatgctttat gtacatgttt ctgctggggg ttgttgagga cagcgatccc 14820
ctagggcctc caatcgggcg agcatttggg tccctgccct taggtgttgg cagatccaca 14880
gcaaagcccg aaaaactcct caaagaggcc actgagcttg acatagttgt tagacgtaca 14940
gcagggctca atgaaaaact ggtgttctac aacaacaccc cactaactct cctcacacct 15000
tggagaaagg tcctaacaac agggagtgtc ttcaacgcaa accaagtgtg caatgcggtt 15060
aatctgatac cgctcgatac cccgcagagg ttccgtgttg tttatatgag catcacccgt 15120
ctttcggata acgggtatta caccgttcct agaagaatgc tggaattcag atcggtcaat 15180
gcagtggcct tcaacctgct ggtgaccctt aggattgaca aggcgatagg ccctgggaag 15240
atcatcgaca atacagagca acttcctgag gcaacattta tggtccacat cgggaacttc 15300
aggagaaaga agagtgaagt ctactctgcc gattattgca aaatgaaaat cgaaaagatg 15360
ggcctggttt ttgcacttgg tgggataggg ggcaccagtc ttcacattag aagcacaggc 15420
aaaatgagca agactctcca tgcacaactc gggttcaaga agaccttatg ttacccgctg 15480
atagatatca atgaagacct taatcgatta ctctggagga gcagatgcaa gatagtaaga 15540
atccaggcag ttttgcagcc atcagttcct caagaattcc gcatttacga cgacgtgatc 15600
ataaatgatg accaaggact attcaaagtt ctgtagaccg tagtgcccag caatgcccga 15660
aaacgacccc cctcacaatg acagccagaa ggcccggaca aaaaagcccc ctccgaaaga 15720
ctccacggac caagcgagag gccagccagc agccgacggc aagcgcgaac accaggcggc 15780
cccagcacag aacagccctg atacaaggcc accaccagcc accccaatct gcatcctcct 15840
cgtgggaccc ccgaggacca acccccaagg ctgcccccga tccaaaccac caaccgcatc 15900
cccaccaccc ccgggaaaga aacccccagc aattggaagg cccctccccc tcttcctcaa 15960
cacaagaact ccacaaccga accgcacaag cgaccgaggt gacccaaccg caggcatccg 16020
actccctaga cagatcctct ctccccggca aactaaacaa aacttagggc caaggaacat 16080
acacacccaa cagaacccag accccggccc acggcgccgc gcccccaacc cccgacaacc 16140
agagggagcc cccaaccaat cccgccggct cccccggtgc ccacaggcag ggacaccaac 16200
ccccgaacag acccagcacc caaccatcga caatccaaga cggggggcc cccccaaaaa 16260
aaggccccca ggggccgaca gccagcaccg cgaggaagcc cacccacccc acacacgacc 16320
acggcaacca aaccagaacc cagaccaccc tgggccacca gctcccagac tcggccatca 16380
ccccgcagaa aggaaaggcc acaacccgcg caccccagcc ccgatccggc ggggagccac 16440
ccaacccgaa ccagcaccca agagcgatcc ccgaaggacc cccgaaccgc aaaggacatc 16500
agtatcccac agcctctcca agtcccccgg tctcctcccc ttctcgaagg gaccaaaaga 16560
tcaatccacc acacccgacg acactcaact ccccacccct aaaggagaca ccgggaatcc 16620
cagaatcaag actcatccaa tgtccatcat gggtctcaag gtgaacgtct ctgccatatt 16680
catggcagta ctgttaactc tccaaacacc caccggtcaa atccattggg gcaatctctc 16740
taagataggg gtggtaggaa taggaagtgc aagctacaaa gttatgactc gttccagcca 16800
tcaatcatta gtcataaaat taatgcccaa tataactctc ctcaataact gcacgagggt 16860
agagattgca gaatacagga gactactgag aacagttttg gaaccaatta gagatgcact 16920
taatgcaatg acccagaata taagaccggt tcagagtgta gcttcaagta ggagacacaa 16980
gagatttgcg ggagtagtcc tggcaggtgc ggccctaggc gttgccacag ctgctcagat 17040
aacagccggc attgcacttc accagtccat gctgaactct caagccatcg acaatctgag 17100
agcgagcctg gaaactacta atcaggcaat tgaggcaatc agacaagcag ggcaggagat 17160
gatattggct gttcagggtg tccaagacta catcaataat gagctgatac cgtctatgaa 17220
ccaactatct tgtgatttaa tcggccagaa gctcgggctc aaattgctca gatactatac 17280
agaaatcctg tcattatttg gccccagctt acgggacccc atatctgcgg agatatctat 17340
ccaggctttg agctatgcgc ttggaggaga catcaataag gtgttagaaa agctcggata 17400
cagtggaggt gatttactgg gcatcttaga gagcagagga ataaaggccc ggataactca 17460
cgtcgacaca gagtcctact tcattgtcct cagtatagcc tatccgacgc tgtccgagat 17520
taagggggtg attgtccacc ggctagaggg ggtctcgtac aacataggct ctcaagagtg 17580
gtataccact gtgcccaagt atgttgcaac ccaagggtac cttatctcga attttgatga 17640
gtcatcgtgt actttcatgc cagaggggac tgtgtgcagc caaaatgcct tgtacccgat 17700
gagtcctctg ctccaagaat gcctccgggg gtccaccaag tcctgtgctc gtacactcgt 17760
atccgggtct tttgggaacc ggttcatttt atcacaaggg aacctaatag ccaattgtgc 17820
atcaatcctt tgcaagtgtt acacaacagg aacgatcatt aatcaagacc ctgacaagat 17880
cctaacatac attgctgccg atcactgccc ggtagtcgag gtgaacggcg tgaccatcca 17940
agtcgggagc aggaggtatc cagatgctgt gtacttgcac agaattgacc tcggtcctcc 18000
catatcattg gagaggttgg acgtagggac aaatctgggg aatgcaattg ctaagttgga 18060
ggatgccaag gaattgttgg agtcatcgga ccagatattg aggagtatga aaggtttatc 18120
gagcactagc atagtctaca tcctgattgc agtgtgtctt ggagggttga tagggatccc 18180
cgctttaata tgttgctgca gggggcgttg taacaaaaag ggagaacaag ttggtatgtc 18240

```
aagaccaggc ctaaagcctg atcttacggg aacatcaaaa tcctatgtaa ggtcgctctg  18300
atcctctaca actcttgaaa cacaaatgtc ccacaagtct cctcttcgtc atcaagcaac  18360
caccgcaccc agcatcaagc ccacctgaaa ttatctccgg cttccctctg gccgaacaat  18420
atcggtagtt aattaaaact tagggtgcaa gatcatccac aatgtcacca caacgagacc  18480
ggataaatgc cttctacaaa gataaccccc atcccaaggg aagtaggata gtcattaaca  18540
gagaacatct tatgattgat agaccttatg ttttgctggc tgttctgttt gtcatgtttc  18600
tgagcttgat cgggttgcta gccattgcag gcattagact tcatcgggca gccatctaca  18660
ccgcagagat ccataaaagc ctcagcacca atctagatgt aactaactca atcgagcatc  18720
aggtcaagga cgtgctgaca ccactcttca aaatcatcgg tgatgaagtg ggcctgagga  18780
cacctcagag attcactgac ctagtgaaat tcatctctga caagattaaa ttccttaatc  18840
cggataggga gtacgacttc agagatctca cttggtgtat caacccgcca gagagaatca  18900
aattggatta tgatcaatac tgtgcagatg tggctgctga agagctcatg aatgcattgg  18960
tgaactcaac tctactggag accagaacaa ccaatcagtt cctagctgtc tcaaagggaa  19020
actgctcagg gcccactaca atcagaggtc aattctcaaa catgtcgctg tccctgttag  19080
acttgtattt aggtcgaggt tacaatgtgt catctatagt cactatgaca tcccagggaa  19140
tgtatggggg aacttaccta gtggaaaagc ctaatctgag cagcaaaagg tcagagttgt  19200
cacaactgag catgtaccga gtgtttgaag taggtgttat cagaaatccg ggtttggggg  19260
ctccggtgtt ccatatgaca aactatcttg agcaaccagc cagtaatgat ctcagcaact  19320
gtatggtggc tttgggggag ctcaaactcg cagccctttg tcacggggaa gattctatca  19380
caattcccta tcagggatca gggaaaggtg tcagcttcca gctcgtcaag ctaggtgtct  19440
ggaaatcccc aaccgacatg caatcctggg tccccttatc aacggatgat ccagtgatag  19500
acaggcttta cctctcatct cacagaggtg ttatcgctga caatcaagca aaatgggctg  19560
tcccgacaac acgaacagat gacaagttgc gaatggagac atgcttccaa caggcgtgta  19620
agggtaaaat ccaagcactc tgcgagaatc ccgagtgggc accattgaag gataacagga  19680
ttccttcata cggggtcttg tctgttgatc tgagtctgac agttgagctt aaaatcaaaa  19740
ttgcttcggg attcgggcca ttgatcacac acggttcagg gatggaccta tacaaatcca  19800
accacaacaa tgtgtattgg ctgactatcc cgccaatgaa gaacctagcc ttaggtgtaa  19860
tcaacacatt ggagtggata ccgagattca aggttagtcc ctacctcttc aatgtcccaa  19920
ttaaggaagc aggcgaagac tgccatgccc caacatacct acctgcggag gtggatggtg  19980
atgtcaaact cagttccaat ctggtgattc tacctggtca agatctccaa tatgttttgg  20040
caacctacga tacttccagg gttgaacatg ctgtggttta ttacgtttac agcccaggcc  20100
gctcattttc ttacttttat ccttttaggt tgcctataaa gggggtcccc atcgaattac  20160
aagtggaatg cttcacatgg gaccaaaaac tctggtgccg tcacttctgt gtgcttgcgg  20220
actcagaatc tggtggacat atcactcact ctgggatggt gggcatggga gtcagctgca  20280
cagtcacccg ggaagatgga accaatcgca gatagggctg ctagtgaacc aatctcatga  20340
tgtcacccag acatcaggca taccca                                        20366
```

<210> SEQ ID NO 10
<211> LENGTH: 1643
<212> TYPE: DNA
<213> ORGANISM: Artificial Sequence
<220> FEATURE:

-continued

<223> OTHER INFORMATION: Artificial DNA containing coding regions of
GMCSF and PAP

<400> SEQUENCE: 10

```
atgtggctgc agagcctgct gctcttgggc actgtggcct gcagcatctc tgcacccgcc     60
cgctcgccca gccccagcac gcagccctgg gagcatgtga atgccatcca ggaggcccgg    120
cgtctcctga acctgagtag agacactgct gctgagatga atgaaacagt agaagtcatc    180
tcagaaatgt ttgacctcca ggagccgacc tgcctacaga cccgcctgga gctgtacaag    240
cagggcctgc ggggcagcct caccaagctc aagggcccct tgaccatgat ggccagccac    300
tacaagcagc actgccctcc aaccccggaa acttcctgtg caacccagat tatcaccttt    360
gaaagtttca aagagaacct gaaggacttt ctgcttgtca tcccctttga ctgctgggag    420
ccagtccagg agtgatagtt tctgacatcc ggcgggtgac tcacaacgcg gccgcagcca    480
ccatgagagc tgcacccctc ctcctggcca gggcagcaag ccttagcctt ggcttcttgt    540
ttctgctttt tttctggcta gaccgaagtg tactagccaa ggagttgaag tttgtgactt    600
tggtgtttcg gcatggagac cgaagtccca ttgacacctt tcccactgac cccataaagg    660
aatcctcatg gccacaagga tttggccaac tcacccagct gggcatggag cagcattatg    720
aacttggaga gtatataaga aagagatata gaaaattctt gaatgagtcc tataaacatg    780
aacaggttta tattcgaagc acagacgttg accggacttt gatgagtgct atgacaaacc    840
tggcagccct gtttccccca gaaggtgtca gcatctggaa tcctatccta ctctggcagc    900
ccatcccggt gcacacagtt cctctttctg aagatcagtt gctatacctg cctttcagga    960
actgccctcg ttttcaagaa cttgagagtg agactttgaa atcagaggaa ttccagaaga   1020
ggctgcaccc ttataaggat tttatagcta ccttgggaaa actttcagga ttacatggcc   1080
aggacctttt tggaatttgg agtaaagtct acgacccttt atattgtgag agtgttcaca   1140
atttcacttt accctcctgg gccactgagg acaccatgac taagttgaga gaattgtcag   1200
aattgtccct cctgtccctc tatggaattc acaagcagaa agagaaatct aggctccaag   1260
ggggtgtcct ggtcaatgaa atcctcaatc acatgaagag agcaactcag ataccaagct   1320
acaaaaaact tatcatgtat tctgcgcatg acactactgt gagtggccta cagatggcgc   1380
tagatgttta caacggactc cttcctccct atgcttcttg ccacttgacg gaattgtact   1440
ttgagaaggg ggagtacttt gtggagatgt actatcggaa tgagacgcag cacgagccgt   1500
atcccctcat gctacctggc tgcagcccta gctgtcctct ggagaggttt gctgagctgg   1560
ttggccctgt gatccctcaa gactggtcca cggagtgtat gaccacaaac agccatcaag   1620
gtactgagga cagtacagat tag                                           1643
```

<210> SEQ ID NO 11
<211> LENGTH: 1601
<212> TYPE: DNA
<213> ORGANISM: Artificial Sequence
<220> FEATURE:
<223> OTHER INFORMATION: Artificial DNA containing coding regions of
GMCSF and CytD

<400> SEQUENCE: 11

```
atgtggctgc agagcctgct gctcttgggc actgtggcct gcagcatctc tgcacccgcc     60
cgctcgccca gccccagcac gcagccctgg gagcatgtga atgccatcca ggaggcccgg    120
cgtctcctga acctgagtag agacactgct gctgagatga atgaaacagt agaagtcatc    180
tcagaaatgt ttgacctcca ggagccgacc tgcctacaga cccgcctgga gctgtacaag    240
```

```
cagggcctgc ggggcagcct caccaagctc aagggcccct tgaccatgat ggccagccac    300

tacaagcagc actgccctcc aaccccggaa acttcctgtg caacccagat tatcaccttt    360

gaaagtttca aagagaacct gaaggacttt ctgcttgtca tcccctttga ctgctgggag    420

ccagtccagg agtgatttct gacatccggc gggtgactca caacgcggcc gcagccacca    480

tggtgacagg gggaatggca agcaagtggg atcagaaggg tatggacatt gcctatgagg    540

aggcggcctt aggttacaaa gagggtggtg ttcctattgg cggatgtctt atcaataaca    600

aagacggaag tgttctcggt cgtggtcaca acatgagatt tcaaaaggga tctgccacac    660

tacatggtga gatctccact ttggaaaact gtgggagatt agagggcaaa gtgtacaaag    720

ataccacttt gtatacgacg ctgtctccat gcgacatgtg tacaggtgcc atcatcatgt    780

atggtattcc acgctgtgtt gtcggtgaga acgttaattt caaaagtaag ggcgagaaat    840

atttacaaac tagaggtcac gaggttgttg ttgttgacga tgagaggtgt aaaaagatca    900

tgaaacaatt tatcgatgaa agacctcagg attggtttga agatattggt gaggcttcgg    960

aaccatttaa gaacgtctac ttgctacctc aaacaaacca attgctgggt ttgtacacca   1020

tcatcagaaa taagaataca actagacctg atttcatttt ctactccgat agaatcatca   1080

gattgttggt tgaagaaggt ttgaaccatc tacctgtgca aaagcaaatt gtggaaactg   1140

acaccaacga aaacttcgaa ggtgtctcat tcatgggtaa aatctgtggt gtttccattg   1200

tcagagctgg tgaatcgatg gagcaaggat taagagactg ttgtaggtct gtgcgtatcg   1260

gtaaaatttt aattcaaagg gacgaggaga ctgctttacc aaagttattc tacgaaaaat   1320

taccagagga tatatctgaa aggtatgtct tcctattaga cccaatgctg gccaccggtg   1380

gtagtgctat catggctaca gaagtcttga ttaagagagg tgttaagcca gagagaattt   1440

acttcttaaa cctaatctgt agtaaggaag ggattgaaaa ataccatgcc gccttcccag   1500

aggtcagaat tgttactggt gccctcgaca gaggtctaga tgaaaacaag tatctagttc   1560

cagggttggg tgactttggt gacagatact actgtgttta a                       1601
```

<210> SEQ ID NO 12
<211> LENGTH: 2210
<212> TYPE: DNA
<213> ORGANISM: Artificial Sequence
<220> FEATURE:
<223> OTHER INFORMATION: Artificial DNA containing coding regions of
      gMCSF, soluble PD-1 & PAP

<400> SEQUENCE: 12

```
atgtggctgc agagcctgct gctcttgggc actgtggcct gcagcatctc tgcacccgcc     60

cgctcgccca gccccagcac gcagccctgg gagcatgtga atgccatcca ggaggcccgg    120

cgtctcctga acctgagtag agacactgct gctgagatga atgaaacagt agaagtcatc    180

tcagaaatgt ttgacctcca ggagccgacc tgcctacaga cccgcctgga gctgtacaag    240

cagggcctgc ggggcagcct caccaagctc aagggcccct tgaccatgat ggccagccac    300

tacaagcagc actgccctcc aaccccggaa acttcctgtg caacccagat tatcaccttt    360

gaaagtttca aagagaacct gaaggacttt ctgcttgtca tcccctttga ctgctgggag    420

ccagtccagg agtgatagtt tctgacatcc ggcgggtgac tcacaacgcg gccgcagcca    480

ccatgcagat cccacaggcg ccctggccag tcgtctgggc ggtgctacaa ctgggctggc    540

ggccaggatg gttcttagac tccccagaca ggccctggaa cccccccacc ttctccccag    600

ccctgctcgt ggtgaccgaa ggggacaacg ccaccttcac ctgcagcttc tccaacacat    660
```

```
cggagagctt cgtgctaaac tggtaccgca tgagccccag caaccagacg gacaagctgg    720

ccgccttccc cgaggaccgc agccagcccg gccaggactg ccgcttccgt gtcacacaac    780

tgcccaacgg gcgtgacttc cacatgagcg tggtcagggc ccggcgcaat gacagcggca    840

cctacctctg tggggccatc tccctggccc ccaaggcgca gatcaaagag agcctgcggg    900

cagagctcag ggtgacagag agaagggcag aagtgcccac agcccacccc agcccctcac    960

ccaggtcagc cggccagttc caaggctccg gagccacgaa cttctctctg ttaaagcaag   1020

caggagacgt ggaagaaaac cccggtccca tgagagctgc acccctcctc ctggccaggg   1080

cagcaagcct tagccttggc ttcttgtttc tgcttttttt ctggctagac cgaagtgtac   1140

tagccaagga gttgaagttt gtgactttgg tgtttcggca tggagaccga agtcccattg   1200

acacctttcc cactgacccc ataaaggaat cctcatggcc acaaggattt ggccaactca   1260

cccagctggg catggagcag cattatgaac ttggagagta tataagaaag agatatagaa   1320

aattcttgaa tgagtcctat aaacatgaac aggtttatat tcgaagcaca gacgttgacc   1380

ggactttgat gagtgctatg acaaacctgg cagccctgtt tcccccagaa ggtgtcagca   1440

tctggaatcc tatcctactc tggcagccca tcccggtgca cacagttcct ctttctgaag   1500

atcagttgct atacctgcct ttcaggaact gccctcgttt tcaagaactt gagagtgaga   1560

ctttgaaatc agaggaattc cagaagaggc tgcaccctta taaggatttt atagctacct   1620

tgggaaaact ttcaggatta catggccagg accttttttgg aatttggagt aaagtctacg   1680

accctttata ttgtgagagt gttcacaatt tcactttacc ctcctgggcc actgaggaca   1740

ccatgactaa gttgagagaa ttgtcagaat tgtccctcct gtccctctat ggaattcaca   1800

agcagaaaga gaaatctagg ctccaagggg gtgtcctggt caatgaaatc ctcaatcaca   1860

tgaagagagc aactcagata ccaagctaca aaaaacttat catgtattct gcgcatgaca   1920

ctactgtgag tggcctacag atggcgctag atgtttacaa cggactcctt cctccctatg   1980

cttcttgcca cttgacggaa ttgtactttg agaaggggga gtactttgtg gagatgtact   2040

atcggaatga gacgcagcac gagccgtatc ccctcatgct acctggctgc agccctagct   2100

gtcctctgga gaggtttgct gagctggttg gccctgtgat ccctcaagac tggtccacgg   2160

agtgtatgac cacaaacagc catcaaggta ctgaggacag tacagattag              2210
```

```
<210> SEQ ID NO 13
<211> LENGTH: 2171
<212> TYPE: DNA
<213> ORGANISM: Artificial Sequence
<220> FEATURE:
<223> OTHER INFORMATION: Artificial DNA containing coding regions of
      GMCSF, soluble PD-1 & CytD

<400> SEQUENCE: 13

atgtggctgc agagcctgct gctcttgggc actgtggcct gcagcatctc tgcacccgcc     60

cgctcgccca gccccagcac gcagccctgg gagcatgtga atgccatcca ggaggcccgg    120

cgtctcctga acctgagtag agacactgct gctgagatga atgaaacagt agaagtcatc    180

tcagaaatgt ttgacctcca ggagccgacc tgcctacaga cccgcctgga gctgtacaag    240

cagggcctgc ggggcagcct caccaagctc aagggcccct tgaccatgat ggccagccac    300

tacaagcagc actgccctcc aaccccggaa acttcctgtg caacccagat tatcaccttt    360

gaaagtttca aagagaacct gaaggacttt ctgcttgtca tcccctttga ctgctgggag    420

ccagtccagg agtgatagtt tctgacatcc ggcgggtgac tcacaacgcg gccgcagcca    480
```

```
ccatgcagat cccacaggcg ccctggccag tcgtctgggc ggtgctacaa ctgggctggc    540

ggccaggatg gttcttagac tccccagaca ggccctggaa cccccccacc ttctccccag    600

ccctgctcgt ggtgaccgaa ggggacaacg ccaccttcac ctgcagcttc tccaacacat    660

cggagagctt cgtgctaaac tggtaccgca tgagccccag caaccagacg gacaagctgg    720

ccgccttccc cgaggaccgc agccagcccg gccaggactg ccgcttccgt gtcacacaac    780

tgcccaacgg gcgtgacttc cacatgagcg tggtcagggc ccggcgcaat gacagcggca    840

cctacctctg tggggccatc tccctggccc ccaaggcgca gatcaaagag agcctgcggg    900

cagagctcag ggtgacagag agaagggcag aagtgcccac agcccacccc agcccctcac    960

ccaggtcagc cggccagttc caaggctccg gagccacgaa cttctctctg ttaaagcaag   1020

caggagacgt ggaagaaaac cccggtccca tggtgacagg ggaatggca agcaagtggg   1080

atcagaaggg tatggacatt gcctatgagg aggcggcctt aggttacaaa gagggtggtg   1140

ttcctattgg cggatgtctt atcaataaca aagacggaag tgttctcggt cgtggtcaca   1200

acatgagatt tcaaaaggga tctgccacac tacatggtga gatctccact ttggaaaact   1260

gtgggagatt agagggcaaa gtgtacaaag ataccacttt gtatacgacg ctgtctccat   1320

gcgacatgtg tacaggtgcc atcatcatgt atggtattcc acgctgtgtt gtcggtgaga   1380

acgttaattt caaaagtaag ggcgagaaat atttacaaac tagaggtcac gaggttgttg   1440

ttgttgacga tgagaggtgt aaaaagatca tgaaacaatt tatcgatgaa agacctcagg   1500

attggtttga agatattggt gaggcttcgg aaccatttaa gaacgtctac ttgctacctc   1560

aaacaaacca attgctgggt ttgtacacca tcatcagaaa taagaataca actagacctg   1620

atttcatttt ctactccgat agaatcatca gattgttggt tgaagaaggt ttgaaccatc   1680

tacctgtgca aaagcaaatt gtggaaactg acaccaacga aaacttcgaa ggtgtctcat   1740

tcatgggtaa aatctgtggt gtttccattg tcagagctgg tgaatcgatg gagcaaggat   1800

taagagactg ttgtaggtct gtgcgtatcg gtaaaatttt aattcaaagg gacgaggaga   1860

ctgctttacc aaagttattc tacgaaaaat taccagagga tatatctgaa aggtatgtct   1920

tcctattaga cccaatgctg gccaccggtg gtagtgctat catggctaca gaagtcttga   1980

ttaagagagg tgttaagcca gagagaattt acttcttaaa cctaatctgt agtaaggaag   2040

ggattgaaaa ataccatgcc gccttcccag aggtcagaat tgttactggt gccctcgaca   2100

gaggtctaga tgaaaacaag tatctagttc cagggttggg tgactttggt gacagatact   2160

actgtgttta a                                                         2171
```

```
<210> SEQ ID NO 14
<211> LENGTH: 2885
<212> TYPE: DNA
<213> ORGANISM: Artificial Sequence
<220> FEATURE:
<223> OTHER INFORMATION: Artificial DNA containing coding regions of
      GMCSF, soluble PD-1, dominant negative mutant of cyclin G1 & PAP

<400> SEQUENCE: 14

atgtggctgc agagcctgct gctcttgggc actgtggcct gcagcatctc tgcacccgcc     60

cgctcgccca gccccagcac gcagccctgg gagcatgtga atgccatcca ggaggcccgg    120

cgtctcctga acctgagtag agacactgct gctgagatga atgaaacagt agaagtcatc    180

tcagaaatgt ttgacctcca ggagccgacc tgcctacaga cccgcctgga gctgtacaag    240

cagggcctgc ggggcagcct caccaagctc aagggcccct tgaccatgat ggccagccac    300
```

-continued

```
tacaagcagc actgccctcc aaccccggaa acttcctgtg caacccagat tatcaccttt    360
gaaagtttca aagagaacct gaaggacttt ctgcttgtca tccccctttga ctgctgggag    420
ccagtccagg agtgatagtt tctgacatcc ggcgggtgac tcacaacgcg gccgcagcca    480
ccatgcagat cccacaggcg ccctggccag tcgtctgggc ggtgctacaa ctgggctggc    540
ggccaggatg gttcttagac tccccagaca ggccctggaa cccccccacc ttctccccag    600
ccctgctcgt ggtgaccgaa ggggacaacg ccaccttcac ctgcagcttc tccaacacat    660
cggagagctt cgtgctaaac tggtaccgca tgagccccag caaccagacg gacaagctgg    720
ccgccttccc cgaggaccgc agccagcccg gccaggactg ccgcttccgt gtcacacaac    780
tgcccaacgg gcgtgacttc cacatgagcg tggtcagggc ccggcgcaat gacagcggca    840
cctacctctg tggggccatc tccctggccc ccaaggcgca gatcaaagag agcctgcggg    900
cagagctcag ggtgacagag agaagggcag aagtgcccac agcccacccc agcccctcac    960
ccaggtcagc cggccagttc caaggctccg gagccacgaa cttctctctg ttaaagcaag   1020
caggagacgt ggaagaaaac cccggtccca tgaaggtaca gcccaagcac cttgggtgtg   1080
ttggactgag ctgcttttat ttggctgtaa aatcaataga agaggaaagg aatgtcccat   1140
tggcaactga cttgatccga ataagtcaat ataggtttac ggtttcagac ttgatgagaa   1200
tggaaaagat tgtattggag aaggtgtgtt ggaaagtcaa agctactact gcctttcaat   1260
ttctgcaact gtattattca ctccttcaag agaacttgcc acttgaaagg agaaatagca   1320
ttaattttga aagactagaa gctcaactga aggcatgtca ttgcaggatc atattttcta   1380
aagcaaagcc ttctgtgttg gcattgtcta tcattgcatt agagatccaa gcacagaagt   1440
gtgtagagtt aacagaagga atagaatgtc ttcagaaaca ttccaagata aatggcagag   1500
atctgacctt ctggcaagag cttgtatcca aatgtttaac tgaatattca tcaaataagt   1560
gttccaaacc aaatgttcag aagttgaaat ggattgtttc tgggcgtact gcacggcaat   1620
tgaagcatag ctactacaga ataactcacc ttccaacaat tcctgaaatg gtcccttaaa   1680
tttctgacat ccggcgggtg actcacaacg cggccgcagc caccatgaga gctgcacccc   1740
tcctcctggc cagggcagca agccttagcc ttggcttctt gtttctgctt tttttctggc   1800
tagaccgaag tgtactagcc aaggagttga agtttgtgac tttggtgttt cggcatggag   1860
accgaagtcc cattgacacc tttcccactg accccataaa ggaatcctca tggccacaag   1920
gatttggcca actcacccag ctgggcatgg agcagcatta tgaacttgga gagtatataa   1980
gaaagagata tagaaaattc ttgaatgagt cctataaaca tgaacaggtt tatattcgaa   2040
gcacagacgt tgaccggact ttgatgagtg ctatgacaaa cctggcagcc ctgtttcccc   2100
cagaaggtgt cagcatctgg aatcctatcc tactctggca gcccatcccg gtgcacacag   2160
ttcctctttc tgaagatcag ttgctatacc tgcctttcag gaactgccct cgttttcaag   2220
aacttgagag tgagactttg aaatcagagg aattccagaa gaggctgcac ccttataagg   2280
attttatagc taccttggga aaactttcag gattacatgg ccaggacctt tttggaattt   2340
ggagtaaagt ctacgaccct ttatattgtg agagtgttca caatttcact ttaccctcct   2400
gggccactga ggacaccatg actaagttga gagaattgtc agaattgtcc ctcctgtccc   2460
tctatggaat tcacaagcag aaagagaaat ctaggctcca agggggtgtc ctggtcaatg   2520
aaatcctcaa tcacatgaag agagcaactc agataccaag ctacaaaaaa cttatcatgt   2580
attctgcgca tgacactact gtgagtggcc tacagatggc gctagatgtt tacaacggac   2640
```

```
tccttcctcc ctatgcttct tgccacttga cggaattgta ctttgagaag ggggagtact   2700

ttgtggagat gtactatcgg aatgagacgc agcacgagcc gtatcccctc atgctacctg   2760

gctgcagccc tagctgtcct ctggagaggt ttgctgagct ggttggccct gtgatccctc   2820

aagactggtc cacggagtgt atgaccacaa acagccatca aggtactgag gacagtacag   2880

attag                                                               2885


<210> SEQ ID NO 15
<211> LENGTH: 2843
<212> TYPE: DNA
<213> ORGANISM: Artificial Sequence
<220> FEATURE:
<223> OTHER INFORMATION: Artificial DNA containing coding regions of
      GMCSF, soluble PD-1, dominant negative mutant of cyclin G1 & Cyt D

<400> SEQUENCE: 15

atgtggctgc agagcctgct gctcttgggc actgtggcct gcagcatctc tgcacccgcc     60

cgctcgccca gccccagcac gcagccctgg gagcatgtga atgccatcca ggaggcccgg    120

cgtctcctga acctgagtag agacactgct gctgagatga atgaaacagt agaagtcatc    180

tcagaaatgt ttgacctcca ggagccgacc tgcctacaga cccgcctgga gctgtacaag    240

cagggcctgc ggggcagcct caccaagctc aagggcccct tgaccatgat ggccagccac    300

tacaagcagc actgccctcc aaccccggaa acttcctgtg caacccagat tatcaccttt    360

gaaagtttca aagagaacct gaaggacttt ctgcttgtca tcccctttga ctgctgggag    420

ccagtccagg agtgatttct gacatccggc gggtgactca caacgcggcc gcagccacca    480

tgcagatccc acaggcgccc tggccagtcg tctgggcggt gctacaactg ggctggcggc    540

caggatggtt cttagactcc ccagacaggc cctggaaccc ccccaccttc tccccagccc    600

tgctcgtggt gaccgaaggg gacaacgcca ccttcacctg cagcttctcc aacacatcgg    660

agagcttcgt gctaaactgg taccgcatga gccccagcaa ccagacggac aagctggccg    720

ccttccccga ggaccgcagc cagcccggcc aggactgccg cttccgtgtc acacaactgc    780

ccaacgggcg tgacttccac atgagcgtgg tcagggcccg gcgcaatgac agcggcacct    840

acctctgtgg ggccatctcc ctggccccca aggcgcagat caaagagagc ctgcgggcag    900

agctcagggt gacagagaga agggcagaag tgcccacagc ccaccccagc ccctcaccca    960

ggtcagccgg ccagttccaa ggctccggag ccacgaactt ctctctgtta aagcaagcag   1020

gagacgtgga agaaaacccc ggtcccatga aggtacagcc caagcacctt gggtgtgttg   1080

gactgagctg cttttatttg gctgtaaaat caatagaaga ggaaaggaat gtcccattgg   1140

caactgactt gatccgaata agtcaatata ggtttacggt ttcagacttg atgagaatgg   1200

aaaagattgt attggagaag gtgtgttgga aagtcaaagc tactactgcc tttcaatttc   1260

tgcaactgta ttattcactc cttcaagaga acttgccact tgaaaggaga aatagcatta   1320

attttgaaag actagaagct caactgaagg catgtcattg caggatcata ttttctaaag   1380

caaagccttc tgtgttggca ttgtctatca ttgcattaga gatccaagca cagaagtgtg   1440

tagagttaac agaaggaata gaatgtcttc agaaacattc caagataaat ggcagagatc   1500

tgaccttctg gcaagagctt gtatccaaat gtttaactga atattcatca aataagtgtt   1560

ccaaaccaaa tgttcagaag ttgaaatgga ttgtttctgg gcgtactgca cggcaattga   1620

agcatagcta ctacagaata actcaccttc caacaattcc tgaaatggtc ccttaaattt   1680

ctgacatccg gcgggtgact cacaacgcgg ccgcagccac catggtgaca gggggaatgg   1740
```

```
caagcaagtg ggatcagaag ggtatggaca ttgcctatga ggaggcggcc ttaggttaca   1800

aagagggtgg tgttcctatt ggcggatgtc ttatcaataa caaagacgga agtgttctcg   1860

gtcgtggtca caacatgaga tttcaaaagg gatctgccac actacatggt gagatctcca   1920

ctttggaaaa ctgtgggaga ttagagggca aagtgtacaa agataccact ttgtatacga   1980

cgctgtctcc atgcgacatg tgtacaggtg ccatcatcat gtatggtatt ccacgctgtg   2040

ttgtcggtga gaacgttaat ttcaaaagta agggcgagaa atatttacaa actagaggtc   2100

acgaggttgt tgttgttgac gatgagaggt gtaaaaagat catgaaacaa tttatcgatg   2160

aaagacctca ggattggttt gaagatattg gtgaggcttc ggaaccattt aagaacgtct   2220

acttgctacc tcaaacaaac caattgctgg gtttgtacac catcatcaga aataagaata   2280

caactagacc tgatttcatt ttctactccg atagaatcat cagattgttg gttgaagaag   2340

gtttgaacca tctacctgtg caaaagcaaa ttgtggaaac tgacaccaac gaaaacttcg   2400

aaggtgtctc attcatgggt aaaatctgtg gtgtttccat tgtcagagct ggtgaatcga   2460

tggagcaagg attaagagac tgttgtaggt ctgtgcgtat cggtaaaatt ttaattcaaa   2520

gggacgagga gactgcttta ccaaagttat tctacgaaaa attaccagag gatatatctg   2580

aaaggtatgt cttcctatta gacccaatgc tggccaccgg tggtagtgct atcatggcta   2640

cagaagtctt gattaagaga ggtgttaagc cagagagaat ttacttctta aacctaatct   2700

gtagtaagga agggattgaa aaataccatg ccgccttccc agaggtcaga attgttactg   2760

gtgccctcga cagaggtcta gatgaaaaca agtatctagt tccagggttg ggtgactttg   2820

gtgacagata ctactgtgtt taa                                           2843
```

```
<210> SEQ ID NO 16
<211> LENGTH: 22130
<212> TYPE: DNA
<213> ORGANISM: Artificial Sequence
<220> FEATURE:
<223> OTHER INFORMATION: Artificial DNA containing MV genome modified by
      inserting GMCSF-ires-PAP

<400> SEQUENCE: 16

gggaagagaa ggcaggcagt tcgggtctca gcaaaccatg cctctcagca attggatcaa     60

ctgaaggcgg tgcacctcgc atccgcggtc agggacctgg agagagcgat gacgacgctg    120

aaactttggg aatcccccca agaaatctcc aggcatcaag cactgggtta cagtgttatt    180

atgtttatga tcacagcggt gaagcggtta agggaatcca agatgctgac tctatcatgg    240

ttcaatcagg ccttgatggt gatagcaccc tctcaggagg agacaatgaa tctgaaaaca    300

gcgatgtgga tattggcgaa cctgataccg agggatatgc tatcactgac cggggatctg    360

ctcccatctc tatggggttc agggcttctg atgttgaaac tgcagaagga ggggagatcc    420

acgagctcct gagactccaa tccagaggca acaactttcc gaagcttggg aaaactctca    480

atgttcctcc gcctccggac cccggtaggg ccagcacttc cgggacaccc attaaaaagg    540

gcacagacgc gagattagcc tcatttggaa cggagatcgc gtctttattg acaggtggtg    600

caacccaatg tgctcgaaag tcaccctcgg aaccatcagg gccaggtgca cctgcgggga    660

atgtccccga gtgtgtgagc aatgccgcac tgatacagga gtggacaccc gaatctggta    720

ccacaatctc cccgagatcc cagaataatg aagaaggggg agactattat gatgatgagc    780

tgttctctga tgtccaagat attaaaacag ccttggccaa aatacacgag gataatcaga    840

agataatctc caagctagaa tcactgctgt tattgaaggg agaagttgag tcaattaaga    900
```

-continued

```
agcagatcaa caggcaaaat atcagcatat ccaccctgga aggacacctc tcaagcatca    960
tgatcgccat tcctggactt gggaaggatc ccaacgaccc cactgcagat gtcgaaatca   1020
atcccgactt gaaacccatc ataggcagag attcaggccg agcactggcc gaagttctca   1080
agaaacccgt tgccagccga caactccaag gaatgacaaa tggacggacc agttccagag   1140
gacagctgct gaaggaattt cagctaaagc cgatcgggaa aaagatgagc tcagccgtcg   1200
ggtttgttcc tgacaccggc cctgcatcac gcagtgtaat ccgctccatt ataaaatcca   1260
gccggctaga ggaggatcgg aagcgttacc tgatgactct ccttgatgat atcaaaggag   1320
ccaatgatct tgccaagttc caccagatgc tgatgaagat aataatgaag tagctacagc   1380
tcaacttacc tgccaacccc atgccagtcg acccaactag tacaacctaa atccattata   1440
aaaaacttag gagcaaagtg attgcctccc aagttccaca atgacagaga tctacgactt   1500
cgacaagtcg gcatgggaca tcaaagggtt gatcgctccg atacaaccca ccacctacag   1560
tgatggcagg ctggtgcccc aggtcagagt catagatcct ggtctaggcg acaggaagga   1620
tgaatgcttt atgtacatgt ttctgctggg ggttgttgag gacagcgatc ccctagggcc   1680
tccaatcggg cgagcatttg ggtccctgcc cttaggtgtt ggcagatcca cagcaaagcc   1740
cgaaaaactc ctcaaagagg ccactgagct tgacatagtt gttagacgta cagcagggct   1800
caatgaaaaa ctggtgttct acaacaacac ccccactaact ctcctcacac cttggagaaa   1860
ggtcctaaca acagggagtg tcttcaacgc aaaccaagtg tgcaatgcgg ttaatctgat   1920
accgctcgat accccgcaga ggttccgtgt tgtttatatg agcatcaccc gtctttcgga   1980
taacgggtat tacaccgttc ctagaagaat gctggaattc agatcggtca atgcagtggc   2040
cttcaacctg ctggtgaccc ttaggattga caaggcgata ggccctggga agatcatcga   2100
caatacagag caacttcctg aggcaacatt tatggtccac atcgggaact tcaggagaaa   2160
gaagagtgaa gtctactctg ccgattattg caaaatgaaa atcgaaaaga tgggcctggt   2220
ttttgcactt ggtgggatag ggggcaccag tcttcacatt agaagcacag gcaaaatgag   2280
caagactctc catgcacaac tcgggttcaa gaagacctta tgttacccgc tgatagatat   2340
caatgaagac cttaatcgat tactctggag gagcagatgc aagatagtaa gaatccaggc   2400
agttttgcag ccatcagttc ctcaagaatt ccgcatttac gacgacgtga tcataaatga   2460
tgaccaagga ctattcaaag ttctgtagac cgtagtgccc agcaatgccc gaaaacgacc   2520
cccctcacaa tgacagccag aaggcccgga caaaaaagcc ccctccgaaa gactccacgg   2580
accaagcgag aggccagcca gcagccgacg gcaagcgcga acaccaggcg gccccagcac   2640
agaacagccc tgatacaagg ccaccaccag ccaccccaat ctgcatcctc ctcgtgggac   2700
ccccgaggac caacccccaa ggctgccccc gatccaaacc accaaccgca tccccaccac   2760
ccccgggaaa gaaaccccca gcaattggaa ggcccctccc cctcttcctc aacacaagaa   2820
ctccacaacc gaaccgcaca agcgaccgag gtgacccaac cgcaggcatc cgactcccta   2880
gacagatcct ctctccccgg caaactaaac aaaacttagg gccaaggaac atacacaccc   2940
aacagaaccc agaccccggc ccacggcgcc gcgcccccaa cccccgacaa ccagagggag   3000
cccccaacca atcccgccgg ctcccccggt gcccacaggc agggacacca acccccgaac   3060
agacccagca cccaaccatc gacaatccaa gacggggggg cccccccaaa aaaaggcccc   3120
caggggccga cagccagcac cgcgaggaag cccacccacc ccacacacga ccacggcaac   3180
caaaccagaa cccagaccac cctgggccac cagctcccag actcggccat caccccgcag   3240
aaaggaaagg ccacaacccg cgcaccccag ccccgatccg gcggggagcc acccaacccg   3300
```

aaccagcacc caagagcgat ccccgaagga cccccgaacc gcaaaggaca tcagtatccc 3360
acagcctctc caagtccccc ggtctcctcc ccttctcgaa gggaccaaaa gatcaatcca 3420
ccacacccga cgacactcaa ctccccaccc ctaaaggaga caccgggaat cccagaatca 3480
agactcatcc aatgtccatc atgggtctca aggtgaacgt ctctgccata ttcatggcag 3540
tactgttaac tctccaaaca cccaccggtc aaatccattg ggcaatctc tctaagatag 3600 gggtggtagg aataggaagt gcaagctaca aagttatgac tcgttccagc catcaatcat 3660
tagtcataaa attaatgccc aatataactc tcctcaataa ctgcacgagg gtagagattg 3720
cagaatacag gagactactg agaacagttt tggaaccaat tagagatgca cttaatgcaa 3780
tgacccagaa tataagaccg gttcagagtg tagcttcaag taggagacac aagagatttg 3840
cgggagtagt cctggcaggt gcggccctag gcgttgccac agctgctcag ataacagccg 3900
gcattgcact tcaccagtcc atgctgaact ctcaagccat cgacaatctg agagcgagcc 3960
tggaaactac taatcaggca attgaggcaa tcagacaagc agggcaggag atgatattgg 4020
ctgttcaggg tgtccaagac tacatcaata atgagctgat accgtctatg aaccaactat 4080
cttgtgattt aatcggccag aagctcgggc tcaaattgct cagatactat acagaaatcc 4140
tgtcattatt tggccccagc ttacgggacc ccatatctgc ggagatatct atccaggctt 4200
tgagctatgc gcttggagga gacatcaata aggtgttaga aaagctcgga tacagtggag 4260
gtgatttact gggcatctta gagagcagag gaataaaggc ccggataact cacgtcgaca 4320
cagagtccta cttcattgtc ctcagtatag cctatccgac gctgtccgag attaaggggg 4380
tgattgtcca ccggctagag ggggtctcgt acaacatagg ctctcaagag tggtatacca 4440
ctgtgcccaa gtatgttgca acccaagggt accttatctc gaattttgat gagtcatcgt 4500
gtactttcat gccagagggg actgtgtgca gccaaaatgc cttgtacccg atgagtcctc 4560
tgctccaaga atgcctccgg gggtccacca agtcctgtgc tcgtacactc gtatccgggt 4620
cttttgggaa ccggttcatt ttatcacaag ggaacctaat agccaattgt gcatcaatcc 4680
tttgcaagtg ttacacaaca ggaacgatca ttaatcaaga ccctgacaag atcctaacat 4740
acattgctgc cgatcactgc ccggtagtcg aggtgaacgg cgtgaccatc caagtcggga 4800
gcaggaggta tccagatgct gtgtacttgc acagaattga cctcggtcct cccatatcat 4860
tggagaggtt ggacgtaggg acaaatctgg ggaatgcaat tgctaagttg gaggatgcca 4920
aggaattgtt ggagtcatcg gaccagatat tgaggagtat gaaaggttta tcgagcacta 4980
gcatagtcta catcctgatt gcagtgtgtc ttggagggtt gatagggatc cccgctttaa 5040
tatgttgctg caggggggcgt tgtaacaaaa agggagaaca agttggtatg tcaagaccag 5100
gcctaaagcc tgatcttacg ggaacatcaa aatcctatgt aaggtcgctc tgatcctcta 5160
caactcttga aacacaaatg tcccacaagt ctcctcttcg tcatcaagca accaccgcac 5220
ccagcatcaa gcccacctga aattatctcc ggcttccctc tggccgaaca atatcggtag 5280
ttaattaaaa cttagggtgc aagatcatcc acaatgtcac cacaacgaga ccggataaat 5340
gccttctaca aagataaccc ccatcccaag ggaagtagga tagtcattaa cagagaacat 5400
cttatgattg atagacctta tgttttgctg gctgttctgt ttgtcatgtt tctgagcttg 5460
atcgggttgc tagccattgc aggcattaga cttcatcggg cagccatcta caccgcagag 5520
atccataaaa gcctcagcac caatctagat gtaactaact caatcgagca tcaggtcaag 5580
gacgtgctga caccactctt caaaatcatc ggtgatgaag tgggcctgag gacacctcag 5640

-continued

```
agattcactg acctagtgaa attcatctct gacaagatta aattccttaa tccggatagg   5700
gagtacgact tcagagatct cacttggtgt atcaacccgc cagagagaat caaattggat   5760
tatgatcaat actgtgcaga tgtggctgct gaagagctca tgaatgcatt ggtgaactca   5820
actctactgg agaccagaac aaccaatcag ttcctagctg tctcaaaggg aaactgctca   5880
gggcccacta caatcagagg tcaattctca aacatgtcgc tgtccctgtt agacttgtat   5940
ttaggtcgag gttacaatgt gtcatctata gtcactatga catcccaggg aatgtatggg   6000
ggaacttacc tagtggaaaa gcctaatctg agcagcaaaa ggtcagagtt gtcacaactg   6060
agcatgtacc gagtgtttga agtaggtgtt atcagaaatc cgggtttggg ggctccggtg   6120
ttccatatga caaactatct tgagcaacca gccagtaatg atctcagcaa ctgtatggtg   6180
gctttggggg agctcaaact cgcagccctt tgtcacgggg aagattctat cacaattccc   6240
tatcagggat cagggaaagg tgtcagcttc cagctcgtca agctaggtgt ctggaaatcc   6300
ccaaccgaca tgcaatcctg ggtcccctta tcaacggatg atccagtgat agacaggctt   6360
tacctctcat ctcacagagg tgttatcgct gacaatcaag caaaatgggc tgtcccgaca   6420
acacgaacag atgacaagtt gcgaatggag acatgcttcc aacaggcgtg taagggtaaa   6480
atccaagcac tctgcgagaa tcccgagtgg gcaccattga aggataacag gattccttca   6540
tacggggtct tgtctgttga tctgagtctg acagttgagc ttaaaatcaa aattgcttcg   6600
ggattcgggc cattgatcac acacggttca gggatggacc tatacaaatc caaccacaac   6660
aatgtgtatt ggctgactat cccgccaatg aagaacctag ccttaggtgt aatcaacaca   6720
ttggagtgga taccgagatt caaggttagt ccctacctct tcaatgtccc aattaaggaa   6780
gcaggcgaag actgccatgc cccaacatac ctacctgcgg aggtggatgg tgatgtcaaa   6840
ctcagttcca atctggtgat tctacctggt caagatctcc aatatgtttt ggcaacctac   6900
gatacttcca gggttgaaca tgctgtggtt tattacgttt acagcccagg ccgctcattt   6960
tcttactttt atccttttag gttgcctata aagggggtcc ccatcgaatt acaagtggaa   7020
tgcttcacat gggaccaaaa actctggtgc cgtcacttct gtgtgcttgc ggactcagaa   7080
tctggtggac atatcactca ctctgggatg gtgggcatgg gagtcagctg cacagtcacc   7140
cgggaagatg gaaccaatcg cagatagggc tgctagtgaa ccaatctcat gatgtcaccc   7200
agacatcagg catacccact agtgtgaaat agacatcaga attaagaaaa acgtagggtc   7260
caagtggttc cccgttatgg actcgctatc tgtcaaccag atcttatacc ctgaagttca   7320
cctagatagc ccgatagtta ccaataagat agtagccatc ctggagtatg ctcgagtccc   7380
tcacgcttac agcctggagg accctacact gtgtcagaac atcaagcacc gcctaaaaaa   7440
cggattttcc aaccaaatga ttataaacaa tgtggaagtt gggaatgtca tcaagtccaa   7500
gcttaggagt tatccggccc actctcatat tccatatcca aattgtaatc aggatttatt   7560
taacatagaa gacaaagagt caacgaggaa gatccgtgaa ctcctcaaaa aggggaattc   7620
gctgtactcc aaagtcagtg ataaggtttt ccaatgctta agggacacta actcacggct   7680
tggcctaggc tccgaattga gggaggacat caaggagaaa gttattaact tgggagttta   7740
catgcacagc tcccagtggt ttgagccctt tctgttttgg tttacagtca agactgagat   7800
gaggtcagtg attaaatcac aaacccatac ttgccatagg aggagacaca cacctgtatt   7860
cttcactggt agttcagttg agttgctaat ctctcgtgac cttgttgcta taatcagtaa   7920
agagtctcaa catgtatatt acctgacatt tgaactggtt ttgatgtatt gtgatgtcat   7980
agaggggagg ttaatgacag agaccgctat gactattgat gctaggtata cagagcttct   8040
```

```
aggaagagtc agatacatgt ggaaactgat agatggtttc ttccctgcac tcgggaatcc   8100
aacttatcaa attgtagcca tgctggagcc tctttcactt gcttacctgc agctgaggga   8160
tataacagta gaactcagag gtgctttcct taaccactgc tttactgaaa tacatgatgt   8220
tcttgaccaa aacgggtttt ctgatgaagg tacttatcat gagttaattg aagctctaga   8280
ttacattttc ataactgatg acatacatct gacaggggag attttctcat tttcagaag    8340
tttcggccac cccagacttg aagcagtaac ggctgctgaa aatgttagga aatacatgaa   8400
tcagcctaaa gtcattgtgt atgagactct gatgaaaggt catgccatat tttgtggaat   8460
cataatcaac ggctatcgtg acaggcacgg aggcagttgg ccaccgctga ccctccccct   8520
gcatgctgca gacacaatcc ggaatgctca agcttcaggt gaagggttaa cacatgagca   8580
gtgcgttgat aactggagat cttttgctgg agtgaaattt ggctgcttta tgcctcttag   8640
cctggatagt gatctgacaa tgtacctaaa ggacaaggca cttgctgctc tccaaaggga   8700
atgggattca gtttacccga aagagttcct gcgttacgac cctcccaagg gaaccgggtc   8760
acggaggctt gtagatgttt tccttaatga ttcgagcttt gacccatatg atgtgataat   8820
gtatgttgta agtggagctt acctccatga ccctgagttc aacctgtctt acagcctgaa   8880
agaaaaggag atcaaggaaa caggtagact tttgctaaa atgacttaca aaatgagggc    8940
atgccaagtg attgctgaaa atctaatctc aaacgggatt ggcaaatatt ttaaggacaa   9000
tgggatggcc aaggatgagc acgatttgac taaggcactc cacactctag ctgtctcagg   9060
agtccccaaa gatctcaaag aaagtcacag gggggggcca gtcttaaaaa cctactcccg   9120
aagcccagtc cacacaagta ccaggaacgt gagagcagca aaagggttta tagggttccc   9180
tcaagtaatt cggcaggacc aagacactga tcatccggag aatatggaag cttacgagac   9240
agtcagtgca tttatcacga ctgatctcaa gaagtactgc cttaattgga gatatgagac   9300
catcagcttg tttgcacaga ggctaaatga gatttacgga ttgccctcat tttccagtg    9360
gctgcataag aggcttgaga cctctgtcct gtatgtaagt gaccctcatt gcccccccga   9420
ccttgacgcc catatcccgt tatataaagt ccccaatgat caaatcttca ttaagtaccc   9480
tatgggaggt atagaagggt attgtcagaa gctgtggacc atcagcacca ttccctatct   9540
atacctggct gcttatgaga gcggagtaag gattgcttcg ttagtgcaag gggacaatca   9600
gaccatagcc gtaacaaaaa gggtacccag cacatggccc tacaacctta agaaacggga   9660
agctgctaga gtaactagag attactttgt aattcttagg caaaggctac atgatattgg   9720
ccatcacctc aaggcaaatg agacaattgt ttcatcacat ttttttgtct attcaaaagg   9780
aatatattat gatgggctac ttgtgtccca atcactcaag agcatcgcaa gatgtgtatt   9840
ctggtcagag actatagttg atgaaacaag ggcagcatgc agtaatattg ctacaacaat   9900
ggctaaaagc atcgagagag gttatgaccg ttaccttgca tattccctga acgtcctaaa   9960
agtgatacag caaattctga tctctcttgg cttcacaatc aattcaacca tgacccggga  10020
tgtagtcata cccctcctca cgaacaacga cctcttaata aggatggcac tgttgcccgc  10080
tcctattggg ggatgaatt atctgaatat gagcaggctg tttgtcagaa acatcggtga   10140
tccagtaaca tcatcaattg ctgatctcaa gagaatgatt ctcgcctcac taatgcctga  10200
agagaccctc catcaagtaa tgacacaaca accgggggac tcttcattcc tagactgggc  10260
tagcgaccct tactcagcaa atcttgtatg tgtccagagc atcactagac tcctcaagaa  10320
cataactgca aggtttgtcc tgatccatag tccaaaccca atgttaaaag gattattcca  10380
```

-continued tgatgacagt aaagaagagg acgagggact ggcggcattc ctcatggaca ggcatattat 10440
agtacctagg gcagctcatg aaatcctgga tcatagtgtc acaggggcaa gagagtctat 10500
tgcaggcatg ctggatacca caaaaggcct gattcgagcc agcatgagga agggggggtt 10560
aacctctcga gtgataacca gattgtccaa ttatgactat gaacaattca gagcagggat 10620
ggtgctattg acaggaagaa agagaaatgt cctcattgac aaagagtcat gttcagtgca 10680
gctggcgaga gctctaagaa gccatatgtg ggcgaggcta gctcgaggac ggcctattta 10740
cggccttgag gtccctgatg tactagaatc tatgcgaggc caccttattc ggcgtcatga 10800
gacatgtgtc atctgcgagt gtggatcagt caactacgga tggtttttg tcccctcggg 10860 ttgccaactg gatgatattg acaaggaaac atcatccttg agagtcccat atattggttc 10920
taccactgat gagagaacag acatgaagct tgccttcgta agagccccaa gtcgatcctt 10980
gcgatctgct gttagaatag caacagtgta ctcatgggct tacggtgatg atgatagctc 11040
ttggaacgaa gcctggttgt tggctaggca aagggccaat gtgagcctgg aggagctaag 11100
ggtgatcact cccatctcaa cttcgactaa tttagcgcat aggttgaggg atcgtagcac 11160
tcaagtgaaa tactcaggta catcccttgt ccgagtggcg aggtatacca caatctccaa 11220
cgacaatctc tcatttgtca tatcagataa gaaggttgat actaacttta tataccaaca 11280
aggaatgctt ctagggttgg gtgttttaga aacattgttt cgactcgaga aagataccgg 11340
atcatctaac acggtattac atcttcacgt cgaaacagat tgttgcgtga tcccgatgat 11400
agatcatccc aggataccca gctcccgcaa gctagagctg agggcagagc tatgtaccaa 11460
cccattgata tatgataatg cacctttaat tgacagagat acaacaaggc tatacaccca 11520
gagccatagg aggcaccttg tggaatttgt tacatggtcc acaccccaac tatatcacat 11580
tttagctaag tccacagcac tatctatgat tgacctggta acaaaatttg agaaggacca 11640
tatgaatgaa atttcagctc tcatagggga tgacgatatc aatagtttca taactgagtt 11700
tctgctcata gagccaagat tattcactat ctacttgggc cagtgtgcgg ccatcaattg 11760
ggcatttgat gtacattatc atagaccatc agggaaatat cagatgggtg agctgttgtc 11820
atcgttcctt tctagaatga gcaaaggagt gtttaaggtg cttgtcaatg ctctaagcca 11880
cccaaagatc tacaagaaat tctggcattg tggtattata gagcctatcc atggtccttc 11940
acttgatgct caaaacttgc acacaactgt gtgcaacatg gtttacacat gctatatgac 12000
ctacctcgac ctgttgttga atgaagagtt agaagagttc acatttctct tgtgtgaaag 12060
cgacgaggat gtagtaccgg acagattcga caacatccag gcaaaacact tatgtgttct 12120
ggcagatttg tactgtcaac cagggacctg cccaccaatt cgaggtctaa gaccggtaga 12180
gaaatgtgca gttctaaccg accatatcaa ggcagaggct aggttatctc cagcaggatc 12240
ttcgtggaac ataaatccaa ttattgtaga ccattactca tgctctctga cttatctccg 12300
gcgaggatcg atcaaacaga taagattgag agttgatcca ggattcattt tcgacgccct 12360
cgctgaggta aatgtcagtc agccaaagat cggcagcaac aacatctcaa atatgagcat 12420
caaggctttc agacccccac acgatgatgt tgcaaaattg ctcaaagata tcaacacaag 12480
caagcacaat cttcccattt cagggggcaa tctcgccaat tatgaaatcc atgctttccg 12540
cagaatcggg ttgaactcat ctgcttgcta caaagctgtt gagatatcaa cattaattag 12600
gagatgcctt gagccagggg aggacggctt gttcttgggt gagggatcgg gttccatgtt 12660
gatcacttat aaggagatac ttaaactaaa caagtgcttc tataatagtg ggtttccgc 12720 caattctaga tctggtcaaa gggaattagc accctatccc tccgaagttg gccttgtcga 12780

-continued

```
acacagaatg ggagtaggta atattgtcaa agtgctcttt aacgggaggc ccgaagtcac  12840
gtgggtaggc agtgtagatt gcttcaattt catagttagt aatatcccta cctctagtgt  12900
ggggtttatc cattcagata tagagacctt gcctaacaaa gatactatag agaagctaga  12960
ggaattggca gccatcttat cgatggctct gctcctgggc aaaataggat caatactggt  13020
gattaagctt atgcctttca gcggggattt tgttcaggga tttataagtt atgtagggtc  13080
ccattataga gaagtgaacc ttgtataccc tagatacagc aacttcatat ctactgaatc  13140
ttatttggtt atgacagatc tcaaggctaa ccggctaatg aatcctgaaa agattaagca  13200
gcagataatt gaatcatctg tgaggacttc acctggactt ataggtcaca tcctatccat  13260
taagcaacta agctgcatac aagcaattgt gggagacgca gttagtagag gtgatatcaa  13320
tcctactctg aaaaaactta cacctataga gcaggtgctg atcaattgcg ggttggcaat  13380
taacggacct aagctgtgca aagaattgat ccaccatgat gttgcctcag ggcaagatgg  13440
attgcttaat tctatactca tcctctacag ggagttggca agattcaaag acaaccaaag  13500
aagtcaacaa gggatgttcc acgcttaccc cgtattggta agtagcaggc aacgagaact  13560
tatatctagg atcacccgca aattttgggg gcacattctt ctttactccg ggaacagaaa  13620
gttgataaat aagtttatcc agaatctcaa gtccggctat ctgatactag acttacacca  13680
gaatatcttc gttaagaatc tatccaagtc agagaaacag attattatga cgggggggttt  13740
gaaacgtgag tgggttttta aggtaacagt caaggagacc aaagaatggt ataagttagt  13800
cggatacagt gccctgatta aggactaatt ggttgaactc cggaacccta atcctgccct  13860
aggtggttag gcattatttg caatagatta aagaaaactt tgaaaatacg aagtttctat  13920
tcccagcttt gtctggtttt tttccccccc aacttcggag gtcgaccagt actccgggcg  13980
acactttgtt tttttttttt cccccgatgc tggaggtcga ccagatgtcc gaaagtgtcc  14040
cccccccccc cccccccccc ccggcgcgga gcggcggggc caccccggac ccctttttttt  14100
tttttttttt tttttttaaa ttcctggaac ctttaggtcg accagttgtc cgtcttttac  14160
tccttcatat aggtcgacca gtactccggg tggtactttg tctttttctg aaaatcccag  14220
aggtcgacca gatatccgcg gccgccgagc tcgttaacaa caacaattgc attcatttta  14280
tgtttcaggt tcagggggag atgtgggagg tttttttaaag caagtaaaac ctctacaaat  14340
gtggtaaaat ccgataagga tcgatccggg ctggcgtaat agcgaagagg cccgcaccga  14400
tcgcccttcc caacagttgc gcagcctgaa tggcgaatgg acgcgccctg tagcggcgca  14460
ttaagcgcgg cgggtgtggt ggttacgcgc agcgtgaccg ctacacttgc cagcgcccta  14520
gcgcccgctc ctttcgcttt cttcccttcc tttctcgcca cgttcgccgg ctttccccgt  14580
caagctctaa atcgggggct ccctttaggg ttccgattta gagctttacg gcacctcgac  14640
cgcaaaaaac ttgatttggg tgatggttca cgtagtgggc catcgccctg atagacggtt  14700
tttcgccctt tgacgttgga gtccacgttc tttaatagtg gactcttgtt ccaaactgga  14760
acaacactca accctatctc ggtctattct tttgatttat aagggatttt gccgatttcg  14820
gcctattggt taaaaaatga gctgatttaa caaatattta acgcgaattt taacaaaata  14880
ttaacgttta caatttcgcc tgatgcggta ttttctcctt acgcatctgt gcggtatttc  14940
acaccgcata cgcggatctg cgcagcacca tggcctgaaa taacctctga aagaggaact  15000
tggttaggta ccttctgagg cggaaagaac cagctgtgga atgtgtgtca gttagggtgt  15060
ggaaagtccc caggctcccc agcaggcaga agtatgcaaa gcatgcatct caattagtca  15120
```

gcaaccaggt gtggaaagtc cccaggctcc ccagcaggca gaagtatgca aagcatgcat 15180
ctcaattagt cagcaaccat agtcccgccc ctaactccgc ccatcccgcc cctaactccg 15240
cccagttccg cccattctcc gccccatggc tgactaattt tttttattta tgcagaggcc 15300
gaggccgcct cggcctctga gctattccag aagtagtgag gaggcttttt tggaggccta 15360
ggcttttgca aaaagcttga ttcttctgac acaacagtct cgaacttaag gctagagcca 15420
ccatggttcg accattgaac tgcatcgtcg ccgtgtccca aaatatgggg attggcaaga 15480
acggagacct accctggcct ccgctcagga acgagttcaa gtacttccaa agaatgacca 15540
caacctcttc agtggaaggt aaacagaatc tggtgattat gggtaggaaa acctggttct 15600
ccattcctga gaagaatcga cctttaaagg acagaattaa tatagttctc agtagagaac 15660
tcaaagaacc accacgagga gctcattttc ttgccaaaag tttggatgat gccttaagac 15720
ttattgaaca accggaattg gcaagtaaag tagacatggt ttggatagtc ggaggcagtt 15780
ctgtttacca ggaagccatg aatcaaccag gccacctcag actctttgtg acaaggatca 15840
tgcaggaatt tgaaagtgac acgtttttcc cagaaattga tttggggaaa tataaacttc 15900
tcccagaata cccaggcgtc ctctctgagg tccaggagga aaaaggcatc aagtataagt 15960
ttgaagtcta cgagaagaaa gactaagcgg gactctgggg ttcgaaatga ccgaccaagc 16020
gacgcccaac ctgccatcac gatggccgca ataaaatatc tttattttca ttacatctgt 16080
gtgttggttt tttgtgtgaa tcgatagcga taaggatccg cgtatggtgc actctcagta 16140
caatctgctc tgatgccgca tagttaagcc agccccgaca cccgccaaca cccgctgacg 16200
cgccctgacg ggcttgtctg ctcccggcat ccgcttacag acaagctgtg accgtctccg 16260
ggagctgcat gtgtcagagg ttttcaccgt catcaccgaa acgcgcgaga cgaaagggcc 16320
tcgtgatacg cctattttta taggttaatg tcatgataat aatggtttct tagacgtcag 16380
gtggcacttt tcggggaaat gtgcgcggaa cccctatttg tttatttttc taaatacatt 16440
caaatatgta tccgctcatg agacaataac cctgataaat gcttcaataa tattgaaaaa 16500
ggaagagtat gagtattcaa catttccgtg tcgcccttat tccctttttt gcggcatttt 16560
gccttcctgt ttttgctcac ccagaaacgc tggtgaaagt aaaagatgct gaagatcagt 16620
tgggtgcacg agtgggttac atcgaactgg atctcaacag cggtaagatc cttgagagtt 16680
ttcgccccga agaacgtttt ccaatgatga gcacttttaa agttctgcta tgtggcgcgg 16740
tattatcccg tattgacgcc gggcaagagc aactcggtcg ccgcatacac tattctcaga 16800
atgacttggt tgagtactca ccagtcacag aaaagcatct tacggatggc atgacagtaa 16860
gagaattatg cagtgctgcc ataaccatga gtgataacac tgcggccaac ttacttctga 16920
caacgatcgg aggaccgaag gagctaaccg cttttttgca caacatgggg gatcatgtaa 16980
ctcgccttga tcgttgggaa ccggagctga atgaagccat accaaacgac gagcgtgaca 17040
ccacgatgcc tgtagcaatg gcaacaacgt tgcgcaaact attaactggc gaactactta 17100
ctctagcttc ccggcaacaa ttaatagact ggatggaggc ggataaagtt gcaggaccac 17160
ttctgcgctc ggcccttccg gctggctggt ttattgctga taaatctgga gccggtgagc 17220
gtgggtctcg cggtatcatt gcagcactgg ggccagatgg taagccctcc cgtatcgtag 17280
ttatctacac gacggggagt caggcaacta tggatgaacg aaatagacag atcgctgaga 17340
taggtgcctc actgattaag cattggtaac tgtcagacca agtttactca tatatacttt 17400
agattgattt aaaacttcat ttttaattta aaaggatcta ggtgaagatc ctttttgata 17460
atctcatgac caaaatccct taacgtgagt tttcgttcca ctgagcgtca gaccccgtag 17520
aaaagatcaa aggatcttct tgagatcctt tttttctgcg cgtaatctgc tgcttgcaaa 17580
caaaaaaacc accgctacca gcggtggttt gtttgccgga tcaagagcta ccaactcttt 17640
ttccgaaggt aactggcttc agcagagcgc agataccaaa tactgtcctt ctagtgtagc 17700
cgtagttagg ccaccacttc aagaactctg tagcaccgcc tacatacctc gctctgctaa 17760
tcctgttacc agtggctgct gccagtggcg ataagtcgtg tcttaccggg ttggactcaa 17820
gacgatagtt accggataag gcgcagcggt cgggctgaac ggggggttcg tgcacacagc 17880
ccagcttgga gcgaacgacc tacaccgaac tgagatacct acagcgtgag ctatgagaaa 17940
gcgccacgct tcccgaaggg agaaaggcgg acaggtatcc ggtaagcggc agggtcggaa 18000
caggagagcg cacgagggag cttccagggg gaaacgcctg gtatctttat agtcctgtcg 18060
ggtttcgcca cctctgactt gagcgtcgat ttttgtgatg ctcgtcaggg gggcggagcc 18120
tatggaaaaa cgccagcaac gcggcctttt tacggttcct ggccttttgc tggccttttg 18180
ctcacatggc tcgacaagct tggctagcac atcctcttgg tcctatcacg gttatgaggt 18240
cgaccagttg ttgctttgat gttcggttct ctcgttgatt gggacaatat ttggggcact 18300
tcgccggtcc cgacttccag aatttccgtg tggtctgtga atttatcacc gctacactgt 18360
catcatattc cagttttgca atctgctctc tttgtacctg cagataggta ccaaacaaag 18420
ttgggtaagg atagttcaat caatgatcat tttctagtgc acttaggatt caagatccta 18480
ttatcaggga caagagcagg attaaggata tccgagatgt ggctgcagag cctgctgctc 18540
ttgggcactg tggcctgcag catctctgca cccgcccgct cgcccagccc cagcacgcag 18600
ccctgggagc atgtgaatgc catccaggag gcccggcgtc tcctgaacct gagtagagac 18660
actgctgctg agatgaatga aacagtagaa gtcatctcag aaatgtttga cctccaggag 18720
ccgacctgcc tacagacccg cctggagctg tacaagcagg gcctgcgggg cagcctcacc 18780
aagctcaagg gccccttgac catgatggcc agccactaca agcagcactg ccctccaacc 18840
ccggaaactt cctgtgcaac ccagattatc acctttgaaa gtttcaaaga gaacctgaag 18900
gactttctgc ttgtcatccc ctttgactgc tgggagccag tccaggagtg atagtttctg 18960
acatccggcg ggtgactcac aacgcggccg cagccaccat gagagctgca cccctcctcc 19020
tggccagggc agcaagcctt agccttggct tcttgtttct gctttttttc tggctagacc 19080
gaagtgtact agccaaggag ttgaagtttg tgactttggt gtttcggcat ggagaccgaa 19140
gtcccattga cacctttccc actgacccca taaaggaatc ctcatggcca caaggatttg 19200
gccaactcac ccagctgggc atggagcagc attatgaact tggagagtat ataagaaaga 19260
gatatagaaa attcttgaat gagtcctata aacatgaaca ggtttatatt cgaagcacag 19320
acgttgaccg gactttgatg agtgctatga caaacctggc agccctgttt cccccagaag 19380
gtgtcagcat ctggaatcct atcctactct ggcagcccat cccggtgcac acagttcctc 19440
tttctgaaga tcagttgcta tacctgcctt tcaggaactg ccctcgtttt caagaacttg 19500
agagtgagac tttgaaatca gaggaattcc agaagaggct gcacccttat aaggatttta 19560
tagctacctt gggaaaactt tcaggattac atggccagga cctttttgga atttggagta 19620
aagtctacga ccctttatat tgtgagagtg ttcacaattt cactttaccc tcctgggcca 19680
ctgaggacac catgactaag ttgagagaat tgtcagaatt gtccctcctg tccctctatg 19740
gaattcacaa gcagaaagag aaatctaggc tccaaggggg tgtcctggtc aatgaaatcc 19800
tcaatcacat gaagagagca actcagatac caagctacaa aaaacttatc atgtattctg 19860

```
cgcatgacac tactgtgagt ggcctacaga tggcgctaga tgtttacaac ggactccttc  19920
ctccctatgc ttcttgccac ttgacggaat tgtactttga gaagggggag tactttgtgg  19980
agatgtacta tcggaatgag acgcagcacg agccgtatcc cctcatgcta cctggctgca  20040
gccctagctg tcctctggag aggtttgctg agctggttgg ccctgtgatc cctcaagact  20100
ggtccacgga gtgtatgacc acaaacagcc atcaaggtac tgaggacagt acagattagg  20160
tgcgagaggc cgaggaccag aacaacatcc gcctaccctc catcattgtt ataaaaaact  20220
taggaaccag gtccacacag ccgccagccc atcaaccatc cactcccacg attggagccg  20280
atggccacac ttttaaggag cttagcattg ttcaaaagaa acaaggacaa accacccatt  20340
acatcaggat ccggtggagc catcagagga atcaaacaca ttattatagt accaatccct  20400
ggagattcct caattaccac tcgatccaga cttctggacc ggttggtcag gttaattgga  20460
aacccggatg tgagcgggcc caaactaaca ggggcactaa taggtatatt atccttattt  20520
gtggagtctc caggtcaatt gattcagagg atcaccgatg accctgacgt tagcataagg  20580
ctgttagagg ttgtccagag tgaccagtca caatctggcc ttaccttcgc atcaagaggt  20640
accaacatgg aggatgaggc ggaccaatac ttttcacatg atgatccaat tagtagtgat  20700
caatccaggt tcggatggtt cgagaacaag gaaatctcag atattgaagt gcaagaccct  20760
gagggattca acatgattct gggtaccatc ctagctcaaa tttgggtctt gctcgcaaag  20820
gcggttacgg ccccagacac ggcagctgat tcggagctaa gaaggtggat aaagtacacc  20880
caacaaagaa gggtagttgg tgaatttaga ttggagagaa aatggttgga tgtggtgagg  20940
aacaggattg ccgaggacct ctccttacgc cgattcatgg tcgctctaat cctggatatc  21000
aagagaacac ccggaaacaa acccaggatt gctgaaatga tatgtgacat tgatacatat  21060
atcgtagagg caggattagc cagttttatc ctgactatta agtttgggat agaaactatg  21120
tatcctgctc ttggactgca tgaatttgct ggtgagttat ccacacttga gtccttgatg  21180
aacctttacc agcaaatggg ggaaactgca ccctacatgg taatcctgga gaactcaatt  21240
cagaacaagt tcagtgcagg atcataccct ctgctctgga gctatgccat gggagtagga  21300
gtggaacttg aaaactccat gggaggtttg aactttggcc gatcttactt tgatccagca  21360
tattttagat tagggcaaga gatggtaagg aggtcagctg gaaaggtcag ttccacattg  21420
gcatctgaac tcggtatcac tgccgaggat gcaaggcttg tttcagagat tgcaatgcat  21480
actactgagg acaagatcag tagagcggtt ggacccagac aagcccaagt atcatttcta  21540
cacggtgatc aaagtgagaa tgagctaccg agattggggg gcaaggaaga taggagggtc  21600
aaacagagtc gaggagaagc cagggagagc tacagagaaa ccgggcccag cagagcaagt  21660
gatgcgagag ctgcccatct tccaaccggc acacccctag acattgacac tgcatcggag  21720
tccagccaag atccgcagga cagtcgaagg tcagctgacg ccctgcttag gctgcaagcc  21780
atggcaggaa tctcggaaga acaaggctca gacacggaca cccctatagt gtacaatgac  21840
agaaatcttc tagactaggt gcgagaggcc gaggaccaga acaacatccg cctaccctcc  21900
atcattgtta taaaaaactt aggaaccagg tccacacagc cgccagccca tcaaccatcc  21960
actcccacga ttggagccga tggcagaaga gcaggcacgc catgtcaaaa acggactgga  22020
atgcatccgg gctctcaagg ccgagcccat cggctcactg gccatcgagg aagctatggc  22080
agcatggtca gaaatatcag acaacccagg acaggagcga gccacctgca             22130
```

<210> SEQ ID NO 17
<211> LENGTH: 22091

<212> TYPE: DNA
<213> ORGANISM: Artificial Sequence
<220> FEATURE:
<223> OTHER INFORMATION: Artificial DNA containing MV genome modified by inserting GMCSF-ires-CytD

<400> SEQUENCE: 17
gggaagagaa ggcaggcagt tcgggtctca gcaaaccatg cctctcagca attggatcaa 60
ctgaaggcgg tgcacctcgc atccgcggtc agggacctgg agagagcgat gacgacgctg 120
aaactttggg aatcccccca agaaatctcc aggcatcaag cactgggtta cagtgttatt 180
atgtttatga tcacagcggt gaagcggtta agggaatcca agatgctgac tctatcatgg 240
ttcaatcagg ccttgatggt gatagcaccc tctcaggagg agacaatgaa tctgaaaaca 300
gcgatgtgga tattggcgaa cctgataccg agggatatgc tatcactgac cggggatctg 360
ctcccatctc tatggggttc agggcttctg atgttgaaac tgcagaagga ggggagatcc 420
acgagctcct gagactccaa tccagaggca acaactttcc gaagcttggg aaaactctca 480
atgttcctcc gcctccggac cccggtaggg ccagcacttc cgggacaccc attaaaaagg 540
gcacagacgc gagattagcc tcatttggaa cggagatcgc gtctttattg acaggtggtg 600
caacccaatg tgctcgaaag tcaccctcgg aaccatcagg gccaggtgca cctgcgggga 660
atgtccccga gtgtgtgagc aatgccgcac tgatacagga gtggacaccc gaatctggta 720
ccacaatctc cccgagatcc cagaataatg aagaaggggg agactattat gatgatgagc 780
tgttctctga tgtccaagat attaaaacag ccttggccaa aatacacgag gataatcaga 840
agataatctc caagctagaa tcactgctgt tattgaaggg agaagttgag tcaattaaga 900
agcagatcaa caggcaaaat atcagcatat ccaccctgga aggacacctc tcaagcatca 960
tgatcgccat tcctggactt gggaaggatc ccaacgaccc cactgcagat gtcgaaatca 1020
atcccgactt gaaacccatc ataggcagag attcaggccg agcactggcc gaagttctca 1080
agaaacccgt tgccagccga caactccaag gaatgacaaa tggacggacc agttccagag 1140
gacagctgct gaaggaattt cagctaaagc cgatcgggaa aaagatgagc tcagccgtcg 1200
ggtttgttcc tgacaccggc cctgcatcac gcagtgtaat ccgctccatt ataaaatcca 1260
gccggctaga ggaggatcgg aagcgttacc tgatgactct ccttgatgat atcaaaggag 1320
ccaatgatct tgccaagttc caccagatgc tgatgaagat aataatgaag tagctacagc 1380
tcaacttacc tgccaacccc atgccagtcg acccaactag tacaacctaa atccattata 1440
aaaaacttag gagcaaagtg attgcctccc aagttccaca atgacagaga tctacgactt 1500
cgacaagtcg gcatgggaca tcaaagggtt gatcgctccg atacaaccca ccacctacag 1560
tgatggcagg ctggtgcccc aggtcagagt catagatcct ggtctaggcg acaggaagga 1620
tgaatgcttt atgtacatgt ttctgctggg ggttgttgag gacagcgatc ccctagggcc 1680
tccaatcggg cgagcatttg ggtccctgcc cttaggtgtt ggcagatcca cagcaaagcc 1740
cgaaaaactc ctcaaagagg ccactgagct tgacatagtt gttagacgta cagcagggct 1800
caatgaaaaa ctggtgttct acaacaacac ccccactaact ctcctcacac cttggagaaa 1860
ggtcctaaca acagggagtg tcttcaacgc aaaccaagtg tgcaatgcgg ttaatctgat 1920
accgctcgat accccgcaga ggttccgtgt tgtttatatg agcatcaccc gtctttcgga 1980
taacgggtat tacaccgttc ctagaagaat gctggaattc agatcggtca atgcagtggc 2040
cttcaacctg ctggtgaccc ttaggattga caaggcgata ggccctggga agatcatcga 2100
caatacagag caacttcctg aggcaacatt tatggtccac atcgggaact tcaggagaaa 2160

-continued

```
gaagagtgaa gtctactctg ccgattattg caaaatgaaa atcgaaaaga tgggcctggt   2220
ttttgcactt ggtgggatag gggcaccag tcttcacatt agaagcacag gcaaaatgag   2280
caagactctc catgcacaac tcgggttcaa gaagacctta tgttacccgc tgatagatat   2340
caatgaagac cttaatcgat tactctggag gagcagatgc aagatagtaa gaatccaggc   2400
agttttgcag ccatcagttc ctcaagaatt ccgcatttac gacgacgtga tcataaatga   2460
tgaccaagga ctattcaaag ttctgtagac cgtagtgccc agcaatgccc gaaaacgacc   2520
cccctcacaa tgacagccag aaggcccgga caaaaaagcc ccctccgaaa gactccacgg   2580
accaagcgag aggccagcca gcagccgacg gcaagcgcga acaccaggcg gccccagcac   2640
agaacagccc tgatacaagg ccaccaccag ccaccccaat ctgcatcctc ctcgtgggac   2700
ccccgaggac caacccccaa ggctgccccc gatccaaacc accaaccgca tccccaccac   2760
ccccgggaaa gaaacccccca gcaattggaa ggcccctccc cctcttcctc aacacaagaa   2820
ctccacaacc gaaccgcaca agcgaccgag gtgacccaac cgcaggcatc cgactcccta   2880
gacagatcct ctctccccgg caaactaaac aaaacttagg gccaaggaac atacacaccc   2940
aacagaaccc agaccccggc ccacggcgcc gcgcccccaa cccccgacaa ccagagggag   3000
cccccaacca atcccgccgg ctcccccggt gcccacaggc agggacacca acccccgaac   3060
agacccagca cccaaccatc gacaatccaa gacgggggggg cccccccaaa aaaaggcccc   3120
caggggccga cagccagcac cgcgaggaag cccacccacc ccacacacga ccacggcaac   3180
caaaccagaa cccagaccac cctgggccac cagctcccag actcggccat caccccgcag   3240
aaaggaaagg ccacaacccg cgcaccccag ccccgatccg gcggggagcc acccaacccg   3300
aaccagcacc caagagcgat ccccgaagga cccccgaacc gcaaaggaca tcagtatccc   3360
acagcctctc caagtccccc ggtctcctcc ccttctcgaa gggaccaaaa gatcaatcca   3420
ccacacccga cgacactcaa ctccccaccc ctaaaggaga caccgggaat cccagaatca   3480
agactcatcc aatgtccatc atgggtctca aggtgaacgt ctctgccata ttcatggcag   3540
tactgttaac tctccaaaca cccaccggtc aaatccattg ggcaatctc tctaagatag   3600
gggtggtagg aataggaagt gcaagctaca aagttatgac tcgttccagc catcaatcat   3660
tagtcataaa attaatgccc aatataactc tcctcaataa ctgcacgagg gtagagattg   3720
cagaatacag gagactactg agaacagttt tggaaccaat tagagatgca cttaatgcaa   3780
tgacccagaa tataagaccg gttcagagtg tagcttcaag taggagacac aagagatttg   3840
cgggagtagt cctggcaggt gcggccctag gcgttgccac agctgctcag ataacagccg   3900
gcattgcact tcaccagtcc atgctgaact ctcaagccat cgacaatctg agagcgagcc   3960
tggaaactac taatcaggca attgaggcaa tcagacaagc agggcaggag atgatattgg   4020
ctgttcaggg tgtccaagac tacatcaata atgagctgat accgtctatg aaccaactat   4080
cttgtgattt aatcggccag aagctcgggc tcaaattgct cagatactat acagaaatcc   4140
tgtcattatt tggccccagc ttacgggacc ccatatctgc ggagatatct atccaggctt   4200
tgagctatgc gcttggagga gacatcaata aggtgttaga aaagctcgga tacagtggag   4260
gtgatttact gggcatctta gagagcagag gaataaaggc ccggataact cacgtcgaca   4320
cagagtccta cttcattgtc ctcagtatag cctatccgac gctgtccgag attaaggggg   4380
tgattgtcca ccggctagag gggtctcgt acaacatagg ctctcaagag tggtatacca   4440
ctgtgcccaa gtatgttgca acccaagggt accttatctc gaattttgat gagtcatcgt   4500
```

-continued

```
gtactttcat gccagagggg actgtgtgca gccaaaatgc cttgtacccg atgagtcctc   4560
tgctccaaga atgcctccgg gggtccacca agtcctgtgc tcgtacactc gtatccgggt   4620
cttttgggaa ccggttcatt ttatcacaag ggaacctaat agccaattgt gcatcaatcc   4680
tttgcaagtg ttacacaaca ggaacgatca ttaatcaaga ccctgacaag atcctaacat   4740
acattgctgc cgatcactgc ccggtagtcg aggtgaacgg cgtgaccatc caagtcggga   4800
gcaggaggta tccagatgct gtgtacttgc acagaattga cctcggtcct cccatatcat   4860
tggagaggtt ggacgtaggg acaaatctgg ggaatgcaat tgctaagttg gaggatgcca   4920
aggaattgtt ggagtcatcg gaccagatat tgaggagtat gaaaggttta tcgagcacta   4980
gcatagtcta catcctgatt gcagtgtgtc ttggagggtt gatagggatc cccgctttaa   5040
tatgttgctg cagggggcgt tgtaacaaaa agggagaaca agttggtatg tcaagaccag   5100
gcctaaagcc tgatcttacg ggaacatcaa aatcctatgt aaggtcgctc tgatcctcta   5160
caactcttga aacacaaatg tcccacaagt ctcctcttcg tcatcaagca accaccgcac   5220
ccagcatcaa gcccacctga aattatctcc ggcttccctc tggccgaaca atatcggtag   5280
ttaattaaaa cttagggtgc aagatcatcc acaatgtcac cacaacgaga ccggataaat   5340
gccttctaca aagataaccc ccatcccaag ggaagtagga tagtcattaa cagagaacat   5400
cttatgattg atagacctta tgttttgctg gctgttctgt ttgtcatgtt tctgagcttg   5460
atcgggttgc tagccattgc aggcattaga cttcatcggg cagccatcta caccgcagag   5520
atccataaaa gcctcagcac caatctagat gtaactaact caatcgagca tcaggtcaag   5580
gacgtgctga caccactctt caaaatcatc ggtgatgaag tgggcctgag gacacctcag   5640
agattcactg acctagtgaa attcatctct gacaagatta aattccttaa tccggatagg   5700
gagtacgact tcagagatct cacttggtgt atcaacccgc cagagagaat caaattggat   5760
tatgatcaat actgtgcaga tgtggctgct gaagagctca tgaatgcatt ggtgaactca   5820
actctactgg agaccagaac aaccaatcag ttcctagctg tctcaaaggg aaactgctca   5880
gggcccacta caatcagagg tcaattctca aacatgtcgc tgtccctgtt agacttgtat   5940
ttaggtcgag gttacaatgt gtcatctata gtcactatga catcccaggg aatgtatggg   6000
ggaacttacc tagtggaaaa gcctaatctg agcagcaaaa ggtcagagtt gtcacaactg   6060
agcatgtacc gagtgtttga agtaggtgtt atcagaaatc cgggtttggg ggctccggtg   6120
ttccatatga caaactatct tgagcaacca gccagtaatg atctcagcaa ctgtatggtg   6180
gctttggggg agctcaaact cgcagccctt tgtcacgggg aagattctat cacaattccc   6240
tatcagggat cagggaaagg tgtcagcttc cagctcgtca agctaggtgt ctggaaatcc   6300
ccaaccgaca tgcaatcctg ggtcccctta tcaacggatg atccagtgat agacaggctt   6360
tacctctcat ctcacagagg tgttatcgct gacaatcaag caaaatgggc tgtcccgaca   6420
acacgaacag atgacaagtt gcgaatggag acatgcttcc aacaggcgtg taagggtaaa   6480
atccaagcac tctgcgagaa tcccgagtgg gcaccattga aggataacag gattccttca   6540
tacggggtct tgtctgttga tctgagtctg acagttgagc ttaaaatcaa aattgcttcg   6600
ggattcgggc cattgatcac acacggttca gggatggacc tatacaaatc caaccacaac   6660
aatgtgtatt ggctgactat cccgccaatg aagaacctag ccttaggtgt aatcaacaca   6720
ttggagtgga taccgagatt caaggttagt ccctacctct tcaatgtccc aattaaggaa   6780
gcaggcgaag actgccatgc cccaacatac ctacctgcgg aggtggatgg tgatgtcaaa   6840
ctcagttcca atctggtgat tctacctggt caagatctcc aatatgtttt ggcaacctac   6900
```

-continued

```
gatacttcca gggttgaaca tgctgtggtt tattacgttt acagcccagg ccgctcattt   6960
tcttactttt atccttttag gttgcctata aagggggtcc ccatcgaatt acaagtggaa   7020
tgcttcacat gggaccaaaa actctggtgc cgtcacttct gtgtgcttgc ggactcagaa   7080
tctggtggac atatcactca ctctgggatg gtgggcatgg gagtcagctg cacagtcacc   7140
cgggaagatg gaaccaatcg cagatagggc tgctagtgaa ccaatctcat gatgtcaccc   7200
agacatcagg catacccact agtgtgaaat agacatcaga attaagaaaa acgtagggtc   7260
caagtggttc cccgttatgg actcgctatc tgtcaaccag atcttatacc ctgaagttca   7320
cctagatagc ccgatagtta ccaataagat agtagccatc ctggagtatg ctcgagtccc   7380
tcacgcttac agcctggagg accctacact gtgtcagaac atcaagcacc gcctaaaaaa   7440
cggattttcc aaccaaatga ttataaacaa tgtggaagtt gggaatgtca tcaagtccaa   7500
gcttaggagt tatccggccc actctcatat tccatatcca aattgtaatc aggatttatt   7560
taacatagaa gacaaagagt caacgaggaa gatccgtgaa ctcctcaaaa aggggaattc   7620
gctgtactcc aaagtcagtg ataaggtttt ccaatgctta agggacacta actcacggct   7680
tggcctaggc tccgaattga gggaggacat caaggagaaa gttattaact tgggagttta   7740
catgcacagc tcccagtggt ttgagccctt tctgttttgg tttacagtca agactgagat   7800
gaggtcagtg attaaatcac aaacccatac ttgccatagg aggagacaca cacctgtatt   7860
cttcactggt agttcagttg agttgctaat ctctcgtgac cttgttgcta taatcagtaa   7920
agagtctcaa catgtatatt acctgacatt tgaactggtt ttgatgtatt gtgatgtcat   7980
agaggggagg ttaatgacag agaccgctat gactattgat gctaggtata cagagcttct   8040
aggaagagtc agatacatgt ggaaactgat agatggtttc ttccctgcac tcgggaatcc   8100
aacttatcaa attgtagcca tgctggagcc tctttcactt gcttacctgc agctgaggga   8160
tataacagta gaactcagag gtgctttcct taaccactgc tttactgaaa tacatgatgt   8220
tcttgaccaa aacgggtttt ctgatgaagg tacttatcat gagttaattg aagctctaga   8280
ttacattttc ataactgatg acatacatct gacaggggag attttctcat ttttcagaag   8340
tttcggccac cccagacttg aagcagtaac ggctgctgaa aatgttagga aatacatgaa   8400
tcagcctaaa gtcattgtgt atgagactct gatgaaaggt catgccatat tttgtggaat   8460
cataatcaac ggctatcgtg acaggcacgg aggcagttgg ccaccgctga ccctccccct   8520
gcatgctgca gacacaatcc ggaatgctca agcttcaggt gaagggttaa cacatgagca   8580
gtgcgttgat aactggagat cttttgctgg agtgaaattt ggctgcttta tgcctcttag   8640
cctggatagt gatctgacaa tgtacctaaa ggacaaggca cttgctgctc tccaaaggga   8700
atgggattca gtttacccga aagagttcct gcgttacgac cctcccaagg gaaccgggtc   8760
acggaggctt gtagatgttt tccttaatga ttcgagcttt gacccatatg atgtgataat   8820
gtatgttgta agtggagctt acctccatga ccctgagttc aacctgtctt acagcctgaa   8880
agaaaaggag atcaaggaaa caggtagact tttgctaaa atgacttaca aaatgagggc   8940
atgccaagtg attgctgaaa atctaatctc aaacgggatt ggcaaatatt ttaaggacaa   9000
tgggatggcc aaggatgagc acgatttgac taaggcactc cacactctag ctgtctcagg   9060
agtccccaaa gatctcaaag aaagtcacag gggggggcca gtcttaaaaa cctactcccg   9120
aagcccagtc cacacaagta ccaggaacgt gagagcagca aaagggttta tagggttccc   9180
tcaagtaatt cggcaggacc aagacactga tcatccggag aatatggaag cttacgagac   9240
```

-continued

```
agtcagtgca tttatcacga ctgatctcaa gaagtactgc cttaattgga gatatgagac   9300
catcagcttg tttgcacaga ggctaaatga gatttacgga ttgccctcat ttttccagtg   9360
gctgcataag aggcttgaga cctctgtcct gtatgtaagt gaccctcatt gcccccccga   9420
ccttgacgcc catatcccgt tatataaagt ccccaatgat caaatcttca ttaagtaccc   9480
tatgggaggt atagaagggt attgtcagaa gctgtggacc atcagcacca ttccctatct   9540
atacctggct gcttatgaga gcggagtaag gattgcttcg ttagtgcaag ggacaatca    9600
gaccatagcc gtaacaaaaa gggtacccag cacatggccc tacaacctta agaaacggga   9660
agctgctaga gtaactagag attactttgt aattcttagg caaaggctac atgatattgg   9720
ccatcacctc aaggcaaatg agacaattgt ttcatcacat ttttttgtct attcaaaagg   9780
aatatattat gatgggctac ttgtgtccca atcactcaag agcatcgcaa gatgtgtatt   9840
ctggtcagag actatagttg atgaaacaag ggcagcatgc agtaatattg ctacaacaat   9900
ggctaaaagc atcgagagag gttatgaccg ttaccttgca tattccctga acgtcctaaa   9960
agtgatacag caaattctga tctctcttgg cttcacaatc aattcaacca tgacccggga  10020
tgtagtcata cccctcctca cgaacaacga cctcttaata aggatggcac tgttgcccgc  10080
tcctattggg ggatgaatt  atctgaatat gagcaggctg tttgtcagaa acatcggtga  10140
tccagtaaca tcatcaattg ctgatctcaa gagaatgatt ctcgcctcac taatgcctga  10200
agagaccctc catcaagtaa tgacacaaca accgggggac tcttcattcc tagactgggc  10260
tagcgaccct tactcagcaa atcttgtatg tgtccagagc atcactagac tcctcaagaa  10320
cataactgca aggtttgtcc tgatccatag tccaaaccca atgttaaaag gattattcca  10380
tgatgacagt aaagaagagg acgagggact ggcggcattc ctcatggaca ggcatattat  10440
agtacctagg gcagctcatg aaatcctgga tcatagtgtc acaggggcaa gagagtctat  10500
tgcaggcatg ctggatacca caaaaggcct gattcgagcc agcatgagga aggggggtt   10560
aacctctcga gtgataacca gattgtccaa ttatgactat gaacaattca gagcagggat  10620
ggtgctattg acaggaagaa agagaaatgt cctcattgac aaagagtcat gttcagtgca  10680
gctggcgaga gctctaagaa gccatatgtg ggcgaggcta gctcgaggac ggcctattta  10740
cggccttgag gtccctgatg tactagaatc tatgcgaggc caccttattc ggcgtcatga  10800
gacatgtgtc atctgcgagt gtggatcagt caactacgga tggtttttg  tcccctcggg  10860
ttgccaactg gatgatattg acaaggaaac atcatccttg agagtcccat atattggttc  10920
taccactgat gagagaacag acatgaagct tgccttcgta agagccccaa gtcgatcctt  10980
gcgatctgct gttagaatag caacagtgta ctcatgggct tacggtgatg atgatagctc  11040
ttggaacgaa gcctggttgt tggctaggca aagggccaat gtgagcctgg aggagctaag  11100
ggtgatcact cccatctcaa cttcgactaa tttagcgcat aggttgaggg atcgtagcac  11160
tcaagtgaaa tactcaggta catcccttgt ccgagtggcg aggtatacca caatctccaa  11220
cgacaatctc tcatttgtca tatcagataa gaaggttgat actaacttta tataccaaca  11280
aggaatgctt ctagggttgg gtgttttaga aacattgttt cgactcgaga aagataccgg  11340
atcatctaac acggtattac atcttcacgt cgaaacagat tgttgcgtga tcccgatgat  11400
agatcatccc aggataccca gctcccgcaa gctagagctg agggcagagc tatgtaccaa  11460
cccattgata tatgataatg cacctttaat tgacagagat acaacaaggc tatacaccca  11520
gagccatagg aggcaccttg tggaatttgt tacatggtcc acaccccaac tatatcacat  11580
tttagctaag tccacagcac tatctatgat tgacctggta acaaaatttg agaaggacca  11640
```

-continued

```
tatgaatgaa atttcagctc tcatagggga tgacgatatc aatagtttca taactgagtt  11700
tctgctcata gagccaagat tattcactat ctacttgggc cagtgtgcgg ccatcaattg  11760
ggcatttgat gtacattatc atagaccatc agggaaatat cagatgggtg agctgttgtc  11820
atcgttcctt tctagaatga gcaaaggagt gtttaaggtg cttgtcaatg ctctaagcca  11880
cccaaagatc tacaagaaat tctggcattg tggtattata gagcctatcc atggtccttc  11940
acttgatgct caaaacttgc acacaactgt gtgcaacatg gtttacacat gctatatgac  12000
ctacctcgac ctgttgttga atgaagagtt agaagagttc acatttctct tgtgtgaaag  12060
cgacgaggat gtagtaccgg acagattcga caacatccag gcaaaacact tatgtgttct  12120
ggcagatttg tactgtcaac cagggacctg cccaccaatt cgaggtctaa gaccggtaga  12180
gaaatgtgca gttctaaccg accatatcaa ggcagaggct aggttatctc cagcaggatc  12240
ttcgtggaac ataaatccaa ttattgtaga ccattactca tgctctctga cttatctccg  12300
gcgaggatcg atcaaacaga taagattgag agttgatcca ggattcattt tcgacgccct  12360
cgctgaggta aatgtcagtc agccaaagat cggcagcaac aacatctcaa atatgagcat  12420
caaggctttc agacccccac acgatgatgt tgcaaaattg ctcaaagata tcaacacaag  12480
caagcacaat cttcccattt caggggggcaa tctcgccaat tatgaaatcc atgctttccg  12540
cagaatcggg ttgaactcat ctgcttgcta caaagctgtt gagatatcaa cattaattag  12600
gagatgcctt gagccagggg aggacggctt gttcttgggt gagggatcgg gttccatgtt  12660
gatcacttat aaggagatac ttaaactaaa caagtgcttc tataatagtg gggtttccgc  12720
caattctaga tctggtcaaa gggaattagc accctatccc tccgaagttg gccttgtcga  12780
acacagaatg ggagtaggta atattgtcaa agtgctcttt aacgggaggc ccgaagtcac  12840
gtgggtaggc agtgtagatt gcttcaattt catagttagt aatatcccta cctctagtgt  12900
ggggtttatc cattcagata tagagacctt gcctaacaaa gatactatag agaagctaga  12960
ggaattggca gccatcttat cgatggctct gctcctgggc aaaataggat caatactggt  13020
gattaagctt atgcctttca gcggggattt tgttcaggga tttataagtt atgtagggtc  13080
ccattataga gaagtgaacc ttgtataccc tagatacagc aacttcatat ctactgaatc  13140
ttatttggtt atgacagatc tcaaggctaa ccggctaatg aatcctgaaa agattaagca  13200
gcagataatt gaatcatctg tgaggacttc acctggactt ataggtcaca tcctatccat  13260
taagcaacta agctgcatac aagcaattgt gggagacgca gttagtagag gtgatatcaa  13320
tcctactctg aaaaaactta cacctataga gcaggtgctg atcaattgcg ggttggcaat  13380
taacggacct aagctgtgca aagaattgat ccaccatgat gttgcctcag ggcaagatgg  13440
attgcttaat tctatactca tcctctacag ggagttggca agattcaaag acaaccaaag  13500
aagtcaacaa gggatgttcc acgcttaccc cgtattggta agtagcaggc aacgagaact  13560
tatatctagg atcacccgca aattttgggg gcacattctt ctttactccg ggaacagaaa  13620
gttgataaat aagtttatcc agaatctcaa gtccggctat ctgatactag acttacacca  13680
gaatatcttc gttaagaatc tatccaagtc agagaaacag attattatga cgggggggttt  13740
gaaacgtgag tgggttttta aggtaacagt caaggagacc aaagaatggt ataagttagt  13800
cggatacagt gccctgatta aggactaatt ggttgaactc cggaacccta atcctgccct  13860
aggtggttag gcattatttg caatagatta aagaaaactt tgaaaatacg aagtttctat  13920
tcccagcttt gtctggtttt tttccccccc aacttcggag gtcgaccagt actccgggcg  13980
```

-continued

```
acactttgtt tttttttttt cccccgatgc tggaggtcga ccagatgtcc gaaagtgtcc  14040
cccccccccc cccccccccc ccggcgcgga gcggcggggc caccccggac cccttttttt  14100
tttttttttt ttttttaaa ttcctggaac ctttaggtcg accagttgtc cgtcttttac  14160
tccttcatat aggtcgacca gtactccggg tggtactttg tctttttctg aaaatcccag  14220
aggtcgacca gatatccgcg gccgccgagc tcgttaacaa caacaattgc attcatttta  14280
tgtttcaggt tcagggggag atgtgggagg tttttaaag caagtaaaac ctctacaaat  14340
gtggtaaaat ccgataagga tcgatccggg ctggcgtaat agcgaagagg cccgcaccga  14400
tcgcccttcc caacagttgc gcagcctgaa tggcgaatgg acgcgccctg tagcggcgca  14460
ttaagcgcgg cgggtgtggt ggttacgcgc agcgtgaccg ctacacttgc cagcgcccta  14520
gcgcccgctc ctttcgcttt cttcccttcc tttctcgcca cgttcgccgg ctttccccgt  14580
caagctctaa atcgggggct ccctttaggg ttccgattta gagctttacg gcacctcgac  14640
cgcaaaaaac ttgatttggg tgatggttca cgtagtgggc catcgccctg atagacggtt  14700
tttcgccctt tgacgttgga gtccacgttc tttaatagtg gactcttgtt ccaaactgga  14760
acaacactca accctatctc ggtctattct tttgatttat aagggatttt gccgatttcg  14820
gcctattggt taaaaaatga gctgatttaa caaatattta acgcgaattt taacaaaata  14880
ttaacgttta caatttcgcc tgatgcggta ttttctcctt acgcatctgt gcggtatttc  14940
acaccgcata cgcggatctg cgcagcacca tggcctgaaa taacctctga aagaggaact  15000
tggttaggta ccttctgagg cggaaagaac cagctgtgga atgtgtgtca gttagggtgt  15060
ggaaagtccc caggctcccc agcaggcaga agtatgcaaa gcatgcatct caattagtca  15120
gcaaccaggt gtggaaagtc cccaggctcc ccagcaggca gaagtatgca aagcatgcat  15180
ctcaattagt cagcaaccat agtcccgccc ctaactccgc ccatcccgcc cctaactccg  15240
cccagttccg cccattctcc gccccatggc tgactaattt ttttatttta tgcagaggcc  15300
gaggccgcct cggcctctga gctattccag aagtagtgag gaggcttttt tggaggccta  15360
ggcttttgca aaaagcttga ttcttctgac acaacagtct cgaacttaag gctagagcca  15420
ccatggttcg accattgaac tgcatcgtcg ccgtgtccca aaatatgggg attggcaaga  15480
acggagacct accctggcct ccgctcagga acgagttcaa gtacttccaa agaatgacca  15540
caacctcttc agtggaaggt aaacagaatc tggtgattat gggtaggaaa acctggttct  15600
ccattcctga gaagaatcga cctttaaagg acagaattaa tatagttctc agtagagaac  15660
tcaaagaacc accacgagga gctcattttc ttgccaaaag tttggatgat gccttaagac  15720
ttattgaaca accggaattg gcaagtaaag tagacatggt ttggatagtc ggaggcagtt  15780
ctgtttacca ggaagccatg aatcaaccag gccacctcag actctttgtg acaaggatca  15840
tgcaggaatt tgaaagtgac acgtttttcc cagaaattga tttggggaaa tataaacttc  15900
tcccagaata cccaggcgtc ctctctgagg tccaggagga aaaaggcatc aagtataagt  15960
ttgaagtcta cgagaagaaa gactaagcgg gactctgggg ttcgaaatga ccgaccaagc  16020
gacgcccaac ctgccatcac gatggccgca ataaaatatc tttattttca ttacatctgt  16080
gtgttggttt tttgtgtgaa tcgatagcga taaggatccg cgtatggtgc actctcagta  16140
caatctgctc tgatgccgca tagttaagcc agccccgaca cccgccaaca cccgctgacg  16200
cgccctgacg ggcttgtctg ctcccggcat ccgcttacag acaagctgtg accgtctccg  16260
ggagctgcat gtgtcagagg ttttcaccgt catcaccgaa acgcgcgaga cgaaagggcc  16320
tcgtgatacg cctattttta taggttaatg tcatgataat aatggtttct tagacgtcag  16380
```

gtggcacttt tcggggaaat gtgcgcggaa cccctatttg tttatttttc taaatacatt 16440
caaatatgta tccgctcatg agacaataac cctgataaat gcttcaataa tattgaaaaa 16500
ggaagagtat gagtattcaa catttccgtg tcgcccttat tccctttttt gcggcatttt 16560
gccttcctgt ttttgctcac ccagaaacgc tggtgaaagt aaaagatgct gaagatcagt 16620
tgggtgcacg agtgggttac atcgaactgg atctcaacag cggtaagatc cttgagagtt 16680
ttcgccccga agaacgtttt ccaatgatga gcacttttaa agttctgcta tgtggcgcgg 16740
tattatcccg tattgacgcc gggcaagagc aactcggtcg ccgcatacac tattctcaga 16800
atgacttggt tgagtactca ccagtcacag aaaagcatct tacggatggc atgacagtaa 16860
gagaattatg cagtgctgcc ataaccatga gtgataacac tgcggccaac ttacttctga 16920
caacgatcgg aggaccgaag gagctaaccg cttttttgca caacatgggg gatcatgtaa 16980
ctcgccttga tcgttgggaa ccggagctga atgaagccat accaaacgac gagcgtgaca 17040
ccacgatgcc tgtagcaatg gcaacaacgt tgcgcaaact attaactggc gaactactta 17100
ctctagcttc ccggcaacaa ttaatagact ggatggaggc ggataaagtt gcaggaccac 17160
ttctgcgctc ggcccttccg gctggctggt ttattgctga taaatctgga gccggtgagc 17220
gtgggtctcg cggtatcatt gcagcactgg ggccagatgg taagccctcc cgtatcgtag 17280
ttatctacac gacggggagt caggcaacta tggatgaacg aaatagacag atcgctgaga 17340
taggtgcctc actgattaag cattggtaac tgtcagacca agtttactca tatatacttt 17400
agattgattt aaaacttcat ttttaattta aaaggatcta ggtgaagatc ctttttgata 17460
atctcatgac caaaatccct taacgtgagt tttcgttcca ctgagcgtca gaccccgtag 17520
aaaagatcaa aggatcttct tgagatcctt tttttctgcg cgtaatctgc tgcttgcaaa 17580
caaaaaaacc accgctacca gcggtggttt gtttgccgga tcaagagcta ccaactcttt 17640
ttccgaaggt aactggcttc agcagagcgc agataccaaa tactgtcctt ctagtgtagc 17700
cgtagttagg ccaccacttc aagaactctg tagcaccgcc tacatacctc gctctgctaa 17760
tcctgttacc agtggctgct gccagtggcg ataagtcgtg tcttaccggg ttggactcaa 17820
gacgatagtt accggataag gcgcagcggt cgggctgaac ggggggttcg tgcacacagc 17880
ccagcttgga gcgaacgacc tacaccgaac tgagatacct acagcgtgag ctatgagaaa 17940
gcgccacgct tcccgaaggg agaaaggcgg acaggtatcc ggtaagcggc agggtcggaa 18000
caggagagcg cacgagggag cttccagggg gaaacgcctg gtatctttat agtcctgtcg 18060
ggtttcgcca cctctgactt gagcgtcgat ttttgtgatg ctcgtcaggg gggcggagcc 18120
tatggaaaaa cgccagcaac gcggcctttt tacggttcct ggccttttgc tggccttttg 18180
ctcacatggc tcgacaagct tggctagcac atcctcttgg tcctatcacg gttatgaggt 18240
cgaccagttg ttgctttgat gttcggttct ctcgttgatt gggacaatat ttggggcact 18300
tcgccggtcc cgacttccag aatttccgtg tggtctgtga atttatcacc gctacactgt 18360
catcatattc cagttttgca atctgctctc tttgtacctg cagataggta ccaaacaaag 18420
ttgggtaagg atagttcaat caatgatcat tttctagtgc acttaggatt caagatccta 18480
ttatcaggga caagagcagg attaaggata tccgagatgt ggctgcagag cctgctgctc 18540
ttgggcactg tggcctgcag catctctgca cccgcccgct cgcccagccc cagcacgcag 18600
ccctgggagc atgtgaatgc catccaggag gcccggcgtc tcctgaacct gagtagagac 18660
actgctgctg agatgaatga aacagtagaa gtcatctcag aaatgtttga cctccaggag 18720

-continued

```
ccgacctgcc tacagacccg cctggagctg tacaagcagg gcctgcgggg cagcctcacc  18780
aagctcaagg gccccttgac catgatggcc agccactaca agcagcactg ccctccaacc  18840
ccggaaactt cctgtgcaac ccagattatc acctttgaaa gtttcaaaga gaacctgaag  18900
gactttctgc ttgtcatccc ctttgactgc tgggagccag tccaggagtg atagtttctg  18960
acatccggcg ggtgactcac aacgcggccg cagccaccat ggtgacaggg ggaatggcaa  19020
gcaagtggga tcagaagggt atggacattg cctatgagga ggcggcctta ggttacaaag  19080
agggtggtgt tcctattggc ggatgtctta tcaataacaa agacggaagt gttctcggtc  19140
gtggtcacaa catgagattt caaaagggat ctgccacact acatggtgag atctccactt  19200
tggaaaactg tgggagatta gagggcaaag tgtacaaaga taccactttg tatacgacgc  19260
tgtctccatg cgacatgtgt acaggtgcca tcatcatgta tggtattcca cgctgtgttg  19320
tcggtgagaa cgttaatttc aaaagtaagg gcgagaaata tttacaaact agaggtcacg  19380
aggttgttgt tgttgacgat gagaggtgta aaaagatcat gaaacaattt atcgatgaaa  19440
gacctcagga ttggtttgaa gatattggtg aggcttcgga accatttaag aacgtctact  19500
tgctacctca aacaaaccaa ttgctgggtt tgtacaccat catcagaaat aagaatacaa  19560
ctagacctga tttcattttc tactccgata gaatcatcag attgttggtt gaagaaggtt  19620
tgaaccatct acctgtgcaa aagcaaattg tggaaactga caccaacgaa aacttcgaag  19680
gtgtctcatt catgggtaaa atctgtggtg tttccattgt cagagctggt gaatcgatgg  19740
agcaaggatt aagagactgt tgtaggtctg tgcgtatcgg taaaatttta attcaaaggg  19800
acgaggagac tgctttacca aagttattct acgaaaaatt accagaggat atatctgaaa  19860
ggtatgtctt cctattagac ccaatgctgg ccaccggtgg tagtgctatc atggctacag  19920
aagtcttgat taagagaggt gttaagccag agagaattta cttcttaaac ctaatctgta  19980
gtaaggaagg gattgaaaaa taccatgccg ccttcccaga ggtcagaatt gttactggtg  20040
ccctcgacag aggtctagat gaaaacaagt atctagttcc agggttgggt gactttggtg  20100
acagatacta ctgtgtttaa gtgcgagagg ccgaggacca gaacaacatc cgcctaccct  20160
ccatcattgt tataaaaaac ttaggaacca ggtccacaca gccgccagcc catcaaccat  20220
ccactcccac gattggagcc gatggccaca cttttaagga gcttagcatt gttcaaaaga  20280
aacaaggaca aaccacccat tacatcagga tccggtggag ccatcagagg aatcaaacac  20340
attattatag taccaatccc tggagattcc tcaattacca ctcgatccag acttctggac  20400
cggttggtca ggttaattgg aaacccggat gtgagcgggc ccaaactaac aggggcacta  20460
ataggtatat tatccttatt tgtggagtct ccaggtcaat tgattcagag gatcaccgat  20520
gaccctgacg ttagcataag gctgttagag gttgtccaga gtgaccagtc acaatctggc  20580
cttaccttcg catcaagagg taccaacatg gaggatgagg cggaccaata cttttcacat  20640
gatgatccaa ttagtagtga tcaatccagg ttcggatggt tcgagaacaa ggaaatctca  20700
gatattgaag tgcaagaccc tgagggattc aacatgattc tgggtaccat cctagctcaa  20760
atttgggtct tgctcgcaaa ggcggttacg gccccagaca cggcagctga ttcggagcta  20820
agaaggtgga taaagtacac ccaacaaaga agggtagttg gtgaatttag attggagaga  20880
aaatggttgg atgtggtgag gaacaggatt gccgaggacc tctccttacg ccgattcatg  20940
gtcgctctaa tcctggatat caagagaaca cccggaaaca aacccaggat tgctgaaatg  21000
atatgtgaca ttgatacata tatcgtagag gcaggattag ccagttttat cctgactatt  21060
aagtttggga tagaaactat gtatcctgct cttggactgc atgaatttgc tggtgagtta  21120
```

tccacacttg agtccttgat gaacctttac cagcaaatgg gggaaactgc accctacatg 21180
gtaatcctgg agaactcaat tcagaacaag ttcagtgcag gatcataccc tctgctctgg 21240
agctatgcca tgggagtagg agtggaactt gaaaactcca tgggaggttt gaactttggc 21300
cgatcttact ttgatccagc atattttaga ttagggcaag agatggtaag gaggtcagct 21360
ggaaaggtca gttccacatt ggcatctgaa ctcggtatca ctgccgagga tgcaaggctt 21420
gtttcagaga ttgcaatgca tactactgag gacaagatca gtagagcggt tggacccaga 21480
caagcccaag tatcatttct acacggtgat caaagtgaga atgagctacc gagattgggg 21540
ggcaaggaag ataggagggt caaacagagt cgaggagaag ccagggagag ctacagagaa 21600
accgggccca gcagagcaag tgatgcgaga gctgcccatc ttccaaccgg cacaccccta 21660
gacattgaca ctgcatcgga gtccagccaa gatccgcagg acagtcgaag gtcagctgac 21720
gccctgctta ggctgcaagc catggcagga atctcggaag aacaaggctc agacacggac 21780
acccctatag tgtacaatga cagaaatctt ctagactagg tgcgagaggc cgaggaccag 21840
aacaacatcc gcctaccctc catcattgtt ataaaaaact taggaaccag gtccacacag 21900
ccgccagccc atcaaccatc cactcccacg attggagccg atggcagaag agcaggcacg 21960
ccatgtcaaa aacggactgg aatgcatccg ggctctcaag gccgagccca tcggctcact 22020
ggccatcgag gaagctatgg cagcatggtc agaaatatca gacaacccag gacaggagcg 22080
agccacctgc a 22091

<210> SEQ ID NO 18
<211> LENGTH: 15795
<212> TYPE: DNA
<213> ORGANISM: Artificial Sequence
<220> FEATURE:
<223> OTHER INFORMATION: Artificial DNA containing selected elements
from MV sequence - Helper plasmid

<400> SEQUENCE: 18
ggccgcttcc ctttagtgag ggttaatgct tcgagcagac atgataagat acattgatga 60
gtttggacaa accacaacta gaatgcagtg aaaaaaatgc tttatttgtg aaatttgtga 120
tgctattgct ttatttgtaa ccattataag ctgcaataaa caagttaaca acaacaattg 180
cattcatttt atgtttcagg ttcaggggga gatgtgggag gtttttttaaa gcaagtaaaa 240 cctctacaaa tgtggtaaaa tccgataagg atcgatccgg gctggcgtaa tagcgaagag 300
gcccgcaccg atcgcccttc ccaacagttg cgcagcctga atggcgaatg gacgcgccct 360
gtagcggcgc attaagcgcg gcgggtgtgg tggttacgcg cagcgtgacc gctacacttg 420
ccagcgccct agcgcccgct cctttcgctt tcttcccttc ctttctcgcc acgttcgccg 480
gctttccccg tcaagctcta aatcgggggc tccctttagg gttccgattt agagctttac 540
ggcacctcga ccgcaaaaaa cttgatttgg gtgatggttc acgtagtggg ccatcgccct 600
gatagacggt ttttcgccct ttgacgttgg agtccacgtt ctttaatagt ggactcttgt 660
tccaaactgg aacaacactc aaccctatct cggtctattc ttttgattta taagggattt 720
tgccgatttc ggcctattgg ttaaaaaatg agctgattta acaaatattt aacgcgaatt 780
ttaacaaaat attaacgttt acaatttcgc ctgatgcggt attttctcct tacgcatctg 840
tgcggtattt cacaccgcat acgcggatct gcgcagcacc atggcctgaa ataacctctg 900
aaagaggaac ttggttaggt accttctgag gcggaaagaa ccagctgtgg aatgtgtgtc 960
agttagggtg tggaaagtcc ccaggctccc cagcaggcag aagtatgcaa agcatgcatc 1020
tcaattagtc agcaaccagg tgtggaaagt ccccaggctc cccagcaggc agaagtatgc 1080
aaagcatgca tctcaattag tcagcaacca tagtcccgcc cctaactccg cccatcccgc 1140
ccctaactcc gcccagttcc gcccattctc cgccccatgg ctgactaatt ttttttattt 1200
atgcagaggc cgaggccgcc tcggcctctg agctattcca gaagtagtga ggaggctttt 1260
ttggaggcct aggcttttgc aaaaagcttg attcttctga cacaacagtc tcgaacttaa 1320
ggctagagcc accatgattg aacaagatgg attgcacgca ggttctccgg ccgcttgggt 1380
ggagaggcta ttcggctatg actgggcaca acagacaatc ggctgctctg atgccgccgt 1440
gttccggctg tcagcgcagg ggcgcccggt tctttttgtc aagaccgacc tgtccggtgc 1500
cctgaatgaa ctgcaggacg aggcagcgcg gctatcgtgg ctggccacga cgggcgttcc 1560
ttgcgcagct gtgctcgacg ttgtcactga agcgggaagg gactggctgc tattgggcga 1620
agtgccgggg caggatctcc tgtcatctca ccttgctcct gccgagaaag tatccatcat 1680
ggctgatgca atgcggcggc tgcatacgct tgatccggct acctgcccat tcgaccacca 1740
agcgaaacat cgcatcgagc gagcacgtac tcggatggaa gccggtcttg tcgatcagga 1800
tgatctggac gaagagcatc aggggctcgc gccagccgaa ctgttcgcca ggctcaaggc 1860
gcgcatgccc gacggcgagg atctcgtcgt gacccatggc gatgcctgct tgccgaatat 1920
catggtggaa aatggccgct tttctggatt catcgactgt ggccggctgg gtgtggcgga 1980
ccgctatcag gacatagcgt tggctacccg tgatattgct gaagagcttg gcggcgaatg 2040
ggctgaccgc ttcctcgtgc tttacggtat cgccgctccc gattcgcagc gcatcgcctt 2100
ctatcgcctt cttgacgagt tcttctgagc gggactctgg ggttcgaaat gaccgaccaa 2160
gcgacgccca acctgccatc acgatggccg caataaaata tctttatttt cattacatct 2220
gtgtgttggt tttttgtgtg aatcgatagc gataaggatc cgcgtatggt gcactctcag 2280
tacaatctgc tctgatgccg catagttaag ccagccccga cacccgccaa cacccgctga 2340
cgcgccctga cgggcttgtc tgctcccggc atccgcttac agacaagctg tgaccgtctc 2400
cgggagctgc atgtgtcaga ggttttcacc gtcatcaccg aaacgcgcga gacgaaaggg 2460
cctcgtgata cgcctatttt tataggttaa tgtcatgata ataatggttt cttagacgtc 2520
aggtggcact tttcggggaa atgtgcgcgg aacccctatt tgtttatttt tctaaataca 2580
ttcaaatatg tatccgctca tgagacaata accctgataa atgcttcaat aatattgaaa 2640
aaggaagagt atgagtattc aacatttccg tgtcgccctt attccctttt ttgcggcatt 2700
ttgccttcct gtttttgctc acccagaaac gctggtgaaa gtaaaagatg ctgaagatca 2760
gttgggtgca cgagtgggtt acatcgaact ggatctcaac agcggtaaga tccttgagag 2820
ttttcgcccc gaagaacgtt ttccaatgat gagcactttt aaagttctgc tatgtggcgc 2880
ggtattatcc cgtattgacg ccgggcaaga gcaactcggt cgccgcatac actattctca 2940
gaatgacttg gttgagtact caccagtcac agaaaagcat cttacggatg gcatgacagt 3000
aagagaatta tgcagtgctg ccataaccat gagtgataac actgcggcca acttacttct 3060
gacaacgatc ggaggaccga aggagctaac cgcttttttg cacaacatgg gggatcatgt 3120
aactcgcctt gatcgttggg aaccggagct gaatgaagcc ataccaaacg acgagcgtga 3180
caccacgatg cctgtagcaa tggcaacaac gttgcgcaaa ctattaactg gcgaactact 3240
tactctagct tcccggcaac aattaataga ctggatggag gcggataaag ttgcaggacc 3300
acttctgcgc tcggcccttc cggctggctg gtttattgct gataaatctg gagccggtga 3360

-continued

```
gcgtgggtct cgcggtatca ttgcagcact ggggccagat ggtaagccct cccgtatcgt   3420
agttatctac acgacgggga gtcaggcaac tatggatgaa cgaaatagac agatcgctga   3480
gataggtgcc tcactgatta agcattggta actgtcagac caagtttact catatatact   3540
ttagattgat ttaaaacttc atttttaatt taaaaggatc taggtgaaga tcctttttga   3600
taatctcatg accaaaatcc cttaacgtga gttttcgttc cactgagcgt cagaccccgt   3660
agaaaagatc aaaggatctt cttgagatcc tttttttctg cgcgtaatct gctgcttgca   3720
aacaaaaaaa ccaccgctac cagcggtggt ttgtttgccg gatcaagagc taccaactct   3780
ttttccgaag gtaactggct tcagcagagc gcagatacca aatactgtcc ttctagtgta   3840
gccgtagtta ggccaccact tcaagaactc tgtagcaccg cctacatacc tcgctctgct   3900
aatcctgtta ccagtggctg ctgccagtgg cgataagtcg tgtcttaccg ggttggactc   3960
aagacgatag ttaccggata aggcgcagcg gtcgggctga acggggggtt cgtgcacaca   4020
gcccagcttg gagcgaacga cctacaccga actgagatac ctacagcgtg agctatgaga   4080
aagcgccacg cttcccgaag ggagaaaggc ggacaggtat ccggtaagcg gcagggtcgg   4140
aacaggagag cgcacgaggg agcttccagg gggaaacgcc tggtatcttt atagtcctgt   4200
cgggtttcgc cacctctgac ttgagcgtcg atttttgtga tgctcgtcag gggggcggag   4260
cctatggaaa aacgccagca acgcggcctt tttacggttc ctggcctttt gctggccttt   4320
tgctcacatg gctcgacaga tcttcaatat tggccattag ccatattatt cattggttat   4380
atagcataaa tcaatattgg ctattggcca ttgcatacgt tgtatctata tcataatatg   4440
tacatttata ttggctcatg tccaatatga ccgccatgtt ggcattgatt attgactagt   4500
tattaatagt aatcaattac ggggtcatta gttcatagcc catatatgga gttccgcgtt   4560
acataactta cggtaaatgg cccgcctggc tgaccgccca acgacccccg cccattgacg   4620
tcaataatga cgtatgttcc catagtaacg ccaataggga ctttccattg acgtcaatgg   4680
gtggagtatt tacggtaaac tgcccacttg gcagtacatc aagtgtatca tatgccaagt   4740
ccgcccccta ttgacgtcaa tgacggtaaa tggcccgcct ggcattatgc ccagtacatg   4800
accttacggg actttcctac ttggcagtac atctacgtat tagtcatcgc tattaccatg   4860
gtgatgcggt tttggcagta caccaatggg cgtggatagc ggtttgactc acggggattt   4920
ccaagtctcc accccattga cgtcaatggg agtttgtttt ggcaccaaaa tcaacgggac   4980
tttccaaaat gtcgtaacaa ctgcgatcgc ccgccccgtt gacgcaaatg ggcggtaggc   5040
gtgtacggtg ggaggtctat ataagcagag ctcgtttagt gaaccgtcag atcactagaa   5100
gctttattgc ggtagtttat cacagttaaa ttgctaacgc agtcagtgct tctgacacaa   5160
cagtctcgaa cttaagctgc agtgactctc ttaaggtagc cttgcagaag ttggtcgtga   5220
ggcactgggc aggtaagtat caaggttaca agacaggttt aaggagacca atagaaactg   5280
ggcttgtcga gacagagaag actcttgcgt ttctgatagg cacctattgg tcttactgac   5340
atccactttg cctttctctc cacaggtgtc cactcccagt tcaattacag ctcttaaggc   5400
tagagtactt aatacgactc actataggct agcatggcca cacttttaag gagcttagca   5460
ttgttcaaaa gaaacaagga caaaccaccc attacatcag gatccggtgg agccatcaga   5520
ggaatcaaac acattattat agtaccaatc cctggagatt cctcaattac cactcgatcc   5580
agacttctgg accggttggt caggttaatt ggaaacccgg atgtgagcgg gcccaaacta   5640
acaggggcac taataggtat attatcctta tttgtggagt ctccaggtca attgattcag   5700
aggatcaccg atgaccctga cgttagcata aggctgttag aggttgtcca gagtgaccag   5760
```

```
tcacaatctg gccttacctt cgcatcaaga ggtaccaaca tggaggatga ggcggaccaa   5820
tacttttcac atgatgatcc aattagtagt gatcaatcca ggttcggatg gttcgagaac   5880
aaggaaatct cagatattga agtgcaagac cctgagggat tcaacatgat tctgggtacc   5940
atcctagctc aaatttgggt cttgctcgca aaggcggtta cggccccaga cacggcagct   6000
gattcggagc taagaaggtg gataaagtac acccaacaaa gaagggtagt tggtgaattt   6060
agattggaga gaaaatggtt ggatgtggtg aggaacagga ttgccgagga cctctcctta   6120
cgccgattca tggtcgctct aatcctggat atcaagagaa cacccggaaa caaacccagg   6180
attgctgaaa tgatatgtga cattgataca tatatcgtag aggcaggatt agccagtttt   6240
atcctgacta ttaagtttgg gatagaaact atgtatcctg ctcttggact gcatgaattt   6300
gctggtgagt tatccacact tgagtccttg atgaaccttt accagcaaat gggggaaact   6360
gcaccctaca tggtaatcct ggagaactca attcagaaca agttcagtgc aggatcatac   6420
cctctgctct ggagctatgc catgggagta ggagtggaac ttgaaaactc catgggaggt   6480
ttgaactttg gccgatctta ctttgatcca gcatatttta gattagggca agagatggta   6540
aggaggtcag ctggaaaggt cagttccaca ttggcatctg aactcggtat cactgccgag   6600
gatgcaaggc ttgtttcaga gattgcaatg catactactg aggacaagat cagtagagcg   6660
gttggaccca gacaagccca agtatcattt ctacacggtg atcaaagtga gaatgagcta   6720
ccgagattgg ggggcaagga agataggagg gtcaaacaga gtcgaggaga agccagggag   6780
agctacagag aaaccgggcc cagcagagca agtgatgcga gagctgccca tcttccaacc   6840
ggcacacccc tagacattga cactgcatcg gagtccagcc aagatccgca ggacagtcga   6900
aggtcagctg acgccctgct taggctgcaa gccatggcag gaatctcgga agaacaaggc   6960
tcagacacgg acacccctat agtgtacaat gacagaaatc ttctagacta gttctgacat   7020
ccggcgggtg actcacaacg cggccgcagc caccatggca gaagagcagg cacgccatgt   7080
caaaaacgga ctggaatgca tccgggctct caaggccgag cccatcggct cactggccat   7140
cgaggaagct atggcagcat ggtcagaaat atcagacaac ccaggacagg agcgagccac   7200
ctgcagggaa gagaaggcag gcagttcggg tctcagcaaa ccatgcctct cagcaattgg   7260
atcaactgaa ggcggtgcac ctcgcatccg cggtcaggga cctggagaga gcgatgacga   7320
cgctgaaact ttgggaatcc ccccaagaaa tctccaggca tcaagcactg ggttacagtg   7380
ttattatgtt tatgatcaca gcggtgaagc ggttaaggga atccaagatg ctgactctat   7440
catggttcaa tcaggccttg atggtgatag caccctctca ggaggagaca atgaatctga   7500
aaacagcgat gtggatattg gcgaacctga taccgaggga tatgctatca ctgaccgggg   7560
atctgctccc atctctatgg ggttcagggc ttctgatgtt gaaactgcag aaggaggga    7620
gatccacgag ctcctgagac tccaatccag aggcaacaac tttccgaagc ttgggaaaac   7680
tctcaatgtt cctccgcctc cggaccccgg tagggccagc acttccggga cacccattaa   7740
aaagggcaca gacgcgagat tagcctcatt tggaacggag atcgcgtctt tattgacagg   7800
tggtgcaacc caatgtgctc gaaagtcacc ctcggaacca tcagggccag gtgcacctgc   7860
ggggaatgtc cccgagtgtg tgagcaatgc cgcactgata caggagtgga cacccgaatc   7920
tggtaccaca atctccccga gatcccagaa taatgaagaa gggggagact attatgatga   7980
tgagctgttc tctgatgtcc aagatattaa aacagccttg gccaaaatac acgaggataa   8040
tcagaagata atctccaagc tagaatcact gctgttattg aagggagaag ttgagtcaat   8100
```

-continued

```
taagaagcag atcaacaggc aaaatatcag catatccacc ctggaaggac acctctcaag   8160
catcatgatc gccattcctg gacttgggaa ggatcccaac gaccccactg cagatgtcga   8220
aatcaatccc gacttgaaac ccatcatagg cagagattca ggccgagcac tggccgaagt   8280
tctcaagaaa cccgttgcca gccgacaact ccaaggaatg acaaatggac ggaccagttc   8340
cagaggacag ctgctgaagg aatttcagct aaagccgatc gggaaaaaga tgagctcagc   8400
cgtcgggttt gttcctgaca ccggccctgc atcacgcagt gtaatccgct ccattataaa   8460
atccagccgg ctagaggagg atcggaagcg ttacctgatg actctccttg atgatatcaa   8520
aggagccaat gatcttgcca agttccacca gatgctgatg aagataataa tgaagtagcg   8580
gccgacgcgt cgagcatgca tctagggcgg ccaattccgc ccctctcccc cccccccctc   8640
tccctccccc cccccctaacg ttactggccg aagccgcttg gaataaggcc ggtgtgcgtt   8700
tgtctatatg tgattttcca ccatattgcc gtcttttggc aatgtgaggg cccggaaacc   8760
tggccctgtc ttcttgacga gcattcctag gggtctttcc cctctcgcca aaggaatgca   8820
aggtctgttg aatgtcgtga aggaagcagt tcctctggaa gcttcttgaa gacaaacaac   8880
gtctgtagcg accctttgca ggcagcggaa ccccccacct ggcgacaggt gcctctgcgg   8940
ccaaaagcca cgtgtataag atacacctgc aaaggcggca caaccccagt gccacgttgt   9000
gagttggata gttgtggaaa gagtcaaatg gctctcctca agcgtattca acaaggggct   9060
gaaggatgcc cagaaggtac cccattgtat gggatctgat ctggggcctc ggtgcacatg   9120
ctttacatgt gtttagtcga ggttaaaaaa acgtctaggc cccccgaacc acggggacgt   9180
ggttttcctt tgaaaaacac gatgataagc ttgccacaac ccgggatcct ctagagtcga   9240
catggactcg ctatctgtca accagatctt ataccctgaa gttcacctag atagcccgat   9300
agttaccaat aagatagtag ccatcctgga gtatgctcga gtccctcacg cttacagcct   9360
ggaggaccct acactgtgtc agaacatcaa gcaccgccta aaaaacggat tttccaacca   9420
aatgattata aacaatgtgg aagttgggaa tgtcatcaag tccaagctta ggagttatcc   9480
ggcccactct catattccat atccaaattg taatcaggat ttatttaaca tagaagacaa   9540
agagtcaacg aggaagatcc gtgaactcct caaaaagggg aattcgctgt actccaaagt   9600
cagtgataag gttttccaat gcttaaggga cactaactca cggcttggcc taggctccga   9660
attgagggag gacatcaagg agaaagttat taacttggga gtttacatgc acagctccca   9720
gtggtttgag ccctttctgt tttggtttac agtcaagact gagatgaggt cagtgattaa   9780
atcacaaacc catacttgcc ataggaggag acacacacct gtattcttca ctggtagttc   9840
agttgagttg ctaatctctc gtgaccttgt tgctataatc agtaaagagt ctcaacatgt   9900
atattacctg acatttgaac tggttttgat gtattgtgat gtcatagagg ggaggttaat   9960
gacagagacc gctatgacta ttgatgctag gtatacagag cttctaggaa gagtcagata  10020
catgtggaaa ctgatagatg gtttcttccc tgcactcggg aatccaactt atcaaattgt  10080
agccatgctg gagcctcttt cacttgctta cctgcagctg agggatataa cagtagaact  10140
cagaggtgct ttccttaacc actgctttac tgaaatacat gatgttcttg accaaaacgg  10200
gttttctgat gaaggtactt atcatgagtt aattgaagct ctagattaca ttttcataac  10260
tgatgacata catctgacag gggagatttt ctcatttttc agaagtttcg gccaccccag  10320
acttgaagca gtaacggctg ctgaaaatgt taggaaatac atgaatcagc ctaaagtcat  10380
tgtgtatgag actctgatga aaggtcatgc catattttgt ggaatcataa tcaacggcta  10440
tcgtgacagg cacggaggca gttggccacc gctgaccctc cccctgcatg ctgcagacac  10500
```

-continued

```
aatccggaat gctcaagctt caggtgaagg gttaacacat gagcagtgcg ttgataactg  10560
gagatctttt gctggagtga aatttggctg ctttatgcct cttagcctgg atagtgatct  10620
gacaatgtac ctaaaggaca aggcacttgc tgctctccaa agggaatggg attcagttta  10680
cccgaaagag ttcctgcgtt acgaccctcc caagggaacc gggtcacgga ggcttgtaga  10740
tgttttcctt aatgattcga gctttgaccc atatgatgtg ataatgtatg ttgtaagtgg  10800
agcttacctc catgaccctg agttcaacct gtcttacagc ctgaaagaaa aggagatcaa  10860
ggaaacaggt agactttttg ctaaaatgac ttacaaaatg agggcatgcc aagtgattgc  10920
tgaaaatcta atctcaaacg ggattggcaa atattttaag gacaatggga tggccaagga  10980
tgagcacgat ttgactaagg cactccacac tctagctgtc tcaggagtcc ccaaagatct  11040
caaagaaagt cacagggggg ggccagtctt aaaaacctac tcccgaagcc cagtccacac  11100
aagtaccagg aacgtgagag cagcaaaagg gtttataggg ttccctcaag taattcggca  11160
ggaccaagac actgatcatc cggagaatat ggaagcttac gagacagtca gtgcatttat  11220
cacgactgat ctcaagaagt actgccttaa ttggagatat gagaccatca gcttgtttgc  11280
acagaggcta aatgagattt acggattgcc ctcatttttc cagtggctgc ataagaggct  11340
tgagacctct gtcctgtatg taagtgaccc tcattgcccc cccgaccttg acgcccatat  11400
cccgttatat aaagtcccca atgatcaaat cttcattaag taccctatgg gaggtataga  11460
agggtattgt cagaagctgt ggaccatcag caccattccc tatctatacc tggctgctta  11520
tgagagcgga gtaaggattg cttcgttagt gcaaggggac aatcagacca tagccgtaac  11580
aaaaagggta cccagcacat ggccctacaa ccttaagaaa cgggaagctg ctagagtaac  11640
tagagattac tttgtaattc ttaggcaaag gctacatgat attggccatc acctcaaggc  11700
aaatgagaca attgtttcat cacatttttt tgtctattca aaaggaatat attatgatgg  11760
gctacttgtg tcccaatcac tcaagagcat cgcaagatgt gtattctggt cagagactat  11820
agttgatgaa acaagggcag catgcagtaa tattgctaca acaatggcta aaagcatcga  11880
gagaggttat gaccgttacc ttgcatattc cctgaacgtc ctaaaagtga tacagcaaat  11940
tctgatctct cttggcttca caatcaattc aaccatgacc cgggatgtag tcataccccct  12000
cctcacgaac aacgacctct taataaggat ggcactgttg cccgctccta ttggggggat  12060
gaattatctg aatatgagca ggctgtttgt cagaaacatc ggtgatccag taacatcatc  12120
aattgctgat ctcaagagaa tgattctcgc ctcactaatg cctgaagaga ccctccatca  12180
agtaatgaca caacaaccgg gggactcttc attcctagac tgggctagcg acccttactc  12240
agcaaatctt gtatgtgtcc agagcatcac tagactcctc aagaacataa ctgcaaggtt  12300
tgtcctgatc catagtccaa acccaatgtt aaaaggatta ttccatgatg acagtaaaga  12360
agaggacgag ggactggcgg cattcctcat ggacaggcat attatagtac ctagggcagc  12420
tcatgaaatc ctggatcata gtgtcacagg ggcaagagag tctattgcag gcatgctgga  12480
taccacaaaa ggcctgattc gagccagcat gaggaagggg gggttaacct ctcgagtgat  12540
aaccagattg tccaattatg actatgaaca attcagagca gggatggtgc tattgacagg  12600
aagaaagaga aatgtcctca ttgacaaaga gtcatgttca gtgcagctgg cgagagctct  12660
aagaagccat atgtgggcga ggctagctcg aggacggcct atttacggcc ttgaggtccc  12720
tgatgtacta gaatctatgc gaggccacct tattcggcgt catgagacat gtgtcatctg  12780
cgagtgtgga tcagtcaact acggatggtt ttttgtcccc tcgggttgcc aactggatga  12840
```

-continued

```
tattgacaag gaaacatcat ccttgagagt cccatatatt ggttctacca ctgatgagag  12900
aacagacatg aagcttgcct tcgtaagagc cccaagtcga tccttgcgat ctgctgttag  12960
aatagcaaca gtgtactcat gggcttacgg tgatgatgat agctcttgga acgaagcctg  13020
gttgttggct aggcaaaggg ccaatgtgag cctggaggag ctaagggtga tcactcccat  13080
ctcaacttcg actaatttag cgcataggtt gagggatcgt agcactcaag tgaaatactc  13140
aggtacatcc cttgtccgag tggcgaggta taccacaatc tccaacgaca atctctcatt  13200
tgtcatatca gataagaagg ttgatactaa ctttatatac caacaaggaa tgcttctagg  13260
gttgggtgtt ttagaaacat tgtttcgact cgagaaagat accggatcat ctaacacggt  13320
attacatctt cacgtcgaaa cagattgttg cgtgatcccg atgatagatc atcccaggat  13380
acccagctcc cgcaagctag agctgagggc agagctatgt accaacccat tgatatatga  13440
taatgcacct ttaattgaca gagatacaac aaggctatac acccagagcc ataggaggca  13500
ccttgtggaa tttgttacat ggtccacacc ccaactatat cacattttag ctaagtccac  13560
agcactatct atgattgacc tggtaacaaa atttgagaag gaccatatga atgaaatttc  13620
agctctcata ggggatgacg atatcaatag tttcataact gagtttctgc tcatagagcc  13680
aagattattc actatctact tgggccagtg tgcggccatc aattgggcat ttgatgtaca  13740
ttatcataga ccatcaggga aatatcagat gggtgagctg ttgtcatcgt tcctttctag  13800
aatgagcaaa ggagtgttta aggtgcttgt caatgctcta agccacccaa agatctacaa  13860
gaaattctgg cattgtggta ttatagagcc tatccatggt ccttcacttg atgctcaaaa  13920
cttgcacaca actgtgtgca acatggttta cacatgctat atgacctacc tcgacctgtt  13980
gttgaatgaa gagttagaag agttcacatt tctcttgtgt gaaagcgacg aggatgtagt  14040
accggacaga ttcgacaaca tccaggcaaa acacttatgt gttctggcag atttgtactg  14100
tcaaccaggg acctgcccac caattcgagg tctaagaccg gtagagaaat gtgcagttct  14160
aaccgaccat atcaaggcag aggctaggtt atctccagca ggatcttcgt ggaacataaa  14220
tccaattatt gtagaccatt actcatgctc tctgacttat ctccggcgag gatcgatcaa  14280
acagataaga ttgagagttg atccaggatt cattttcgac gccctcgctg aggtaaatgt  14340
cagtcagcca aagatcggca gcaacaacat ctcaaatatg agcatcaagg ctttcagacc  14400
cccacacgat gatgttgcaa aattgctcaa agatatcaac acaagcaagc acaatcttcc  14460
catttcaggg ggcaatctcg ccaattatga aatccatgct ttccgcagaa tcgggttgaa  14520
ctcatctgct tgctacaaag ctgttgagat atcaacatta attaggagat gccttgagcc  14580
aggggaggac ggcttgttct tgggtgaggg atcgggttcc atgttgatca cttataagga  14640
gatacttaaa ctaaacaagt gcttctataa tagtggggtt tccgccaatt ctagatctgg  14700
tcaaagggaa ttagcaccct atccctccga agttggcctt gtcgaacaca gaatgggagt  14760
aggtaatatt gtcaaagtgc tctttaacgg gaggcccgaa gtcacgtggg taggcagtgt  14820
agattgcttc aatttcatag ttagtaatat ccctacctct agtgtggggt ttatccattc  14880
agatatagag accttgccta acaaagatac tatagagaag ctagaggaat tggcagccat  14940
cttatcgatg gctctgctcc tgggcaaaat aggatcaata ctggtgatta agcttatgcc  15000
tttcagcggg gattttgttc agggatttat aagttatgta gggtcccatt atagagaagt  15060
gaaccttgta taccctagat acagcaactt catatctact gaatcttatt tggttatgac  15120
agatctcaag gctaaccggc taatgaatcc tgaaaagatt aagcagcaga taattgaatc  15180
atctgtgagg acttcacctg gacttatagg tcacatccta tccattaagc aactaagctg  15240
```

```
catacaagca attgtgggag acgcagttag tagaggtgat atcaatccta ctctgaaaaa  15300

acttacacct atagagcagg tgctgatcaa ttgcgggttg gcaattaacg gacctaagct  15360

gtgcaaagaa ttgatccacc atgatgttgc ctcagggcaa gatggattgc ttaattctat  15420

actcatcctc tacagggagt tggcaagatt caaagacaac caaagaagtc aacaagggat  15480

gttccacgct taccccgtat tggtaagtag caggcaacga gaacttatat ctaggatcac  15540

ccgcaaattt tgggggcaca ttcttcttta ctccgggaac agaaagttga taaataagtt  15600

tatccagaat ctcaagtccg gctatctgat actagactta caccagaata tcttcgttaa  15660

gaatctatcc aagtcagaga aacagattat tatgacgggg ggtttgaaac gtgagtgggt  15720

ttttaaggta acagtcaagg agaccaaaga atggtataag ttagtcggat acagtgccct  15780

gattaaggac taagc                                                    15795
```

<210> SEQ ID NO 19
<211> LENGTH: 557
<212> TYPE: DNA
<213> ORGANISM: Artificial Sequence
<220> FEATURE:
<223> OTHER INFORMATION: Artificial DNA sequence - Modified AfeI-NotI fragment

<400> SEQUENCE: 19

```
gctcacgtgg tgcgagaggc cgaggaccag aacaacatcc gcctaccctc catcattgtt     60

ataaaaaact taggaaccag gtccacacag ccgccagccc atcaaccatc cactcccacg    120

attggagccg atgggaattc tcgcgattgg ttgaactccg gaaccctaat cctgccctag    180

gtggttaggc attatttgca atagattaaa gaaaactttg aaaatacgaa gtttctattc    240

ccagctttgt ctggtttttt tccccccaa cttcggaggt cgaccagtac tccgggcgac    300

actttgtttt tttttttcc cccgatgctg gaggtcgacc agatgtccga aagtgtcccc    360

cccccccccc cccccccccc ggcgcggagc ggcggggcca ccccggaccc cttttttttt    420

tttttttttt tttttaaatt cctggaacct ttaggtcgac cagttgtccg tcttttactc    480

cttcatatag gtcgaccagt actccgggtg gtactttgtc tttttctgaa aatcccagag    540

gtcgaccaga tatccgc                                                   557
```

<210> SEQ ID NO 20
<211> LENGTH: 15172
<212> TYPE: DNA
<213> ORGANISM: Artificial Sequence
<220> FEATURE:
<223> OTHER INFORMATION: Artificial DNA containing selected elements from MV sequence - pNPFH_GCG

<400> SEQUENCE: 20

```
gctaccgtag tgcccagcaa tgcccgaaaa cgaccccccct cacaatgaca gccagaaggc     60

ccggacaaaa aagcccccctc cgaaagactc cacggaccaa gcgagaggcc agccagcagc    120

cgacggcaag cgcgaacacc aggcggcccc agcacagaac agccctgata caaggccacc    180

accagccacc ccaatctgca tcctcctcgt gggacccccg aggaccaacc cccaaggctg    240

cccccgatcc aaaccaccaa ccgcatcccc accacccccg ggaaagaaac ccccagcaat    300

tggaaggccc ctccccctct tcctcaacac aagaactcca caaccgaacc gcacaagcga    360

ccgaggtgac ccaaccgcag gcatccgact ccctagacag atcctctctc cccggcaaac    420

taaacaaaac ttagggccaa ggaacataca cacccaacag aacccagacc ccggcccacg    480
```

-continued

```
gcgccgcgcc cccaaccccc gacaaccaga gggagccccc aaccaatccc gccggctccc    540
ccggtgccca caggcaggga caccaacccc cgaacagacc cagcacccaa ccatcgacaa    600
tccaagacgg gggggccccc ccaaaaaaag gcccccaggg gccgacagcc agcaccgcga    660
ggaagcccac ccaccccaca cacgaccacg gcaaccaaac cagaacccag accaccctgg    720
gccaccagct cccagactcg gccatcaccc cgcagaaagg aaaggccaca acccgcgcac    780
cccagccccg atccggcggg gagccaccca acccgaacca gcacccaaga gcgatccccg    840
aaggaccccc gaaccgcaaa ggacatcagt atcccacagc ctctccaagt cccccggtct    900
cctccccttc tcgaagggac caaaagatca atccaccaca cccgacgaca ctcaactccc    960
caccccctaaa ggagacaccg ggaatcccag aatcaagact catccaatgt ccatcatggg   1020
tctcaaggtg aacgtctctg ccatattcat ggcagtactg ttaactctcc aaacacccac   1080
cggtcaaatc cattggggca atctctctaa gataggggtg gtaggaatag gaagtgcaag   1140
ctacaaagtt atgactcgtt ccagccatca atcattagtc ataaaattaa tgcccaatat   1200
aactctcctc aataactgca cgagggtaga gattgcagaa tacaggagac tactgagaac   1260
agttttggaa ccaattagag atgcacttaa tgcaatgacc cagaatataa gaccggttca   1320
gagtgtagct tcaagtagga gacacaagag atttgcggga gtagtcctgg caggtgcggc   1380
cctaggcgtt gccacagctg ctcagataac agccggcatt gcacttcacc agtccatgct   1440
gaactctcaa gccatcgaca atctgagagc gagcctggaa actactaatc aggcaattga   1500
ggcaatcaga caagcagggc aggagatgat attggctgtt cagggtgtcc aagactacat   1560
caataatgag ctgataccgt ctatgaacca actatcttgt gatttaatcg gccagaagct   1620
cgggctcaaa ttgctcagat actatacaga aatcctgtca ttatttggcc ccagcttacg   1680
ggaccccata tctgcggaga tatctatcca ggctttgagc tatgcgcttg gaggagacat   1740
caataaggtg ttagaaaagc tcggatacag tggaggtgat ttactgggca tcttagagag   1800
cagaggaata aaggcccgga taactcacgt cgacacagag tcctacttca ttgtcctcag   1860
tatagcctat ccgacgctgt ccgagattaa gggggtgatt gtccaccggc tagagggggt   1920
ctcgtacaac ataggctctc aagagtggta taccactgtg cccaagtatg ttgcaaccca   1980
agggtacctt atctcgaatt ttgatgagtc atcgtgtact ttcatgccag aggggactgt   2040
gtgcagccaa aatgccttgt acccgatgag tcctctgctc caagaatgcc tccgggggtc   2100
caccaagtcc tgtgctcgta cactcgtatc cgggtctttt gggaaccggt tcattttatc   2160
acaagggaac ctaatagcca attgtgcatc aatcctttgc aagtgttaca caacaggaac   2220
gatcattaat caagaccctg acaagatcct aacatacatt gctgccgatc actgcccggt   2280
agtcgaggtg aacggcgtga ccatccaagt cgggagcagg aggtatccag atgctgtgta   2340
cttgcacaga attgacctcg gtcctcccat atcattggag aggttggacg tagggacaaa   2400
tctggggaat gcaattgcta agttggagga tgccaaggaa ttgttggagt catcggacca   2460
gatattgagg agtatgaaag gtttatcgag cactagcata gtctacatcc tgattgcagt   2520
gtgtcttgga gggttgatag ggatccccgc tttaatatgt tgctgcaggg ggcgttgtaa   2580
caaaaaggga gaacaagttg gtatgtcaag accaggccta aagcctgatc ttacgggaac   2640
atcaaaatcc tatgtaaggt cgctctgatc ctctacaact cttgaaacac aaatgtccca   2700
caagtctcct cttcgtcatc aagcaaccac cgcacccagc atcaagccca cctgaaatta   2760
tctccggctt ccctctggcc gaacaatatc ggtagttaat taaaacttag ggtgcaagat   2820
catccacaat gtcaccacaa cgagaccgga taaatgcctt ctacaaagat aacccccatc   2880
```

-continued

```
ccaagggaag taggatagtc attaacagag aacatcttat gattgataga ccttatgttt   2940
tgctggctgt tctgtttgtc atgtttctga gcttgatcgg gttgctagcc attgcaggca   3000
ttagacttca tcgggcagcc atctacaccg cagagatcca taaaagcctc agcaccaatc   3060
tagatgtaac taactcaatc gagcatcagg tcaaggacgt gctgacacca ctcttcaaaa   3120
tcatcggtga tgaagtgggc ctgaggacac ctcagagatt cactgaccta gtgaaattca   3180
tctctgacaa gattaaattc cttaatccgg atagggagta cgacttcaga gatctcactt   3240
ggtgtatcaa cccgccagag agaatcaaat tggattatga tcaatactgt gcagatgtgg   3300
ctgctgaaga gctcatgaat gcattggtga actcaactct actggagacc agaacaacca   3360
atcagttcct agctgtctca aagggaaact gctcagggcc cactacaatc agaggtcaat   3420
tctcaaacat gtcgctgtcc ctgttagact tgtatttagg tcgaggttac aatgtgtcat   3480
ctatagtcac tatgacatcc cagggaatgt atgggggaac ttacctagtg gaaaagccta   3540
atctgagcag caaaaggtca gagttgtcac aactgagcat gtaccgagtg tttgaagtag   3600
gtgttatcag aaatccgggt ttgggggctc cggtgttcca tatgacaaac tatcttgagc   3660
aaccagccag taatgatctc agcaactgta tggtggcttt gggggagctc aaactcgcag   3720
ccctttgtca cggggaagat tctatcacaa ttccctatca gggatcaggg aaaggtgtca   3780
gcttccagct cgtcaagcta ggtgtctgga aatccccaac cgacatgcaa tcctgggtcc   3840
ccttatcaac ggatgatcca gtgatagaca ggctttacct ctcatctcac agaggtgtta   3900
tcgctgacaa tcaagcaaaa tgggctgtcc cgacaacacg aacagatgac aagttgcgaa   3960
tggagacatg cttccaacag gcgtgtaagg gtaaaatcca agcactctgc gagaatcccg   4020
agtgggcacc attgaaggat aacaggattc cttcatacgg ggtcttgtct gttgatctga   4080
gtctgacagt tgagcttaaa atcaaaattg cttcgggatt cgggccattg atcacacacg   4140
gttcagggat ggacctatac aaatccaacc acaacaatgt gtattggctg actatcccgc   4200
caatgaagaa cctagcctta ggtgtaatca acacattgga gtggataccg agattcaagg   4260
ttagtcccta cctcttcaat gtcccaatta aggaagcagg cgaagactgc catgccccaa   4320
catacctacc tgcggaggtg gatggtgatg tcaaactcag ttccaatctg gtgattctac   4380
ctggtcaaga tctccaatat gttttggcaa cctacgatac ttccagggtt gaacatgctg   4440
tggtttatta cgtttacagc ccaggccgct cattttctta cttttatcct tttaggttgc   4500
ctataaaggg ggtccccatc gaattacaag tggaatgctt cacatgggac caaaaactct   4560
ggtgccgtca cttctgtgtg cttgcggact cagaatctgg tggacatatc actcactctg   4620
ggatggtggg catgggagtc agctgcacag tcacccggga agatggaacc aatcgcagat   4680
agggctgcta gtgaaccaat ctcatgatgt cacccagaca tcaggcatac ccactagtgt   4740
gaaatagaca tcagaattaa gaaaaacgta gggtccaagt ggttccccgt tctcgaggcc   4800
gccatgtggc tgcagagcct gctgctcttg ggcactgtgg cctgcagcat ctctgcaccc   4860
gcccgctcgc ccagccccag cacgcagccc tgggagcatg tgaatgccat ccaggaggcc   4920
cggcgtctcc tgaacctgag tagagacact gctgctgaga tgaatgaaac agtagaagtc   4980
atctcagaaa tgtttgacct ccaggagccg acctgcctac agacccgcct ggagctgtac   5040
aagcagggcc tgcggggcag cctcaccaag ctcaagggcc ccttgaccat gatggccagc   5100
cactacaagc agcactgccc tccaaccccg gaaacttcct gtgcaaccca gattatcacc   5160
tttgaaagtt tcaaagagaa cctgaaggac tttctgcttg tcatcccctt tgactgctgg   5220
```

-continued

```
gagccagtcc aggagtgaca cgtggtgcga gaggccgagg accagaacaa catccgccta   5280
ccctccatca ttgttataaa aaacttagga accaggtcca cacagccgcc agcccatcaa   5340
ccatccactc ccacgattgg agccgatggg aattcgccac catgaaggta cagcccaagc   5400
accttgggtg tgttggactg agctgctttt atttggctgt aaaatcaata gaagaggaaa   5460
ggaatgtccc attggcaact gacttgatcc gaataagtca atataggttt acggtttcag   5520
acttgatgag aatggaaaag attgtattgg agaaggtgtg ttggaaagtc aaagctacta   5580
ctgcctttca atttctgcaa ctgtattatt cactccttca agagaacttg ccacttgaaa   5640
ggagaaatag cattaatttt gaaagactag aagctcaact gaaggcatgt cattgcagga   5700
tcatattttc taaagcaaag ccttctgtgt tggcattgtc tatcattgca ttagagatcc   5760
aagcacagaa gtgtgtagag ttaacagaag gaatagaatg tcttcagaaa cattccaaga   5820
taaatggcag agatctgacc ttctggcaag agcttgtatc caaatgttta actgaatatt   5880
catcaaataa gtgttccaaa ccaaatgttc agaagttgaa atggattgtt tctgggcgta   5940
ctgcacggca attgaagcat agctactaca gaataactca ccttccaaca attcctgaaa   6000
tggtccctta atcgcgattg gttgaactcc ggaaccctaa tcctgcccta ggtggttagg   6060
cattatttgc aatagattaa agaaaacttt gaaaatacga agtttctatt cccagctttg   6120
tctggttttt ttcccccca acttcggagg tcgaccagta ctccgggcga cactttgttt   6180
ttttttttc ccccgatgct ggaggtcgac cagatgtccg aaagtgtccc cccccccccc   6240
cccccccccc cggcgcggag cggcggggcc accccggacc cctttttttt tttttttttt   6300
tttttaaat tcctggaacc tttaggtcga ccagttgtcc gtcttttact ccttcatata   6360
ggtcgaccag tactccgggt ggtactttgt ctttttctga aaatcccaga ggtcgaccag   6420
atatccgcgg ccgccgagct cgttaacaac aacaattgca ttcattttat gtttcaggtt   6480
caggggggaga tgtgggaggt tttttaaagc aagtaaaacc tctacaaatg tggtaaaatc   6540
cgataaggat cgatccgggc tggcgtaata gcgaagaggc ccgcaccgat cgcccttccc   6600
aacagttgcg cagcctgaat ggcgaatgga cgcgccctgt agcggcgcat taagcgcggc   6660
gggtgtggtg gttacgcgca gcgtgaccgc tacacttgcc agcgccctag cgcccgctcc   6720
tttcgctttc ttcccttcct ttctcgccac gttcgccggc tttccccgtc aagctctaaa   6780
tcgggggctc cctttagggt tccgatttag agctttacgg cacctcgacc gcaaaaaact   6840
tgatttgggt gatggttcac gtagtgggcc atcgccctga tagacggttt ttcgcccttt   6900
gacgttggag tccacgttct ttaatagtgg actcttgttc caaactggaa caacactcaa   6960
ccctatctcg gtctattctt ttgatttata agggattttg ccgatttcgg cctattggtt   7020
aaaaaatgag ctgatttaac aaatatttaa cgcgaatttt aacaaaatat taacgtttac   7080
aatttcgcct gatgcggtat tttctcctta cgcatctgtg cggtatttca caccgcatac   7140
gcggatctgc gcagcaccat ggcctgaaat aacctctgaa agaggaactt ggttaggtac   7200
cttctgaggc ggaaagaacc agctgtggaa tgtgtgtcag ttagggtgtg gaaagtcccc   7260
aggctcccca gcaggcagaa gtatgcaaag catgcatctc aattagtcag caaccaggtg   7320
tggaaagtcc ccaggctccc cagcaggcag aagtatgcaa agcatgcatc tcaattagtc   7380
agcaaccata gtcccgcccc taactccgcc catcccgccc ctaactccgc ccagttccgc   7440
ccattctccg ccccatggct gactaatttt ttttatttat gcagaggccg aggccgcctc   7500
ggcctctgag ctattccaga agtagtgagg aggctttttt ggaggcctag gcttttgcaa   7560
aaagcttgat tcttctgaca caacagtctc gaacttaagg ctagagccac catggttcga   7620
```

-continued

```
ccattgaact gcatcgtcgc cgtgtcccaa aatatgggga ttggcaagaa cggagaccta   7680
ccctggcctc cgctcaggaa cgagttcaag tacttccaaa gaatgaccac aacctcttca   7740
gtggaaggta aacagaatct ggtgattatg ggtaggaaaa cctggttctc cattcctgag   7800
aagaatcgac ctttaaagga cagaattaat atagttctca gtagagaact caaagaacca   7860
ccacgaggag ctcattttct tgccaaaagt ttggatgatg ccttaagact tattgaacaa   7920
ccggaattgg caagtaaagt agacatggtt tggatagtcg gaggcagttc tgtttaccag   7980
gaagccatga atcaaccagg ccacctcaga ctctttgtga caaggatcat gcaggaattt   8040
gaaagtgaca cgtttttccc agaaattgat ttggggaaat ataaacttct cccagaatac   8100
ccaggcgtcc tctctgaggt ccaggaggaa aaaggcatca agtataagtt tgaagtctac   8160
gagaagaaag actaagcggg actctggggt tcgaaatgac cgaccaagcg acgcccaacc   8220
tgccatcacg atggccgcaa taaaatatct ttattttcat tacatctgtg tgttggtttt   8280
ttgtgtgaat cgatagcgat aaggatccgc gtatggtgca ctctcagtac aatctgctct   8340
gatgccgcat agttaagcca gccccgacac ccgccaacac ccgctgacgc gccctgacgg   8400
gcttgtctgc tcccggcatc cgcttacaga caagctgtga ccgtctccgg gagctgcatg   8460
tgtcagaggt tttcaccgtc atcaccgaaa cgcgcgagac gaaagggcct cgtgatacgc   8520
ctatttttat aggttaatgt catgataata atggtttctt agacgtcagg tggcactttt   8580
cggggaaatg tgcgcggaac ccctatttgt ttatttttct aaatacattc aaatatgtat   8640
ccgctcatga gacaataacc ctgataaatg cttcaataat attgaaaaag gaagagtatg   8700
agtattcaac atttccgtgt cgcccttatt cccttttttg cggcattttg ccttcctgtt   8760
tttgctcacc cagaaacgct ggtgaaagta aaagatgctg aagatcagtt gggtgcacga   8820
gtgggttaca tcgaactgga tctcaacagc ggtaagatcc ttgagagttt tcgccccgaa   8880
gaacgttttc caatgatgag cacttttaaa gttctgctat gtggcgcggt attatcccgt   8940
attgacgccg ggcaagagca actcggtcgc cgcatacact attctcagaa tgacttggtt   9000
gagtactcac cagtcacaga aaagcatctt acggatggca tgacagtaag agaattatgc   9060
agtgctgcca taaccatgag tgataacact gcggccaact tacttctgac aacgatcgga   9120
ggaccgaagg agctaaccgc ttttttgcac aacatggggg atcatgtaac tcgccttgat   9180
cgttgggaac cggagctgaa tgaagccata ccaaacgacg agcgtgacac cacgatgcct   9240
gtagcaatgg caacaacgtt gcgcaaacta ttaactggcg aactacttac tctagcttcc   9300
cggcaacaat taatagactg gatggaggcg gataaagttg caggaccact tctgcgctcg   9360
gcccttccgg ctggctggtt tattgctgat aaatctggag ccggtgagcg tgggtctcgc   9420
ggtatcattg cagcactggg gccagatggt aagccctccc gtatcgtagt tatctacacg   9480
acggggagtc aggcaactat ggatgaacga aatagacaga tcgctgagat aggtgcctca   9540
ctgattaagc attggtaact gtcagaccaa gtttactcat atatacttta gattgattta   9600
aaacttcatt tttaatttaa aaggatctag gtgaagatcc tttttgataa tctcatgacc   9660
aaaatccctt aacgtgagtt ttcgttccac tgagcgtcag accccgtaga aaagatcaaa   9720
ggatcttctt gagatccttt ttttctgcgc gtaatctgct gcttgcaaac aaaaaaacca   9780
ccgctaccag cggtggtttg tttgccggat caagagctac caactctttt tccgaaggta   9840
actggcttca gcagagcgca gataccaaat actgtccttc tagtgtagcc gtagttaggc   9900
caccacttca agaactctgt agcaccgcct acatacctcg ctctgctaat cctgttacca   9960
```

```
gtggctgctg ccagtggcga taagtcgtgt cttaccgggt tggactcaag acgatagtta  10020
ccggataagg cgcagcggtc gggctgaacg gggggttcgt gcacacagcc cagcttggag  10080
cgaacgacct acaccgaact gagataccta cagcgtgagc tatgagaaag cgccacgctt  10140
cccgaaggga gaaaggcgga caggtatccg gtaagcggca gggtcggaac aggagagcgc  10200
acgagggagc ttccaggggg aaacgcctgg tatctttata gtcctgtcgg gtttcgccac  10260
ctctgacttg agcgtcgatt tttgtgatgc tcgtcagggg ggcggagcct atggaaaaac  10320
gccagcaacg cggccttttt acggttcctg gccttttgct ggccttttgc tcacatggct  10380
cgacaagctt ggctagcaca tcctcttggt cctatcacgg ttatgaggtc gaccagttgt  10440
tgctttgatg ttcggttctc tcgttgattg ggacaatatt tggggcactt cgccggtccc  10500
gacttccaga atttccgtgt ggtctgtgaa tttatcaccg ctacactgtc atcatattcc  10560
agttttgcaa tctgctctct ttgtacctgc agataggtac caaacaaagt tgggtaagga  10620
tagttcaatc aatgatcatt ttctagtgca cttaggattc aagatcctat tatcagggac  10680
aagagcagga ttaaggatat ccgagatggc cacactttta aggagcttag cattgttcaa  10740
aagaaacaag gacaaaccac ccattacatc aggatccggt ggagccatca gaggaatcaa  10800
acacattatt atagtaccaa tccctggaga ttcctcaatt accactcgat ccagacttct  10860
ggaccggttg gtcaggttaa ttggaaaccc ggatgtgagc gggcccaaac taacaggggc  10920
actaataggt atattatcct tatttgtgga gtctccaggt caattgattc agaggatcac  10980
cgatgaccct gacgttagca taaggctgtt agaggttgtc cagagtgacc agtcacaatc  11040
tggccttacc ttcgcatcaa gaggtaccaa catggaggat gaggcggacc aatacttttc  11100
acatgatgat ccaattagta gtgatcaatc caggttcgga tggttcgaga acaaggaaat  11160
ctcagatatt gaagtgcaag accctgaggg attcaacatg attctgggta ccatcctagc  11220
tcaaatttgg gtcttgctcg caaaggcggt tacggcccca gacacggcag ctgattcgga  11280
gctaagaagg tggataaagt acacccaaca aagaagggta gttggtgaat ttagattgga  11340
gagaaaatgg ttggatgtgg tgaggaacag gattgccgag gacctctcct tacgccgatt  11400
catggtcgct ctaatcctgg atatcaagag aacacccgga aacaaaccca ggattgctga  11460
aatgatatgt gacattgata catatatcgt agaggcagga ttagccagtt ttatcctgac  11520
tattaagttt gggatagaaa ctatgtatcc tgctcttgga ctgcatgaat ttgctggtga  11580
gttatccaca cttgagtcct tgatgaacct ttaccagcaa atgggggaaa ctgcacccta  11640
catggtaatc ctggagaact caattcagaa caagttcagt gcaggatcat accctctgct  11700
ctggagctat gccatgggag taggagtgga acttgaaaac tccatgggag gtttgaactt  11760
tggccgatct tactttgatc cagcatattt tagattaggg caagagatgg taaggaggtc  11820
agctggaaag gtcagttcca cattggcatc tgaactcggt atcactgccg aggatgcaag  11880
gcttgtttca gagattgcaa tgcatactac tgaggacaag atcagtagag cggttggacc  11940
cagacaagcc caagtatcat ttctacacgg tgatcaaagt gagaatgagc taccgagatt  12000
gggggggcaag gaagatagga gggtcaaaca gagtcgagga gaagccaggg agagctacag  12060
agaaaccggg cccagcagag caagtgatgc gagagctgcc catcttccaa ccggcacacc  12120
cctagacatt gacactgcat cggagtccag ccaagatccg caggacagtc gaaggtcagc  12180
tgacgccctg cttaggctgc aagccatggc aggaatctcg gaagaacaag gctcagacac  12240
ggacacccct atagtgtaca atgacagaaa tcttctagac taggtgcgag aggccgagga  12300
ccagaacaac atccgcctac cctccatcat tgttataaaa aacttaggaa ccaggtccac  12360
```

-continued acagccgcca gcccatcaac catccactcc cacgattgga gccgatggca gaagagcagg 12420
cacgccatgt caaaaacgga ctggaatgca tccgggctct caaggccgag cccatcggct 12480
cactggccat cgaggaagct atggcagcat ggtcagaaat atcagacaac ccaggacagg 12540
agcgagccac ctgcagggaa gagaaggcag gcagttcggg tctcagcaaa ccatgcctct 12600
cagcaattgg atcaactgaa ggcggtgcac ctcgcatccg cggtcaggga cctggagaga 12660
gcgatgacga cgctgaaact ttgggaatcc ccccaagaaa tctccaggca tcaagcactg 12720
ggttacagtg ttattatgtt tatgatcaca gcggtgaagc ggttaaggga atccaagatg 12780
ctgactctat catggttcaa tcaggccttg atggtgatag caccctctca ggaggagaca 12840
atgaatctga aaacagcgat gtggatattg gcgaacctga taccgaggga tatgctatca 12900
ctgaccgggg atctgctccc atctctatgg ggttcagggc ttctgatgtt gaaactgcag 12960
aaggagggga gatccacgag ctcctgagac tccaatccag aggcaacaac tttccgaagc 13020
ttgggaaaac tctcaatgtt cctccgcctc cggaccccgg tagggccagc acttccggga 13080
cacccattaa aaagggcaca gacgcgagat tagcctcatt tggaacggag atcgcgtctt 13140
tattgacagg tggtgcaacc caatgtgctc gaaagtcacc ctcggaacca tcagggccag 13200
gtgcacctgc ggggaatgtc cccgagtgtg tgagcaatgc cgcactgata caggagtgga 13260
cacccgaatc tggtaccaca atctccccga gatcccagaa taatgaagaa gggggagact 13320
attatgatga tgagctgttc tctgatgtcc aagatattaa aacagccttg gccaaaatac 13380
acgaggataa tcagaagata atctccaagc tagaatcact gctgttattg aagggagaag 13440
ttgagtcaat taagaagcag atcaacaggc aaaatatcag catatccacc ctggaaggac 13500
acctctcaag catcatgatc gccattcctg gacttgggaa ggatcccaac gaccccactg 13560
cagatgtcga aatcaatccc gacttgaaac ccatcatagg cagagattca ggccgagcac 13620
tggccgaagt tctcaagaaa cccgttgcca gccgacaact ccaaggaatg acaaatggac 13680
ggaccagttc cagaggacag ctgctgaagg aatttcagct aaagccgatc gggaaaaaga 13740
tgagctcagc cgtcgggttt gttcctgaca ccggccctgc atcacgcagt gtaatccgct 13800
ccattataaa atccagccgg ctagaggagg atcggaagcg ttacctgatg actctccttg 13860
atgatatcaa aggagccaat gatcttgcca agttccacca gatgctgatg aagataataa 13920
tgaagtagct acagctcaac ttacctgcca accccatgcc agtcgaccca actagtacaa 13980
cctaaatcca ttataaaaaa cttaggagca aagtgattgc ctcccaagtt ccacaacgcg 14040
tgccaccatg gtgacagggg gaatggcaag caagtgggat cagaagggta tggacattgc 14100
ctatgaggag gcggccttag gttacaaaga gggtggtgtt cctattggcg gatgtcttat 14160
caataacaaa gacggaagtg ttctcggtcg tggtcacaac atgagatttc aaaagggatc 14220
cgccacacta catggtgaga tctccacttt ggaaaactgt gggagattag agggcaaagt 14280
gtacaaagat accactttgt atacgacgct gtctccatgc gacatgtgta caggtgccat 14340
catcatgtat ggtattccac gctgtgttgt cggtgagaac gttaatttca aaagtaaggg 14400
cgagaaatat ttacaaacta gaggtcacga ggttgttgtt gttgacgatg agaggtgtaa 14460
aaagatcatg aaacaattta tcgatgaaag acctcaggat tggtttgaag atattggtga 14520
ggcttcggaa ccatttaaga acgtctactt gctacctcaa acaaaccaat tgctgggttt 14580
gtacaccatc atcagaaata agaatacaac tagacctgat ttcattttct actccgatag 14640
aatcatcaga ttgttggttg aagaaggttt gaaccatcta cctgtgcaaa agcaaattgt 14700

-continued

```
ggaaactgac accaacgaaa acttcgaagg tgtctcattc atgggtaaaa tctgtggtgt  14760

ttccattgtc agagctggtg aatcgatgga gcaaggatta agagactgtt gtaggtctgt  14820

gcgtatcggt aaaattttaa ttcaaaggga cgaggagact gctttaccaa agttattcta  14880

cgaaaaatta ccagaggata tatctgaaag gtatgtcttc ctattagacc caatgctggc  14940

caccggtggt agtgctatca tggctacaga agtcttgatt aagagaggtg ttaagccaga  15000

gagaatttac ttcttaaacc taatctgtag taaggaaggg attgaaaaat accatgccgc  15060

cttcccagag gtcagaattg ttactggtgc cctcgacaga ggtctagatg aaaacaagta  15120

tctagttcca gggttgggtg actttggtga cagatactac tgtgtttaaa gc          15172
```

<210> SEQ ID NO 21
<211> LENGTH: 7670
<212> TYPE: DNA
<213> ORGANISM: Artificial Sequence
<220> FEATURE:
<223> OTHER INFORMATION: Artificial DNA containing Dengue virus prM & E protein coding region cloned into pMTXP1T - pMTX-P1T-D2G

<400> SEQUENCE: 21

```
aagcttggct agcacatcct cttggtccta tcacggttat gaggtcgacc agttgttgct     60

ttgatgttcg gttctctcgt tgattgggac aatatttggg gcacttcgcc ggtcccgact    120

tccagaattt ccgtgtggtc tgtgaattta tcaccgctac actgtcatca tattccagtt    180

ttgcaatctg ctctctttgt acctgcagat aggtaccaaa caaagttggg taaggatagt    240

tcaatcaatg atcattttct agtgcactta ggattcaaga tcctattatc agggacaaga    300

gcaggattaa ggatatccga gtcgcgacgc gtacatgtag cgctcgcacc ggtccgcggg    360

gcgcgccgcc accatgaaat gtctgctgta cctggccttc ctgttcatcg gcgtgaattg    420

tttccattta accacacgta acggagaacc acacatgatc gtcagtagac aagagaaagg    480

gaaaagtctt ctgtttaaaa cagaggatgg tgtgaacatg tgtaccctca tggccatgga    540

ccttggtgaa ttgtgtgaag atacaatcac gtacaagtgt ccttttctca agcagaatga    600

accagaagac atagattgtt ggtgcaactc tacgtccaca tgggtaactt atgggacgtg    660

taccaccaca ggagaacaca gaagagaaaa aagatcagtg gcactcgttc cacatgtggg    720

aatgggactg gagacacgaa ctgaaacatg gatgtcatca gaaggggcct ggaaacatgc    780

ccagagaatt gaaacttgga tcttgagaca tccaggcttt accataatgg cagcaatcct    840

ggcatacacc ataggaacga cacatttcca aagagccctg attttcatct tactgacagc    900

tgtcgctcct tcaatgacaa tgcgttgcat aggaatatca aatagagact ttgtagaagg    960

ggtttcagga ggaagctggg ttgacatagt cttagaacat ggaagctgtg tgacgacgat   1020

ggcaaaaaac aaaccaacat tggattttga actgatagaa acagaagcca aacaacctgc   1080

cactctaagg aagtactgta tagaggcaaa gctgaccaac acaacaacag attctcgctg   1140

cccaacacaa ggagaaccca gcctaaatga agagcaggac aaaaggttcg tctgcaaaca   1200

ctccatggtg gacagaggat ggggaaatgg atgtggacta tttggaaaag gaggcattgt   1260

gacctgtgct atgttcacat gcaaaaagaa catgaaagga aaagtcgtgc aaccagaaaa   1320

cttggaatac accattgtga taacacctca ctcaggggaa gagcatgcag tcggaaatga   1380

cacaggaaaa catggcaagg aaatcaaaat aacaccacag agttccatca cagaagcaga   1440

gttgacaggc tatggcactg tcacgatgga gtgctctccg agaacgggcc tcgacttcaa   1500

tgagatggtg ttgctgcaaa tggaaaataa agcttggctg gtgcacaggc aatggttcct   1560
```

-continued

```
agacctgccg ttgccatggc tgcccggagc ggacacacaa ggatcaaatt ggatacagaa   1620
agagacattg gtcactttca aaaatcccca tgcgaagaaa caggatgttg ttgttttggg   1680
atcccaagaa ggggccatgc acacagcact cacaggggcc acagaaatcc agatgtcatc   1740
aggaaactta ctgttcacag gacatctcaa gtgcaggctg aggatggaca aactacagct   1800
caaaggaatg tcatactcta tgtgcacagg aaagtttaaa gttgtgaagg aaatagcaga   1860
aacacaacat ggaacaatag ttatcagagt acaatatgaa ggggacggtt ctccatgtaa   1920
gatccctttt gagataatgg atttggaaaa aagacatgtt ttaggtcgcc tgattacagt   1980
caacccaatc gtaacagaaa aagatagccc agtcaacata gaagcagaac ctccattcgg   2040
agacagctac atcatcatag gagtagagcc gggacaattg aagctcaact ggtttaagaa   2100
aggaagttct atcggccaaa tgattgagac aacaatgagg ggagcgaaga gaatggccat   2160
tttaggtgac acagcttggg attttggatc cctgggagga gtgtttacat ctataggaaa   2220
ggctctccac caagttttcg gagcaatcta tggggctgcc ttcagtgggg tctcatggat   2280
tatgaaaatc ctcataggag tcattatcac atggatagga atgaattcac gcagcacctc   2340
actgtctgtg tcactagtat tggtgggagt cgtgacgctg tatttgggag ttatggtgca   2400
ggcctgaaac tcgaggtgcg agaggccgag gaccagaaca acatccgcct accctccatc   2460
attgttataa aaaacttagg aaccaggtcc acacagccgc cagcccatca accatccact   2520
cccacgattg gagccgcacg tggccaccat ggtgagcaag ggcgaggagc tgttcaccgg   2580
ggtggtgccc atcctggtcg agctggacgg cgacgtaaac ggccacaagt tcagcgtgtc   2640
cggcgagggc gagggcgatg ccacctacgg caagctgacc ctgaagttca tctgcaccac   2700
cggcaagctg cccgtgccct ggcccaccct cgtgaccacc ctgacctacg gcgtgcagtg   2760
cttcagccgc taccccgacc acatgaagca gcacgacttc ttcaagtccg ccatgcccga   2820
aggctacgtc caggagcgca ccatcttctt caaggacgac ggcaactaca agacccgcgc   2880
cgaggtgaag ttcgagggcg acaccctggt gaaccgcatc gagctgaagg gcatcgactt   2940
caaggaggac ggcaacatcc tggggcacaa gctggagtac aactacaaca gccacaacgt   3000
ctatatcatg gccgacaagc agaagaacgg catcaaggtg aacttcaaga tccgccacaa   3060
catcgaggac ggcagcgtgc agctcgccga ccactaccag cagaacaccc ccatcggcga   3120
cggccccgtg ctgctgcccg acaaccacta cctgagcacc cagtccgccc tgagcaaaga   3180
ccccaacgag aagcgcgatc acatggtcct gctggagttc gtgaccgccg ccgggatcac   3240
tctcggcatg gacgagctgt acaagtaata agtttaaacc ctgcaggtta attaagtgaa   3300
ttcttggttg aactccggaa ccctaatcct gccctaggtg gttaggcatt atttgcaata   3360
gattaaagaa aactttgaaa atacgaagtt tctattccca gctttgtctg gttttttttcc   3420
cccccaactt cggaggtcga ccagtactcc gggcgacact ttgttttttt tttttccccc   3480
gatgctggag gtcgaccaga tgtccgaaag tgtccccccc cccccccccc cccccccggc   3540
gcggagcggc ggggccaccc cggacccctt tttttttttt tttttttttt ttaaattcct   3600
ggaaccttta ggtcgaccag ttgtccgtct tttactcctt catataggtc gaccagtact   3660
ccgggtggta ctttgtcttt ttctgaaaat cccagaggtc gaccagatat ccgcggccgc   3720
cgagctcgtt aacaacaaca attgcattca ttttatgttt caggttcagg gggagatgtg   3780
ggaggttttt taaagcaagt aaaacctcta caaatgtggt aaaatccgat aaggatcgat   3840
ccgggctggc gtaatagcga agaggcccgc accgatcgcc cttcccaaca gttgcgcagc   3900
ctgaatggcg aatggacgcg ccctgtagcg gcgcattaag cgcggcgggt gtggtggtta   3960
```

```
cgcgcagcgt gaccgctaca cttgccagcg ccctagcgcc cgctcctttc gctttcttcc   4020
cttcctttct cgccacgttc gccggctttc cccgtcaagc tctaaatcgg gggctccctt   4080
tagggttccg atttagagct ttacggcacc tcgaccgcaa aaaacttgat ttgggtgatg   4140
gttcacgtag tgggccatcg ccctgataga cggtttttcg ccctttgacg ttggagtcca   4200
cgttctttaa tagtggactc ttgttccaaa ctggaacaac actcaaccct atctcggtct   4260
attcttttga tttataaggg attttgccga tttcggccta ttggttaaaa aatgagctga   4320
tttaacaaat atttaacgcg aattttaaca aaatattaac gtttacaatt tcgcctgatg   4380
cggtattttc tccttacgca tctgtgcggt atttcacacc gcatacgcgg atctgcgcag   4440
caccatggcc tgaaataacc tctgaaagag gaacttggtt aggtaccttc tgaggcggaa   4500
agaaccagct gtggaatgtg tgtcagttag ggtgtggaaa gtccccaggc tccccagcag   4560
gcagaagtat gcaaagcatg catctcaatt agtcagcaac caggtgtgga aagtccccag   4620
gctccccagc aggcagaagt atgcaaagca tgcatctcaa ttagtcagca accatagtcc   4680
cgcccctaac tccgcccatc ccgcccctaa ctccgcccag ttccgcccat tctccgcccc   4740
atggctgact aatttttttt atttatgcag aggccgaggc cgcctcggcc tctgagctat   4800
tccagaagta gtgaggaggc ttttttggag gcctaggctt ttgcaaaaag cttgattctt   4860
ctgacacaac agtctcgaac ttaaggctag agccaccatg gttcgaccat tgaactgcat   4920
cgtcgccgtg tcccaaaata tggggattgg caagaacgga gacctaccct ggcctccgct   4980
caggaacgag ttcaagtact tccaaagaat gaccacaacc tcttcagtgg aaggtaaaca   5040
gaatctggtg attatgggta ggaaaacctg gttctccatt cctgagaaga atcgaccttt   5100
aaaggacaga attaatatag ttctcagtag agaactcaaa gaaccaccac gaggagctca   5160
ttttcttgcc aaaagtttgg atgatgcctt aagacttatt gaacaaccgg aattggcaag   5220
taaagtagac atggtttgga tagtcggagg cagttctgtt taccaggaag ccatgaatca   5280
accaggccac ctcagactct ttgtgacaag gatcatgcag gaatttgaaa gtgacacgtt   5340
tttcccagaa attgatttgg ggaaatataa acttctccca gaatacccag gcgtcctctc   5400
tgaggtccag gaggaaaaag gcatcaagta taagtttgaa gtctacgaga agaaagacta   5460
agcgggactc tggggttcga aatgaccgac caagcgacgc ccaacctgcc atcacgatgg   5520
ccgcaataaa atatctttat tttcattaca tctgtgtgtt ggttttttgt gtgaatcgat   5580
agcgataagg atccgcgtat ggtgcactct cagtacaatc tgctctgatg ccgcatagtt   5640
aagccagccc cgacacccgc caacacccgc tgacgcgccc tgacgggctt gtctgctccc   5700
ggcatccgct tacagacaag ctgtgaccgt ctccgggagc tgcatgtgtc agaggttttc   5760
accgtcatca ccgaaacgcg cgagacgaaa gggcctcgtg atacgcctat ttttataggt   5820
taatgtcatg ataataatgg tttcttagac gtcaggtggc acttttcggg gaaatgtgcg   5880
cggaacccct atttgtttat ttttctaaat acattcaaat atgtatccgc tcatgagaca   5940
ataaccctga taaatgcttc aataatattg aaaaaggaag agtatgagta ttcaacattt   6000
ccgtgtcgcc cttattccct tttttgcggc attttgcctt cctgtttttg ctcacccaga   6060
aacgctggtg aaagtaaaag atgctgaaga tcagttgggt gcacgagtgg gttacatcga   6120
actggatctc aacagcggta agatccttga gagttttcgc cccgaagaac gttttccaat   6180
gatgagcact tttaaagttc tgctatgtgg cgcggtatta tcccgtattg acgccgggca   6240
agagcaactc ggtcgccgca tacactattc tcagaatgac ttggttgagt actcaccagt   6300
```

-continued

```
cacagaaaag catcttacgg atggcatgac agtaagagaa ttatgcagtg ctgccataac   6360

catgagtgat aacactgcgg ccaacttact tctgacaacg atcggaggac cgaaggagct   6420

aaccgctttt ttgcacaaca tgggggatca tgtaactcgc cttgatcgtt gggaaccgga   6480

gctgaatgaa gccataccaa acgacgagcg tgacaccacg atgcctgtag caatggcaac   6540

aacgttgcgc aaactattaa ctggcgaact acttactcta gcttcccggc aacaattaat   6600

agactggatg gaggcggata aagttgcagg accacttctg cgctcggccc ttccggctgg   6660

ctggtttatt gctgataaat ctggagccgg tgagcgtggg tctcgcggta tcattgcagc   6720

actggggcca gatggtaagc cctcccgtat cgtagttatc tacacgacgg ggagtcaggc   6780

aactatggat gaacgaaata gacagatcgc tgagataggt gcctcactga ttaagcattg   6840

gtaactgtca gaccaagttt actcatatat actttagatt gatttaaaac ttcattttta   6900

atttaaaagg atctaggtga agatcctttt tgataatctc atgaccaaaa tcccttaacg   6960

tgagttttcg ttccactgag cgtcagaccc cgtagaaaag atcaaaggat cttcttgaga   7020

tccttttttt ctgcgcgtaa tctgctgctt gcaaacaaaa aaaccaccgc taccagcggt   7080

ggtttgtttg ccggatcaag agctaccaac tctttttccg aaggtaactg gcttcagcag   7140

agcgcagata ccaaatactg tccttctagt gtagccgtag ttaggccacc acttcaagaa   7200

ctctgtagca ccgcctacat acctcgctct gctaatcctg ttaccagtgg ctgctgccag   7260

tggcgataag tcgtgtctta ccgggttgga ctcaagacga tagttaccgg ataaggcgca   7320

gcggtcgggc tgaacggggg gttcgtgcac acagcccagc ttggagcgaa cgacctacac   7380

cgaactgaga tacctacagc gtgagctatg agaaagcgcc acgcttcccg aagggagaaa   7440

ggcggacagg tatccggtaa gcggcagggt cggaacagga gagcgcacga gggagcttcc   7500

agggggaaac gcctggtatc tttatagtcc tgtcgggttt cgccacctct gacttgagcg   7560

tcgatttttg tgatgctcgt caggggggcg gagcctatgg aaaaacgcca gcaacgcggc   7620

ctttttacgg ttcctggcct tttgctggcc ttttgctcac atggctcgac              7670


<210> SEQ ID NO 22
<211> LENGTH: 273
<212> TYPE: DNA
<213> ORGANISM: Artificial Sequence
<220> FEATURE:
<223> OTHER INFORMATION: Artificial DNA that was deleted from
      pMTXP1T-D2G

<400> SEQUENCE: 22

ttccatttaa ccacacgtaa cggagaacca cacatgatcg tcagtagaca agagaaaggg     60

aaaagtcttc tgtttaaaac agaggatggt gtgaacatgt gtaccctcat ggccatggac    120

cttggtgaat tgtgtgaaga tacaatcacg tacaagtgtc cttttctcaa gcagaatgaa    180

ccagaagaca tagattgttg gtgcaactct acgtccacat gggtaactta tgggacgtgt    240

accaccacag gagaacacag aagagaaaaa aga                                 273


<210> SEQ ID NO 23
<211> LENGTH: 23770
<212> TYPE: DNA
<213> ORGANISM: Artificial Sequence
<220> FEATURE:
<223> OTHER INFORMATION: Artificial DNA containing MV genome modified by
      inserting GMCSF-ires-sPD-1-2a-PAP - pMV-GsPP

<400> SEQUENCE: 23

taactggcga actacttact ctagcttccc ggcaacaatt aatagactgg atggaggcgg     60
```

-continued

```
ataaagttgc aggaccactt ctgcgctcgg cccttccggc tggctggttt attgctgata    120
aatctggagc cggtgagcgt gggtctcgcg gtatcattgc agcactgggg ccagatggta    180
agccctcccg tatcgtagtt atctacacga cggggagtca ggcaactatg gatgaacgaa    240
atagacagat cgctgagata ggtgcctcac tgattaagca ttggtaactg tcagaccaag    300
tttactcata tatactttag attgatttaa aacttcattt ttaatttaaa aggatctagg    360
tgaagatcct ttttgataat ctcatgacca aaatccctta acgtgagttt tcgttccact    420
gagcgtcaga ccccgtagaa aagatcaaag gatcttcttg agatcctttt tttctgcgcg    480
taatctgctg cttgcaaaca aaaaaaccac cgctaccagc ggtggtttgt ttgccggatc    540
aagagctacc aactcttttt ccgaaggtaa ctggcttcag cagagcgcag ataccaaata    600
ctgttcttct agtgtagccg tagttaggcc accacttcaa gaactctgta gcaccgccta    660
catacctcgc tctgctaatc ctgttaccag tggctgctgc cagtggcgat aagtcgtgtc    720
ttaccgggtt ggactcaaga cgatagttac cggataaggc gcagcggtcg ggctgaacgg    780
ggggttcgtg cacacagccc agcttggagc gaacgaccta caccgaactg agatacctac    840
agcgtgagct atgagaaagc gccacgcttc ccgaagggag aaaggcggac aggtatccgg    900
taagcggcag ggtcggaaca ggagagcgca cgagggagct tccaggggga aacgcctggt    960
atctttatag tcctgtcggg tttcgccacc tctgacttga gcgtcgattt ttgtgatgct   1020
cgtcaggggg gcggagccta tggaaaaacg ccagcaacgc ggccttttta cggttcctgg   1080
ccttttgctg gccttttgct cacatgttct ttcctgcgtt atcccctgat tctgtggata   1140
accgtattac cgcctttgag tgagctgata ccgctcgccg cagccgaacg accgagcgca   1200
gcgagtcagt gagcgaggaa gcggaagagc gcccaatacg caaaccgcct ctccccgcgc   1260
gttggccgat tcattaatgc agctggcacg acaggtttcc cgactggaaa gcgggcagtg   1320
agcgcaacgc aattaatgtg agttagctca ctcattaggc accccaggct ttacacttta   1380
tgcttccggc tcgtatgttg tgtggaattg tgagcggata acaatttcac acaggaaaca   1440
gctatgacca tgattacgcc aagctctagc tagaggtcga cggtatacag acatgataag   1500
atacattgat gagtttggac aaaccacaac tagaatgcag tgaaaaaaat gctttatttg   1560
tgaaatttgt gatgctattg ctttatttgt aaccattata agctgcaata aacaagttgg   1620
ggtgggcgaa gaactccagc atgagatccc cgcgctggag gatcatccag ccggcgtccc   1680
ggaaaacgat tccgaagccc aacctttcat agaaggcggc ggtggaatcg aaatctcgtg   1740
atggcaggtt gggcgtcgct tggtcggtca tttcgaaccc cagagtcccg ctcagaagaa   1800
ctcgtcaaga aggcgataga aggcgatgcg ctgcgaatcg ggagcggcga taccgtaaag   1860
cacgaggaag cggtcagccc attcgccgcc aagctcttca gcaatatcac gggtagccaa   1920
cgctatgtcc tgatagcggt ccgccacacc cagccggcca cagtcgatga atccagaaaa   1980
gcggccattt tccaccatga tattcggcaa gcaggcatcg ccatgggtca cgacgagatc   2040
ctcgccgtcg ggcatgcgcg ccttgagcct ggcgaacagt tcggctggcg cgagcccctg   2100
atgctcttcg tccagatcat cctgatcgac aagaccggct tccatccgag tacgtgctcg   2160
ctcgatgcga tgtttcgctt ggtggtcgaa tgggcaggta gccggatcaa gcgtatgcag   2220
ccgccgcatt gcatcagcca tgatggatac tttctcggca ggagcaaggt gagatgacag   2280
gagatcctgc cccggcactt cgcccaatag cagccagtcc cttcccgctt cagtgacaac   2340
gtcgagcaca gctgcgcaag gaacgcccgt cgtggccagc cacgatagcc gcgctgcctc   2400
```

-continued

```
gtcctgcagt tcattcaggg caccggacag gtcggtcttg acaaaaagaa ccgggcgccc   2460
ctgcgctgac agccggaaca cggcggcatc agagcagccg attgtctgtt gtgcccagtc   2520
atagccgaat agcctctcca cccaagcggc cggagaacct gcgtgcaatc catcttgttc   2580
aatcatgcga aacgatcctc atcctgtctc ttgatcagat ccgaaaatgg atatacaagc   2640
tcccgggagc tttttgcaaa agcctaggcc tccaaaaaag cctcctcact acttctggaa   2700
tagctcagag gcagaggcgg cctcggcctc tgcataaata aaaaaaatta gtcagccatg   2760
gggcggagaa tgggcggaac tgggcggagt taggggcggg atgggcggag ttaggggcgg   2820
gactatggtt gctgactaat tgagatgcat gctttgcata cttctgcctg ctggggagcc   2880
tggggacttt ccacacctgg ttgctgacta attgagatgc atgctttgca tacttctgcc   2940
tgctggggag cctggggact ttccacaccc taactgacac acattccaca gaattaattc   3000
gcgttaaatt tttgttaaat cagctcattt tttaaccaat aggccgaaat cggcaaaatc   3060
ccttataaat caaaagaata gaccgagata gggttgagtg ttgttccagt ttggaacaag   3120
agtccactat taaagaacgt ggactccaac gtcaaagggc gaaaaaccgt ctatcagggc   3180
gatggcccac tacgtgaacc atcaccctaa tcaagttttt tggggtcgag gtgccgtaaa   3240
gcactaaatc ggaaccctaa agggagcccc cgatttagag cttgacgggg aaagccggcg   3300
aacgtggcga gaaaggaagg gaagaaagcg aaaggagcgg gcgctagggc gctggcaagt   3360
gtagcggtca cgctgcgcgt aaccaccaca cccgccgcgc ttaatgcgcc gctacagggc   3420
gcgtggggat accccctaga gccccagctg gttctttccg cctcagaagc catagagccc   3480
accgcatccc cagcatgcct gctattgtct tcccaatcct cccccttgct gtcctgcccc   3540
accccacccc ccagaataga atgacaccta ctcagacaat gcgatgcaat ttcctcattt   3600
tattaggaaa ggacagtggg agtggcacct tccagggtca aggaaggcac gggggagggg   3660
caaacaacag atggctggca actagaaggc acagtcgagg ctgatcagcg gtttaaacag   3720
cgctaccaac tttgtttggt ctgatgagtc cgtgaggacg aaacccggag tcccgggtca   3780
ccaaacaaag ttgggtaagg atagttcaat caatgatcat ttctagtgc acttaggatt   3840
caagatccta ttatcaggga caagagcagg attaaggata tccgagatgt ggctgcagag   3900
cctgctgctc ttgggcactg tggcctgcag catctctgca cccgcccgct cgcccagccc   3960
cagcacgcag ccctgggagc atgtgaatgc catccaggag gcccggcgtc tcctgaacct   4020
gagtagagac actgctgctg agatgaatga aacagtagaa gtcatctcag aaatgtttga   4080
cctccaggag ccgacctgcc tacagacccg cctggagctg tacaagcagg gcctgcgggg   4140
cagcctcacc aagctcaagg gccccttgac catgatggcc agccactaca agcagcactg   4200
ccctccaacc ccggaaactt cctgtgcaac ccagattatc acctttgaaa gtttcaaaga   4260
gaacctgaag gactttctgc ttgtcatccc ctttgactgc tgggagccag tccaggagtg   4320
atagtttctg acatccggcg ggtgactcac aacgcggccg cagccaccat gcagatccca   4380
caggcgccct ggccagtcgt ctgggcggtg ctacaactgg gctggcggcc aggatggttc   4440
ttagactccc cagacaggcc ctggaacccc cccaccttct ccccagccct gctcgtggtg   4500
accgaagggg acaacgccac cttcacctgc agcttctcca acacatcgga gagcttcgtg   4560
ctaaactggt accgcatgag ccccagcaac cagacggaca agctggccgc cttccccgag   4620
gaccgcagcc agcccggcca ggactgccgc ttccgtgtca cacaactgcc caacgggcgt   4680
gacttccaca tgagcgtggt cagggcccgg cgcaatgaca gcggcaccta cctctgtggg   4740
gccatctccc tggcccccaa ggcgcagatc aaagagagcc tgcgggcaga gctcagggtg   4800
```

-continued

```
acagagagaa gggcagaagt gcccacagcc caccccagcc cctcacccag gtcagccggc   4860
cagttccaag gaggtggtgg atccggcggt ggcggttctg gtggaggtgg atctcaccac   4920
catcatcacc atggctccgg agccacgaac ttctctctgt taaagcaagc aggagacgtg   4980
gaagaaaacc ccggtcccat gagagctgca cccctcctcc tggccagggc agcaagcctt   5040
agccttggct tcttgtttct gctttttttc tggctagacc gaagtgtact agccaaggag   5100
ttgaagtttg tgactttggt gtttcggcat ggagaccgaa gtcccattga cacctttccc   5160
actgacccca taaaggaatc ctcatggcca caaggatttg gccaactcac ccagctgggc   5220
atggagcagc attatgaact tggagagtat ataagaaaga gatatagaaa attcttgaat   5280
gagtcctata aacatgaaca ggtttatatt cgaagcacag acgttgaccg gactttgatg   5340
agtgctatga caaacctggc agccctgttt cccccagaag gtgtcagcat ctggaatcct   5400
atcctactct ggcagcccat cccggtgcac acagttcctc tttctgaaga tcagttgcta   5460
tacctgcctt tcaggaactg ccctcgtttt caagaacttg agagtgagac tttgaaatca   5520
gaggaattcc agaagaggct gcacccttat aaggatttta tagctacctt gggaaaactt   5580
tcaggattac atggccagga cctttttgga atttggagta aagtctacga ccctttatat   5640
tgtgagagtg ttcacaattt cactttaccc tcctgggcca ctgaggacac catgactaag   5700
ttgagagaat tgtcagaatt gtccctcctg tccctctatg gaattcacaa gcagaaagag   5760
aaatctaggc tccaaggggg tgtcctggtc aatgaaatcc tcaatcacat gaagagagca   5820
actcagatac caagctacaa aaaacttatc atgtattctg cgcatgacac tactgtgagt   5880
ggcctacaga tggcgctaga tgtttacaac ggactccttc ctccctatgc ttcttgccac   5940
ttgacggaat tgtactttga gaagggggag tactttgtgg agatgtacta tcggaatgag   6000
acgcagcacg agccgtatcc cctcatgcta cctggctgca gccctagctg tcctctggag   6060
aggtttgctg agctggttgg ccctgtgatc cctcaagact ggtccacgga gtgtatgacc   6120
acaaacagcc atcaaggtac tgaggacagt acagattagg tgcgagaggc cgaggaccag   6180
aacaacatcc gcctaccctc catcattgtt ataaaaaact taggaaccag gtccacacag   6240
ccgccagccc atcaaccatc cactcccacg attggagccg atggccacac ttttaaggag   6300
cttagcattg ttcaaaagaa acaaggacaa accacccatt acatcaggat ccggtggagc   6360
catcagagga atcaaacaca ttattatagt accaatccct ggagattcct caattaccac   6420
tcgatccaga cttctggacc ggttggtcag gttaattgga aacccggatg tgagcgggcc   6480
caaactaaca ggggcactaa taggtatatt atccttattt gtggagtctc caggtcaatt   6540
gattcagagg atcaccgatg accctgacgt tagcataagg ctgttagagg ttgtccagag   6600
tgaccagtca caatctggcc ttaccttcgc atcaagaggt accaacatgg aggatgaggc   6660
ggaccaatac ttttcacatg atgatccaat tagtagtgat caatccaggt tcggatggtt   6720
cgagaacaag gaaatctcag atattgaagt gcaagaccct gagggattca acatgattct   6780
gggtaccatc ctagctcaaa tttgggtctt gctcgcaaag gcggttacgg ccccagacac   6840
ggcagctgat tcggagctaa gaaggtggat aaagtacacc caacaaagaa gggtagttgg   6900
tgaatttaga ttggagagaa aatggttgga tgtggtgagg aacaggattg ccgaggacct   6960
ctccttacgc cgattcatgg tcgctctaat cctggatatc aagagaacac ccggaaacaa   7020
acccaggatt gctgaaatga tatgtgacat tgatacatat atcgtagagg caggattagc   7080
cagttttatc ctgactatta agtttgggat agaaactatg tatcctgctc ttggactgca   7140
```

-continued

```
tgaatttgct ggtgagttat ccacacttga gtccttgatg aacctttacc agcaaatggg   7200
ggaaactgca ccctacatgg taatcctgga gaactcaatt cagaacaagt tcagtgcagg   7260
atcataccct ctgctctgga gctatgccat gggagtagga gtggaacttg aaaactccat   7320
gggaggtttg aactttggcc gatcttactt tgatccagca tattttagat tagggcaaga   7380
gatggtaagg aggtcagctg gaaaggtcag ttccacattg gcatctgaac tcggtatcac   7440
tgccgaggat gcaaggcttg tttcagagat tgcaatgcat actactgagg acaagatcag   7500
tagagcggtt ggacccagac aagcccaagt atcatttcta cacggtgatc aaagtgagaa   7560
tgagctaccg agattggggg gcaaggaaga taggagggtc aaacagagtc gaggagaagc   7620
cagggagagc tacagagaaa ccgggcccag cagagcaagt gatgcgagag ctgcccatct   7680
tccaaccggc acacccctag acattgacac tgcatcggag tccagccaag atccgcagga   7740
cagtcgaagg tcagctgacg ccctgcttag gctgcaagcc atggcaggaa tctcggaaga   7800
acaaggctca gacacggaca cccctatagt gtacaatgac agaaatcttc tagactaggt   7860
gcgagaggcc gaggaccaga acaacatccg cctaccctcc atcattgtta taaaaaactt   7920
aggaaccagg tccacacagc cgccagccca tcaaccatcc actcccacga ttggagccga   7980
tggcagaaga gcaggcacgc catgtcaaaa acggactgga atgcatccgg gctctcaagg   8040
ccgagcccat cggctcactg gccatcgagg aagctatggc agcatggtca gaaatatcag   8100
acaacccagg acaggagcga gccacctgca gggaagagaa ggcaggcagt tcgggtctca   8160
gcaaaccatg cctctcagca attggatcaa ctgaaggcgg tgcacctcgc atccgcggtc   8220
agggacctgg agagagcgat gacgacgctg aaactttggg aatcccccca agaaatctcc   8280
aggcatcaag cactgggtta cagtgttatt atgtttatga tcacagcggt gaagcggtta   8340
agggaatcca agatgctgac tctatcatgg ttcaatcagg ccttgatggt gatagcaccc   8400
tctcaggagg agacaatgaa tctgaaaaca gcgatgtgga tattggcgaa cctgataccg   8460
agggatatgc tatcactgac cggggatctg ctcccatctc tatggggttc agggcttctg   8520
atgttgaaac tgcagaagga ggggagatcc acgagctcct gagactccaa tccagaggca   8580
acaactttcc gaagcttggg aaaactctca atgttcctcc gcctccggac cccggtaggg   8640
ccagcacttc cgggacaccc attaaaaagg gcacagacgc gagattagcc tcatttggaa   8700
cggagatcgc gtctttattg acaggtggtg caacccaatg tgctcgaaag tcaccctcgg   8760
aaccatcagg gccaggtgca cctgcgggga atgtccccga gtgtgtgagc aatgccgcac   8820
tgatacagga gtggacaccc gaatctggta ccacaatctc cccgagatcc cagaataatg   8880
aagaaggggg agactattat gatgatgagc tgttctctga tgtccaagat attaaaacag   8940
ccttggccaa aatacacgag gataatcaga agataatctc caagctagaa tcactgctgt   9000
tattgaaggg agaagttgag tcaattaaga agcagatcaa caggcaaaat atcagcatat   9060
ccaccctgga aggacacctc tcaagcatca tgatcgccat tcctggactt gggaaggatc   9120
ccaacgaccc cactgcagat gtcgaaatca atcccgactt gaaacccatc ataggcagag   9180
attcaggccg agcactggcc gaagttctca agaaacccgt tgccagccga caactccaag   9240
gaatgacaaa tggacggacc agttccagag gacagctgct gaaggaattt cagctaaagc   9300
cgatcgggaa aaagatgagc tcagccgtcg ggtttgttcc tgacaccggc cctgcatcac   9360
gcagtgtaat ccgctccatt ataaaatcca gccggctaga ggaggatcgg aagcgttacc   9420
tgatgactct ccttgatgat atcaaaggag ccaatgatct tgccaagttc caccagatgc   9480
tgatgaagat aataatgaag tagctacagc tcaacttacc tgccaacccc atgccagtcg   9540
```

acccaactag tacaacctaa atccattata aaaaacttag gagcaaagtg attgcctccc 9600
aagttccaca atgacagaga tctacgactt cgacaagtcg gcatgggaca tcaaagggtt 9660
gatcgctccg atacaaccca ccacctacag tgatggcagg ctggtgcccc aggtcagagt 9720
catagatcct ggtctaggcg acaggaagga tgaatgcttt atgtacatgt ttctgctggg 9780
ggttgttgag gacagcgatc ccctagggcc tccaatcggg cgagcatttg ggtccctgcc 9840
cttaggtgtt ggcagatcca cagcaaagcc cgaaaaactc ctcaaagagg ccactgagct 9900
tgacatagtt gttagacgta cagcagggct caatgaaaaa ctggtgttct acaacaacac 9960
cccactaact ctcctcacac cttggagaaa ggtcctaaca acagggagtg tcttcaacgc 10020
aaaccaagtg tgcaatgcgg ttaatctgat accgctcgat accccgcaga ggttccgtgt 10080
tgtttatatg agcatcaccc gtctttcgga taacgggtat tacaccgttc ctagaagaat 10140
gctggaattc agatcggtca atgcagtggc cttcaacctg ctggtgaccc ttaggattga 10200
caaggcgata ggccctggga agatcatcga caatacagag caacttcctg aggcaacatt 10260
tatggtccac atcgggaact tcaggagaaa gaagagtgaa gtctactctg ccgattattg 10320
caaaatgaaa atcgaaaaga tgggcctggt tttgcactt ggtgggatag ggggcaccag 10380
tcttcacatt agaagcacag gcaaaatgag caagactctc catgcacaac tcgggttcaa 10440
gaagacctta tgttacccgc tgatagatat caatgaagac cttaatcgat tactctggag 10500
gagcagatgc aagatagtaa gaatccaggc agttttgcag ccatcagttc ctcaagaatt 10560
ccgcatttac gacgacgtga tcataaatga tgaccaagga ctattcaaag ttctgtagac 10620
cgtagtgccc agcaatgccc gaaaacgacc cccctcacaa tgacagccag aaggcccgga 10680
caaaaaagcc ccctccgaaa gactccacgg accaagcgag aggccagcca gcagccgacg 10740
gcaagcgcga acaccaggcg gccccagcac agaacagccc tgatacaagg ccaccaccag 10800
ccaccccaat ctgcatcctc ctcgtgggac ccccgaggac caacccccaa ggctgccccc 10860
gatccaaacc accaaccgca tccccaccac ccccgggaaa gaaacccccca gcaattggaa 10920
ggcccctccc cctcttcctc aacacaagaa ctccacaacc gaaccgcaca agcgaccgag 10980
gtgacccaac cgcaggcatc cgactcccta gacagatcct ctctccccgg caaactaaac 11040
aaaacttagg gccaaggaac atacacaccc aacagaaccc agaccccggc ccacggcgcc 11100
gcgcccccaa cccccgacaa ccagagggag cccccaacca atcccgccgg ctcccccggt 11160
gcccacaggc agggacacca acccccgaac agacccagca cccaaccatc gacaatccaa 11220
gacgggggggg cccccccaaa aaaaggcccc caggggccga cagccagcac cgcgaggaag 11280
cccacccacc ccacacacga ccacggcaac caaaccagaa cccagaccac cctgggccac 11340
cagctcccag actcggccat caccccgcag aaaggaaagg ccacaacccg cgcaccccag 11400
ccccgatccg gcggggagcc acccaacccg aaccagcacc caagagcgat ccccgaagga 11460
cccccgaacc gcaaaggaca tcagtatccc acagcctctc caagtccccc ggtctcctcc 11520
ccttctcgaa gggaccaaaa gatcaatcca ccacacccga cgacactcaa ctccccaccc 11580
ctaaaggaga caccgggaat cccagaatca agactcatcc aatgtccatc atgggtctca 11640
aggtgaacgt ctctgccata ttcatggcag tactgttaac tctccaaaca cccaccggtc 11700
aaatccattg ggcaatctc tctaagatag gggtggtagg aataggaagt gcaagctaca 11760
aagttatgac tcgttccagc catcaatcat tagtcataaa attaatgccc aatataactc 11820
tcctcaataa ctgcacgagg gtagagattg cagaatacag gagactactg agaacagttt 11880

-continued

```
tggaaccaat tagagatgca cttaatgcaa tgacccagaa tataagaccg gttcagagtg  11940
tagcttcaag taggagacac aagagatttg cgggagtagt cctggcaggt gcggccctag  12000
gcgttgccac agctgctcag ataacagccg gcattgcact tcaccagtcc atgctgaact  12060
ctcaagccat cgacaatctg agagcgagcc tggaaactac taatcaggca attgaggcaa  12120
tcagacaagc agggcaggag atgatattgg ctgttcaggg tgtccaagac tacatcaata  12180
atgagctgat accgtctatg aaccaactat cttgtgattt aatcggccag aagctcgggc  12240
tcaaattgct cagatactat acagaaatcc tgtcattatt tggccccagc ttacgggacc  12300
ccatatctgc ggagatatct atccaggctt tgagctatgc gcttggagga gacatcaata  12360
aggtgttaga aaagctcgga tacagtggag gtgatttact gggcatctta gagagcagag  12420
gaataaaggc ccggataact cacgtcgaca cagagtccta cttcattgtc ctcagtatag  12480
cctatccgac gctgtccgag attaaggggg tgattgtcca ccggctagag ggggtctcgt  12540
acaacatagg ctctcaagag tggtatacca ctgtgcccaa gtatgttgca acccaagggt  12600
accttatctc gaattttgat gagtcatcgt gtactttcat gccagagggg actgtgtgca  12660
gccaaaatgc cttgtacccg atgagtcctc tgctccaaga atgcctccgg gggtccacca  12720
agtcctgtgc tcgtacactc gtatccgggt cttttgggaa ccggttcatt ttatcacaag  12780
ggaacctaat agccaattgt gcatcaatcc tttgcaagtg ttacacaaca ggaacgatca  12840
ttaatcaaga ccctgacaag atcctaacat acattgctgc cgatcactgc ccggtagtcg  12900
aggtgaacgg cgtgaccatc caagtcggga gcaggaggta tccagatgct gtgtacttgc  12960
acagaattga cctcggtcct cccatatcat tggagaggtt ggacgtaggg acaaatctgg  13020
ggaatgcaat tgctaagttg gaggatgcca aggaattgtt ggagtcatcg gaccagatat  13080
tgaggagtat gaaaggttta tcgagcacta gcatagtcta catcctgatt gcagtgtgtc  13140
ttggagggtt gatagggatc cccgctttaa tatgttgctg caggggggcgt tgtaacaaaa  13200
agggagaaca agttggtatg tcaagaccag gcctaaagcc tgatcttacg ggaacatcaa  13260
aatcctatgt aaggtcgctc tgatcctcta caactcttga aacacaaatg tcccacaagt  13320
ctcctcttcg tcatcaagca accaccgcac ccagcatcaa gcccacctga aattatctcc  13380
ggcttccctc tggccgaaca atatcggtag ttaattaaaa cttagggtgc aagatcatcc  13440
acaatgtcac cacaacgaga ccggataaat gccttctaca aagataaccc ccatcccaag  13500
ggaagtagga tagtcattaa cagagaacat cttatgattg atagacctta tgttttgctg  13560
gctgttctgt ttgtcatgtt tctgagcttg atcgggttgc tagccattgc aggcattaga  13620
cttcatcggg cagccatcta caccgcagag atccataaaa gcctcagcac caatctagat  13680
gtaactaact caatcgagca tcaggtcaag gacgtgctga caccactctt caaaatcatc  13740
ggtgatgaag tgggcctgag gacacctcag agattcactg acctagtgaa attcatctct  13800
gacaagatta aattccttaa tccggatagg gagtacgact tcagagatct cacttggtgt  13860
atcaacccgc cagagagaat caaattggat tatgatcaat actgtgcaga tgtggctgct  13920
gaagagctca tgaatgcatt ggtgaactca actctactgg agaccagaac aaccaatcag  13980
ttcctagctg tctcaaaggg aaactgctca gggcccacta caatcagagg tcaattctca  14040
aacatgtcgc tgtccctgtt agacttgtat ttaggtcgag gttacaatgt gtcatctata  14100
gtcactatga catcccaggg aatgtatggg ggaacttacc tagtggaaaa gcctaatctg  14160
agcagcaaaa ggtcagagtt gtcacaactg agcatgtacc gagtgtttga agtaggtgtt  14220
atcagaaatc cgggtttggg ggctccggtg ttccatatga caaactatct tgagcaacca  14280
```

-continued

```
gccagtaatg atctcagcaa ctgtatggtg gctttggggg agctcaaact cgcagccctt  14340
tgtcacgggg aagattctat cacaattccc tatcagggat cagggaaagg tgtcagcttc  14400
cagctcgtca agctaggtgt ctggaaatcc ccaaccgaca tgcaatcctg ggtcccctta  14460
tcaacggatg atccagtgat agacaggctt tacctctcat ctcacagagg tgttatcgct  14520
gacaatcaag caaaatgggc tgtcccgaca acacgaacag atgacaagtt gcgaatggag  14580
acatgcttcc aacaggcgtg taagggtaaa atccaagcac tctgcgagaa tcccgagtgg  14640
gcaccattga aggataacag gattccttca tacggggtct tgtctgttga tctgagtctg  14700
acagttgagc ttaaaatcaa aattgcttcg ggattcgggc cattgatcac acacggttca  14760
gggatggacc tatacaaatc caaccacaac aatgtgtatt ggctgactat cccgccaatg  14820
aagaacctag ccttaggtgt aatcaacaca ttggagtgga taccgagatt caaggttagt  14880
ccctacctct tcaatgtccc aattaaggaa gcaggcgaag actgccatgc cccaacatac  14940
ctacctgcgg aggtggatgg tgatgtcaaa ctcagttcca atctggtgat tctacctggt  15000
caagatctcc aatatgtttt ggcaacctac gatacttcca gggttgaaca tgctgtggtt  15060
tattacgttt acagcccagg ccgctcattt tcttactttt atccttttag gttgcctata  15120
aaggggggtcc ccatcgaatt acaagtggaa tgcttcacat gggaccaaaa actctggtgc  15180
cgtcacttct gtgtgcttgc ggactcagaa tctggtggac atatcactca ctctgggatg  15240
gtgggcatgg gagtcagctg cacagtcacc cgggaagatg gaaccaatcg cagatagggc  15300
tgctagtgaa ccaatctcat gatgtcaccc agacatcagg catacccact agtgtgaaat  15360
agacatcaga attaagaaaa acgtagggtc caagtggttc cccgttatgg actcgctatc  15420
tgtcaaccag atcttatacc ctgaagttca cctagatagc ccgatagtta ccaataagat  15480
agtagccatc ctggagtatg ctcgagtccc tcacgcttac agcctggagg accctacact  15540
gtgtcagaac atcaagcacc gcctaaaaaa cggattttcc aaccaaatga ttataaacaa  15600
tgtggaagtt gggaatgtca tcaagtccaa gcttaggagt tatccggccc actctcatat  15660
tccatatcca aattgtaatc aggatttatt taacatagaa gacaaagagt caacgaggaa  15720
gatccgtgaa ctcctcaaaa aggggaattc gctgtactcc aaagtcagtg ataaggtttt  15780
ccaatgctta agggacacta actcacggct tggcctaggc tccgaattga gggaggacat  15840
caaggagaaa gttattaact tgggagttta catgcacagc tcccagtggt ttgagccctt  15900
tctgttttgg tttacagtca agactgagat gaggtcagtg attaaatcac aaacccatac  15960
ttgccatagg aggagacaca cacctgtatt cttcactggt agttcagttg agttgctaat  16020
ctctcgtgac cttgttgcta taatcagtaa agagtctcaa catgtatatt acctgacatt  16080
tgaactggtt ttgatgtatt gtgatgtcat agaggggagg ttaatgacag agaccgctat  16140
gactattgat gctaggtata cagagcttct aggaagagtc agatacatgt ggaaactgat  16200
agatggtttc ttccctgcac tcgggaatcc aacttatcaa attgtagcca tgctggagcc  16260
tctttcactt gcttacctgc agctgaggga tataacagta gaactcagag gtgctttcct  16320
taaccactgc tttactgaaa tacatgatgt tcttgaccaa aacgggtttt ctgatgaagg  16380
tacttatcat gagttaattg aagctctaga ttacattttc ataactgatg acatacatct  16440
gacaggggag attttctcat tttcagaag tttcggccac cccagacttg aagcagtaac  16500
ggctgctgaa aatgttagga aatacatgaa tcagcctaaa gtcattgtgt atgagactct  16560
gatgaaaggt catgccatat tttgtggaat cataatcaac ggctatcgtg acaggcacgg  16620
```

-continued

```
aggcagttgg ccaccgctga ccctccccct gcatgctgca gacacaatcc ggaatgctca  16680

agcttcaggt gaagggttaa cacatgagca gtgcgttgat aactggagat cttttgctgg  16740

agtgaaattt ggctgcttta tgcctcttag cctggatagt gatctgacaa tgtacctaaa  16800

ggacaaggca cttgctgctc tccaaaggga atgggattca gtttacccga aagagttcct  16860

gcgttacgac cctcccaagg gaaccgggtc acggaggctt gtagatgttt tccttaatga  16920

ttcgagcttt gacccatatg atgtgataat gtatgttgta agtggagctt acctccatga  16980

ccctgagttc aacctgtctt acagcctgaa agaaaaggag atcaaggaaa caggtagact  17040

ttttgctaaa atgacttaca aaatgagggc atgccaagtg attgctgaaa atctaatctc  17100

aaacgggatt ggcaaatatt ttaaggacaa tgggatggcc aaggatgagc acgatttgac  17160

taaggcactc cacactctag ctgtctcagg agtccccaaa gatctcaaag aaagtcacag  17220

gggggggcca gtcttaaaaa cctactcccg aagcccagtc cacacaagta ccaggaacgt  17280

gagagcagca aaagggttta tagggttccc tcaagtaatt cggcaggacc aagacactga  17340

tcatccggag aatatggaag cttacgagac agtcagtgca tttatcacga ctgatctcaa  17400

gaagtactgc cttaattgga gatatgagac catcagcttg tttgcacaga ggctaaatga  17460

gatttacgga ttgccctcat ttttccagtg gctgcataag aggcttgaga cctctgtcct  17520

gtatgtaagt gaccctcatt gcccccccga ccttgacgcc catatcccgt tatataaagt  17580

ccccaatgat caaatcttca ttaagtaccc tatgggaggt atagaagggt attgtcagaa  17640

gctgtggacc atcagcacca ttccctatct atacctggct gcttatgaga gcggagtaag  17700

gattgcttcg ttagtgcaag ggacaatca gaccatagcc gtaacaaaaa gggtacccag  17760

cacatggccc tacaacctta agaaacggga agctgctaga gtaactagag attactttgt  17820

aattcttagg caaaggctac atgatattgg ccatcacctc aaggcaaatg agacaattgt  17880

ttcatcacat ttttttgtct attcaaaagg aatatattat gatgggctac ttgtgtccca  17940

atcactcaag agcatcgcaa gatgtgtatt ctggtcagag actatagttg atgaaacaag  18000

ggcagcatgc agtaatattg ctacaacaat ggctaaaagc atcgagagag gttatgaccg  18060

ttaccttgca tattccctga acgtcctaaa agtgatacag caaattctga tctctcttgg  18120

cttcacaatc aattcaacca tgacccggga tgtagtcata cccctcctca cgaacaacga  18180

cctcttaata aggatggcac tgttgcccgc tcctattggg gggatgaatt atctgaatat  18240

gagcaggctg tttgtcagaa acatcggtga tccagtaaca tcatcaattg ctgatctcaa  18300

gagaatgatt ctcgcctcac taatgcctga agagaccctc catcaagtaa tgacacaaca  18360

accgggggac tcttcattcc tagactgggc tagcgaccct tactcagcaa atcttgtatg  18420

tgtccagagc atcactagac tcctcaagaa cataactgca aggtttgtcc tgatccatag  18480

tccaaaccca atgttaaaag gattattcca tgatgacagt aaagaagagg acgagggact  18540

ggcggcattc ctcatggaca ggcatattat agtacctagg gcagctcatg aaatcctgga  18600

tcatagtgtc acaggggcaa gagagtctat tgcaggcatg ctggatacca caaaaggcct  18660

gattcgagcc agcatgagga aggggggtt aacctctcga gtgataacca gattgtccaa  18720

ttatgactat gaacaattca gagcagggat ggtgctattg acaggaagaa agagaaatgt  18780

cctcattgac aaagagtcat gttcagtgca gctggcgaga gctctaagaa gccatatgtg  18840

ggcgaggcta gctcgaggac ggcctattta cggccttgag gtccctgatg tactagaatc  18900

tatgcgaggc caccttattc ggcgtcatga gacatgtgtc atctgcgagt gtggatcagt  18960

caactacgga tggtttttg tcccctcggg ttgccaactg gatgatattg acaaggaaac  19020
```

-continued atcatccttg agagtcccat atattggttc taccactgat gagagaacag acatgaagct 19080
tgccttcgta agagccccaa gtcgatcctt gcgatctgct gttagaatag caacagtgta 19140
ctcatgggct tacggtgatg atgatagctc ttggaacgaa gcctggttgt tggctaggca 19200
aagggccaat gtgagcctgg aggagctaag ggtgatcact cccatctcaa cttcgactaa 19260
tttagcgcat aggttgaggg atcgtagcac tcaagtgaaa tactcaggta catcccttgt 19320
ccgagtggcg aggtatacca caatctccaa cgacaatctc tcatttgtca tatcagataa 19380
gaaggttgat actaacttta tataccaaca aggaatgctt ctagggttgg gtgttttaga 19440
aacattgttt cgactcgaga aagataccgg atcatctaac acggtattac atcttcacgt 19500
cgaaacagat tgttgcgtga tcccgatgat agatcatccc aggataccca gctcccgcaa 19560
gctagagctg agggcagagc tatgtaccaa cccattgata tatgataatg cacctttaat 19620
tgacagagat acaacaaggc tatacaccca gagccatagg aggcaccttg tggaatttgt 19680
tacatggtcc acaccccaac tatatcacat tttagctaag tccacagcac tatctatgat 19740
tgacctggta acaaaatttg agaaggacca tatgaatgaa atttcagctc tcatagggga 19800
tgacgatatc aatagtttca taactgagtt tctgctcata gagccaagat tattcactat 19860
ctacttgggc cagtgtgcgg ccatcaattg ggcatttgat gtacattatc atagaccatc 19920
agggaaatat cagatgggtg agctgttgtc atcgttcctt tctagaatga gcaaaggagt 19980
gtttaaggtg cttgtcaatg ctctaagcca cccaaagatc tacaagaaat tctggcattg 20040
tggtattata gagcctatcc atggtccttc acttgatgct caaaacttgc acacaactgt 20100
gtgcaacatg gtttacacat gctatatgac ctacctcgac ctgttgttga atgaagagtt 20160
agaagagttc acatttctct tgtgtgaaag cgacgaggat gtagtaccgg acagattcga 20220
caacatccag gcaaaacact tatgtgttct ggcagatttg tactgtcaac cagggacctg 20280
cccaccaatt cgaggtctaa gaccggtaga gaaatgtgca gttctaaccg accatatcaa 20340
ggcagaggct aggttatctc cagcaggatc ttcgtggaac ataaatccaa ttattgtaga 20400
ccattactca tgctctctga cttatctccg gcgaggatcg atcaaacaga taagattgag 20460
agttgatcca ggattcattt tcgacgccct cgctgaggta aatgtcagtc agccaaagat 20520
cggcagcaac aacatctcaa atatgagcat caaggctttc agacccccac acgatgatgt 20580
tgcaaaattg ctcaaagata tcaacacaag caagcacaat cttcccattt caggggggcaa 20640
tctcgccaat tatgaaatcc atgctttccg cagaatcggg ttgaactcat ctgcttgcta 20700
caaagctgtt gagatatcaa cattaattag gagatgcctt gagccagggg aggacggctt 20760
gttcttgggt gagggatcgg gttccatgtt gatcacttat aaggagatac ttaaactaaa 20820
caagtgcttc tataatagtg ggtttccgc caattctaga tctggtcaaa gggaattagc 20880
accctatccc tccgaagttg gccttgtcga acacagaatg ggagtaggta atattgtcaa 20940
agtgctcttt aacgggaggc ccgaagtcac gtgggtaggc agtgtagatt gcttcaattt 21000
catagttagt aatatcccta cctctagtgt ggggtttatc cattcagata tagagacctt 21060
gcctaacaaa gatactatag agaagctaga ggaattggca gccatcttat cgatggctct 21120
gctcctgggc aaaataggat caatactggt gattaagctt atgcctttca gcggggattt 21180
tgttcaggga tttataagtt atgtagggtc ccattataga gaagtgaacc ttgtataccc 21240
tagatacagc aacttcatat ctactgaatc ttatttggtt atgacagatc tcaaggctaa 21300
ccggctaatg aatcctgaaa agattaagca gcagataatt gaatcatctg tgaggacttc 21360

-continued

```
acctggactt ataggtcaca tcctatccat taagcaacta agctgcatac aagcaattgt  21420
gggagacgca gttagtagag gtgatatcaa tcctactctg aaaaaactta cacctataga  21480
gcaggtgctg atcaattgcg ggttggcaat taacggacct aagctgtgca aagaattgat  21540
ccaccatgat gttgcctcag ggcaagatgg attgcttaat tctatactca tcctctacag  21600
ggagttggca agattcaaag acaaccaaag aagtcaacaa gggatgttcc acgcttaccc  21660
cgtattggta agtagcaggc aacgagaact tatatctagg atcacccgca aattttgggg  21720
gcacattctt ctttactccg ggaacagaaa gttgataaat aagtttatcc agaatctcaa  21780
gtccggctat ctgatactag acttacacca gaatatcttc gttaagaatc tatccaagtc  21840
agagaaacag attattatga cggggggttt gaaacgtgag tgggttttta aggtaacagt  21900
caaggagacc aaagaatggt ataagttagt cggatacagt gccctgatta aggactaatt  21960
ggttgaactc cggaacccta atcctgccct aggtggttag gcattatttg caatagatta  22020
aagaaaactt tgaaaatacg aagtttctat tcccagcttt gtctggtgcc ggccatggtc  22080
ccagcctcct cgctggcggc cggtgggcaa cattccgagg ggaccgtccc ctcggtaatg  22140
gcgaatggga ccgtttaaac gctagccagc ttgggtctcc ctatagtgag tcgtattaat  22200
ttcgataagc cagtaagcag tgggttctct agttagccag agagctctgc ttatatagac  22260
ctcccaccgt acacgcctac cgcccatttg cgtcaatggg gcggagttgt tacgacattt  22320
tggaaagtcc cgttgatttt ggtgccaaaa caaactccca ttgacgtcaa tggggtggag  22380
acttggaaat ccccgtgagt caaaccgcta tccacgccca ttgatgtact gccaaaaccg  22440
catcaccatg gtaatagcga tgactaatac gtagatgtac tgccaagtag gaaagtccca  22500
taaggtcatg tactgggcat aatgccaggc gggccattta ccgtcattga cgtcaatagg  22560
gggcgtactt ggcatatgat acacttgatg tactgccaag tgggcagttt accgtaaata  22620
ctccacccat tgacgtcaat ggaaagtccc tattggcgtt actatgggaa catacgtcat  22680
tattgacgtc aatgggcggg ggtcgttggg cggtcagcca ggcgggccat ttaccgtaag  22740
ttatgtaacg cggaactcca tatatgggct atgaactaat gaccccgtaa ttgattacta  22800
ttaataacta gtcaataatc aatgtcaacg cgtatatctg gcccgtacat cgcgaagcag  22860
cgcaaaacgc ctaaccctaa gcagattctt catgcaattg tcggtcaagc cttgccttgt  22920
tgtagcttaa attttgctcg cgcactactc agcgacctcc aacacacaag cagggagcag  22980
atactggctt aactatgcgg catcagagca gattgtactg agagtgcacc ataggggatc  23040
gggagatctc ccgatccgtc gacgtcaggt ggcacttttc ggggaaatgt gcgcggaacc  23100
cctatttgtt tatttttcta aatacattca aatatgtatc cgctcatgag acaataaccc  23160
tgataaatgc ttcaataata ttgaaaaagg aagagtatga gtattcaaca tttccgtgtc  23220
gcccttattc ccttttttgc ggcattttgc cttcctgttt ttgctcaccc agaaacgctg  23280
gtgaaagtaa aagatgctga agatcagttg ggtgcacgag tgggttacat cgaactggat  23340
ctcaacagcg gtaagatcct tgagagtttt cgccccgaag aacgttttcc aatgatgagc  23400
acttttaaag ttctgctatg tggcgcggta ttatcccgta ttgacgccgg gcaagagcaa  23460
ctcggtcgcc gcatacacta ttctcagaat gacttggttg agtactcacc agtcacagaa  23520
aagcatctta cggatggcat gacagtaaga gaattatgca gtgctgccat aaccatgagt  23580
gataacactg cggccaactt acttctgaca acgatcggag gaccgaagga gctaaccgct  23640
tttttgcaca acatggggga tcatgtaact cgccttgatc gttgggaacc ggagctgaat  23700
gaagccatac caaacgacga gcgtgacacc acgatgcctg tagcaatggc aacaacgttg  23760
```

cgcaaactat 23770

<210> SEQ ID NO 24
<211> LENGTH: 21780
<212> TYPE: DNA
<213> ORGANISM: Artificial Sequence
<220> FEATURE:
<223> OTHER INFORMATION: Artificial DNA containing MV genome modified by inserting GMCSF-ires-sPD-1-2A-DnG1-ires-PAP - pMV-GsPDP

<400> SEQUENCE: 24
ggtcagggac ctggagagag cgatgacgac gctgaaactt tgggaatccc cccaagaaat 60
ctccaggcat caagcactgg gttacagtgt tattatgttt atgatcacag cggtgaagcg 120
gttaagggaa tccaagatgc tgactctatc atggttcaat caggccttga tggtgatagc 180
accctctcag gaggagacaa tgaatctgaa aacagcgatg tggatattgg cgaacctgat 240
accgagggat atgctatcac tgaccgggga tctgctccca tctctatggg gttcagggct 300
tctgatgttg aaactgcaga aggaggggag atccacgagc tcctgagact ccaatccaga 360
ggcaacaact ttccgaagct tgggaaaact ctcaatgttc ctccgcctcc ggaccccggt 420
agggccagca cttccgggac acccattaaa aagggcacag acgcgagatt agcctcattt 480
ggaacggaga tcgcgtcttt attgacaggt ggtgcaaccc aatgtgctcg aaagtcaccc 540
tcggaaccat cagggccagg tgcacctgcg gggaatgtcc ccgagtgtgt gagcaatgcc 600
gcactgatac aggagtggac acccgaatct ggtaccacaa tctccccgag atcccagaat 660
aatgaagaag gggagactta ttatgatgat gagctgttct ctgatgtcca agatattaaa 720
acagccttgg ccaaaataca cgaggataat cagaagataa tctccaagct agaatcactg 780
ctgttattga agggagaagt tgagtcaatt aagaagcaga tcaacaggca aaatatcagc 840
atatccaccc tggaaggaca cctctcaagc atcatgatcg ccattcctgg acttgggaag 900
gatcccaacg accccactgc agatgtcgaa atcaatcccg acttgaaacc catcataggc 960
agagattcag gccgagcact ggccgaagtt ctcaagaaac ccgttgccag ccgacaactc 1020
caaggaatga caaatggacg gaccagttcc agaggacagc tgctgaagga atttcagcta 1080
aagccgatcg ggaaaaagat gagctcagcc gtcgggtttg ttcctgacac cggccctgca 1140
tcacgcagtg taatccgctc cattataaaa tccagccggc tagaggagga tcggaagcgt 1200
tacctgatga ctctccttga tgatatcaaa ggagccaatg atcttgccaa gttccaccag 1260
atgctgatga agataataat gaagtagcta cagctcaact tacctgccaa ccccatgcca 1320
gtcgacccaa ctagtacaac ctaaatccat tataaaaaac ttaggagcaa agtgattgcc 1380
tcccaagttc cacaatgaca gagatctacg acttcgacaa gtcggcatgg gacatcaaag 1440
ggttgatcgc tccgatacaa cccaccacct acagtgatgg caggctggtg ccccaggtca 1500
gagtcataga tcctggtcta ggcgacagga aggatgaatg ctttatgtac atgtttctgc 1560
tgggggttgt tgaggacagc gatcccctag ggcctccaat cgggcgagca tttgggtccc 1620
tgcccttagg tgttggcaga tccacagcaa agcccgaaaa actcctcaaa gaggccactg 1680
agcttgacat agttgttaga cgtacagcag ggctcaatga aaaactggtg ttctacaaca 1740
acaccccact aactctcctc acaccttgga gaaaggtcct aacaacaggg agtgtcttca 1800
acgcaaacca agtgtgcaat gcggttaatc tgataccgct cgataccccg cagaggttcc 1860
gtgttgttta tatgagcatc acccgtcttt cggataacgg gtattacacc gttcctagaa 1920
gaatgctgga attcagatcg gtcaatgcag tggccttcaa cctgctggtg acccttagga 1980

-continued

```
ttgacaaggc gataggccct gggaagatca tcgacaatac agagcaactt cctgaggcaa   2040
catttatggt ccacatcggg aacttcagga gaaagaagag tgaagtctac tctgccgatt   2100
attgcaaaat gaaaatcgaa aagatgggcc tggtttttgc acttggtggg ataggggggca  2160
ccagtcttca cattagaagc acaggcaaaa tgagcaagac tctccatgca caactcgggt   2220
tcaagaagac cttatgttac ccgctgatag atatcaatga agaccttaat cgattactct   2280
ggaggagcag atgcaagata gtaagaatcc aggcagtttt gcagccatca gttcctcaag   2340
aattccgcat ttacgacgac gtgatcataa atgatgacca aggactattc aaagttctgt   2400
agaccgtagt gcccagcaat gcccgaaaac gacccccctc acaatgacag ccagaaggcc   2460
cggacaaaaa agcccctcc gaaagactcc acggaccaag cgagaggcca gccagcagcc    2520
gacggcaagc gcgaacacca ggcggcccca gcacagaaca gccctgatac aaggccacca   2580
ccagccaccc caatctgcat cctcctcgtg ggacccccga ggaccaaccc ccaaggctgc   2640
ccccgatcca aaccaccaac cgcatcccca ccacccccgg gaaagaaacc cccagcaatt   2700
ggaaggcccc tcccctctt cctcaacaca agaactccac aaccgaaccg cacaagcgac    2760
cgaggtgacc caaccgcagg catccgactc cctagacaga tcctctctcc ccggcaaact   2820
aaacaaaact tagggccaag gaacatacac acccaacaga acccagaccc cggcccacgg   2880
cgccgcgccc ccaaccccg acaaccagag ggagccccca accaatcccg ccggctcccc    2940
cggtgcccac aggcagggac accaaccccc gaacagaccc agcacccaac catcgacaat   3000
ccaagacggg ggggcccccc caaaaaaagg cccccagggg ccgacagcca gcaccgcgag   3060
gaagcccacc caccccacac acgaccacgg caaccaaacc agaacccaga ccaccctggg   3120
ccaccagctc ccagactcgg ccatcacccc gcagaaagga aaggccacaa cccgcgcacc   3180
ccagccccga tccggcgggg agccacccaa cccgaaccag cacccaagag cgatccccga   3240
aggaccccg aaccgcaaag gacatcagta tcccacagcc tctccaagtc ccccggtctc    3300
ctcccttct cgaagggacc aaaagatcaa tccaccacac ccgacgacac tcaactcccc    3360
accctaaag gagacaccgg gaatcccaga atcaagactc atccaatgtc catcatgggt    3420
ctcaaggtga acgtctctgc catattcatg gcagtactgt taactctcca aacacccacc   3480
ggtcaaatcc attggggcaa tctctctaag atagggggtgg taggaatagg aagtgcaagc  3540
tacaaagtta tgactcgttc cagccatcaa tcattagtca taaaattaat gcccaatata   3600
actctcctca ataactgcac gagggtagag attgcagaat acaggagact actgagaaca   3660
gttttggaac caattagaga tgcacttaat gcaatgaccc agaatataag accggttcag   3720
agtgtagctt caagtaggag acacaagaga tttgcgggag tagtcctggc aggtgcggcc   3780
ctaggcgttg ccacagctgc tcagataaca gccggcattg cacttcacca gtccatgctg   3840
aactctcaag ccatcgacaa tctgagagcg agcctggaaa ctactaatca ggcaattgag   3900
gcaatcagac aagcagggca ggagatgata ttggctgttc agggtgtcca agactacatc   3960
aataatgagc tgataccgtc tatgaaccaa ctatcttgtg atttaatcgg ccagaagctc   4020
gggctcaaat tgctcagata ctatacagaa atcctgtcat tatttggccc cagcttacgg   4080
gaccccatat ctgcggagat atctatccag gctttgagct atgcgcttgg aggagacatc   4140
aataaggtgt tagaaaagct cggatacagt ggaggtgatt tactgggcat cttagagagc   4200
agaggaataa aggcccggat aactcacgtc gacacagagt cctacttcat tgtcctcagt   4260
atagcctatc cgacgctgtc cgagattaag gggtgattg tccaccggct agagggggtc    4320
```

-continued tcgtacaaca taggctctca agagtggtat accactgtgc ccaagtatgt tgcaacccaa 4380
gggtacctta tctcgaattt tgatgagtca tcgtgtactt tcatgccaga ggggactgtg 4440
tgcagccaaa atgccttgta cccgatgagt cctctgctcc aagaatgcct ccgggggtcc 4500
accaagtcct gtgctcgtac actcgtatcc gggtcttttg ggaaccggtt cattttatca 4560
caagggaacc taatagccaa ttgtgcatca atcctttgca agtgttacac aacaggaacg 4620
atcattaatc aagaccctga caagatccta acatacattg ctgccgatca ctgcccggta 4680
gtcgaggtga acggcgtgac catccaagtc gggagcagga ggtatccaga tgctgtgtac 4740
ttgcacagaa ttgacctcgg tcctcccata tcattggaga ggttggacgt agggacaaat 4800
ctggggaatg caattgctaa gttggaggat gccaaggaat tgttggagtc atcggaccag 4860
atattgagga gtatgaaagg tttatcgagc actagcatag tctacatcct gattgcagtg 4920
tgtcttggag ggttgatagg gatccccgct ttaatatgtt gctgcagggg gcgttgtaac 4980
aaaaagggag aacaagttgg tatgtcaaga ccaggcctaa agcctgatct tacgggaaca 5040
tcaaaatcct atgtaaggtc gctctgatcc tctacaactc ttgaaacaca aatgtcccac 5100
aagtctcctc ttcgtcatca agcaaccacc gcacccagca tcaagcccac ctgaaattat 5160
ctccggcttc cctctggccg aacaatatcg gtagttaatt aaaacttagg gtgcaagatc 5220
atccacaatg tcaccacaac gagaccggat aaatgccttc tacaaagata acccccatcc 5280
caagggaagt aggatagtca ttaacagaga acatcttatg attgatagac cttatgtttt 5340
gctggctgtt ctgtttgtca tgtttctgag cttgatcggg ttgctagcca ttgcaggcat 5400
tagacttcat cgggcagcca tctacaccgc agagatccat aaaagcctca gcaccaatct 5460
agatgtaact aactcaatcg agcatcaggt caaggacgtg ctgacaccac tcttcaaaat 5520
catcggtgat gaagtgggcc tgaggacacc tcagagattc actgacctag tgaaattcat 5580
ctctgacaag attaaattcc ttaatccgga tagggagtac gacttcagag atctcacttg 5640
gtgtatcaac ccgccagaga gaatcaaatt ggattatgat caatactgtg cagatgtggc 5700
tgctgaagag ctcatgaatg cattggtgaa ctcaactcta ctggagacca gaacaaccaa 5760
tcagttccta gctgtctcaa agggaaactg ctcagggccc actacaatca gaggtcaatt 5820
ctcaaacatg tcgctgtccc tgttagactt gtatttaggt cgaggttaca atgtgtcatc 5880
tatagtcact atgacatccc agggaatgta tgggggaact tacctagtgg aaaagcctaa 5940
tctgagcagc aaaaggtcag agttgtcaca actgagcatg taccgagtgt ttgaagtagg 6000
tgttatcaga aatccgggtt tgggggctcc ggtgttccat atgacaaact atcttgagca 6060
accagccagt aatgatctca gcaactgtat ggtggctttg gggggagctca aactcgcagc 6120 cctttgtcac ggggaagatt ctatcacaat tccctatcag ggatcaggga aaggtgtcag 6180
cttccagctc gtcaagctag gtgtctggaa atccccaacc gacatgcaat cctgggtccc 6240
cttatcaacg gatgatccag tgatagacag gctttacctc tcatctcaca gaggtgttat 6300
cgctgacaat caagcaaaat gggctgtccc gacaacacga acagatgaca agttgcgaat 6360
ggagacatgc ttccaacagg cgtgtaaggg taaaatccaa gcactctgcg agaatcccga 6420
gtgggcacca ttgaaggata acaggattcc ttcatacggg gtcttgtctg ttgatctgag 6480
tctgacagtt gagcttaaaa tcaaaattgc ttcgggattc gggccattga tcacacacgg 6540
ttcagggatg gacctataca aatccaacca caacaatgtg tattggctga ctatcccgcc 6600
aatgaagaac ctagccttag gtgtaatcaa cacattggag tggataccga gattcaaggt 6660
tagtccctac ctcttcaatg tcccaattaa ggaagcaggc gaagactgcc atgccccaac 6720

```
atacctacct gcggaggtgg atggtgatgt caaactcagt tccaatctgg tgattctacc   6780
tggtcaagat ctccaatatg ttttggcaac ctacgatact tccagggttg aacatgctgt   6840
ggtttattac gtttacagcc caggccgctc attttcttac ttttatcctt ttaggttgcc   6900
tataaagggg gtccccatcg aattacaagt ggaatgcttc acatgggacc aaaaactctg   6960
gtgccgtcac ttctgtgtgc ttgcggactc agaatctggt ggacatatca ctcactctgg   7020
gatggtgggc atgggagtca gctgcacagt cacccgggaa gatggaacca atcgcagata   7080
gggctgctag tgaaccaatc tcatgatgtc acccagacat caggcatacc cactagtgtg   7140
aaatagacat cagaattaag aaaaacgtag ggtccaagtg gttccccgtt atggactcgc   7200
tatctgtcaa ccagatctta taccctgaag ttcacctaga tagcccgata gttaccaata   7260
agatagtagc catcctggag tatgctcgag tccctcacgc ttacagcctg gaggacccta   7320
cactgtgtca gaacatcaag caccgcctaa aaaacggatt ttccaaccaa atgattataa   7380
acaatgtgga agttgggaat gtcatcaagt ccaagcttag gagttatccg gcccactctc   7440
atattccata tccaaattgt aatcaggatt tatttaacat agaagacaaa gagtcaacga   7500
ggaagatccg tgaactcctc aaaaagggga attcgctgta ctccaaagtc agtgataagg   7560
ttttccaatg cttaagggac actaactcac ggcttggcct aggctccgaa ttgagggagg   7620
acatcaagga gaaagttatt aacttgggag tttacatgca cagctcccag tggtttgagc   7680
cctttctgtt ttggtttaca gtcaagactg agatgaggtc agtgattaaa tcacaaaccc   7740
atacttgcca taggaggaga cacacacctg tattcttcac tggtagttca gttgagttgc   7800
taatctctcg tgaccttgtt gctataatca gtaaagagtc tcaacatgta tattacctga   7860
catttgaact ggttttgatg tattgtgatg tcatagaggg gaggttaatg acagagaccg   7920
ctatgactat tgatgctagg tatacagagc ttctaggaag agtcagatac atgtggaaac   7980
tgatagatgg tttcttccct gcactcggga atccaactta tcaaattgta gccatgctgg   8040
agcctctttc acttgcttac ctgcagctga gggatataac agtagaactc agaggtgctt   8100
tccttaacca ctgctttact gaaatacatg atgttcttga ccaaaacggg ttttctgatg   8160
aaggtactta tcatgagtta attgaagctc tagattacat tttcataact gatgacatac   8220
atctgacagg ggagattttc tcatttttca gaagtttcgg ccaccccaga cttgaagcag   8280
taacggctgc tgaaaatgtt aggaaataca tgaatcagcc taaagtcatt gtgtatgaga   8340
ctctgatgaa aggtcatgcc atattttgtg gaatcataat caacggctat cgtgacaggc   8400
acggaggcag ttggccaccg ctgaccctcc ccctgcatgc tgcagacaca atccggaatg   8460
ctcaagcttc aggtgaaggg ttaacacatg agcagtgcgt tgataactgg agatcttttg   8520
ctggagtgaa atttggctgc tttatgcctc ttagcctgga tagtgatctg acaatgtacc   8580
taaaggacaa ggcacttgct gctctccaaa gggaatggga ttcagtttac ccgaaagagt   8640
tcctgcgtta cgaccctccc aagggaaccg ggtcacggag gcttgtagat gttttcctta   8700
atgattcgag ctttgaccca tatgatgtga taatgtatgt tgtaagtgga gcttacctcc   8760
atgaccctga gttcaacctg tcttacagcc tgaaagaaaa ggagatcaag gaaacaggta   8820
gactttttgc taaaatgact tacaaaatga gggcatgcca agtgattgct gaaaatctaa   8880
tctcaaacgg gattggcaaa tattttaagg acaatgggat ggccaaggat gagcacgatt   8940
tgactaaggc actccacact ctagctgtct caggagtccc caaagatctc aaagaaagtc   9000
acaggggggg gccagtctta aaaacctact cccgaagccc agtccacaca agtaccagga   9060
```

-continued

```
acgtgagagc agcaaaaggg tttatagggt tccctcaagt aattcggcag gaccaagaca   9120
ctgatcatcc ggagaatatg gaagcttacg agacagtcag tgcatttatc acgactgatc   9180
tcaagaagta ctgccttaat tggagatatg agaccatcag cttgtttgca cagaggctaa   9240
atgagattta cggattgccc tcatttttcc agtggctgca taagaggctt gagacctctg   9300
tcctgtatgt aagtgaccct cattgccccc ccgaccttga cgcccatatc ccgttatata   9360
aagtccccaa tgatcaaatc ttcattaagt accctatggg aggtatagaa gggtattgtc   9420
agaagctgtg gaccatcagc accattccct atctatacct ggctgcttat gagagcggag   9480
taaggattgc ttcgttagtg caaggggaca atcagaccat agccgtaaca aaaagggtac   9540
ccagcacatg gccctacaac cttaagaaac gggaagctgc tagagtaact agagattact   9600
ttgtaattct taggcaaagg ctacatgata ttggccatca cctcaaggca aatgagacaa   9660
ttgtttcatc acattttttt gtctattcaa aaggaatata ttatgatggg ctacttgtgt   9720
cccaatcact caagagcatc gcaagatgtg tattctggtc agagactata gttgatgaaa   9780
caagggcagc atgcagtaat attgctacaa caatggctaa aagcatcgag agaggttatg   9840
accgttacct tgcatattcc ctgaacgtcc taaaagtgat acagcaaatt ctgatctctc   9900
ttggcttcac aatcaattca accatgaccc gggatgtagt catacccctc ctcacgaaca   9960
acgacctctt aataaggatg gcactgttgc ccgctcctat tggggggatg aattatctga  10020
atatgagcag gctgtttgtc agaaacatcg gtgatccagt aacatcatca attgctgatc  10080
tcaagagaat gattctcgcc tcactaatgc ctgaagagac cctccatcaa gtaatgacac  10140
aacaaccggg ggactcttca ttcctagact gggctagcga cccttactca gcaaatcttg  10200
tatgtgtcca gagcatcact agactcctca agaacataac tgcaaggttt gtcctgatcc  10260
atagtccaaa cccaatgtta aaaggattat tccatgatga cagtaaagaa gaggacgagg  10320
gactggcggc attcctcatg gacaggcata ttatagtacc tagggcagct catgaaatcc  10380
tggatcatag tgtcacaggg gcaagagagt ctattgcagg catgctggat accacaaaag  10440
gcctgattcg agccagcatg aggaaggggg ggttaacctc tcgagtgata accagattgt  10500
ccaattatga ctatgaacaa ttcagagcag ggatggtgct attgacagga agaaagagaa  10560
atgtcctcat tgacaaagag tcatgttcag tgcagctggc gagagctcta agaagccata  10620
tgtgggcgag gctagctcga ggacggccta tttacggcct tgaggtccct gatgtactag  10680
aatctatgcg aggccacctt attcggcgtc atgagacatg tgtcatctgc gagtgtggat  10740
cagtcaacta cggatggttt tttgtcccct cgggttgcca actggatgat attgacaagg  10800
aaacatcatc cttgagagtc ccatatattg gttctaccac tgatgagaga acagacatga  10860
agcttgcctt cgtaagagcc ccaagtcgat ccttgcgatc tgctgttaga atagcaacag  10920
tgtactcatg ggcttacggt gatgatgata gctcttggaa cgaagcctgg ttgttggcta  10980
ggcaaagggc caatgtgagc ctggaggagc taagggtgat cactcccatc tcaacttcga  11040
ctaatttagc gcataggttg agggatcgta gcactcaagt gaaatactca ggtacatccc  11100
ttgtccgagt ggcgaggtat accacaatct ccaacgacaa tctctcattt gtcatatcag  11160
ataagaaggt tgatactaac tttatatacc aacaaggaat gcttctaggg ttgggtgttt  11220
tagaaacatt gtttcgactc gagaaagata ccggatcatc taacacggta ttacatcttc  11280
acgtcgaaac agattgttgc gtgatcccga tgatagatca tcccaggata cccagctccc  11340
gcaagctaga gctgagggca gagctatgta ccaacccatt gatatatgat aatgcacctt  11400
taattgacag agatacaaca aggctataca cccagagcca taggaggcac cttgtggaat  11460
```

-continued ttgttacatg gtccacaccc caactatatc acattttagc taagtccaca gcactatcta 11520
tgattgacct ggtaacaaaa tttgagaagg accatatgaa tgaaatttca gctctcatag 11580
gggatgacga tatcaatagt ttcataactg agtttctgct catagagcca agattattca 11640
ctatctactt gggccagtgt gcggccatca attgggcatt tgatgtacat tatcatagac 11700
catcagggaa atatcagatg ggtgagctgt tgtcatcgtt cctttctaga atgagcaaag 11760
gagtgtttaa ggtgcttgtc aatgctctaa gccacccaaa gatctacaag aaattctggc 11820
attgtggtat tatagagcct atccatggtc cttcacttga tgctcaaaac ttgcacacaa 11880
ctgtgtgcaa catggtttac acatgctata tgacctacct cgacctgttg ttgaatgaag 11940
agttagaaga gttcacattt ctcttgtgtg aaagcgacga ggatgtagta ccggacagat 12000
tcgacaacat ccaggcaaaa cacttatgtg ttctggcaga tttgtactgt caaccaggga 12060
cctgcccacc aattcgaggt ctaagaccgg tagagaaatg tgcagttcta accgaccata 12120
tcaaggcaga ggctaggtta tctccagcag gatcttcgtg gaacataaat ccaattattg 12180
tagaccatta ctcatgctct ctgacttatc tccggcgagg atcgatcaaa cagataagat 12240
tgagagttga tccaggattc attttcgacg ccctcgctga ggtaaatgtc agtcagccaa 12300
agatcggcag caacaacatc tcaaatatga gcatcaaggc tttcagaccc ccacacgatg 12360
atgttgcaaa attgctcaaa gatatcaaca caagcaagca caatcttccc atttcagggg 12420
gcaatctcgc caattatgaa atccatgctt tccgcagaat cgggttgaac tcatctgctt 12480
gctacaaagc tgttgagata tcaacattaa ttaggagatg ccttgagcca ggggaggacg 12540
gcttgttctt gggtgaggga tcgggttcca tgttgatcac ttataaggag atacttaaac 12600
taaacaagtg cttctataat agtggggttt ccgccaattc tagatctggt caaagggaat 12660
tagcacccta tccctccgaa gttggccttg tcgaacacag aatgggagta ggtaatattg 12720
tcaaagtgct ctttaacggg aggcccgaag tcacgtgggt aggcagtgta gattgcttca 12780
atttcatagt tagtaatatc cctacctcta gtgtggggtt tatccattca gatatagaga 12840
ccttgcctaa caaagatact atagagaagc tagaggaatt ggcagccatc ttatcgatgg 12900
ctctgctcct gggcaaaata ggatcaatac tggtgattaa gcttatgcct ttcagcgggg 12960
attttgttca gggatttata agttatgtag ggtcccatta tagagaagtg aaccttgtat 13020
accctagata cagcaacttc atatctactg aatcttattt ggttatgaca gatctcaagg 13080
ctaaccggct aatgaatcct gaaaagatta agcagcagat aattgaatca tctgtgagga 13140
cttcacctgg acttataggt cacatcctat ccattaagca actaagctgc atacaagcaa 13200
ttgtgggaga cgcagttagt agaggtgata tcaatcctac tctgaaaaaa cttacaccta 13260
tagagcaggt gctgatcaat tgcgggttgg caattaacgg acctaagctg tgcaaagaat 13320
tgatccacca tgatgttgcc tcagggcaag atggattgct taattctata ctcatcctct 13380
acagggagtt ggcaagattc aaagacaacc aaagaagtca acaagggatg ttccacgctt 13440
accccgtatt ggtaagtagc aggcaacgag aacttatatc taggatcacc cgcaaatttt 13500
gggggcacat tcttctttac tccgggaaca gaaagttgat aaataagttt atccagaatc 13560
tcaagtccgg ctatctgata ctagacttac accagaatat cttcgttaag aatctatcca 13620
agtcagagaa acagattatt atgacggggg gtttgaaacg tgagtgggtt tttaaggtaa 13680
cagtcaagga gaccaaagaa tggtataagt tagtcggata cagtgccctg attaaggact 13740
aattggttga actccggaac cctaatcctg ccctaggtgg ttaggcatta tttgcaatag 13800

-continued

```
attaaagaaa actttgaaaa tacgaagttt ctattcccag ctttgtctgg tgccggccat  13860
ggtcccagcc tcctcgctgg cggccggtgg gcaacattcc gaggggaccg tcccctcggt  13920
aatggcgaat gggaccgttt aaaccccgct atcggatccc gggcccgtcg actgcagagg  13980
cctgcatgca agcttggcgt aatcatggtc atagctgttt cctgtgtgaa attgttatcc  14040
gctcacaatt ccacacaaca tacgagccgg aagcataaag tgtaaagcct ggggtgccta  14100
atgagtgagc taactcacat taattgcgtt gcgctcactg cccgctttcc agtcgggaaa  14160
cctgtcgtgc cagctgcatt aatgaatcgg ccaacgcgcg gggagaggcg gtttgcgtat  14220
tgggcgctct tccgcttcct cgctcactga ctcgctgcgc tcggtcgttc ggctgcggcg  14280
agcggtatca gctcactcaa aggcggtaat acggttatcc acagaatcag gggataacgc  14340
aggaaagaac atgtgagcaa aaggccagca aaaggccagg aaccgtaaaa aggccgcgtt  14400
gctggcgttt ttccataggc tccgcccccc tgacgagcat cacaaaaatc gacgctcaag  14460
tcagaggtgg cgaaacccga caggactata aagataccag gcgtttcccc ctggaagctc  14520
cctcgtgcgc tctcctgttc cgaccctgcc gcttaccgga tacctgtccg cctttctccc  14580
ttcgggaagc gtggcgcttt ctcatagctc acgctgtagg tatctcagtt cggtgtaggt  14640
cgttcgctcc aagctgggct gtgtgcacga accccccgtt cagcccgacc gctgcgcctt  14700
atccggtaac tatcgtcttg agtccaaccc ggtaagacac gacttatcgc cactggcagc  14760
agccactggt aacaggatta gcagagcgag gtatgtaggc ggtgctacag agttcttgaa  14820
gtggtggcct aactacggct acactagaag aacagtattt ggtatctgcg ctctgctgaa  14880
gccagttacc ttcggaaaaa gagttggtag ctcttgatcc ggcaaacaaa ccaccgctgg  14940
tagcggtggt ttttttgttt gcaagcagca gattacgcgc agaaaaaaag gatctcaaga  15000
agatcctttg atcttttcta cggggtctga cgctcagtgg aacgaaaact cacgttaagg  15060
gattttggtc atgagattat caaaaaggat cttcacctag atccttttaa attaaaaatg  15120
aagttttaaa tcaatctaaa gtatatatga gtaaacttgg tctgacagtt accaatgctt  15180
aatcagtgag gcacctatct cagcgatctg tctatttcgt tcatccatag ttgcctgact  15240
ccccgtcgtg tagataacta cgatacggga gggcttacca tctggcccca gtgctgcaat  15300
gataccgcga gacccacgct caccggctcc agatttatca gcaataaacc agccagccgg  15360
aagggccgag cgcagaagtg gtcctgcaac tttatccgcc tccatccagt ctattaattg  15420
ttgccgggaa gctagagtaa gtagttcgcc agttaatagt ttgcgcaacg ttgttgccat  15480
tgctacaggc atcgtggtgt cacgctcgtc gtttggtatg gcttcattca gctccggttc  15540
ccaacgatca aggcgagtta catgatcccc catgttgtgc aaaaaagcgg ttagctcctt  15600
cggtcctccg atcgttgtca gaagtaagtt ggccgcagtg ttatcactca tggttatggc  15660
agcactgcat aattctctta ctgtcatgcc atccgtaaga tgcttttctg tgactggtga  15720
gtactcaacc aagtcattct gagaatagtg tatgcggcga ccgagttgct cttgcccggc  15780
gtcaatacgg gataataccg cgccacatag cagaacttta aaagtgctca tcattggaaa  15840
acgttcttcg gggcgaaaac tctcaaggat cttaccgctg ttgagatcca gttcgatgta  15900
acccactcgt gcacccaact gatcttcagc atcttttact ttcaccagcg tttctgggtg  15960
agcaaaaaca ggaaggcaaa atgccgcaaa aaagggaata agggcgacac ggaaatgttg  16020
aatactcata ctcttccttt ttcaatatta ttgaagcatt tatcagggtt attgtctcat  16080
gagcggatac atatttgaat gtatttagaa aaataaacaa ataggggttc cgcgcacatt  16140
tccccgaaaa gtgccacctg acgtctaaga aaccattatt atcatgacat taacctataa  16200
```

aaataggcgt atcacgaggc cctttcgtct cgcgcgtttc ggtgatgacg gtgaaaacct 16260
ctgacacatg cagctcccgg agacggtcac agcttgtctg taagcggatg ccgggagcag 16320
acaagcccgt cagggcgcgt cagcgggtgt tggcgggtgt cggggctggc ttaactatgc 16380
ggcatcagag cagattgtac tgagagtgca ccatatgcgg tgtgaaatac cgcacagatg 16440
cgtaaggaga aaataccgca tcaggcgcca ttcgccattc aggctgcgca actgttggga 16500
agggcgatcg gtgcgggcct cttcgctatt acgccagctg gcgaaagggg gatgtgctgc 16560
aaggcgatta agttgggtaa cgccagggtt ttcccagtca cgacgttgta aaacgacggc 16620
cagtgaattc gagctcggta cctcgcgaat gcatctagat acgtttaaac agcgctacca 16680
actttgtttg gtctgatgag tccgtgagga cgaaacccgg agtcccgggt caccaaacaa 16740
agttgggtaa ggatagttca atcaatgatc attttctagt gcacttagga ttcaagatcc 16800
tattatcagg gacaagagca ggattaagga tatccgagat gtggctgcag agcctgctgc 16860
tcttgggcac tgtggcctgc agcatctctg cacccgcccg ctcgcccagc cccagcacgc 16920
agccctggga gcatgtgaat gccatccagg aggcccggcg tctcctgaac ctgagtagag 16980
acactgctgc tgagatgaat gaaacagtag aagtcatctc agaaatgttt gacctccagg 17040
agccgacctg cctacagacc cgcctggagc tgtacaagca gggcctgcgg ggcagcctca 17100
ccaagctcaa gggccccttg accatgatgg ccagccacta caagcagcac tgccctccaa 17160
ccccggaaac ttcctgtgca acccagatta tcacctttga aagtttcaaa gagaacctga 17220
aggactttct gcttgtcatc ccctttgact gctgggagcc agtccaggag tgatagtttc 17280
tgacatccgg cgggtgactc acaacgcggc cgcagccacc atgcagatcc cacaggcgcc 17340
ctggccagtc gtctgggcgg tgctacaact gggctggcgg ccaggatggt tcttagactc 17400
cccagacagg ccctggaacc cccccacctt ctccccagcc ctgctcgtgg tgaccgaagg 17460
ggacaacgcc accttcacct gcagcttctc caacacatcg gagagcttcg tgctaaactg 17520
gtaccgcatg agccccagca accagacgga caagctggcc gccttccccg aggaccgcag 17580
ccagcccggc caggactgcc gcttccgtgt cacacaactg cccaacgggc gtgacttcca 17640
catgagcgtg gtcagggccc ggcgcaatga cagcggcacc tacctctgtg gggccatctc 17700
cctggccccc aaggcgcaga tcaaagagag cctgcgggca gagctcaggg tgacagagag 17760
aagggcagaa gtgcccacag cccaccccag cccctcaccc aggtcagccg gccagttcca 17820
aggctccgga gccacgaact tctctctgtt aaagcaagca ggagacgtgg aagaaaaccc 17880
cggtcccatg aaggtacagc ccaagcacct tgggtgtgtt ggactgagct gcttttattt 17940
ggctgtaaaa tcaatagaag aggaaaggaa tgtcccattg gcaactgact tgatccgaat 18000
aagtcaatat aggtttacgg tttcagactt gatgagaatg gaaaagattg tattggagaa 18060
ggtgtgttgg aaagtcaaag ctactactgc ctttcaattt ctgcaactgt attattcact 18120
ccttcaagag aacttgccac ttgaaaggag aaatagcatt aattttgaaa gactagaagc 18180
tcaactgaag gcatgtcatt gcaggatcat attttctaaa gcaaagcctt ctgtgttggc 18240
attgtctatc attgcattag agatccaagc acagaagtgt gtagagttaa cagaaggaat 18300
agaatgtctt cagaaacatt ccaagataaa tggcagagat ctgaccttct ggcaagagct 18360
tgtatccaaa tgtttaactg aatattcatc aaataagtgt tccaaaccaa atgttcagaa 18420
gttgaaatgg attgtttctg ggcgtactgc acggcaattg aagcatagct actacagaat 18480
aactcacctt ccaacaattc ctgaaatggt cccttaaatt tctgacatcc ggcgggtgac 18540

-continued tcacaacgcg gccgcagcca ccatgagagc tgcacccctc ctcctggcca gggcagcaag 18600
ccttagcctt ggcttcttgt ttctgctttt tttctggcta gaccgaagtg tactagccaa 18660
ggagttgaag tttgtgactt tggtgtttcg gcatggagac cgaagtccca ttgacacctt 18720
tcccactgac cccataaagg aatcctcatg gccacaagga tttggccaac tcacccagct 18780
gggcatggag cagcattatg aacttggaga gtatataaga aagagatata gaaaattctt 18840
gaatgagtcc tataaacatg aacaggttta tattcgaagc acagacgttg accggacttt 18900
gatgagtgct atgacaaacc tggcagccct gtttcccca gaaggtgtca gcatctggaa 18960
tcctatccta ctctggcagc ccatcccggt gcacacagtt cctctttctg aagatcagtt 19020
gctatacctg cctttcagga actgccctcg ttttcaagaa cttgagagtg agactttgaa 19080
atcagaggaa ttccagaaga ggctgcaccc ttataaggat tttatagcta ccttgggaaa 19140
actttcagga ttacatggcc aggacctttt tggaatttgg agtaaagtct acgacccttt 19200
atattgtgag agtgttcaca atttcacttt accctcctgg gccactgagg acaccatgac 19260
taagttgaga gaattgtcag aattgtccct cctgtccctc tatggaattc acaagcagaa 19320
agagaaatct aggctccaag gggtgtcct ggtcaatgaa atcctcaatc acatgaagag 19380
agcaactcag ataccaagct acaaaaaact tatcatgtat tctgcgcatg acactactgt 19440
gagtggccta cagatggcgc tagatgttta caacggactc cttcctccct atgcttcttg 19500
ccacttgacg gaattgtact ttgagaaggg ggagtacttt gtggagatgt actatcggaa 19560
tgagacgcag cacgagccgt atcccctcat gctacctggc tgcagcccta gctgtcctct 19620
ggagaggttt gctgagctgg ttggccctgt gatccctcaa gactggtcca cggagtgtat 19680
gaccacaaac agccatcaag gtactgagga cagtacagat taggtgcgag aggccgagga 19740
ccagaacaac atccgcctac cctccatcat tgttataaaa aacttaggaa ccaggtccac 19800
acagccgcca gcccatcaac catccactcc cacgattgga gccgatggcc acacttttaa 19860
ggagcttagc attgttcaaa agaaacaagg acaaaccacc cattacatca ggatccggtg 19920
gagccatcag aggaatcaaa cacattatta tagtaccaat ccctggagat tcctcaatta 19980
ccactcgatc cagacttctg gaccggttgg tcaggttaat tggaaacccg gatgtgagcg 20040
ggcccaaact aacaggggca ctaataggta tattatcctt atttgtggag tctccaggtc 20100
aattgattca gaggatcacc gatgaccctg acgttagcat aaggctgtta gaggttgtcc 20160
agagtgacca gtcacaatct ggccttacct tcgcatcaag aggtaccaac atggaggatg 20220
aggcggacca atacttttca catgatgatc caattagtag tgatcaatcc aggttcggat 20280
ggttcgagaa caaggaaatc tcagatattg aagtgcaaga ccctgaggga ttcaacatga 20340
ttctgggtac catcctagct caaatttggg tcttgctcgc aaaggcggtt acggccccag 20400
acacggcagc tgattcggag ctaagaaggt ggataaagta cacccaacaa agaagggtag 20460
ttggtgaatt tagattggag agaaaatggt tggatgtggt gaggaacagg attgccgagg 20520
acctctcctt acgccgattc atggtcgctc taatcctgga tatcaagaga acacccggaa 20580
acaaacccag gattgctgaa atgatatgtg acattgatac atatatcgta gaggcaggat 20640
tagccagttt tatcctgact attaagtttg ggatagaaac tatgtatcct gctcttggac 20700
tgcatgaatt tgctggtgag ttatccacac ttgagtcctt gatgaacctt taccagcaaa 20760
tgggggaaac tgcaccctac atggtaatcc tggagaactc aattcagaac aagttcagtg 20820
caggatcata ccctctgctc tggagctatg ccatgggagt aggagtggaa cttgaaaact 20880
ccatgggagg tttgaacttt ggccgatctt actttgatcc agcatatttt agattagggc 20940
aagagatggt aaggaggtca gctggaaagg tcagttccac attggcatct gaactcggta 21000
tcactgccga ggatgcaagg cttgtttcag agattgcaat gcatactact gaggacaaga 21060
tcagtagagc ggttggaccc agacaagccc aagtatcatt tctacacggt gatcaaagtg 21120
agaatgagct accgagattg gggggcaagg aagataggag ggtcaaacag agtcgaggag 21180
aagccaggga gagctacaga gaaaccgggc ccagcagagc aagtgatgcg agagctgccc 21240
atcttccaac cggcacaccc ctagacattg acactgcatc ggagtccagc caagatccgc 21300
aggacagtcg aaggtcagct gacgccctgc ttaggctgca agccatggca ggaatctcgg 21360
aagaacaagg ctcagacacg gacaccccta tagtgtacaa tgacagaaat cttctagact 21420
aggtgcgaga ggccgaggac cagaacaaca tccgcctacc ctccatcatt gttataaaaa 21480
acttaggaac caggtccaca cagccgccag cccatcaacc atccactccc acgattggag 21540
ccgatggcag aagagcaggc acgccatgtc aaaaacggac tggaatgcat ccgggctctc 21600
aaggccgagc ccatcggctc actggccatc gaggaagcta tggcagcatg gtcagaaata 21660
tcagacaacc caggacagga gcgagccacc tgcagggaag agaaggcagg cagttcgggt 21720
ctcagcaaac catgcctctc agcaattgga tcaactgaag gcggtgcacc tcgcatccgc 21780

<210> SEQ ID NO 25
<211> LENGTH: 21062
<212> TYPE: DNA
<213> ORGANISM: Artificial Sequence
<220> FEATURE:
<223> OTHER INFORMATION: Artificial DNA containing MV genome modified by inserting GMCSF-ires-sPD1-2A-CytD - pMV-GsPC

<400> SEQUENCE: 25
accaaacaaa gttgggtaag gatagttcaa tcaatgatca ttttctagtg cacttaggat 60
tcaagatcct attatcaggg acaagagcag gattaaggat atccgagatg tggctgcaga 120
gcctgctgct cttgggcact gtggcctgca gcatctctgc acccgcccgc tcgcccagcc 180
ccagcacgca gccctgggag catgtgaatg ccatccagga ggcccggcgt ctcctgaacc 240
tgagtagaga cactgctgct gagatgaatg aaacagtaga agtcatctca gaaatgtttg 300
acctccagga gccgacctgc ctacagaccc gcctggagct gtacaagcag ggcctgcggg 360
gcagcctcac caagctcaag ggccccttga ccatgatggc cagccactac aagcagcact 420
gccctccaac cccggaaact tcctgtgcaa cccagattat cacctttgaa agtttcaaag 480
agaacctgaa ggactttctg cttgtcatcc cctttgactg ctgggagcca gtccaggagt 540
gatagtttct gacatccggc gggtgactca caacgcggcc gcagccacca tgcagatccc 600
acaggcgccc tggccagtcg tctgggcggt gctacaactg ggctggcggc caggatggtt 660
cttagactcc ccagacaggc cctggaaccc ccccaccttc tccccagccc tgctcgtggt 720
gaccgaaggg gacaacgcca ccttcacctg cagcttctcc aacacatcgg agagcttcgt 780
gctaaactgg taccgcatga gccccagcaa ccagacggac aagctggccg ccttccccga 840
ggaccgcagc cagcccggcc aggactgccg cttccgtgtc acacaactgc ccaacgggcg 900
tgacttccac atgagcgtgg tcagggcccg gcgcaatgac agcggcacct acctctgtgg 960
ggccatctcc ctggccccca aggcgcagat caaagagagc ctgcgggcag agctcagggt 1020
gacagagaga agggcagaag tgcccacagc ccaccccagc ccctcaccca ggtcagccgg 1080
ccagttccaa ggctccggag ccacgaactt ctctctgtta aagcaagcag gagacgtgga 1140
agaaaacccc ggtcccatgg tgacaggggg aatggcaagc aagtgggatc agaagggtat 1200
ggacattgcc tatgaggagg cggccttagg ttacaaagag ggtggtgttc ctattggcgg 1260
atgtcttatc aataacaaag acggaagtgt tctcggtcgt ggtcacaaca tgagatttca 1320
aaagggatct gccacactac atggtgagat ctccactttg gaaaactgtg ggagattaga 1380
gggcaaagtg tacaaagata ccactttgta tacgacgctg tctccatgcg acatgtgtac 1440
aggtgccatc atcatgtatg gtattccacg ctgtgttgtc ggtgagaacg ttaatttcaa 1500
aagtaagggc gagaaatatt tacaaactag aggtcacgag gttgttgttg ttgacgatga 1560
gaggtgtaaa aagatcatga aacaatttat cgatgaaaga cctcaggatt ggtttgaaga 1620
tattggtgag gcttcggaac catttaagaa cgtctacttg ctacctcaaa caaaccaatt 1680
gctgggtttg tacaccatca tcagaaataa gaatacaact agacctgatt tcattttcta 1740
ctccgataga atcatcagat tgttggttga agaaggtttg aaccatctac ctgtgcaaaa 1800
gcaaattgtg gaaactgaca ccaacgaaaa cttcgaaggt gtctcattca tgggtaaaat 1860
ctgtggtgtt tccattgtca gagctggtga atcgatggag caaggattaa gagactgttg 1920
taggtctgtg cgtatcggta aaattttaat tcaaagggac gaggagactg ctttaccaaa 1980
gttattctac gaaaaattac cagaggatat atctgaaagg tatgtcttcc tattagaccc 2040
aatgctggcc accggtggta gtgctatcat ggctacagaa gtcttgatta agagaggtgt 2100
taagccagag agaatttact tcttaaacct aatctgtagt aaggaaggga ttgaaaaata 2160
ccatgccgcc ttcccagagg tcagaattgt tactggtgcc ctcgacagag gtctagatga 2220
aaacaagtat ctagttccag ggttgggtga ctttggtgac agatactact gtgtttaagt 2280
gcgagaggcc gaggaccaga acaacatccg cctaccctcc atcattgtta taaaaaactt 2340
aggaaccagg tccacacagc cgccagccca tcaaccatcc actcccacga ttggagccga 2400
tggccacact tttaaggagc ttagcattgt tcaaaagaaa caaggacaaa ccacccatta 2460
catcaggatc cggtggagcc atcagaggaa tcaaacacat tattatagta ccaatccctg 2520
gagattcctc aattaccact cgatccagac ttctggaccg gttggtcagg ttaattggaa 2580
acccggatgt gagcgggccc aaactaacag gggcactaat aggtatatta tccttatttg 2640
tggagtctcc aggtcaattg attcagagga tcaccgatga ccctgacgtt agcataaggc 2700
tgttagaggt tgtccagagt gaccagtcac aatctggcct taccttcgca tcaagaggta 2760
ccaacatgga ggatgaggcg gaccaatact tttcacatga tgatccaatt agtagtgatc 2820
aatccaggtt cggatggttc gagaacaagg aaatctcaga tattgaagtg caagaccctg 2880
agggattcaa catgattctg ggtaccatcc tagctcaaat ttgggtcttg ctcgcaaagg 2940
cggttacggc cccagacacg gcagctgatt cggagctaag aaggtggata aagtacaccc 3000
aacaaagaag ggtagttggt gaatttagat tggagagaaa atggttggat gtggtgagga 3060
acaggattgc cgaggacctc tccttacgcc gattcatggt cgctctaatc ctggatatca 3120
agagaacacc cggaaacaaa cccaggattg ctgaaatgat atgtgacatt gatacatata 3180
tcgtagaggc aggattagcc agttttatcc tgactattaa gtttgggata gaaactatgt 3240
atcctgctct tggactgcat gaatttgctg gtgagttatc cacacttgag tccttgatga 3300
acctttacca gcaaatgggg gaaactgcac cctacatggt aatcctggag aactcaattc 3360
agaacaagtt cagtgcagga tcataccctc tgctctggag ctatgccatg ggagtaggag 3420
tggaacttga aaactccatg ggaggtttga actttggccg atcttacttt gatccagcat 3480
attttagatt agggcaagag atggtaagga ggtcagctgg aaaggtcagt tccacattgg 3540

-continued

```
catctgaact cggtatcact gccgaggatg caaggcttgt ttcagagatt gcaatgcata   3600
ctactgagga caagatcagt agagcggttg gacccagaca agcccaagta tcatttctac   3660
acggtgatca aagtgagaat gagctaccga gattgggggg caaggaagat aggagggtca   3720
aacagagtcg aggagaagcc agggagagct acagagaaac cgggcccagc agagcaagtg   3780
atgcgagagc tgcccatctt ccaaccggca caccccctaga cattgacact gcatcggagt  3840
ccagccaaga tccgcaggac agtcgaaggt cagctgacgc cctgcttagg ctgcaagcca   3900
tggcaggaat ctcggaagaa caaggctcag acacggacac ccctatagtg tacaatgaca   3960
gaaatcttct agactaggtg cgagaggccg aggaccagaa caacatccgc ctaccctcca   4020
tcattgttat aaaaaactta ggaaccaggt ccacacagcc gccagcccat caaccatcca   4080
ctcccacgat tggagccgat ggcagaagag caggcacgcc atgtcaaaaa cggactggaa   4140
tgcatccggg ctctcaaggc cgagcccatc ggctcactgg ccatcgagga agctatggca   4200
gcatggtcag aaatatcaga caacccagga caggagcgag ccacctgcag ggaagagaag   4260
gcaggcagtt cgggtctcag caaaccatgc ctctcagcaa ttggatcaac tgaaggcggt   4320
gcacctcgca tccgcggtca gggacctgga gagagcgatg acgacgctga aactttggga   4380
atccccccaa gaaatctcca ggcatcaagc actgggttac agtgttatta tgtttatgat   4440
cacagcggtg aagcggttaa gggaatccaa gatgctgact ctatcatggt tcaatcaggc   4500
cttgatggtg atagcaccct ctcaggagga gacaatgaat ctgaaaacag cgatgtggat   4560
attggcgaac ctgataccga gggatatgct atcactgacc ggggatctgc tcccatctct   4620
atggggttca gggcttctga tgttgaaact gcagaaggag gggagatcca cgagctcctg   4680
agactccaat ccagaggcaa caactttccg aagcttggga aaactctcaa tgttcctccg   4740
cctccggacc ccggtagggc cagcacttcc gggacaccca ttaaaaaggg cacagacgcg   4800
agattagcct catttggaac ggagatcgcg tctttattga caggtggtgc aacccaatgt   4860
gctcgaaagt caccctcgga accatcaggg ccaggtgcac ctgcggggaa tgtccccgag   4920
tgtgtgagca atgccgcact gatacaggag tggacacccg aatctggtac cacaatctcc   4980
ccgagatccc agaataatga agaaggggga gactattatg atgatgagct gttctctgat   5040
gtccaagata ttaaaacagc cttggccaaa atacacgagg ataatcagaa gataatctcc   5100
aagctagaat cactgctgtt attgaaggga gaagttgagt caattaagaa gcagatcaac   5160
aggcaaaata tcagcatatc caccctggaa ggacacctct caagcatcat gatcgccatt   5220
cctggacttg ggaaggatcc caacgacccc actgcagatg tcgaaatcaa tcccgacttg   5280
aaacccatca taggcagaga ttcaggccga gcactggccg aagttctcaa gaaacccgtt   5340
gccagccgac aactccaagg aatgacaaat ggacggacca gttccagagg acagctgctg   5400
aaggaatttc agctaaagcc gatcgggaaa aagatgagct cagccgtcgg gtttgttcct   5460
gacaccggcc ctgcatcacg cagtgtaatc cgctccatta taaaatccag ccggctagag   5520
gaggatcgga agcgttacct gatgactctc cttgatgata tcaaaggagc caatgatctt   5580
gccaagttcc accagatgct gatgaagata ataatgaagt agctacagct caacttacct   5640
gccaacccca tgccagtcga cccaactagt acaacctaaa tccattataa aaaacttagg   5700
agcaaagtga ttgcctccca agttccacaa tgacagagat ctacgacttc gacaagtcgg   5760
catgggacat caaagggttg atcgctccga tacaacccac cacctacagt gatggcaggc   5820
tggtgcccca ggtcagagtc atagatcctg gtctaggcga caggaaggat gaatgcttta   5880
tgtacatgtt tctgctgggg gttgttgagg acagcgatcc cctagggcct ccaatcgggc   5940
```

gagcatttgg gtccctgccc ttaggtgttg gcagatccac agcaaagccc gaaaaactcc 6000
tcaaagaggc cactgagctt gacatagttg ttagacgtac agcagggctc aatgaaaaac 6060
tggtgttcta caacaacacc ccactaactc tcctcacacc ttggagaaag gtcctaacaa 6120
cagggagtgt cttcaacgca aaccaagtgt gcaatgcggt taatctgata ccgctcgata 6180
ccccgcagag gttccgtgtt gtttatatga gcatcacccg tctttcggat aacgggtatt 6240
acaccgttcc tagaagaatg ctggaattca gatcggtcaa tgcagtggcc ttcaacctgc 6300
tggtgaccct taggattgac aaggcgatag gccctgggaa gatcatcgac aatacagagc 6360
aacttcctga ggcaacattt atggtccaca tcgggaactt caggagaaag aagagtgaag 6420
tctactctgc cgattattgc aaaatgaaaa tcgaaaagat gggcctggtt tttgcacttg 6480
gtgggatagg gggcaccagt cttcacatta gaagcacagg caaaatgagc aagactctcc 6540
atgcacaact cgggttcaag aagaccttat gttacccgct gatagatatc aatgaagacc 6600
ttaatcgatt actctggagg agcagatgca agatagtaag aatccaggca gttttgcagc 6660
catcagttcc tcaagaattc cgcatttacg acgacgtgat cataaatgat gaccaaggac 6720
tattcaaagt tctgtagacc gtagtgccca gcaatgcccg aaaacgaccc ccctcacaat 6780
gacagccaga aggcccggac aaaaaagccc cctccgaaag actccacgga ccaagcgaga 6840
ggccagccag cagccgacgg caagcgcgaa caccaggcgg ccccagcaca gaacagccct 6900
gatacaaggc caccaccagc caccccaatc tgcatcctcc tcgtgggacc cccgaggacc 6960
aacccccaag gctgcccccg atccaaacca ccaaccgcat ccccaccacc cccgggaaag 7020
aaacccccag caattggaag gcccctcccc ctcttcctca acacaagaac tccacaaccg 7080
aaccgcacaa gcgaccgagg tgacccaacc gcaggcatcc gactccctag acagatcctc 7140
tctccccggc aaactaaaca aaacttaggg ccaaggaaca tacacaccca acagaaccca 7200
gaccccggcc cacggcgccg cgcccccaac ccccgacaac cagagggagc ccccaaccaa 7260
tcccgccggc tcccccggtg cccacaggca gggacaccaa cccccgaaca gacccagcac 7320
ccaaccatcg acaatccaag acggggggc cccccaaaa aaaggccccc aggggccgac 7380
agccagcacc gcgaggaagc ccacccaccc cacacacgac cacggcaacc aaaccagaac 7440
ccagaccacc ctgggccacc agctcccaga ctcggccatc accccgcaga aaggaaaggc 7500
cacaacccgc gcaccccagc cccgatccgg cggggagcca cccaacccga accagcaccc 7560
aagagcgatc cccgaaggac ccccgaaccg caaaggacat cagtatccca cagcctctcc 7620
aagtcccccg gtctcctccc cttctcgaag ggaccaaaag atcaatccac cacacccgac 7680
gacactcaac tccccacccc taaaggagac accgggaatc ccagaatcaa gactcatcca 7740
atgtccatca tgggtctcaa ggtgaacgtc tctgccatat tcatggcagt actgttaact 7800
ctccaaacac ccaccggtca aatccattgg ggcaatctct ctaagatagg ggtggtagga 7860
ataggaagtg caagctacaa agttatgact cgttccagcc atcaatcatt agtcataaaa 7920
ttaatgccca atataactct cctcaataac tgcacgaggg tagagattgc agaatacagg 7980
agactactga gaacagtttt ggaaccaatt agagatgcac ttaatgcaat gacccagaat 8040
ataagaccgg ttcagagtgt agcttcaagt aggagacaca agagatttgc gggagtagtc 8100
ctggcaggtg cggccctagg cgttgccaca gctgctcaga taacagccgg cattgcactt 8160
caccagtcca tgctgaactc tcaagccatc gacaatctga gagcgagcct ggaaactact 8220
aatcaggcaa ttgaggcaat cagacaagca gggcaggaga tgatattggc tgttcagggt 8280

-continued gtccaagact acatcaataa tgagctgata ccgtctatga accaactatc ttgtgattta 8340
atcggccaga agctcgggct caaattgctc agatactata cagaaatcct gtcattattt 8400
ggccccagct tacgggaccc catatctgcg gagatatcta tccaggcttt gagctatgcg 8460
cttggaggag acatcaataa ggtgttagaa aagctcggat acagtggagg tgatttactg 8520
ggcatcttag agagcagagg aataaaggcc cggataactc acgtcgacac agagtcctac 8580
ttcattgtcc tcagtatagc ctatccgacg ctgtccgaga ttaagggggt gattgtccac 8640
cggctagagg gggtctcgta caacataggc tctcaagagt ggtataccac tgtgcccaag 8700
tatgttgcaa cccaagggta ccttatctcg aattttgatg agtcatcgtg tactttcatg 8760
ccagagggga ctgtgtgcag ccaaaatgcc ttgtacccga tgagtcctct gctccaagaa 8820
tgcctccggg ggtccaccaa gtcctgtgct cgtacactcg tatccgggtc ttttgggaac 8880
cggttcattt tatcacaagg gaacctaata gccaattgtg catcaatcct ttgcaagtgt 8940
tacacaacag gaacgatcat taatcaagac cctgacaaga tcctaacata cattgctgcc 9000
gatcactgcc cggtagtcga ggtgaacggc gtgaccatcc aagtcgggag caggaggtat 9060
ccagatgctg tgtacttgca cagaattgac ctcggtcctc ccatatcatt ggagaggttg 9120
gacgtaggga caaatctggg gaatgcaatt gctaagttgg aggatgccaa ggaattgttg 9180
gagtcatcgg accagatatt gaggagtatg aaaggtttat cgagcactag catagtctac 9240
atcctgattg cagtgtgtct tggagggttg atagggatcc ccgctttaat atgttgctgc 9300
agggggcgtt gtaacaaaaa gggagaacaa gttggtatgt caagaccagg cctaaagcct 9360
gatcttacgg gaacatcaaa atcctatgta aggtcgctct gatcctctac aactcttgaa 9420
acacaaatgt cccacaagtc tcctcttcgt catcaagcaa ccaccgcacc cagcatcaag 9480
cccacctgaa attatctccg gcttccctct ggccgaacaa tatcggtagt taattaaaac 9540
ttagggtgca agatcatcca caatgtcacc acaacgagac cggataaatg ccttctacaa 9600
agataacccc catcccaagg gaagtaggat agtcattaac agagaacatc ttatgattga 9660
tagaccttat gttttgctgg ctgttctgtt tgtcatgttt ctgagcttga tcgggttgct 9720
agccattgca ggcattagac ttcatcgggc agccatctac accgcagaga tccataaaag 9780
cctcagcacc aatctagatg taactaactc aatcgagcat caggtcaagg acgtgctgac 9840
accactcttc aaaatcatcg gtgatgaagt gggcctgagg acacctcaga gattcactga 9900
cctagtgaaa ttcatctctg acaagattaa attccttaat ccggataggg agtacgactt 9960
cagagatctc acttggtgta tcaacccgcc agagagaatc aaattggatt atgatcaata 10020
ctgtgcagat gtggctgctg aagagctcat gaatgcattg gtgaactcaa ctctactgga 10080
gaccagaaca accaatcagt tcctagctgt ctcaaaggga aactgctcag ggcccactac 10140
aatcagaggt caattctcaa acatgtcgct gtccctgtta gacttgtatt taggtcgagg 10200
ttacaatgtg tcatctatag tcactatgac atcccaggga atgtatgggg gaacttacct 10260
agtggaaaag cctaatctga gcagcaaaag gtcagagttg tcacaactga gcatgtaccg 10320
agtgtttgaa gtaggtgtta tcagaaatcc gggtttgggg gctccggtgt tccatatgac 10380
aaactatctt gagcaaccag ccagtaatga tctcagcaac tgtatggtgg ctttgggggga 10440 gctcaaactc gcagcccttt gtcacgggga agattctatc acaattccct atcagggatc 10500
agggaaaggt gtcagcttcc agctcgtcaa gctaggtgtc tggaaatccc caaccgacat 10560
gcaatcctgg gtccccttat caacggatga tccagtgata gacaggcttt acctctcatc 10620
tcacagaggt gttatcgctg acaatcaagc aaaatgggct gtcccgacaa cacgaacaga 10680
tgacaagttg cgaatggaga catgcttcca acaggcgtgt aagggtaaaa tccaagcact 10740
ctgcgagaat cccgagtggg caccattgaa ggataacagg attccttcat acggggtctt 10800
gtctgttgat ctgagtctga cagttgagct taaaatcaaa attgcttcgg gattcgggcc 10860
attgatcaca cacggttcag ggatggacct atacaaatcc aaccacaaca atgtgtattg 10920
gctgactatc ccgccaatga agaacctagc cttaggtgta atcaacacat tggagtggat 10980
accgagattc aaggttagtc cctacctctt caatgtccca attaaggaag caggcgaaga 11040
ctgccatgcc ccaacatacc tacctgcgga ggtggatggt gatgtcaaac tcagttccaa 11100
tctggtgatt ctacctggtc aagatctcca atatgttttg gcaacctacg atacttccag 11160
ggttgaacat gctgtggttt attacgttta cagcccaggc cgctcatttt cttactttta 11220
tccttttagg ttgcctataa agggggtccc catcgaatta caagtggaat gcttcacatg 11280
ggaccaaaaa ctctggtgcc gtcacttctg tgtgcttgcg gactcagaat ctggtggaca 11340
tatcactcac tctgggatgg tgggcatggg agtcagctgc acagtcaccc gggaagatgg 11400
aaccaatcgc agatagggct gctagtgaac caatctcatg atgtcaccca gacatcaggc 11460
atacccacta gtgtgaaata gacatcagaa ttaagaaaaa cgtagggtcc aagtggttcc 11520
ccgttatgga ctcgctatct gtcaaccaga tcttataccc tgaagttcac ctagatagcc 11580
cgatagttac caataagata gtagccatcc tggagtatgc tcgagtccct cacgcttaca 11640
gcctggagga ccctacactg tgtcagaaca tcaagcaccg cctaaaaaac ggattttcca 11700
accaaatgat tataaacaat gtggaagttg ggaatgtcat caagtccaag cttaggagtt 11760
atccggccca ctctcatatt ccatatccaa attgtaatca ggatttattt aacatagaag 11820
acaaagagtc aacgaggaag atccgtgaac tcctcaaaaa ggggaattcg ctgtactcca 11880
aagtcagtga taaggttttc caatgcttaa gggacactaa ctcacggctt ggcctaggct 11940
ccgaattgag ggaggacatc aaggagaaag ttattaactt gggagtttac atgcacagct 12000
cccagtggtt tgagcccttt ctgttttggt ttacagtcaa gactgagatg aggtcagtga 12060
ttaaatcaca aacccatact tgccatagga ggagacacac acctgtattc ttcactggta 12120
gttcagttga gttgctaatc tctcgtgacc ttgttgctat aatcagtaaa gagtctcaac 12180
atgtatatta cctgacattt gaactggttt tgatgtattg tgatgtcata gaggggaggt 12240
taatgacaga gaccgctatg actattgatg ctaggtatac agagcttcta ggaagagtca 12300
gatacatgtg gaaactgata gatggtttct tccctgcact cgggaatcca acttatcaaa 12360
ttgtagccat gctggagcct ctttcacttg cttacctgca gctgagggat ataacagtag 12420
aactcagagg tgctttcctt aaccactgct ttactgaaat acatgatgtt cttgaccaaa 12480
acgggttttc tgatgaaggt acttatcatg agttaattga agctctagat tacattttca 12540
taactgatga catacatctg acaggggaga ttttctcatt tttcagaagt ttcggccacc 12600
ccagacttga agcagtaacg gctgctgaaa atgttaggaa atacatgaat cagcctaaag 12660
tcattgtgta tgagactctg atgaaaggtc atgccatatt ttgtggaatc ataatcaacg 12720
gctatcgtga caggcacgga ggcagttggc caccgctgac cctccccctg catgctgcag 12780
acacaatccg gaatgctcaa gcttcaggtg aagggttaac acatgagcag tgcgttgata 12840
actggagatc ttttgctgga gtgaaatttg gctgctttat gcctcttagc ctggatagtg 12900
atctgacaat gtacctaaag gacaaggcac ttgctgctct ccaaagggaa tgggattcag 12960
tttacccgaa agagttcctg cgttacgacc ctcccaaggg aaccgggtca cggaggcttg 13020

```
tagatgtttt ccttaatgat tcgagctttg acccatatga tgtgataatg tatgttgtaa  13080
gtggagctta cctccatgac cctgagttca acctgtctta cagcctgaaa gaaaaggaga  13140
tcaaggaaac aggtagactt tttgctaaaa tgacttacaa aatgagggca tgccaagtga  13200
ttgctgaaaa tctaatctca aacgggattg gcaaatattt taaggacaat gggatggcca  13260
aggatgagca cgatttgact aaggcactcc acactctagc tgtctcagga gtccccaaag  13320
atctcaaaga aagtcacagg ggggggccag tcttaaaaac ctactcccga agcccagtcc  13380
acacaagtac caggaacgtg agagcagcaa aagggtttat agggttccct caagtaattc  13440
ggcaggacca agacactgat catccggaga atatggaagc ttacgagaca gtcagtgcat  13500
ttatcacgac tgatctcaag aagtactgcc ttaattggag atatgagacc atcagcttgt  13560
ttgcacagag gctaaatgag atttacggat tgccctcatt tttccagtgg ctgcataaga  13620
ggcttgagac ctctgtcctg tatgtaagtg accctcattg cccccccgac cttgacgccc  13680
atatcccgtt atataaagtc cccaatgatc aaatcttcat taagtaccct atgggaggta  13740
tagaagggta ttgtcagaag ctgtggacca tcagcaccat tccctatcta tacctggctg  13800
cttatgagag cggagtaagg attgcttcgt tagtgcaagg ggacaatcag accatagccg  13860
taacaaaaag ggtacccagc acatggccct acaaccttaa gaaacgggaa gctgctagag  13920
taactagaga ttactttgta attcttaggc aaaggctaca tgatattggc catcacctca  13980
aggcaaatga gacaattgtt tcatcacatt tttttgtcta ttcaaaagga atatattatg  14040
atgggctact tgtgtcccaa tcactcaaga gcatcgcaag atgtgtattc tggtcagaga  14100
ctatagttga tgaaacaagg gcagcatgca gtaatattgc tacaacaatg gctaaaagca  14160
tcgagagagg ttatgaccgt accttgcat attccctgaa cgtcctaaaa gtgatacagc  14220
aaattctgat ctctcttggc ttcacaatca attcaaccat gacccgggat gtagtcatac  14280
ccctcctcac gaacaacgac ctcttaataa ggatggcact gttgcccgct cctattgggg  14340
ggatgaatta tctgaatatg agcaggctgt ttgtcagaaa catcggtgat ccagtaacat  14400
catcaattgc tgatctcaag agaatgattc tcgcctcact aatgcctgaa gagaccctcc  14460
atcaagtaat gacacaacaa ccgggggact cttcattcct agactgggct agcgacccctt  14520
actcagcaaa tcttgtatgt gtccagagca tcactagact cctcaagaac ataactgcaa  14580
ggtttgtcct gatccatagt ccaaacccaa tgttaaaagg attattccat gatgacagta  14640
aagaagagga cgagggactg gcggcattcc tcatggacag gcatattata gtacctaggg  14700
cagctcatga aatcctggat catagtgtca caggggcaag agagtctatt gcaggcatgc  14760
tggataccac aaaaggcctg attcgagcca gcatgaggaa ggggggtta acctctcgag  14820
tgataaccag attgtccaat tatgactatg aacaattcag agcagggatg gtgctattga  14880
caggaagaaa gagaaatgtc ctcattgaca aagagtcatg ttcagtgcag ctggcgagag  14940
ctctaagaag ccatatgtgg gcgaggctag ctcgaggacg gcctatttac ggccttgagg  15000
tccctgatgt actagaatct atgcgaggcc accttattcg gcgtcatgag acatgtgtca  15060
tctgcgagtg tggatcagtc aactacggat ggttttttgt cccctcgggt tgccaactgg  15120
atgatattga caaggaaaca tcatccttga gagtcccata tattggttct accactgatg  15180
agagaacaga catgaagctt gccttcgtaa gagccccaag tcgatccttg cgatctgctg  15240
ttagaatagc aacagtgtac tcatgggctt acggtgatga tgatagctct tggaacgaag  15300
cctggttgtt ggctaggcaa agggccaatg tgagcctgga ggagctaagg gtgatcactc  15360
ccatctcaac ttcgactaat ttagcgcata ggttgaggga tcgtagcact caagtgaaat  15420
```

actcaggtac atcccttgtc cgagtggcga ggtataccac aatctccaac gacaatctct 15480
catttgtcat atcagataag aaggttgata ctaactttat ataccaacaa ggaatgcttc 15540
tagggttggg tgttttagaa acattgtttc gactcgagaa agataccgga tcatctaaca 15600
cggtattaca tcttcacgtc gaaacagatt gttgcgtgat cccgatgata gatcatccca 15660
ggatacccag ctcccgcaag ctagagctga gggcagagct atgtaccaac ccattgatat 15720
atgataatgc acctttaatt gacagagata caacaaggct atacacccag agccatagga 15780
ggcaccttgt ggaatttgtt acatggtcca caccccaact atatcacatt ttagctaagt 15840
ccacagcact atctatgatt gacctggtaa caaaatttga gaaggaccat atgaatgaaa 15900
tttcagctct catagggat gacgatatca atagtttcat aactgagttt ctgctcatag 15960
agccaagatt attcactatc tacttgggcc agtgtgcggc catcaattgg gcatttgatg 16020
tacattatca tagaccatca gggaaatatc agatgggtga gctgttgtca tcgttccttt 16080
ctagaatgag caaaggagtg tttaaggtgc ttgtcaatgc tctaagccac ccaaagatct 16140
acaagaaatt ctggcattgt ggtattatag agcctatcca tggtccttca cttgatgctc 16200
aaaacttgca cacaactgtg tgcaacatgg tttacacatg ctatatgacc tacctcgacc 16260
tgttgttgaa tgaagagtta gaagagttca catttctctt gtgtgaaagc gacgaggatg 16320
tagtaccgga cagattcgac aacatccagg caaaacactt atgtgttctg gcagatttgt 16380
actgtcaacc agggacctgc ccaccaattc gaggtctaag accggtagag aaatgtgcag 16440
ttctaaccga ccatatcaag gcagaggcta ggttatctcc agcaggatct tcgtggaaca 16500
taaatccaat tattgtagac cattactcat gctctctgac ttatctccgg cgaggatcga 16560
tcaaacagat aagattgaga gttgatccag gattcatttt cgacgccctc gctgaggtaa 16620
atgtcagtca gccaaagatc ggcagcaaca acatctcaaa tatgagcatc aaggctttca 16680
gacccccaca cgatgatgtt gcaaaattgc tcaaagatat caacacaagc aagcacaatc 16740
ttcccatttc agggggcaat ctcgccaatt atgaaatcca tgctttccgc agaatcgggt 16800
tgaactcatc tgcttgctac aaagctgttg agatatcaac attaattagg agatgccttg 16860
agccagggga ggacggcttg ttcttgggtg agggatcggg ttccatgttg atcacttata 16920
aggagatact taaactaaac aagtgcttct ataatagtgg ggtttccgcc aattctagat 16980
ctggtcaaag ggaattagca ccctatccct ccgaagttgg ccttgtcgaa cacagaatgg 17040
gagtaggtaa tattgtcaaa gtgctcttta acgggaggcc cgaagtcacg tgggtaggca 17100
gtgtagattg cttcaatttc atagttagta atatccctac ctctagtgtg gggtttatcc 17160
attcagatat agagaccttg cctaacaaag atactataga gaagctagag gaattggcag 17220
ccatcttatc gatggctctg ctcctgggca aaataggatc aatactggtg attaagctta 17280
tgcctttcag cggggatttt gttcagggat ttataagtta tgtagggtcc cattatagag 17340
aagtgaacct tgtataccct agatacagca acttcatatc tactgaatct tatttggtta 17400
tgacagatct caaggctaac cggctaatga atcctgaaaa gattaagcag cagataattg 17460
aatcatctgt gaggacttca cctggactta taggtcacat cctatccatt aagcaactaa 17520
gctgcataca agcaattgtg ggagacgcag ttagtagagg tgatatcaat cctactctga 17580
aaaaacttac acctatagag caggtgctga tcaattgcgg gttggcaatt aacggaccta 17640
agctgtgcaa agaattgatc caccatgatg ttgcctcagg gcaagatgga ttgcttaatt 17700
ctatactcat cctctacagg gagttggcaa gattcaaaga caaccaaaga agtcaacaag 17760
ggatgttcca cgcttacccc gtattggtaa gtagcaggca acgagaactt atatctagga 17820
tcacccgcaa attttggggg cacattcttc tttactccgg gaacagaaag ttgataaata 17880
agtttatcca gaatctcaag tccggctatc tgatactaga cttacaccag aatatcttcg 17940
ttaagaatct atccaagtca gagaaacaga ttattatgac gggggggtttg aaacgtgagt 18000
gggtttttaa ggtaacagtc aaggagacca aagaatggta taagttagtc ggatacagtg 18060
ccctgattaa ggactaattg gttgaactcc ggaaccctaa tcctgcccta ggtggttagg 18120
cattatttgc aatagattaa agaaaacttt gaaaatacga agtttctatt cccagctttg 18180
tctggtgccg gccatggtcc cagcctcctc gctggcggcc ggtgggcaac attccgaggg 18240
gaccgtcccc tcggtaatgg cgaatgggac cgtttaaacg tatctagatg cattcgcgag 18300
gtaccgagct cgaattcact ggccgtcgtt ttacaacgtc gtgactggga aaaccctggc 18360
gttacccaac ttaatcgcct tgcagcacat ccccctttcg ccagctggcg taatagcgaa 18420
gaggcccgca ccgatcgccc ttcccaacag ttgcgcagcc tgaatggcga atggcgcctg 18480
atgcggtatt ttctccttac gcatctgtgc ggtatttcac accgcatatg gtgcactctc 18540
agtacaatct gctctgatgc cgcatagtta agccagcccc gacacccgcc aacacccgct 18600
gacgcgccct gacgggcttg tctgctcccg gcatccgctt acagacaagc tgtgaccgtc 18660
tccgggagct gcatgtgtca gaggttttca ccgtcatcac cgaaacgcgc gagacgaaag 18720
ggcctcgtga tacgcctatt tttataggtt aatgtcatga taataatggt ttcttagacg 18780
tcaggtggca cttttcgggg aaatgtgcgc ggaaccccta tttgtttatt tttctaaata 18840
cattcaaata tgtatccgct catgagacaa taaccctgat aaatgcttca ataatattga 18900
aaaaggaaga gtatgagtat tcaacatttc cgtgtcgccc ttattccctt ttttgcggca 18960
ttttgccttc ctgtttttgc tcacccagaa acgctggtga aagtaaaaga tgctgaagat 19020
cagttgggtg cacgagtggg ttacatcgaa ctggatctca acagcggtaa gatccttgag 19080
agttttcgcc ccgaagaacg ttttccaatg atgagcactt ttaaagttct gctatgtggc 19140
gcggtattat cccgtattga cgccgggcaa gagcaactcg gtcgccgcat acactattct 19200
cagaatgact tggttgagta ctcaccagtc acagaaaagc atcttacgga tggcatgaca 19260
gtaagagaat tatgcagtgc tgccataacc atgagtgata acactgcggc caacttactt 19320
ctgacaacga tcggaggacc gaaggagcta accgcttttt tgcacaacat gggggatcat 19380
gtaactcgcc ttgatcgttg ggaaccggag ctgaatgaag ccataccaaa cgacgagcgt 19440
gacaccacga tgcctgtagc aatggcaaca acgttgcgca aactattaac tggcgaacta 19500
cttactctag cttcccggca acaattaata gactggatgg aggcggataa agttgcagga 19560
ccacttctgc gctcggccct tccggctggc tggtttattg ctgataaatc tggagccggt 19620
gagcgtgggt ctcgcggtat cattgcagca ctggggccag atggtaagcc ctcccgtatc 19680
gtagttatct acacgacggg gagtcaggca actatggatg aacgaaatag acagatcgct 19740
gagataggtg cctcactgat taagcattgg taactgtcag accaagttta ctcatatata 19800
ctttagattg atttaaaact tcatttttaa tttaaaagga tctaggtgaa gatccttttt 19860
gataatctca tgaccaaaat cccttaacgt gagttttcgt tccactgagc gtcagacccc 19920
gtagaaaaga tcaaaggatc ttcttgagat cctttttttc tgcgcgtaat ctgctgcttg 19980
caaacaaaaa aaccaccgct accagcggtg gtttgtttgc cggatcaaga gctaccaact 20040
ctttttccga aggtaactgg cttcagcaga gcgcagatac caaatactgt tcttctagtg 20100
tagccgtagt taggccacca cttcaagaac tctgtagcac cgcctacata cctcgctctg 20160
ctaatcctgt taccagtggc tgctgccagt ggcgataagt cgtgtcttac cgggttggac 20220
tcaagacgat agttaccgga taaggcgcag cggtcgggct gaacgggggg ttcgtgcaca 20280
cagcccagct tggagcgaac gacctacacc gaactgagat acctacagcg tgagctatga 20340
gaaagcgcca cgcttcccga agggagaaag gcggacaggt atccggtaag cggcagggtc 20400
ggaacaggag agcgcacgag ggagcttcca gggggaaacg cctggtatct ttatagtcct 20460
gtcgggtttc gccacctctg acttgagcgt cgatttttgt gatgctcgtc aggggggcgg 20520
agcctatgga aaaacgccag caacgcggcc tttttacggt tcctggcctt ttgctggcct 20580
tttgctcaca tgttctttcc tgcgttatcc cctgattctg tggataaccg tattaccgcc 20640
tttgagtgag ctgataccgc tcgccgcagc cgaacgaccg agcgcagcga gtcagtgagc 20700
gaggaagcgg aagagcgccc aatacgcaaa ccgcctctcc ccgcgcgttg gccgattcat 20760
taatgcagct ggcacgacag gtttcccgac tggaaagcgg gcagtgagcg caacgcaatt 20820
aatgtgagtt agctcactca ttaggcaccc caggctttac actttatgct tccggctcgt 20880
atgttgtgtg gaattgtgag cggataacaa tttcacacag gaaacagcta tgaccatgat 20940
tacgccaagc ttgcatgcag gcctctgcag tcgacgggcc cgggatccga tgggtttaaa 21000
cagcgctacc aactttgttt ggtctgatga gtccgtgagg acgaaacccg gagtcccggg 21060
tc 21062

<210> SEQ ID NO 26
<211> LENGTH: 21734
<212> TYPE: DNA
<213> ORGANISM: Artificial Sequence
<220> FEATURE:
<223> OTHER INFORMATION: Artificial DNA containing MV genome modified by inserting GMCSF-ires-sPD-1-2A-DnG1-ires-CytD - pMV-GsPDC

<400> SEQUENCE: 26
accaaacaaa gttgggtaag gatagttcaa tcaatgatca ttttctagtg cacttaggat 60
tcaagatcct attatcaggg acaagagcag gattaaggat atccgagatg tggctgcaga 120
gcctgctgct cttgggcact gtggcctgca gcatctctgc acccgcccgc tcgcccagcc 180
ccagcacgca gccctgggag catgtgaatg ccatccagga ggcccggcgt ctcctgaacc 240
tgagtagaga cactgctgct gagatgaatg aaacagtaga agtcatctca gaaatgtttg 300
acctccagga gccgacctgc ctacagaccc gcctggagct gtacaagcag ggcctgcggg 360
gcagcctcac caagctcaag ggccccttga ccatgatggc cagccactac aagcagcact 420
gccctccaac cccggaaact tcctgtgcaa cccagattat cacctttgaa agtttcaaag 480
agaacctgaa ggactttctg cttgtcatcc cctttgactg ctgggagcca gtccaggagt 540
gatttctgac atccggcggg tgactcacaa cgcggccgca gccaccatgc agatcccaca 600
ggcgccctgg ccagtcgtct gggcggtgct acaactgggc tggcggccag gatggttctt 660
agactcccca gacaggccct ggaacccccc caccttctcc ccagccctgc tcgtggtgac 720
cgaaggggac aacgccacct tcacctgcag cttctccaac acatcggaga gcttcgtgct 780
aaactggtac cgcatgagcc ccagcaacca gacggacaag ctggccgcct tccccgagga 840
ccgcagccag cccggccagg actgccgctt ccgtgtcaca caactgccca acgggcgtga 900
cttccacatg agcgtggtca gggcccggcg caatgacagc ggcacctacc tctgtggggc 960
catctccctg gcccccaagg cgcagatcaa agagagcctg cgggcagagc tcagggtgac 1020
agagagaagg gcagaagtgc ccacagccca ccccagcccc tcacccaggt cagccggcca 1080

-continued gttccaaggc tccggagcca cgaacttctc tctgttaaag caagcaggag acgtggaaga 1140
aaaccccggt cccatgaagg tacagcccaa gcaccttggg tgtgttggac tgagctgctt 1200
ttatttggct gtaaaatcaa tagaagagga aaggaatgtc ccattggcaa ctgacttgat 1260
ccgaataagt caatataggt ttacggtttc agacttgatg agaatggaaa agattgtatt 1320
ggagaaggtg tgttggaaag tcaaagctac tactgccttt caatttctgc aactgtatta 1380
ttcactcctt caagagaact tgccacttga aaggagaaat agcattaatt ttgaaagact 1440
agaagctcaa ctgaaggcat gtcattgcag gatcatattt tctaaagcaa agccttctgt 1500
gttggcattg tctatcattg cattagagat ccaagcacag aagtgtgtag agttaacaga 1560
aggaatagaa tgtcttcaga aacattccaa gataaatggc agagatctga ccttctggca 1620
agagcttgta tccaaatgtt taactgaata ttcatcaaat aagtgttcca aaccaaatgt 1680
tcagaagttg aaatggattg tttctgggcg tactgcacgg caattgaagc atagctacta 1740
cagaataact caccttccaa caattcctga aatggtccct taaatttctg acatccggcg 1800
ggtgactcac aacgcggccg cagccaccat ggtgacaggg ggaatggcaa gcaagtggga 1860
tcagaagggt atggacattg cctatgagga ggcggcctta ggttacaaag agggtggtgt 1920
tcctattggc ggatgtctta tcaataacaa agacggaagt gttctcggtc gtggtcacaa 1980
catgagattt caaaagggat ctgccacact acatggtgag atctccactt tggaaaactg 2040
tgggagatta gagggcaaag tgtacaaaga taccactttg tatacgacgc tgtctccatg 2100
cgacatgtgt acaggtgcca tcatcatgta tggtattcca cgctgtgttg tcggtgagaa 2160
cgttaatttc aaaagtaagg gcgagaaata tttacaaact agaggtcacg aggttgttgt 2220
tgttgacgat gagaggtgta aaaagatcat gaaacaattt atcgatgaaa gacctcagga 2280
ttggtttgaa gatattggtg aggcttcgga accatttaag aacgtctact tgctacctca 2340
aacaaaccaa ttgctgggtt tgtacaccat catcagaaat aagaatacaa ctagacctga 2400
tttcattttc tactccgata gaatcatcag attgttggtt gaagaaggtt tgaaccatct 2460
acctgtgcaa aagcaaattg tggaaactga caccaacgaa aacttcgaag gtgtctcatt 2520
catgggtaaa atctgtggtg tttccattgt cagagctggt gaatcgatgg agcaaggatt 2580
aagagactgt tgtaggtctg tgcgtatcgg taaaatttta attcaaaggg acgaggagac 2640
tgctttacca aagttattct acgaaaaatt accagaggat atatctgaaa ggtatgtctt 2700
cctattagac ccaatgctgg ccaccggtgg tagtgctatc atggctacag aagtcttgat 2760
taagagaggt gttaagccag agagaattta cttcttaaac ctaatctgta gtaaggaagg 2820
gattgaaaaa taccatgccg ccttcccaga ggtcagaatt gttactggtg ccctcgacag 2880
aggtctagat gaaaacaagt atctagttcc agggttgggt gactttggtg acagatacta 2940
ctgtgtttaa gtgcgagagg ccgaggacca gaacaacatc cgcctaccct ccatcattgt 3000
tataaaaaac ttaggaacca ggtccacaca gccgccagcc catcaaccat ccactcccac 3060
gattggagcc gatggccaca cttttaagga gcttagcatt gttcaaaaga aacaaggaca 3120
aaccacccat tacatcagga tccggtggag ccatcagagg aatcaaacac attattatag 3180
taccaatccc tggagattcc tcaattacca ctcgatccag acttctggac cggttggtca 3240
ggttaattgg aaacccggat gtgagcgggc ccaaactaac aggggcacta ataggtatat 3300
tatccttatt tgtggagtct ccaggtcaat tgattcagag gatcaccgat gaccctgacg 3360
ttagcataag gctgttagag gttgtccaga gtgaccagtc acaatctggc cttaccttcg 3420

```
catcaagagg taccaacatg gaggatgagg cggaccaata cttttcacat gatgatccaa   3480
ttagtagtga tcaatccagg ttcggatggt tcgagaacaa ggaaatctca gatattgaag   3540
tgcaagaccc tgagggattc aacatgattc tgggtaccat cctagctcaa atttgggtct   3600
tgctcgcaaa ggcggttacg gccccagaca cggcagctga ttcggagcta agaaggtgga   3660
taaagtacac ccaacaaaga agggtagttg gtgaatttag attggagaga aaatggttgg   3720
atgtggtgag gaacaggatt gccgaggacc tctccttacg ccgattcatg gtcgctctaa   3780
tcctggatat caagagaaca cccggaaaca aacccaggat tgctgaaatg atatgtgaca   3840
ttgatacata tatcgtagag gcaggattag ccagttttat cctgactatt aagtttggga   3900
tagaaactat gtatcctgct cttggactgc atgaatttgc tggtgagtta tccacacttg   3960
agtccttgat gaacctttac cagcaaatgg gggaaactgc accctacatg gtaatcctgg   4020
agaactcaat tcagaacaag ttcagtgcag gatcataccc tctgctctgg agctatgcca   4080
tgggagtagg agtggaactt gaaaactcca tgggaggttt gaactttggc cgatcttact   4140
ttgatccagc atattttaga ttagggcaag agatggtaag gaggtcagct ggaaaggtca   4200
gttccacatt ggcatctgaa ctcggtatca ctgccgagga tgcaaggctt gtttcagaga   4260
ttgcaatgca tactactgag gacaagatca gtagagcggt tggacccaga caagcccaag   4320
tatcatttct acacggtgat caaagtgaga atgagctacc gagattgggg ggcaaggaag   4380
ataggagggt caaacagagt cgaggagaag ccagggagag ctacagagaa accgggccca   4440
gcagagcaag tgatgcgaga gctgcccatc ttccaaccgg cacacccccta gacattgaca   4500
ctgcatcgga gtccagccaa gatccgcagg acagtcgaag gtcagctgac gccctgctta   4560
ggctgcaagc catggcagga atctcggaag aacaaggctc agacacggac acccctatag   4620
tgtacaatga cagaaatctt ctagactagg tgcgagaggc cgaggaccag aacaacatcc   4680
gcctaccctc catcattgtt ataaaaaact taggaaccag gtccacacag ccgccagccc   4740
atcaaccatc cactcccacg attggagccg atggcagaag agcaggcacg ccatgtcaaa   4800
aacggactgg aatgcatccg ggctctcaag gccgagccca tcggctcact ggccatcgag   4860
gaagctatgg cagcatggtc agaaatatca gacaacccag gacaggagcg agccacctgc   4920
agggaagaga aggcaggcag ttcgggtctc agcaaaccat gcctctcagc aattggatca   4980
actgaaggcg gtgcacctcg catccgcggt cagggacctg gagagagcga tgacgacgct   5040
gaaactttgg gaatcccccc aagaaatctc caggcatcaa gcactgggtt acagtgttat   5100
tatgtttatg atcacagcgg tgaagcggtt aagggaatcc aagatgctga ctctatcatg   5160
gttcaatcag gccttgatgg tgatagcacc ctctcaggag gagacaatga atctgaaaac   5220
agcgatgtgg atattggcga acctgatacc gagggatatg ctatcactga ccggggatct   5280
gctcccatct ctatggggtt cagggcttct gatgttgaaa ctgcagaagg aggggagatc   5340
cacgagctcc tgagactcca atccagaggc aacaactttc cgaagcttgg gaaaactctc   5400
aatgttcctc cgcctccgga ccccggtagg gccagcactt ccgggacacc cattaaaaag   5460
ggcacagacg cgagattagc ctcatttgga acggagatcg cgtctttatt gacaggtggt   5520
gcaacccaat gtgctcgaaa gtcaccctcg gaaccatcag ggccaggtgc acctgcgggg   5580
aatgtccccg agtgtgtgag caatgccgca ctgatacagg agtggacacc cgaatctggt   5640
accacaatct ccccgagatc ccagaataat gaagaagggg gagactatta tgatgatgag   5700
ctgttctctg atgtccaaga tattaaaaca gccttggcca aaatacacga ggataatcag   5760
aagataatct ccaagctaga atcactgctg ttattgaagg gagaagttga gtcaattaag   5820
```

-continued aagcagatca acaggcaaaa tatcagcata tccaccctgg aaggacacct ctcaagcatc 5880
atgatcgcca ttcctggact tgggaaggat cccaacgacc ccactgcaga tgtcgaaatc 5940
aatcccgact tgaaacccat cataggcaga gattcaggcc gagcactggc cgaagttctc 6000
aagaaacccg ttgccagccg acaactccaa ggaatgacaa atggacggac cagttccaga 6060
ggacagctgc tgaaggaatt tcagctaaag ccgatcggga aaaagatgag ctcagccgtc 6120
gggtttgttc ctgacaccgg ccctgcatca cgcagtgtaa tccgctccat tataaaatcc 6180
agccggctag aggaggatcg gaagcgttac ctgatgactc tccttgatga tatcaaagga 6240
gccaatgatc ttgccaagtt ccaccagatg ctgatgaaga taataatgaa gtagctacag 6300
ctcaacttac ctgccaaccc catgccagtc gacccaacta gtacaaccta aatccattat 6360
aaaaaactta ggagcaaagt gattgcctcc caagttccac aatgacagag atctacgact 6420
tcgacaagtc ggcatgggac atcaaagggt tgatcgctcc gatacaaccc accacctaca 6480
gtgatggcag gctggtgccc caggtcagag tcatagatcc tggtctaggc gacaggaagg 6540
atgaatgctt tatgtacatg tttctgctgg gggttgttga ggacagcgat cccctagggc 6600
ctccaatcgg gcgagcattt gggtccctgc ccttaggtgt tggcagatcc acagcaaagc 6660
ccgaaaaact cctcaaagag gccactgagc ttgacatagt tgttagacgt acagcagggc 6720
tcaatgaaaa actggtgttc tacaacaaca ccccactaac tctcctcaca ccttggagaa 6780
aggtcctaac aacagggagt gtcttcaacg caaaccaagt gtgcaatgcg gttaatctga 6840
taccgctcga taccccgcag aggttccgtg ttgtttatat gagcatcacc cgtctttcgg 6900
ataacgggta ttacaccgtt cctagaagaa tgctggaatt cagatcggtc aatgcagtgg 6960
ccttcaacct gctggtgacc cttaggattg acaaggcgat aggccctggg aagatcatcg 7020
acaatacaga gcaacttcct gaggcaacat ttatggtcca catcgggaac ttcaggagaa 7080
agaagagtga agtctactct gccgattatt gcaaaatgaa aatcgaaaag atgggcctgg 7140
tttttgcact tggtgggata gggggcacca gtcttcacat tagaagcaca ggcaaaatga 7200
gcaagactct ccatgcacaa ctcgggttca agaagacctt atgttacccg ctgatagata 7260
tcaatgaaga ccttaatcga ttactctgga ggagcagatg caagatagta agaatccagg 7320
cagttttgca gccatcagtt cctcaagaat tccgcattta cgacgacgtg atcataaatg 7380
atgaccaagg actattcaaa gttctgtaga ccgtagtgcc cagcaatgcc cgaaaacgac 7440
ccccctcaca atgacagcca gaaggcccgg acaaaaaagc cccctccgaa agactccacg 7500
gaccaagcga gaggccagcc agcagccgac ggcaagcgcg aacaccaggc ggccccagca 7560
cagaacagcc ctgatacaag gccaccacca gccaccccaa tctgcatcct cctcgtggga 7620
cccccgagga ccaaccccca aggctgcccc cgatccaaac caccaaccgc atccccacca 7680
cccccgggaa agaaaccccc agcaattgga aggcccctcc ccctcttcct caacacaaga 7740
actccacaac cgaaccgcac aagcgaccga ggtgacccaa ccgcaggcat ccgactccct 7800
agacagatcc tctctccccg gcaaactaaa caaaacttag ggccaaggaa catacacacc 7860
caacagaacc cagaccccgg cccacggcgc cgcgccccca acccccgaca accagaggga 7920
gcccccaacc aatcccgccg gctcccccgg tgcccacagg cagggacacc aacccccgaa 7980
cagacccagc acccaaccat cgacaatcca agacgggggg gcccccccaa aaaaaggccc 8040
ccaggggccg acagccagca ccgcgaggaa gcccacccac cccacacacg accacggcaa 8100
ccaaaccaga acccagacca ccctgggcca ccagctccca gactcggcca tcaccccgca 8160

-continued

```
gaaaggaaag gccacaaccc gcgcacccca gccccgatcc ggcggggagc cacccaaccc   8220
gaaccagcac ccaagagcga tccccgaagg acccccgaac cgcaaaggac atcagtatcc   8280
cacagcctct ccaagtcccc cggtctcctc cccttctcga agggaccaaa agatcaatcc   8340
accacacccg acgacactca actccccacc cctaaaggag acaccgggaa tcccagaatc   8400
aagactcatc caatgtccat catgggtctc aaggtgaacg tctctgccat attcatggca   8460
gtactgttaa ctctccaaac acccaccggt caaatccatt ggggcaatct ctctaagata   8520
ggggtggtag gaataggaag tgcaagctac aaagttatga ctcgttccag ccatcaatca   8580
ttagtcataa aattaatgcc caatataact ctcctcaata actgcacgag ggtagagatt   8640
gcagaataca ggagactact gagaacagtt ttggaaccaa ttagagatgc acttaatgca   8700
atgacccaga atataagacc ggttcagagt gtagcttcaa gtaggagaca caagagattt   8760
gcgggagtag tcctggcagg tgcggcccta ggcgttgcca cagctgctca gataacagcc   8820
ggcattgcac ttcaccagtc catgctgaac tctcaagcca tcgacaatct gagagcgagc   8880
ctggaaacta ctaatcaggc aattgaggca atcagacaag cagggcagga gatgatattg   8940
gctgttcagg gtgtccaaga ctacatcaat aatgagctga taccgtctat gaaccaacta   9000
tcttgtgatt taatcggcca gaagctcggg ctcaaattgc tcagatacta tacagaaatc   9060
ctgtcattat ttggccccag cttacgggac cccatatctg cggagatatc tatccaggct   9120
ttgagctatg cgcttggagg agacatcaat aaggtgttag aaaagctcgg atacagtgga   9180
ggtgatttac tgggcatctt agagagcaga ggaataaagg cccggataac tcacgtcgac   9240
acagagtcct acttcattgt cctcagtata gcctatccga cgctgtccga gattaagggg   9300
gtgattgtcc accggctaga gggggtctcg tacaacatag gctctcaaga gtggtatacc   9360
actgtgccca agtatgttgc aacccaaggg taccttatct cgaattttga tgagtcatcg   9420
tgtactttca tgccagaggg gactgtgtgc agccaaaatg ccttgtaccc gatgagtcct   9480
ctgctccaag aatgcctccg gggtccacc aagtcctgtg ctcgtacact cgtatccggg   9540
tcttttggga accggttcat tttatcacaa gggaacctaa tagccaattg tgcatcaatc   9600
ctttgcaagt gttacacaac aggaacgatc attaatcaag accctgacaa gatcctaaca   9660
tacattgctg ccgatcactg cccggtagtc gaggtgaacg gcgtgaccat ccaagtcggg   9720
agcaggaggt atccagatgc tgtgtacttg cacagaattg acctcggtcc tcccatatca   9780
ttggagaggt tggacgtagg gacaaatctg gggaatgcaa ttgctaagtt ggaggatgcc   9840
aaggaattgt tggagtcatc ggaccagata ttgaggagta tgaaaggttt atcgagcact   9900
agcatagtct acatcctgat tgcagtgtgt cttggagggt tgatagggat ccccgcttta   9960
atatgttgct gcagggggcg ttgtaacaaa aagggagaac aagttggtat gtcaagacca  10020
ggcctaaagc ctgatcttac gggaacatca aaatcctatg taaggtcgct ctgatcctct  10080
acaactcttg aaacacaaat gtcccacaag tctcctcttc gtcatcaagc aaccaccgca  10140
cccagcatca agcccacctg aaattatctc cggcttccct ctggccgaac aatatcggta  10200
gttaattaaa acttagggtg caagatcatc cacaatgtca ccacaacgag accggataaa  10260
tgccttctac aaagataacc cccatcccaa gggaagtagg atagtcatta acagagaaca  10320
tcttatgatt gatagacctt atgttttgct ggctgttctg tttgtcatgt ttctgagctt  10380
gatcgggttg ctagccattg caggcattag acttcatcgg gcagccatct acaccgcaga  10440
gatccataaa agcctcagca ccaatctaga tgtaactaac tcaatcgagc atcaggtcaa  10500
ggacgtgctg acaccactct tcaaaatcat cggtgatgaa gtgggcctga ggacacctca  10560
```

-continued

```
gagattcact gacctagtga aattcatctc tgacaagatt aaattcctta atccggatag  10620
ggagtacgac ttcagagatc tcacttggtg tatcaacccg ccagagagaa tcaaattgga  10680
ttatgatcaa tactgtgcag atgtggctgc tgaagagctc atgaatgcat tggtgaactc  10740
aactctactg gagaccagaa caaccaatca gttcctagct gtctcaaagg gaaactgctc  10800
agggcccact acaatcagag gtcaattctc aaacatgtcg ctgtccctgt tagacttgta  10860
tttaggtcga ggttacaatg tgtcatctat agtcactatg acatcccagg gaatgtatgg  10920
gggaacttac ctagtggaaa agcctaatct gagcagcaaa aggtcagagt tgtcacaact  10980
gagcatgtac cgagtgtttg aagtaggtgt tatcagaaat ccgggtttgg gggctccggt  11040
gttccatatg acaaactatc ttgagcaacc agccagtaat gatctcagca actgtatggt  11100
ggctttgggg gagctcaaac tcgcagccct ttgtcacggg gaagattcta tcacaattcc  11160
ctatcaggga tcagggaaag gtgtcagctt ccagctcgtc aagctaggtg tctggaaatc  11220
cccaaccgac atgcaatcct gggtcccctt atcaacggat gatccagtga tagacaggct  11280
ttacctctca tctcacagag gtgttatcgc tgacaatcaa gcaaaatggg ctgtcccgac  11340
aacacgaaca gatgacaagt tgcgaatgga gacatgcttc caacaggcgt gtaagggtaa  11400
aatccaagca ctctgcgaga atcccgagtg ggcaccattg aaggataaca ggattccttc  11460
atacggggtc ttgtctgttg atctgagtct gacagttgag cttaaaatca aaattgcttc  11520
gggattcggg ccattgatca cacacggttc agggatggac ctatacaaat ccaaccacaa  11580
caatgtgtat tggctgacta tcccgccaat gaagaaccta gccttaggtg taatcaacac  11640
attggagtgg ataccgagat tcaaggttag tccctacctc ttcaatgtcc caattaagga  11700
agcaggcgaa gactgccatg ccccaacata cctacctgcg gaggtggatg gtgatgtcaa  11760
actcagttcc aatctggtga ttctacctgg tcaagatctc caatatgttt tggcaaccta  11820
cgatacttcc agggttgaac atgctgtggt ttattacgtt tacagcccag gccgctcatt  11880
ttcttacttt tatcctttta ggttgcctat aaagggggtc cccatcgaat tacaagtgga  11940
atgcttcaca tgggaccaaa aactctggtg ccgtcacttc tgtgtgcttg cggactcaga  12000
atctggtgga catatcactc actctgggat ggtgggcatg ggagtcagct gcacagtcac  12060
ccgggaagat ggaaccaatc gcagataggg ctgctagtga accaatctca tgatgtcacc  12120
cagacatcag gcatacccac tagtgtgaaa tagacatcag aattaagaaa aacgtagggt  12180
ccaagtggtt ccccgttatg gactcgctat ctgtcaacca gatcttatac cctgaagttc  12240
acctagatag cccgatagtt accaataaga tagtagccat cctggagtat gctcgagtcc  12300
ctcacgctta cagcctggag gaccctacac tgtgtcagaa catcaagcac cgcctaaaaa  12360
acggattttc caaccaaatg attataaaca atgtggaagt tgggaatgtc atcaagtcca  12420
agcttaggag ttatccggcc cactctcata ttccatatcc aaattgtaat caggatttat  12480
ttaacataga agacaaagag tcaacgagga agatccgtga actcctcaaa aaggggaatt  12540
cgctgtactc caaagtcagt gataaggttt tccaatgctt aagggacact aactcacggc  12600
ttggcctagg ctccgaattg agggaggaca tcaaggagaa agttattaac ttgggagttt  12660
acatgcacag ctcccagtgg tttgagccct ttctgttttg gtttacagtc aagactgaga  12720
tgaggtcagt gattaaatca caaacccata cttgccatag gaggagacac acacctgtat  12780
tcttcactgg tagttcagtt gagttgctaa tctctcgtga ccttgttgct ataatcagta  12840
aagagtctca acatgtatat tacctgacat ttgaactggt tttgatgtat tgtgatgtca  12900
```

-continued

```
tagaggggag gttaatgaca gagaccgcta tgactattga tgctaggtat acagagcttc  12960
taggaagagt cagatacatg tggaaactga tagatggttt cttccctgca ctcgggaatc  13020
caacttatca aattgtagcc atgctggagc ctctttcact tgcttacctg cagctgaggg  13080
atataacagt agaactcaga ggtgctttcc ttaaccactg ctttactgaa atacatgatg  13140
ttcttgacca aaacgggttt tctgatgaag gtacttatca tgagttaatt gaagctctag  13200
attacatttt cataactgat gacatacatc tgacagggga gattttctca tttttcagaa  13260
gtttcggcca ccccagactt gaagcagtaa cggctgctga aaatgttagg aaatacatga  13320
atcagcctaa agtcattgtg tatgagactc tgatgaaagg tcatgccata ttttgtggaa  13380
tcataatcaa cggctatcgt gacaggcacg gaggcagttg gccaccgctg accctccccc  13440
tgcatgctgc agacacaatc cggaatgctc aagcttcagg tgaagggtta acacatgagc  13500
agtgcgttga taactggaga tcttttgctg gagtgaaatt tggctgcttt atgcctctta  13560
gcctggatag tgatctgaca atgtacctaa aggacaaggc acttgctgct ctccaaaggg  13620
aatgggattc agtttacccg aaagagttcc tgcgttacga ccctcccaag ggaaccgggt  13680
cacggaggct tgtagatgtt ttccttaatg attcgagctt tgacccatat gatgtgataa  13740
tgtatgttgt aagtggagct tacctccatg accctgagtt caacctgtct tacagcctga  13800
aagaaaagga gatcaaggaa acaggtagac tttttgctaa aatgacttac aaaatgaggg  13860
catgccaagt gattgctgaa aatctaatct caaacgggat tggcaaatat tttaaggaca  13920
atgggatggc caaggatgag cacgatttga ctaaggcact ccacactcta gctgtctcag  13980
gagtccccaa agatctcaaa gaaagtcaca ggggggggcc agtcttaaaa acctactccc  14040
gaagcccagt ccacacaagt accaggaacg tgagagcagc aaaagggttt atagggttcc  14100
ctcaagtaat tcggcaggac caagacactg atcatccgga gaatatggaa gcttacgaga  14160
cagtcagtgc atttatcacg actgatctca agaagtactg ccttaattgg agatatgaga  14220
ccatcagctt gtttgcacag aggctaaatg agatttacgg attgccctca tttttccagt  14280
ggctgcataa gaggcttgag acctctgtcc tgtatgtaag tgaccctcat tgcccccccg  14340
accttgacgc ccatatcccg ttatataaag tccccaatga tcaaatcttc attaagtacc  14400
ctatgggagg tatagaaggg tattgtcaga agctgtggac catcagcacc attccctatc  14460
tatacctggc tgcttatgag agcggagtaa ggattgcttc gttagtgcaa ggggacaatc  14520
agaccatagc cgtaacaaaa agggtaccca gcacatggcc ctacaacctt aagaaacggg  14580
aagctgctag agtaactaga gattactttg taattcttag gcaaaggcta catgatattg  14640
gccatcacct caaggcaaat gagacaattg tttcatcaca tttttttgtc tattcaaaag  14700
gaatatatta tgatgggcta cttgtgtccc aatcactcaa gagcatcgca agatgtgtat  14760
tctggtcaga gactatagtt gatgaaacaa gggcagcatg cagtaatatt gctacaacaa  14820
tggctaaaag catcgagaga ggttatgacc gttaccttgc atattccctg aacgtcctaa  14880
aagtgataca gcaaattctg atctctcttg gcttcacaat caattcaacc atgacccggg  14940
atgtagtcat acccctcctc acgaacaacg acctcttaat aaggatggca ctgttgcccg  15000
ctcctattgg ggggatgaat tatctgaata tgagcaggct gtttgtcaga aacatcggtg  15060
atccagtaac atcatcaatt gctgatctca agagaatgat tctcgcctca ctaatgcctg  15120
aagagaccct ccatcaagta atgacacaac aaccggggga ctcttcattc ctagactggg  15180
ctagcgaccc ttactcagca aatcttgtat gtgtccagag catcactaga ctcctcaaga  15240
acataactgc aaggtttgtc ctgatccata gtccaaaccc aatgttaaaa ggattattcc  15300
```

-continued

```
atgatgacag taaagaagag gacgagggac tggcggcatt cctcatggac aggcatatta  15360
tagtacctag ggcagctcat gaaatcctgg atcatagtgt cacaggggca agagagtcta  15420
ttgcaggcat gctggatacc acaaaaggcc tgattcgagc cagcatgagg aagggggggt  15480
taacctctcg agtgataacc agattgtcca attatgacta tgaacaattc agagcaggga  15540
tggtgctatt gacaggaaga aagagaaatg tcctcattga caaagagtca tgttcagtgc  15600
agctggcgag agctctaaga agccatatgt gggcgaggct agctcgagga cggcctattt  15660
acggccttga ggtccctgat gtactagaat ctatgcgagg ccaccttatt cggcgtcatg  15720
agacatgtgt catctgcgag tgtggatcag tcaactacgg atggtttttt gtcccctcgg  15780
gttgccaact ggatgatatt gacaaggaaa catcatcctt gagagtccca tatattggtt  15840
ctaccactga tgagagaaca gacatgaagc ttgccttcgt aagagcccca agtcgatcct  15900
tgcgatctgc tgttagaata gcaacagtgt actcatgggc ttacggtgat gatgatagct  15960
cttggaacga agcctggttg ttggctaggc aaagggccaa tgtgagcctg gaggagctaa  16020
gggtgatcac tcccatctca acttcgacta atttagcgca taggttgagg gatcgtagca  16080
ctcaagtgaa atactcaggt acatcccttg tccgagtggc gaggtatacc acaatctcca  16140
acgacaatct ctcatttgtc atatcagata agaaggttga tactaacttt atataccaac  16200
aaggaatgct tctagggttg ggtgttttag aaacattgtt tcgactcgag aaagataccg  16260
gatcatctaa cacggtatta catcttcacg tcgaaacaga ttgttgcgtg atcccgatga  16320
tagatcatcc caggataccc agctcccgca agctagagct gagggcagag ctatgtacca  16380
acccattgat atatgataat gcacctttaa ttgacagaga tacaacaagg ctatacaccc  16440
agagccatag gaggcacctt gtggaatttg ttacatggtc cacaccccaa ctatatcaca  16500
ttttagctaa gtccacagca ctatctatga ttgacctggt aacaaaattt gagaaggacc  16560
atatgaatga aatttcagct ctcatagggg atgacgatat caatagtttc ataactgagt  16620
ttctgctcat agagccaaga ttattcacta tctacttggg ccagtgtgcg gccatcaatt  16680
gggcatttga tgtacattat catagaccat cagggaaata tcagatgggt gagctgttgt  16740
catcgttcct ttctagaatg agcaaaggag tgtttaaggt gcttgtcaat gctctaagcc  16800
acccaaagat ctacaagaaa ttctggcatt gtggtattat agagcctatc catggtcctt  16860
cacttgatgc tcaaaacttg cacacaactg tgtgcaacat ggtttacaca tgctatatga  16920
cctacctcga cctgttgttg aatgaagagt tagaagagtt cacatttctc ttgtgtgaaa  16980
gcgacgagga tgtagtaccg gacagattcg acaacatcca ggcaaaacac ttatgtgttc  17040
tggcagattt gtactgtcaa ccagggacct gcccaccaat tcgaggtcta agaccggtag  17100
agaaatgtgc agttctaacc gaccatatca aggcagaggc taggttatct ccagcaggat  17160
cttcgtggaa cataaatcca attattgtag accattactc atgctctctg acttatctcc  17220
ggcgaggatc gatcaaacag ataagattga gagttgatcc aggattcatt ttcgacgccc  17280
tcgctgaggt aaatgtcagt cagccaaaga tcggcagcaa caacatctca aatatgagca  17340
tcaaggcttt cagaccccca cacgatgatg ttgcaaaatt gctcaaagat atcaacacaa  17400
gcaagcacaa tcttcccatt tcagggggca atctcgccaa ttatgaaatc catgctttcc  17460
gcagaatcgg gttgaactca tctgcttgct acaaagctgt tgagatatca acattaatta  17520
ggagatgcct tgagccaggg gaggacggct tgttcttggg tgagggatcg ggttccatgt  17580
tgatcactta taaggagata cttaaactaa acaagtgctt ctataatagt ggggtttccg  17640
```

ccaattctag atctggtcaa agggaattag caccctatcc ctccgaagtt ggccttgtcg 17700
aacacagaat gggagtaggt aatattgtca aagtgctctt taacgggagg cccgaagtca 17760
cgtgggtagg cagtgtagat tgcttcaatt tcatagttag taatatccct acctctagtg 17820
tggggtttat ccattcagat atagagacct tgcctaacaa agatactata gagaagctag 17880
aggaattggc agccatctta tcgatggctc tgctcctggg caaaatagga tcaatactgg 17940
tgattaagct tatgcctttc agcggggatt ttgttcaggg atttataagt tatgtagggt 18000
cccattatag agaagtgaac cttgtatacc ctagatacag caacttcata tctactgaat 18060
cttatttggt tatgacagat ctcaaggcta accggctaat gaatcctgaa aagattaagc 18120
agcagataat tgaatcatct gtgaggactt cacctggact tataggtcac atcctatcca 18180
ttaagcaact aagctgcata caagcaattg tgggagacgc agttagtaga ggtgatatca 18240
atcctactct gaaaaaactt acacctatag agcaggtgct gatcaattgc gggttggcaa 18300
ttaacggacc taagctgtgc aaagaattga tccaccatga tgttgcctca gggcaagatg 18360
gattgcttaa ttctatactc atcctctaca gggagttggc aagattcaaa gacaaccaaa 18420
gaagtcaaca agggatgttc cacgcttacc ccgtattggt aagtagcagg caacgagaac 18480
ttatatctag gatcacccgc aaattttggg ggcacattct tctttactcc gggaacagaa 18540
agttgataaa taagtttatc cagaatctca agtccggcta tctgatacta gacttacacc 18600
agaatatctt cgttaagaat ctatccaagt cagagaaaca gattattatg acgggggggtt 18660
tgaaacgtga gtgggttttt aaggtaacag tcaaggagac caaagaatgg tataagttag 18720
tcggatacag tgccctgatt aaggactaat tggttgaact ccggaaccct aatcctgccc 18780
taggtggtta ggcattattt gcaatagatt aaagaaaact ttgaaaatac gaagtttcta 18840
ttcccagctt tgtctggtgc cggccatggt cccagcctcc tcgctggcgg ccggtgggca 18900
acattccgag ggaccgtcc cctcggtaat ggcgaatggg accgtttaaa cgtatctaga 18960
tgcattcgcg aggtaccgag ctcgaattca ctggccgtcg ttttacaacg tcgtgactgg 19020
gaaaaccctg gcgttaccca acttaatcgc cttgcagcac atccccctttt cgccagctgg 19080
cgtaatagcg aagaggcccg caccgatcgc ccttcccaac agttgcgcag cctgaatggc 19140
gaatggcgcc tgatgcggta ttttctcctt acgcatctgt gcggtatttc acaccgcata 19200
tggtgcactc tcagtacaat ctgctctgat gccgcatagt taagccagcc ccgacacccg 19260
ccaacacccg ctgacgcgcc ctgacgggct tgtctgctcc cggcatccgc ttacagacaa 19320
gctgtgaccg tctccgggag ctgcatgtgt cagaggtttt caccgtcatc accgaaacgc 19380
gcgagacgaa agggcctcgt gatacgccta tttttatagg ttaatgtcat gataataatg 19440
gtttcttaga cgtcaggtgg cacttttcgg ggaaatgtgc gcggaacccc tatttgttta 19500
tttttctaaa tacattcaaa tatgtatccg ctcatgagac aataaccctg ataaatgctt 19560
caataatatt gaaaaaggaa gagtatgagt attcaacatt tccgtgtcgc ccttattccc 19620
ttttttgcgg cattttgcct tcctgttttt gctcacccag aaacgctggt gaaagtaaaa 19680
gatgctgaag atcagttggg tgcacgagtg ggttacatcg aactggatct caacagcggt 19740
aagatccttg agagttttcg ccccgaagaa cgttttccaa tgatgagcac ttttaaagtt 19800
ctgctatgtg gcgcggtatt atcccgtatt gacgccgggc aagagcaact cggtcgccgc 19860
atacactatt ctcagaatga cttggttgag tactcaccag tcacagaaaa gcatcttacg 19920
gatggcatga cagtaagaga attatgcagt gctgccataa ccatgagtga taacactgcg 19980
gccaacttac ttctgacaac gatcggagga ccgaaggagc taaccgcttt tttgcacaac 20040

```
atgggggatc atgtaactcg ccttgatcgt tgggaaccgg agctgaatga agccatacca  20100

aacgacgagc gtgacaccac gatgcctgta gcaatggcaa caacgttgcg caaactatta  20160

actggcgaac tacttactct agcttcccgg caacaattaa tagactggat ggaggcggat  20220

aaagttgcag gaccacttct gcgctcggcc cttccggctg gctggtttat tgctgataaa  20280

tctggagccg gtgagcgtgg gtctcgcggt atcattgcag cactggggcc agatggtaag  20340

ccctcccgta tcgtagttat ctacacgacg gggagtcagg caactatgga tgaacgaaat  20400

agacagatcg ctgagatagg tgcctcactg attaagcatt ggtaactgtc agaccaagtt  20460

tactcatata tactttagat tgatttaaaa cttcattttt aatttaaaag gatctaggtg  20520

aagatccttt ttgataatct catgaccaaa atcccttaac gtgagttttc gttccactga  20580

gcgtcagacc ccgtagaaaa gatcaaagga tcttcttgag atcctttttt tctgcgcgta  20640

atctgctgct tgcaaacaaa aaaaccaccg ctaccagcgg tggtttgttt gccggatcaa  20700

gagctaccaa ctctttttcc gaaggtaact ggcttcagca gagcgcagat accaaatact  20760

gttcttctag tgtagccgta gttaggccac cacttcaaga actctgtagc accgcctaca  20820

tacctcgctc tgctaatcct gttaccagtg gctgctgcca gtggcgataa gtcgtgtctt  20880

accgggttgg actcaagacg atagttaccg gataaggcgc agcggtcggg ctgaacgggg  20940

ggttcgtgca cacagcccag cttggagcga acgacctaca ccgaactgag atacctacag  21000

cgtgagctat gagaaagcgc cacgcttccc gaagggagaa aggcggacag gtatccggta  21060

agcggcaggg tcggaacagg agagcgcacg agggagcttc caggggggaaa cgcctggtat  21120

ctttatagtc ctgtcgggtt tcgccacctc tgacttgagc gtcgattttt gtgatgctcg  21180

tcaggggggc ggagcctatg gaaaaacgcc agcaacgcgg cctttttacg gttcctggcc  21240

ttttgctggc cttttgctca catgttcttt cctgcgttat cccctgattc tgtggataac  21300

cgtattaccg cctttgagtg agctgatacc gctcgccgca gccgaacgac cgagcgcagc  21360

gagtcagtga gcgaggaagc ggaagagcgc ccaatacgca aaccgcctct ccccgcgcgt  21420

tggccgattc attaatgcag ctggcacgac aggtttcccg actggaaagc gggcagtgag  21480

cgcaacgcaa ttaatgtgag ttagctcact cattaggcac cccaggcttt acactttatg  21540

cttccggctc gtatgttgtg tggaattgtg agcggataac aatttcacac aggaaacagc  21600

tatgaccatg attacgccaa gcttgcatgc aggcctctgc agtcgacggg cccgggatcc  21660

gatgggttta aacagcgcta ccaactttgt ttggtctgat gagtccgtga ggacgaaacc  21720

cggagtcccg ggtc                                                   21734
```

<210> SEQ ID NO 27
<211> LENGTH: 1286
<212> TYPE: DNA
<213> ORGANISM: Artificial Sequence
<220> FEATURE:
<223> OTHER INFORMATION: Artificial DNA containing coding regions of soluble PD-1 & dominant negative mutant of cyclin G1

<400> SEQUENCE: 27

```
tttctgacat ccggcgggtg actcacaacg cggccgcagc caccatgcag atcccacagg    60

cgccctggcc agtcgtctgg gcggtgctac aactgggctg gcggccagga tggttcttag   120

actccccaga caggccctgg aacccccccca ccttctcccc agccctgctc gtggtgaccg   180

aaggggacaa cgccaccttc acctgcagct tctccaacac atcggagagc ttcgtgctaa   240

actggtaccg catgagcccc agcaaccaga cggacaagct ggccgccttc cccgaggacc   300
```

gcagccagcc cggccaggac tgccgcttcc gtgtcacaca actgcccaac gggcgtgact 360
tccacatgag cgtggtcagg gcccggcgca atgacagcgg cacctacctc tgtggggcca 420
tctccctggc ccccaaggcg cagatcaaag agagcctgcg ggcagagctc agggtgacag 480
agagaagggc agaagtgccc acagcccacc ccagcccctc acccaggtca gccggccagt 540
tccaaggctc cggagccacg aacttctctc tgttaaagca agcaggagac gtggaagaaa 600
accccggtcc catgaaggta cagcccaagc accttgggtg tgttggactg agctgctttt 660
atttggctgt aaaatcaata gaagaggaaa ggaatgtccc attggcaact gacttgatcc 720
gaataagtca atataggttt acggtttcag acttgatgag aatggaaaag attgtattgg 780
agaaggtgtg ttggaaagtc aaagctacta ctgcctttca atttctgcaa ctgtattatt 840
cactccttca agagaacttg ccacttgaaa ggagaaatag cattaatttt gaaagactag 900
aagctcaact gaaggcatgt cattgcagga tcatattttc taaagcaaag ccttctgtgt 960
tggcattgtc tatcattgca ttagagatcc aagcacagaa gtgtgtagag ttaacagaag 1020
gaatagaatg tcttcagaaa cattccaaga taaatggcag agatctgacc ttctggcaag 1080
agcttgtatc caaatgttta actgaatatt catcaaataa gtgttccaaa ccaaatgttc 1140
agaagttgaa atggattgtt tctgggcgta ctgcacggca attgaagcat agctactaca 1200
gaataactca ccttccaaca attcctgaaa tggtccctta aatttctgac atccggcggg 1260
tgactcacaa cgcggccgca gccacc 1286

<210> SEQ ID NO 28
<211> LENGTH: 18770
<212> TYPE: DNA
<213> ORGANISM: Artificial Sequence
<220> FEATURE:
<223> OTHER INFORMATION: Artificial DNA containing entire MV sequence

<400> SEQUENCE: 28
atcggatccc gggcccgtcg actgcagagg cctgcatgca agcttggcgt aatcatggtc 60
atagctgttt cctgtgtgaa attgttatcc gctcacaatt ccacacaaca tacgagccgg 120
aagcataaag tgtaaagcct ggggtgccta atgagtgagc taactcacat taattgcgtt 180
gcgctcactg cccgctttcc agtcgggaaa cctgtcgtgc cagctgcatt aatgaatcgg 240
ccaacgcgcg gggagaggcg gtttgcgtat tgggcgctct tccgcttcct cgctcactga 300
ctcgctgcgc tcggtcgttc ggctgcggcg agcggtatca gctcactcaa aggcggtaat 360
acggttatcc acagaatcag gggataacgc aggaaagaac atgtgagcaa aaggccagca 420
aaaggccagg aaccgtaaaa aggccgcgtt gctggcgttt ttccataggc tccgcccccc 480
tgacgagcat cacaaaaatc gacgctcaag tcagaggtgg cgaaacccga caggactata 540
aagataccag gcgtttcccc ctggaagctc cctcgtgcgc tctcctgttc cgaccctgcc 600
gcttaccgga tacctgtccg cctttctccc ttcgggaagc gtggcgcttt ctcatagctc 660
acgctgtagg tatctcagtt cggtgtaggt cgttcgctcc aagctgggct gtgtgcacga 720
accccccgtt cagcccgacc gctgcgcctt atccggtaac tatcgtcttg agtccaaccc 780
ggtaagacac gacttatcgc cactggcagc agccactggt aacaggatta gcagagcgag 840
gtatgtaggc ggtgctacag agttcttgaa gtggtggcct aactacggct acactagaag 900
aacagtattt ggtatctgcg ctctgctgaa gccagttacc ttcggaaaaa gagttggtag 960
ctcttgatcc ggcaaacaaa ccaccgctgg tagcggtggt ttttttgttt gcaagcagca 1020
gattacgcgc agaaaaaaag gatctcaaga agatcctttg atcttttcta cggggtctga 1080
cgctcagtgg aacgaaaact cacgttaagg gattttggtc atgagattat caaaaaggat 1140
cttcacctag atccttttaa attaaaaatg aagttttaaa tcaatctaaa gtatatatga 1200
gtaaacttgg tctgacagtt accaatgctt aatcagtgag gcacctatct cagcgatctg 1260
tctatttcgt tcatccatag ttgcctgact ccccgtcgtg tagataacta cgatacggga 1320
gggcttacca tctggcccca gtgctgcaat gataccgcga gacccacgct caccggctcc 1380
agatttatca gcaataaacc agccagccgg aagggccgag cgcagaagtg gtcctgcaac 1440
tttatccgcc tccatccagt ctattaattg ttgccgggaa gctagagtaa gtagttcgcc 1500
agttaatagt ttgcgcaacg ttgttgccat tgctacaggc atcgtggtgt cacgctcgtc 1560
gtttggtatg gcttcattca gctccggttc ccaacgatca aggcgagtta catgatcccc 1620
catgttgtgc aaaaaagcgg ttagctcctt cggtcctccg atcgttgtca gaagtaagtt 1680
ggccgcagtg ttatcactca tggttatggc agcactgcat aattctctta ctgtcatgcc 1740
atccgtaaga tgcttttctg tgactggtga gtactcaacc aagtcattct gagaatagtg 1800
tatgcggcga ccgagttgct cttgcccggc gtcaatacgg gataataccg cgccacatag 1860
cagaacttta aaagtgctca tcattggaaa acgttcttcg gggcgaaaac tctcaaggat 1920
cttaccgctg ttgagatcca gttcgatgta acccactcgt gcacccaact gatcttcagc 1980
atcttttact ttcaccagcg tttctgggtg agcaaaaaca ggaaggcaaa atgccgcaaa 2040
aaagggaata agggcgacac ggaaatgttg aatactcata ctcttccttt ttcaatatta 2100
ttgaagcatt tatcagggtt attgtctcat gagcggatac atatttgaat gtatttagaa 2160
aaataaacaa ataggggttc cgcgcacatt tccccgaaaa gtgccacctg acgtctaaga 2220
aaccattatt atcatgacat taacctataa aaataggcgt atcacgaggc cctttcgtct 2280
cgcgcgtttc ggtgatgacg gtgaaaacct ctgacacatg cagctcccgg agacggtcac 2340
agcttgtctg taagcggatg ccgggagcag acaagcccgt cagggcgcgt cagcgggtgt 2400
tggcgggtgt cggggctggc ttaactatgc ggcatcagag cagattgtac tgagagtgca 2460
ccatatgcgg tgtgaaatac cgcacagatg cgtaaggaga aaataccgca tcaggcgcca 2520
ttcgccattc aggctgcgca actgttggga agggcgatcg gtgcgggcct cttcgctatt 2580
acgccagctg gcgaaagggg gatgtgctgc aaggcgatta agttgggtaa cgccagggtt 2640
ttcccagtca cgacgttgta aaacgacggc cagtgaattc gagctcggta cctcgcgaat 2700
gcatctagat acgtttaaac agcgctacca actttgtttg gtctgatgag tccgtgagga 2760
cgaaacccgg agtcccgggt caccaaacaa agttgggtaa ggatagttca atcaatgatc 2820
attttctagt gcacttagga ttcaagatcc tattatcagg gacaagagca ggattaagga 2880
tatccgagat ggccacactt ttaaggagct tagcattgtt caaaagaaac aaggacaaac 2940
cacccattac atcaggatcc ggtggagcca tcagaggaat caaacacatt attatagtac 3000
caatccctgg agattcctca attaccactc gatccagact tctggaccgg ttggtcaggt 3060
taattggaaa cccggatgtg agcgggccca aactaacagg ggcactaata ggtatattat 3120
ccttatttgt ggagtctcca ggtcaattga ttcagaggat caccgatgac cctgacgtta 3180
gcataaggct gttagaggtt gtccagagtg accagtcaca atctggcctt accttcgcat 3240
caagaggtac caacatggag gatgaggcgg accaatactt ttcacatgat gatccaatta 3300
gtagtgatca atccaggttc ggatggttcg agaacaagga aatctcagat attgaagtgc 3360
aagaccctga gggattcaac atgattctgg gtaccatcct agctcaaatt tgggtcttgc 3420

-continued

```
tcgcaaaggc ggttacggcc ccagacacgg cagctgattc ggagctaaga aggtggataa   3480
agtacaccca acaaagaagg gtagttggtg aatttagatt ggagagaaaa tggttggatg   3540
tggtgaggaa caggattgcc gaggacctct ccttacgccg attcatggtc gctctaatcc   3600
tggatatcaa gagaacaccc ggaaacaaac ccaggattgc tgaaatgata tgtgacattg   3660
atacatatat cgtagaggca ggattagcca gttttatcct gactattaag tttgggatag   3720
aaactatgta tcctgctctt ggactgcatg aatttgctgg tgagttatcc acacttgagt   3780
ccttgatgaa cctttaccag caaatggggg aaactgcacc ctacatggta atcctggaga   3840
actcaattca gaacaagttc agtgcaggat catacccctct gctctggagc tatgccatgg   3900
gagtaggagt ggaacttgaa aactccatgg gaggtttgaa ctttggccga tcttactttg   3960
atccagcata ttttagatta gggcaagaga tggtaaggag gtcagctgga aaggtcagtt   4020
ccacattggc atctgaactc ggtatcactg ccgaggatgc aaggcttgtt tcagagattg   4080
caatgcatac tactgaggac aagatcagta gagcggttgg acccagacaa gcccaagtat   4140
catttctaca cggtgatcaa agtgagaatg agctaccgag attggggggc aaggaagata   4200
ggagggtcaa acagagtcga ggagaagcca gggagagcta cagagaaacc gggcccagca   4260
gagcaagtga tgcgagagct gcccatcttc caaccggcac acccctagac attgacactg   4320
catcggagtc cagccaagat ccgcaggaca gtcgaaggtc agctgacgcc ctgcttaggc   4380
tgcaagccat ggcaggaatc tcggaagaac aaggctcaga cacggacacc cctatagtgt   4440
acaatgacag aaatcttcta gactaggtgc gagaggccga ggaccagaac aacatccgcc   4500
taccctccat cattgttata aaaaacttag gaaccaggtc cacacagccg ccagcccatc   4560
aaccatccac tcccacgatt ggagccgatg gcagaagagc aggcacgcca tgtcaaaaac   4620
ggactggaat gcatccgggc tctcaaggcc gagcccatcg gctcactggc catcgaggaa   4680
gctatggcag catggtcaga aatatcagac aacccaggac aggagcgagc cacctgcagg   4740
gaagagaagg caggcagttc gggtctcagc aaaccatgcc tctcagcaat tggatcaact   4800
gaaggcggtg cacctcgcat ccgcggtcag ggacctggag agagcgatga cgacgctgaa   4860
actttgggaa tccccccaag aaatctccag gcatcaagca ctgggttaca gtgttattat   4920
gtttatgatc acagcggtga agcggttaag ggaatccaag atgctgactc tatcatggtt   4980
caatcaggcc ttgatggtga tagcaccctc tcaggaggag acaatgaatc tgaaaacagc   5040
gatgtggata ttggcgaacc tgataccgag ggatatgcta tcactgaccg gggatctgct   5100
cccatctcta tggggttcag ggcttctgat gttgaaactg cagaaggagg ggagatccac   5160
gagctcctga gactccaatc cagaggcaac aactttccga agcttgggaa aactctcaat   5220
gttcctccgc ctccggaccc cggtagggcc agcacttccg ggacacccat taaaaagggc   5280
acagacgcga gattagcctc atttggaacg gagatcgcgt ctttattgac aggtggtgca   5340
acccaatgtg ctcgaaagtc accctcggaa ccatcagggc caggtgcacc tgcggggaat   5400
gtccccgagt gtgtgagcaa tgccgcactg atacaggagt ggacacccga atctggtacc   5460
acaatctccc cgagatccca gaataatgaa gaagggggag actattatga tgatgagctg   5520
ttctctgatg tccaagatat taaaacagcc ttggccaaaa tacacgagga taatcagaag   5580
ataatctcca agctagaatc actgctgtta ttgaagggag aagttgagtc aattaagaag   5640
cagatcaaca ggcaaaatat cagcatatcc accctggaag gacacctctc aagcatcatg   5700
atcgccattc ctggacttgg gaaggatccc aacgacccca ctgcagatgt cgaaatcaat   5760
```

-continued

```
cccgacttga aacccatcat aggcagagat tcaggccgag cactggccga agttctcaag   5820
aaacccgttg ccagccgaca actccaagga atgacaaatg gacggaccag ttccagagga   5880
cagctgctga aggaatttca gctaaagccg atcgggaaaa agatgagctc agccgtcggg   5940
tttgttcctg acaccggccc tgcatcacgc agtgtaatcc gctccattat aaaatccagc   6000
cggctagagg aggatcggaa gcgttacctg atgactctcc ttgatgatat caaaggagcc   6060
aatgatcttg ccaagttcca ccagatgctg atgaagataa taatgaagta gctacagctc   6120
aacttacctg ccaaccccat gccagtcgac ccaactagta caacctaaat ccattataaa   6180
aaacttagga gcaaagtgat tgcctcccaa gttccacaat gacagagatc tacgacttcg   6240
acaagtcggc atgggacatc aaagggttga tcgctccgat acaacccacc acctacagtg   6300
atggcaggct ggtgccccag gtcagagtca tagatcctgg tctaggcgac aggaaggatg   6360
aatgctttat gtacatgttt ctgctggggg ttgttgagga cagcgatccc ctagggcctc   6420
caatcgggcg agcatttggg tccctgccct taggtgttgg cagatccaca gcaaagcccg   6480
aaaaactcct caaagaggcc actgagcttg acatagttgt tagacgtaca gcagggctca   6540
atgaaaaact ggtgttctac aacaacaccc cactaactct cctcacacct tggagaaagg   6600
tcctaacaac agggagtgtc ttcaacgcaa accaagtgtg caatgcggtt aatctgatac   6660
cgctcgatac cccgcagagg ttccgtgttg tttatatgag catcacccgt ctttcggata   6720
acgggtatta caccgttcct agaagaatgc tggaattcag atcggtcaat gcagtggcct   6780
tcaacctgct ggtgaccctt aggattgaca aggcgatagg ccctgggaag atcatcgaca   6840
atacagagca acttcctgag gcaacattta tggtccacat cgggaacttc aggagaaaga   6900
agagtgaagt ctactctgcc gattattgca aaatgaaaat cgaaaagatg ggcctggttt   6960
ttgcacttgg tgggataggg ggcaccagtc ttcacattag aagcacaggc aaaatgagca   7020
agactctcca tgcacaactc gggttcaaga agaccttatg ttacccgctg atagatatca   7080
atgaagacct taatcgatta ctctggagga gcagatgcaa gatagtaaga atccaggcag   7140
ttttgcagcc atcagttcct caagaattcc gcatttacga cgacgtgatc ataaatgatg   7200
accaaggact attcaaagtt ctgtagaccg tagtgcccag caatgcccga aaacgacccc   7260
cctcacaatg acagccagaa ggcccggaca aaaaagcccc ctccgaaaga ctccacggac   7320
caagcgagag gccagccagc agccgacggc aagcgcgaac accaggcggc cccagcacag   7380
aacagccctg atacaaggcc accaccagcc accccaatct gcatcctcct cgtgggaccc   7440
ccgaggacca acccccaagg ctgcccccga tccaaaccac caaccgcatc cccaccaccc   7500
ccgggaaaga aacccccagc aattggaagg cccctccccc tcttcctcaa cacaagaact   7560
ccacaaccga accgcacaag cgaccgaggt gacccaaccg caggcatccg actccctaga   7620
cagatcctct ctccccggca aactaaacaa aacttagggc caaggaacat acacacccaa   7680
cagaacccag accccggccc acggcgccgc gcccccaacc cccgacaacc agagggagcc   7740
cccaaccaat cccgccggct cccccggtgc ccacaggcag ggacaccaac ccccgaacag   7800
acccagcacc caaccatcga caatccaaga cggggggggcc cccccaaaaa aaggccccca   7860
ggggccgaca gccagcaccg cgaggaagcc cacccacccc acacacgacc acggcaacca   7920
aaccagaacc cagaccaccc tgggccacca gctcccagac tcggccatca ccccgcagaa   7980
aggaaaggcc acaacccgcg caccccagcc ccgatccggc ggggagccac ccaacccgaa   8040
ccagcaccca agagcgatcc ccgaaggacc cccgaaccgc aaaggacatc agtatcccac   8100
agcctctcca agtcccccgg tctcctcccc ttctcgaagg gaccaaaaga tcaatccacc   8160
```

-continued

```
acacccgacg acactcaact ccccacccct aaaggagaca ccgggaatcc cagaatcaag   8220
actcatccaa tgtccatcat gggtctcaag gtgaacgtct ctgccatatt catggcagta   8280
ctgttaactc tccaaacacc caccggtcaa atccattggg gcaatctctc taagataggg   8340
gtggtaggaa taggaagtgc aagctacaaa gttatgactc gttccagcca tcaatcatta   8400
gtcataaaat taatgcccaa tataactctc ctcaataact gcacgagggt agagattgca   8460
gaatacagga gactactgag aacagttttg gaaccaatta gagatgcact taatgcaatg   8520
acccagaata taagaccggt tcagagtgta gcttcaagta ggagacacaa gagatttgcg   8580
ggagtagtcc tggcaggtgc ggccctaggc gttgccacag ctgctcagat aacagccggc   8640
attgcacttc accagtccat gctgaactct caagccatcg acaatctgag agcgagcctg   8700
gaaactacta atcaggcaat tgaggcaatc agacaagcag ggcaggagat gatattggct   8760
gttcagggtg tccaagacta catcaataat gagctgatac cgtctatgaa ccaactatct   8820
tgtgatttaa tcggccagaa gctcgggctc aaattgctca gatactatac agaaatcctg   8880
tcattatttg gccccagctt acgggacccc atatctgcgg agatatctat ccaggctttg   8940
agctatgcgc ttggaggaga catcaataag gtgttagaaa agctcggata cagtggaggt   9000
gatttactgg gcatcttaga gagcagagga ataaaggccc ggataactca cgtcgacaca   9060
gagtcctact tcattgtcct cagtatagcc tatccgacgc tgtccgagat taagggggtg   9120
attgtccacc ggctagaggg ggtctcgtac aacataggct ctcaagagtg gtataccact   9180
gtgcccaagt atgttgcaac ccaagggtac cttatctcga attttgatga gtcatcgtgt   9240
actttcatgc cagaggggac tgtgtgcagc caaaatgcct tgtacccgat gagtcctctg   9300
ctccaagaat gcctccgggg gtccaccaag tcctgtgctc gtacactcgt atccgggtct   9360
tttgggaacc ggttcatttt atcacaaggg aacctaatag ccaattgtgc atcaatcctt   9420
tgcaagtgtt acacaacagg aacgatcatt aatcaagacc ctgacaagat cctaacatac   9480
attgctgccg atcactgccc ggtagtcgag gtgaacggcg tgaccatcca agtcgggagc   9540
aggaggtatc cagatgctgt gtacttgcac agaattgacc tcggtcctcc catatcattg   9600
gagaggttgg acgtagggac aaatctgggg aatgcaattg ctaagttgga ggatgccaag   9660
gaattgttgg agtcatcgga ccagatattg aggagtatga aaggtttatc gagcactagc   9720
atagtctaca tcctgattgc agtgtgtctt ggagggttga tagggatccc cgctttaata   9780
tgttgctgca gggggcgttg taacaaaaag ggagaacaag ttggtatgtc aagaccaggc   9840
ctaaagcctg atcttacggg aacatcaaaa tcctatgtaa ggtcgctctg atcctctaca   9900
actcttgaaa cacaaatgtc ccacaagtct cctcttcgtc atcaagcaac caccgcaccc   9960
agcatcaagc ccacctgaaa ttatctccgg cttccctctg gccgaacaat atcggtagtt  10020
aattaaaact tagggtgcaa gatcatccac aatgtcacca caacgagacc ggataaatgc  10080
cttctacaaa gataaccccc atcccaaggg aagtaggata gtcattaaca gagaacatct  10140
tatgattgat agaccttatg ttttgctggc tgttctgttt gtcatgtttc tgagcttgat  10200
cgggttgcta gccattgcag gcattagact tcatcgggca gccatctaca ccgcagagat  10260
ccataaaagc ctcagcacca atctagatgt aactaactca atcgagcatc aggtcaagga  10320
cgtgctgaca ccactcttca aaatcatcgg tgatgaagtg ggcctgagga cacctcagag  10380
attcactgac ctagtgaaat tcatctctga caagattaaa ttccttaatc cggataggga  10440
gtacgacttc agagatctca cttggtgtat caacccgcca gagagaatca aattggatta  10500
```

-continued

```
tgatcaatac tgtgcagatg tggctgctga agagctcatg aatgcattgg tgaactcaac  10560
tctactggag accagaacaa ccaatcagtt cctagctgtc tcaaagggaa actgctcagg  10620
gcccactaca atcagaggtc aattctcaaa catgtcgctg tccctgttag acttgtattt  10680
aggtcgaggt tacaatgtgt catctatagt cactatgaca tcccagggaa tgtatggggg  10740
aacttaccta gtggaaaagc ctaatctgag cagcaaaagg tcagagttgt cacaactgag  10800
catgtaccga gtgtttgaag taggtgttat cagaaatccg ggtttggggg ctccggtgtt  10860
ccatatgaca aactatcttg agcaaccagc cagtaatgat ctcagcaact gtatggtggc  10920
tttgggggag ctcaaactcg cagccctttg tcacggggaa gattctatca caattcccta  10980
tcagggatca gggaaaggtg tcagcttcca gctcgtcaag ctaggtgtct ggaaatcccc  11040
aaccgacatg caatcctggg tccccttatc aacggatgat ccagtgatag acaggcttta  11100
cctctcatct cacagaggtg ttatcgctga caatcaagca aaatgggctg tcccgacaac  11160
acgaacagat gacaagttgc gaatggagac atgcttccaa caggcgtgta agggtaaaat  11220
ccaagcactc tgcgagaatc ccgagtgggc accattgaag gataacagga ttccttcata  11280
cggggtcttg tctgttgatc tgagtctgac agttgagctt aaaatcaaaa ttgcttcggg  11340
attcgggcca ttgatcacac acggttcagg gatggaccta tacaaatcca accacaacaa  11400
tgtgtattgg ctgactatcc cgccaatgaa gaacctagcc ttaggtgtaa tcaacacatt  11460
ggagtggata ccgagattca aggttagtcc ctacctcttc aatgtcccaa ttaaggaagc  11520
aggcgaagac tgccatgccc caacatacct acctgcggag gtggatggtg atgtcaaact  11580
cagttccaat ctggtgattc tacctggtca agatctccaa tatgttttgg caacctacga  11640
tacttccagg gttgaacatg ctgtggttta ttacgtttac agcccaggcc gctcattttc  11700
ttacttttat ccttttaggt tgcctataaa gggggtcccc atcgaattac aagtggaatg  11760
cttcacatgg gaccaaaaac tctggtgccg tcacttctgt gtgcttgcgg actcagaatc  11820
tggtggacat atcactcact ctgggatggt gggcatggga gtcagctgca cagtcacccg  11880
ggaagatgga accaatcgca gatagggctg ctagtgaacc aatctcatga tgtcacccag  11940
acatcaggca tacccactag tgtgaaatag acatcagaat taagaaaaac gtagggtcca  12000
agtggttccc cgttatggac tcgctatctg tcaaccagat cttataccct gaagttcacc  12060
tagatagccc gatagttacc aataagatag tagccatcct ggagtatgct cgagtccctc  12120
acgcttacag cctggaggac cctacactgt gtcagaacat caagcaccgc ctaaaaaacg  12180
gattttccaa ccaaatgatt ataaacaatg tggaagttgg gaatgtcatc aagtccaagc  12240
ttaggagtta tccggcccac tctcatattc catatccaaa ttgtaatcag gatttattta  12300
acatagaaga caaagagtca acgaggaaga tccgtgaact cctcaaaaag gggaattcgc  12360
tgtactccaa agtcagtgat aaggttttcc aatgcttaag ggacactaac tcacggcttg  12420
gcctaggctc cgaattgagg gaggacatca aggagaaagt tattaacttg ggagtttaca  12480
tgcacagctc ccagtggttt gagccctttc tgttttggtt tacagtcaag actgagatga  12540
ggtcagtgat taaatcacaa acccatactt gccataggag gagacacaca cctgtattct  12600
tcactggtag ttcagttgag ttgctaatct ctcgtgacct tgttgctata atcagtaaag  12660
agtctcaaca tgtatattac ctgacatttg aactggtttt gatgtattgt gatgtcatag  12720
aggggaggtt aatgacagag accgctatga ctattgatgc taggtataca gagcttctag  12780
gaagagtcag atacatgtgg aaactgatag atggtttctt ccctgcactc gggaatccaa  12840
cttatcaaat tgtagccatg ctggagcctc tttcacttgc ttacctgcag ctgagggata  12900
```

-continued

```
taacagtaga actcagaggt gctttcctta accactgctt tactgaaata catgatgttc  12960
ttgaccaaaa cgggttttct gatgaaggta cttatcatga gttaattgaa gctctagatt  13020
acattttcat aactgatgac atacatctga caggggagat tttctcattt ttcagaagtt  13080
tcggccaccc cagacttgaa gcagtaacgg ctgctgaaaa tgttaggaaa tacatgaatc  13140
agcctaaagt cattgtgtat gagactctga tgaaaggtca tgccatattt tgtggaatca  13200
taatcaacgg ctatcgtgac aggcacggag gcagttggcc accgctgacc ctcccccctgc  13260
atgctgcaga cacaatccgg aatgctcaag cttcaggtga agggttaaca catgagcagt  13320
gcgttgataa ctggagatct tttgctggag tgaaatttgg ctgctttatg cctcttagcc  13380
tggatagtga tctgacaatg tacctaaagg acaaggcact tgctgctctc caaagggaat  13440
gggattcagt ttacccgaaa gagttcctgc gttacgaccc tcccaaggga accgggtcac  13500
ggaggcttgt agatgttttc cttaatgatt cgagctttga cccatatgat gtgataatgt  13560
atgttgtaag tggagcttac ctccatgacc ctgagttcaa cctgtcttac agcctgaaag  13620
aaaaggagat caaggaaaca ggtagacttt ttgctaaaat gacttacaaa atgagggcat  13680
gccaagtgat tgctgaaaat ctaatctcaa acgggattgg caaatatttt aaggacaatg  13740
ggatggccaa ggatgagcac gatttgacta aggcactcca cactctagct gtctcaggag  13800
tccccaaaga tctcaaagaa agtcacaggg gggggccagt cttaaaaacc tactcccgaa  13860
gcccagtcca cacaagtacc aggaacgtga gagcagcaaa agggtttata gggttccctc  13920
aagtaattcg gcaggaccaa gacactgatc atccggagaa tatggaagct tacgagacag  13980
tcagtgcatt tatcacgact gatctcaaga agtactgcct taattggaga tatgagacca  14040
tcagcttgtt tgcacagagg ctaaatgaga tttacggatt gccctcattt ttccagtggc  14100
tgcataagag gcttgagacc tctgtcctgt atgtaagtga ccctcattgc ccccccgacc  14160
ttgacgccca tatcccgtta tataaagtcc ccaatgatca aatcttcatt aagtacccta  14220
tgggaggtat agaagggtat tgtcagaagc tgtggaccat cagcaccatt ccctatctat  14280
acctggctgc ttatgagagc ggagtaagga ttgcttcgtt agtgcaaggg gacaatcaga  14340
ccatagccgt aacaaaaagg gtacccagca catggcccta caaccttaag aaacgggaag  14400
ctgctagagt aactagagat tactttgtaa ttcttaggca aaggctacat gatattggcc  14460
atcacctcaa ggcaaatgag acaattgttt catcacattt ttttgtctat tcaaaaggaa  14520
tatattatga tgggctactt gtgtcccaat cactcaagag catcgcaaga tgtgtattct  14580
ggtcagagac tatagttgat gaaacaaggg cagcatgcag taatattgct acaacaatgg  14640
ctaaaagcat cgagagaggt tatgaccgtt accttgcata ttccctgaac gtcctaaaag  14700
tgatacagca aattctgatc tctcttggct tcacaatcaa ttcaaccatg acccgggatg  14760
tagtcatacc cctcctcacg aacaacgacc tcttaataag gatggcactg ttgcccgctc  14820
ctattggggg gatgaattat ctgaatatga gcaggctgtt tgtcagaaac atcggtgatc  14880
cagtaacatc atcaattgct gatctcaaga gaatgattct cgcctcacta atgcctgaag  14940
agaccctcca tcaagtaatg acacaacaac cgggggactc ttcattccta gactgggcta  15000
gcgaccctta ctcagcaaat cttgtatgtg tccagagcat cactagactc ctcaagaaca  15060
taactgcaag gtttgtcctg atccatagtc caaacccaat gttaaaagga ttattccatg  15120
atgacagtaa agaagaggac gagggactgg cggcattcct catggacagg catattatag  15180
tacctagggc agctcatgaa atcctggatc atagtgtcac aggggcaaga gagtctattg  15240
```

-continued

```
caggcatgct ggataccaca aaaggcctga ttcgagccag catgaggaag ggggggttaa  15300
cctctcgagt gataaccaga ttgtccaatt atgactatga acaattcaga gcagggatgg  15360
tgctattgac aggaagaaag agaaatgtcc tcattgacaa agagtcatgt tcagtgcagc  15420
tggcgagagc tctaagaagc catatgtggg cgaggctagc tcgaggacgg cctatttacg  15480
gccttgaggt ccctgatgta ctagaatcta tgcgaggcca ccttattcgg cgtcatgaga  15540
catgtgtcat ctgcgagtgt ggatcagtca actacggatg gtttttgtc ccctcgggtt  15600
gccaactgga tgatattgac aaggaaacat catccttgag agtcccatat attggttcta  15660
ccactgatga gagaacagac atgaagcttg ccttcgtaag agccccaagt cgatccttgc  15720
gatctgctgt tagaatagca acagtgtact catgggctta cggtgatgat gatagctctt  15780
ggaacgaagc ctggttgttg gctaggcaaa gggccaatgt gagcctggag gagctaaggg  15840
tgatcactcc catctcaact tcgactaatt tagcgcatag gttgagggat cgtagcactc  15900
aagtgaaata ctcaggtaca tcccttgtcc gagtggcgag gtataccaca atctccaacg  15960
acaatctctc atttgtcata tcagataaga aggttgatac taactttata taccaacaag  16020
gaatgcttct agggttgggt gttttagaaa cattgtttcg actcgagaaa gataccggat  16080
catctaacac ggtattacat cttcacgtcg aaacagattg ttgcgtgatc ccgatgatag  16140
atcatcccag gatacccagc tcccgcaagc tagagctgag ggcagagcta tgtaccaacc  16200
cattgatata tgataatgca cctttaattg acagagatac aacaaggcta tacacccaga  16260
gccataggag gcaccttgtg gaatttgtta catggtccac accccaacta tatcacattt  16320
tagctaagtc cacagcacta tctatgattg acctggtaac aaaatttgag aaggaccata  16380
tgaatgaaat ttcagctctc ataggggatg acgatatcaa tagtttcata actgagtttc  16440
tgctcataga gccaagatta ttcactatct acttgggcca gtgtgcggcc atcaattggg  16500
catttgatgt acattatcat agaccatcag ggaaatatca gatgggtgag ctgttgtcat  16560
cgttcctttc tagaatgagc aaaggagtgt ttaaggtgct tgtcaatgct ctaagccacc  16620
caaagatcta caagaaattc tggcattgtg gtattataga gcctatccat ggtccttcac  16680
ttgatgctca aaacttgcac acaactgtgt gcaacatggt ttacacatgc tatatgacct  16740
acctcgacct gttgttgaat gaagagttag aagagttcac atttctcttg tgtgaaagcg  16800
acgaggatgt agtaccggac agattcgaca acatccaggc aaaacactta tgtgttctgg  16860
cagatttgta ctgtcaacca gggacctgcc caccaattcg aggtctaaga ccggtagaga  16920
aatgtgcagt tctaaccgac catatcaagg cagaggctag gttatctcca gcaggatctt  16980
cgtggaacat aaatccaatt attgtagacc attactcatg ctctctgact tatctccggc  17040
gaggatcgat caaacagata agattgagag ttgatccagg attcatttc gacgccctcg  17100
ctgaggtaaa tgtcagtcag ccaaagatcg gcagcaacaa catctcaaat atgagcatca  17160
aggctttcag acccccacac gatgatgttg caaaattgct caaagatatc aacacaagca  17220
agcacaatct tcccatttca gggggcaatc tcgccaatta tgaaatccat gctttccgca  17280
gaatcgggtt gaactcatct gcttgctaca aagctgttga gatatcaaca ttaattagga  17340
gatgccttga gccaggggag gacggcttgt tcttgggtga gggatcgggt tccatgttga  17400
tcacttataa ggagatactt aaactaaaca agtgcttcta taatagtggg gtttccgcca  17460
attctagatc tggtcaaagg gaattagcac cctatccctc cgaagttggc cttgtcgaac  17520
acagaatggg agtaggtaat attgtcaaag tgctctttaa cgggaggccc gaagtcacgt  17580
gggtaggcag tgtagattgc ttcaatttca tagttagtaa tatccctacc tctagtgtgg  17640
```

-continued

```
ggtttatcca ttcagatata gagaccttgc ctaacaaaga tactatagag aagctagagg  17700

aattggcagc catcttatcg atggctctgc tcctgggcaa aataggatca atactggtga  17760

ttaagcttat gcctttcagc ggggattttg ttcagggatt tataagttat gtagggtccc  17820

attatagaga agtgaacctt gtatacccta gatacagcaa cttcatatct actgaatctt  17880

atttggttat gacagatctc aaggctaacc ggctaatgaa tcctgaaaag attaagcagc  17940

agataattga atcatctgtg aggacttcac ctggacttat aggtcacatc ctatccatta  18000

agcaactaag ctgcatacaa gcaattgtgg gagacgcagt tagtagaggt gatatcaatc  18060

ctactctgaa aaaacttaca cctatagagc aggtgctgat caattgcggg ttggcaatta  18120

acggacctaa gctgtgcaaa gaattgatcc accatgatgt tgcctcaggg caagatggat  18180

tgcttaattc tatactcatc ctctacaggg agttggcaag attcaaagac aaccaaagaa  18240

gtcaacaagg gatgttccac gcttaccccg tattggtaag tagcaggcaa cgagaactta  18300

tatctaggat cacccgcaaa ttttgggggc acattcttct ttactccggg aacagaaagt  18360

tgataaataa gtttatccag aatctcaagt ccggctatct gatactagac ttacaccaga  18420

atatcttcgt taagaatcta tccaagtcag agaaacagat tattatgacg gggggtttga  18480

aacgtgagtg ggtttttaag gtaacagtca aggagaccaa agaatggtat aagttagtcg  18540

gatacagtgc cctgattaag gactaattgg ttgaactccg gaaccctaat cctgccctag  18600

gtggttaggc attatttgca atagattaaa gaaaactttg aaaatacgaa gtttctattc  18660

ccagctttgt ctggtgccgg ccatggtccc agcctcctcg ctggcggccg gtgggcaaca  18720

ttccgagggg accgtcccct cggtaatggc gaatgggacc gtttaaaccc            18770
```

DNA MOLECULES PRODUCING CUSTOM DESIGNED REPLICATING AND NON-REPLICATING NEGATIVE STRANDED RNA VIRUSES AND USES THERE OF

CROSS-REFERENCE TO RELATED APPLICATIONS

This application is a U.S. National Phase application, under 35 U.S.C. § 371, of International Application no. PCT/IN2016/000004, with an international filing date of Jan. 4, 2016, and claims benefit of India Application no. 39/MUM/2015 filed on Jan. 5, 2015, and which are hereby incorporated by reference for all purposes.

REFERENCE TO SEQUENCE LISTING

The entirety of the electronically filed sequence listing text file named Sequence_ListingCRF_ST25.txt, created Aug. 20, 2018, 359 kB, is incorporated by reference herein.

FIELD OF INVENTION

The present invention relates to the production of recombinant derivatives of negative stranded RNA viruses. More specifically, the present invention relates to the production of replicating derivatives of measles virus (MV) that contain a single additional transcriptional unit (ATU) coding for 2 to 4 non-MV genes. This invention also relates to the production of custom designed non-replicating measles virus derivatives. Moreover, this invention relates to production of replicating measles virus derivatives that are useful for transferring 2 to 4 non-measles genes into animal cells including into human cancer cells and other human cells. The invention also relates to use of replicating MV derivatives for treatment of Cancer. This invention also relates to use of the non-replicating MV derivatives described in this invention as vectors for gene therapy of cancer and other diseases. Non-replicating MV derivatives useful for use as vaccinating agents for prevention of diseases like Measles and Dengue are also described.

BACKGROUND OF THE INVENTION

Measles is an acute potentially lethal respiratory infection of infants & children caused by measlesvirus (MV), a member of morbillivirus genus of negative stranded RNA viruses. Development of live attenuated virus MV vaccine in 1960s has helped reduce the incidence of and deaths caused by Measles to near eradication and MV vaccine is recognized as one of the most effective and safe vaccines available till date. MV is a member of the genus morbillivirus of family Paramyxoviridae. It contains a negative stranded RNA genome that has unique highly conserved 3' and 5' termini called leader and trailer respectively and codes for 6 genes—N (nucleocapsid protein), P (phosphoprotein), M (matrix protein), F (fusion protein), H (hemagglutinin) and L (large protein/a polymerase) separated by similarly conserved intergenic sequences. The H and F genes that code for glycoproteins are essential for entry of MV, into susceptible cells. The H protein binds to its receptor proteins and induces conformational changes in F protein which cause the fusion of cell membrane with viral membrane and releases the MV nucleocapsid into host cells. Once inside the host cell, the viral RNA dependent RNA polymerase initiates the expression of MV genes. The newly expressed H and F proteins in turn are expressed on the cell membrane and mediate cell-cell fusion and transfer of MV into neighbouring cells resulting into large multinuclear syncytia that are a typical of MV cytopathic effect.

Early in 1970s, several case reports described the spontaneous regression of haematological cancers following infection with Measles virus (MV) [1-4] suggesting that MV may exert cancer therapeutic effect. Subsequent observations showed that MV induces preferential lysis of a wide variety of cancer cell types including breast [5], cutaneous T cell leukemia [6, 7], lung cancer [8], mesothelioma [9] etc in vitro and in vivo in xenotransplant models. This oncolytic effect of MV is also observed in clinical setting as reported in case of CTCL [6], ovarian cancer [10] and myeloma [11, 12], which showed that MV treatment is safe even after treatment with extremely high dose ($10^6$ times the vaccine dose) and has potential to induce an objective and dose dependent tumor response [13]; Russell and coworkers showed that MV-NIS induced complete regression of long standing relapsing drug-refractory myeloma and multiple glucose-avid plasmacytomas [12] and the patients remained tumour free for significant albeit different lengths of time.

Thus, MV has emerged as a potent oncolytic virus capable of causing complete regressions of established tumours in clinical setting and several researchers have reported the synthesis of oncolytic MV derivatives—U.S. Pat. Nos. 7,670,598, 8,586,364, 6,896,881, 7,118,740, 7,393,527 and 7,670,598. However, the currently used oncolytic derivatives of MV also have certain limitations. They are developed using the original method developed by Billeter and colleagues [14] (WO 97/06270). However, the nucleotide sequence of the plasmid used to synthesize MV is closer to the wild type Edmonston strain [15, 16]. Additionally, this method uses cell lines like chicken embryo fibroblasts (CEK) or 293 human embryonic kidney (HEK) cells which are not approved for vaccine production. In contrast, strains already used as vaccines for MV (e.g. Edmonston-Zagreb, Edmonston-Enders, Alk C, Edmonston. A, Schwarz and Edmonston B-Moraten) are already manufactured in approved cell lines & processes and have been used clinically since 1960s and shown excellent safety in clinical situations. Their oncolytic derivatives may prove safer clinically & could have a greater chance of reaching the clinic.

Three other important shortcomings may prevent further translation of Measles as a cancer therapeutic agent: (1) Measles virus must be used at extremely high doses which are difficult to manufacture, (2) cancer cells respond heterogeneously to MV treatment and unkilled tumour cells may grow into recurring tumours after different time intervals and harbour MV used for therapy, and (3) most people are immunized against measles and harbour long lasting anti-MV immunity. This pre-existing anti-MV immunity can compromise efficacy of oncolytic MV and development of effective strategies for circumventing anti-MV immunity is essential. As a result, it is necessary to develop new improved oncolytic Measles virotherapies which will be more potent, exert a comprehensive therapeutic effect and may be able to circumvent anti-MV immunity.

The formation of syncytia stimulated by the binding of H protein to its receptors and their subsequent apoptotic death is responsible for the cancer therapeutic effect of MV. Two cell surface molecules—Signalling lymphocyte-activation molecule (SLAM) and CD46 are known [17, 18] to function as specific receptors for MV. CD46 is ubiquitously present on primate cells but is over-expressed on several cancer cells. CD46 is a membrane associated complement regulatory protein that protects human cells against autologous complement mediated lysis. The expression of CD46 is increased in a wide range of cancer cells and helps cancer cells avoid their immunological clearance. The vaccine strain of MV infects cancer cells which express CD46 at high levels preferentially and induces cell death; however, it has no effect on non-cancerous cells which express CD46 at low levels [19].

The oncolytic effect of MV depends on the ability of its fusogenic proteins (H & F) to form syncytia that undergo apoptotic cell death. Since the H and F proteins present in most of the currently reported oncolytic MV derivatives are similar (e.g. U.S. Pat. Nos. 7,670,598, 8,586,364, 6,896,881, 7,118,740, 7,393,527 and 7,670,598), they exhibit similar potency for inducing cancer cell death. Therefore enhancement of the binding affinity & the fusogenic potential of these proteins may represent one method of enhancing the oncolytic potency of MV. Mutational analysis of the H & F proteins have identified several critical aminoacids which determine the efficiency & potency of cell fusion. This information may be used to improve the oncolytic potency of MV. However, the effect of mutating MV H and F proteins on the pathogenic activity of MV is difficult to predict and so this approach may not be desirable.

Another approach may be to Combine oncolytic effect of MV with the therapeutic effect of other genes. Recent gene therapy trials have shown that a large variety of genes including (1) suicide genes which induce cell death [20], (2) genes that increase the susceptibility of cancer cells to chemotherapy [20] (3) genes that restore specific oncogene/tumour suppressor gene function [21-23] and (4) genes that induce anti-tumour immune responses and arm the patient's immune system to eliminate cancer cells [24] have therapeutic benefit and MV derivatives incorporating some of these may be useful. Indeed. MV derivatives encoding genes/proteins that enhance the sensitivity of cancer cells to radiotherapy (MV-NIS), [11, 25] or susceptibility to specific cancer therapeutic agents by arming MV to pro-drug converting enzymes like purine nucleoside phosphorylase have already been developed [26-28]. Similarly, arming MV derivatives with genes encoding human GMCSF [29] or antibodies to CTLA4 or PD-L1 proteins [30] were found to increase the therapeutic efficacy of oncolytic MV.

However, such modifications are not sufficient to make MV uniformly effective as an oncolytic agent against cancer cells. The vaccine strain of MV infects cancer cells which express CD46 at high levels preferentially and induces cell death. However, cancer cells are known to be heterogenous. Different cancer cells are known to harbour genetic defects in specific one or more oncogenes and/or tumour suppressor genes like p53, Ras, Her-2, etc which help them maintain the cancerous phenotype. And introducing the variants of these genes which either restore their function or inhibit their abberent function into cancer cells is known to inhibit cancer cell growth. Similarly, well differentiated cancer cells are more likely to express higher levels of CD46 than less differentiated cells [31]. As a result, MV does not kill the subset of cancer cells which express CD46 at low levels [19]. Therefore, arming oncolytic MV with appropriate genes that help identify & kill cancer cells which may be infected with MV but have escaped oMV-induced cell death is required. Russell and coworkers, armed MV-NIS with sodium iodide symporter gene which allows such cells to be killed by radioiodine therapy selectively. Similar arming of MV to seek and kill MV infected (cancer) cells that escape MV-induced death would be essential.

Arming MV derivatives with prodrug modifying enzymes like Prostate acidic phosphatase, Cytosine deaminase, Thymidine kinase, Purine nucleotide phosphorylase etc can be one way to facilitate the use of the prodrugs of 5FU, acyclovir, etc for killing tumor cells which escape oMV induced death. Such a strategy will also help eliminate all residual MV remaining in the body after successful treatment with oMV. Arming MV derivatives with one or more such genes will help increase the potency of its oncolytic effect and also make the effect more uniform.

Two types of events are known to make establishment and maintenance of tumour cells feasible in human body. Firstly, accumulations of mutations in key tumor suppressor and oncogenes, cell cycle regulatory genes and other genes are well known to induce the cancer phenotype. A parallel failure of human immune response to identify such cancerous/abnormal cells and eliminate them is necessary to promote an uncontrolled growth of these cancer cells. Further accumulation of mutations makes the tumors more aggressive. Therefore, a two pronged attack on cancers and human immune system will help cancer therapy.

A number of cytokines have been shown to be useful for enhancing the immune response against cancer and help its immune elimination. Several of them are currently used as therapeutic agents. Human GMCSF is a potent inducer of granulocyte and macrophage growth. It also attracts and induces maturation of dendritic cells, CD4+ and CD8+ T cells and induces anti-tumor immune responses and causes tumor necrosis. It is used as an adjuvant therapy of cancer. GMCSF-secreting cells have also been shown to be useful tumor vaccines. More recently, virus mediated GMCSF expression (T-Vec, JX 594 and JX929) has also been shown to enhance the oncolytic effect through immune stimulation [29].

Tumor cells also use a number of molecular pathways for evading their clearance by human immune system. They are known to express a number of immunoregulatory molecules including CD46, Fas ligand, the ligands of the Programmed death 1 (PD-1) molecules etc which help in the evasion of immune system. Targeting the PD-1:PD-Ligand pathways has emerged as a very effective way of enhancing the anti-tumour immune response. PD-1 is an immunoinhibitory molecule that belongs to the CD28 family and is expressed on the T cells, B cells, monocytes, natural killer cells and many tumour infiltrating cells. It has 2 ligands PD-L1 and PD-L2. PD-L1 is expressed on resting T and B cells, dendritic cells, macrophages, vascular endothelial cells and pancreatic islet cells where as PD-L2 is expressed on dendritic cells and macrophages alone. A number of tumor cells express PD-L1 at high levels. Some tumor cells are also known to express PD-L2. Various cancers such as melanoma, hepatocellular carcinoma, glioblastoma, lung, kidney, breast, ovarian, pancreatic and esophageal cancers as well as haematological malignancies have positive PD-L1 expression and this is correlated to poor prognosis. Tripple negative breast cancer (TNBC) which is a particularly aggressive type of breast cancer, frequently shows high levels of PD-L1 which is correlated with higher grade, larger tumours, and poor prognosis. Even in case of advanced lung cancer, levels of regulatory T cells (CD4+), which help supress tumour immune surveillance are increased, immune checkpoint pathways involving PD-1/PD-L1 are involved in regulating T cell responses and inhibition of this pathway is suggested to offer a useful means of controlling it. A number of anti-PD-1 and anti-PD-L1 antibodies have emerged as useful therapeutic options for different types of cancer. However, they are associated with immune-related adverse effects such as pneumonitis, vitiligo, colitis, hepatitis, hypophysitis and thyroiditis. In contrast, expression of PD-1 inhibitors within the tumour microenvironment may help limit the effects of PD-1 blockade to the tumours and eliminate these adverse effects [30]. Additionally, it will also remove the inhibitory effect on Tumor Infiltrating lymphocytes and increase the immunological clearance of tumors. GMCSF will attract immune cells into tumour microenvironment. However, their inactivation by PD-L1 mediated immunoregulatory signals will nullify the advantage of GMCSF incorporation into oMV. Therefore, it was decided to introduce a soluble PD-1 molecule into the oncolytic MV.

Several strategies may be used to kill cancer cells which are infected with oMV but escape cell death. Russell and coworkers have used sodium iodide symporter. Cytosine deaminase which degrades prodrugs and sensitizes cells to death caused by 5-fluorouracil has also been used [27, 28].

A large proportion of people are usually immunized against MV in childhood and this pre-existing immunity has been shown to interfere in the therapeutic effect of MV derivatives [12]. Evasion of this anti-MV immunity is essential for using MV virus as anti-cancer agent.

Therefore, strategies like the use of MV-infected cell carriers instead of MV have been used to circumvent the hurdle posed by pre-existing anti-MV immunity [32]. This strategy has been suggested to mask the MV from anti-MV immunity long enough to allow successful therapy. However, its efficiency has yet to be clinically proven and alternate modalities that will help overcome this hurdle are needed. Employing chimeric MV derivatives that express non-MV fusogenic proteins capable of stimulating oncolysis may provide another approach. Indeed, Miest et al, (2011) showed that chimeric MV derivatives expressing glycoproteins of the related canine distemper virus (CDV) were capable of evading anti-MV immunity [33] in animals. Such replacement of fusogenic proteins may give rise to a new virus with unpredictable pathogenic potential and since oMV need to be used at extremely high doses, this approach may not be desirable.

SUMMARY OF THE INVENTION

This invention comprises compositions, methods of making the same, methods of using the same and a reagent kit wherein the compositions comprise non-replictaing and replicating negative stranded RNA virus derivatives comprising a genome coding for two or more non-viral genes inserted in the same, or plasmid molecules coding for the genomes of the said negative stranded RNA virus derivatives comprising two or more non-viral genes inserted in the same. The feature "comprising two or more non-viral genes inserted in the same" is the common technical feature of the above mentioned compositions.

The invention also comprises compositions comprising non-replicating negative stranded RNA virus derivatives, comprising one or more non-viral genes.

This invention comprises a derivative of an attenuated negative stranded RNA virus belonging to family paramyxoviridae, wherein the derivative comprises two or more non-viral genes inserted in the same. The said derivative comprises two or more or three or more or four or more non-viral genes. The said virus may be a Measles Virus (MV) or any other virus with equivalent attenuation, equivalent safety for a human being and with same requirements for rescuing the any other virus from cDNA; the said requirements comprising use of viral N, P and L proteins expressed from three distinct helper plasmids and use of a plasmid coding a viral anti-genomic RNA modified by insertion of a single additional transcriptional unit.

This invention also comprises a process of making the said derivative of attenuated Measles Virus, the process comprises use of (a) a two plasmid system and comprising (i) one cloning plasmid comprising the entire anti-genome of measles virus with or without an additional transcriptional unit (ATU) coding for non-MV genes or MV genome like replicon RNA coding for non-MV genes along with a subset of MV genes wherein MV stands for "Measles Virus", (ii) one helper plasmid coding for and expressing N, P, L proteins respectively, and (iii) a cell line supporting measles virus replication; the cell line may or may not be modified to express one or more of M or F or H proteins of MV stably but not requiring the help of exogenous vaccinia virus or exogenous T7 RNA polymerase.

The derivative of an attenuated negative stranded RNA virus of measles virus of his invention consists of a replicating derivative or a non-replicating derivative. The non-replicating derivative is named as "Virosome" for the purpose of this specification. In one aspect of the invention, the replicating derivative of the attenuated Measles Virus comprises a single additional transcriptional unit (ATU) coding for 2 to 4 non-Measles Virus genes inserted in Measles Virus genome. The non-Measles Virus genes comprise, without limitation, one or more of following features: (a) genes that code for cytokines or chemokines, (b) genes that code for growth factors, (c) genes that code for immuno-regulatory genes, (d) genes that cause death of cancer cells, (e) genes that code for tumour associated antigen, (f) genes that arrest the growth of cancer cells, (g) genes that sensitize cancer cells to death by prodrugs, (h) genes that sensitize cancer cells to death by other therapeutic agents/mechanisms, and the like. The said non-MV genes include, one or more, without limitation, (a) genes that code for cytokine comprise human GMCSF, IL-2, IL-11, IL-15, TNF-alpha, etc, (b) genes that kills or arrests the growth of cancer cell death comprise dominant negative cyclin G1, p53, Bcl-2, etc. (c) genes that code for immune-regulatory genes comprise soluble PD-1, soluble CTLA-4, or antibodies blocking the activity of these molecules, (d) genes that code for tumor specific antigen comprise prostatic acid phosphatase, prostate specific antigen, carcinoembryonic antigen, (e) genes that sensitize cancer cells to death by prodrugs comprising cytosine deaminase, thymidine kinase, prostatic acid phosphatase and the other therapeutic agents comprise sodium iodide symporter. The derivatives of the attenuated Measles Virus of this embodiment of the invention are illustrated by (a) rMV-GP, wherein an ATU comprising sequence ID #10 is inserted upstream of N protein coding region, (b) rMV-GC, wherein an ATU comprising sequence ID #11 is inserted upstream of N protein coding region, (c) rMV-GsPP, wherein an ATU comprising sequence ID #12 is inserted upstream of N protein coding region, (d) rMV-GsPC, wherein an ATU comprising sequence ID #13 is inserted upstream of N protein coding region, (e) rMV-GsPDP, wherein an ATU comprising sequence ID #14 is inserted upstream of N protein coding region or rMV-GsPDC, wherein an ATU comprising sequence ID #15 is inserted upstream of N protein coding region.

The Virosomes comprise (a) Virosomes coding exclusively non-MV genes, and (b) Virosomes coding non-MV genes and/or a subset of MVgenes. Some of the features these Virosomes are capable of include, without limitation, (a) displaying antigens from other pathogenic organisms including viruses like Dengue, (b) delivering and inducing the expression of genes coding for antigens from other pathogenic organisms including viruses like Dengue, (c) inducing immunity against different non-measles virus antigens, (d) delivering non-measles virus genes into human/animal cells for modulating the expression of cellular genes, (e) capable of serving as vaccines against different diseases, and (f) serving as therapeutic agents for treatment of different disease. Some illustrations of Virosome comprise: (a) GFP virosome comprising genome coding for green fluorescent protein and produced from the plasmid pMTX-P1T (Seq ID #1)—by inserting the cDNA encoding green fluorescence protein (GFP) in between Pml I and Pme I sites, (b) Virosome comprising a genome that codes for prM and E proteins of dengue virus and produced from the plasmid pMTX-P1T-D2G comprising Seq ID #21, (c) Virosome comprising a genome that codes for the preM and E proteins of Dengue Virus along with the N, P and L proteins of measles Virus, produced from a plasmid derived from pMTX-P1T-High (Seq ID #7) by inserting the cDNA coding for prM and E proteins in between Asc I and Xho I sites, (d) Virosome comprising a genome that codes for a truncated-prM and E proteins of Dengue virus, and produced by deleting the region corresponding to Seq ID #22 from Seq ID #21, (e) Virosome comprising a genome that codes for a truncated-prM and E proteins of Dengue virus along with N, P and L prroteins of Measles Virus, and produced from a plasmid derived from pMTX-P1T-High by inserting a cDNA corresponding to prM truncated by deleting Seq ID#22 and E proteins at Asc I and Xho I sites, (f) Virosome, comprising a genome that codes the H and F proteins of Measles Virus and is derived from pMV (Seq ID #9 or Seq ID #28) by deleting the sequences corresponding to the N, P, M and L genes of MV, and (g) Virosome, comprising a genome for one or more of therapeutically useful genes and a sub-set of MV genes derived from pMTX-P1T-NP-RE1-FH-RE2-RE3 (Seq ID #8) or by replacing one or more of the MV protein coding regions from pMV (Seq ID #9 or Seq ID #28) with other therapeutically useful genes. Further specific examples of these Virosomes comprise: a Virosome comprising one or more of genes comprising dominant negative mutant of Cyclin G1, cytocidal genes, Cytosine deaminase gene, human granulocyte macrophage colony stimulating factor gene (GMCSF) gene, soluble PD-1 blockade gene, PD1 blocking antibody gene and gene for prostate specific acid phosphatase (PAP).

This invention also includes plasmids coding for the anti-genome of replicating Measles Virus derivatives comprising a single additional transcriptional unit (ATU) that comprises two or more non-viral genes inserted in the same. These plasmids comprise, without limitation, pMV-GP of sequence ID #16, pMV-GC of sequence ID #17, pMV-GsPP of sequence ID #23, pMV-GsPC of sequence ID #25, pMV-GsPDP of sequence ID #24, pMV-GsPDC of sequence ID #26.

This invention also comprises a method for producing a non-replicating derivatives of an attenuated derivative of a Measles Virus, the term "Measles Virus" being abbreviated as "MV" hereafter, the non-replictaing derivative being named as virosome and the method comprising of one or more of following steps: (a) co-transfecting MV Packaging cell line with a Cloning Plasmid and a Helper plasmid, (b) incubating at a temperature between 35° C. to 38° C. for 3 to 10 days, and (c) collecting Virosome containing culture supernatant; wherein the non-replicating derivative of an attenuated derivative of Measles Virus comprisies two or more non-viral genes inserted in the same.

This invention also discloses a plasmid coding for and expressing N, P, and L proteins of Measles Virus. In one embodiment, this plasmid has Seq ID 18 and is used along with plasmid coding for a MV derivative comprising two or more non-viral genes inserted in the same. This invention also discloses a plasmid coding for Measles Virus genome-like replicon RNA, the term "Measles Virus" being abbreviated as "MV" hereafter, comprising one or more of non-MV genes and a subset of MV genes. This embodiment of plasmids of this invention has been illustrated, without limitation, by plasmids pMTX-P1T (Seq ID #1), pMTX-P1T-Intermediate (Seq ID #4), pMTX-P1T-High (Seq ID #7) and pMTX-P1T-NP-RE1-FH-RE2-RE3 (Seq ID #8).

This invention also discloses a Measles Virus packaging cell line for producing derivative of an attenuated negative stratded virus belonging to family paramyxoviridae, the derivative comprising two or more non-viral genes inserted in the same. In one embodiment, this cell line is capable of expressing the M, F and H proteins of MV stably. Illustrations of this type of MV packaging cell lines comprises $Viro_{MFH}$ In another embodiment, this cell line is capable of expressing the M protein of MV stably. Illustration of this type of MV packaging cell line comprises $Viro_{M}$.

This invention discloses a reagent kit for producing the non-replicating Measles Virus derivative, the reagent kit comprising (a) MV Packaging cell lines expressing the one or more of M, F and H proteins of MV stably, (b) cloning plasmid coding for MV genome-like replicon RNA comprising sites for cloning one or more of non-MV genes and a subset of MV genes, (c) helper plasmid coding for and expressing N, P, and L proteins of Measles Virus stably. This kit comprises MV packaging cell line comprising of $VERO_{MFH}$ or $Vero_{M}$ or both; cloning plasmids comprising any one selected from pMTX-P1T (Seq ID #1), pMTX-P1T-Intermediate (Seq ID #4), pMTX-P1T-High (Seq ID #7) and pMTX-P1T-NP-RE1-FH-RE2-RE3 (Seq ID #8), and a helper plasmid comprises plasmid of Seq ID #18; wherein the non-replicating measles Virus derivative comprising two or more non-viral genes inserted in the same.

This invention comprises a composition comprising: (a) replicating and non-replicating derivatives of an attenuated virus wherein the virus is Measles Virus, the term "Measles Virus" being abbreviated as "MV" hereafter, or any other virus with equivalent attenuation, equivalent safety for a human being and with requirements for rescuing the any other virus from cDNA, the requirements comprising use of viral N, P and L proteins expressed from three distinct helper plasmids and use of a plasmid coding a viral anti-genomic RNA modified by insertion of a single additional transcriptional unit, (b) Pharmaceutically acceptable excepients' wherein the replicating and non-replicating derivatives comprise two or more non-viral genes inserted in the same. This composition wherein the derivative of an attenuated virus is a non-replicating derivative, called for the purpose of this invention as "Virosome". The Virosome is one or more, without limitation, comprising a genome that codes for either exclusively non-measles genes or a combination of non-MV and a subset of MV genes. This composition includes a vaccine. The vaccine comprises, without limitation, one or more of: (a) GFP virosome comprising genome coding for green fluorescent protein, (b) Virosome comprising a genome that codes for prM and E proteins of dengue virus, (c) Virosome comprising a genome that codes for the preM and E proteins of Dengue Virus along with the N, P and L proteins of measles Virus, (d) Virosome comprising a genome that codes for a truncated prM and E proteins of Dengue virus, (e) Virosome comprising a genome that codes for a truncated prM and E proteins of Dengue virus along with N, P and L proteins of Measles Virus, and (g) Virosome, comprising a genome that codes the H and F proteins of Measles Virus. The vaccine comprising virosomes of above (b), (c), (d) and (e) corresponds to one or more of serotype 1, serotype 2, serotype 3 or serotype 4 of Dengue Virus. The composition Virosomes of above (b), (c), (d) and (e) are used as vaccine for prevention of Dengue and Virosome of (f) comprises a Measles Vaccine.

The Virosomes also comprise a non-vaccine medication; non-vaccine medication comprising, without limitation, a genome that codes for one or more of therapeutically useful genes and a sub-set of MV genes. This Virosome may be produced using plasmid pNPHF-GCG as a cloning plasmid.

It is also an embodiment of this invention that the composition of the derivative of an attenuated virus is a replicating derivative comprising derivatives that are capable to induce the death of cancer cells but do not adversely affect non-cancerous cells. In this embodiment, the cancer cells comprise breast cancer cells, lung cancer cells or prostate cancer cells and the non-cancerous cells are human non-cancerous cells or Vero cell line. The cancer cells, in such embodiments, comprise at least one of T47D, A-549 or PC-3 and human non-cancerous cells comprising at least one of human normal dermal fibroblasts or mesenchymal stem cells. In these compositions the replicating derivative is one or more selected from the group consisting of rMV-GP, wherein an ATU comprising sequence ID #10 is inserted upstream of N protein coding region, rMV-GC, wherein an ATU comprising sequence ID #11 is inserted upstream of N protein coding region, rMV-GsPP, wherein an ATU comprising sequence ID #12 is inserted upstream of N protein coding region, rMV-GsPC, wherein an ATU comprising sequence ID #13 is inserted upstream of N protein coding region, rMV-GsPDP, wherein an ATU comprising sequence ID #14 is inserted upstream of N protein coding region or rMV-GsPDC, wherein an ATU comprising sequence ID #15 is inserted upstream of N protein coding region.

This invention also includes composition of plasmids comprising: (a) a plasmid coding for the anti-genome of replicating MV derivatives comprising a single additional transcriptional unit (ATU) coding for 2 to 4 non-Measles Virus genes, (b) helper plasmid coding for and expressing N, P, and L proteins of Measles Virus, and (c) Pharmaceutically acceptable excipients; wherein the plasmid coding for anti-genome of replicating MV derivative comprises two or more non-viral genes inserted in the same. These composition comprise plasmid coding for the anti-genome of replicating Measles Virus derivatives comprising a single additional transcriptional unit (ATU) coding for 2 to 4 non-Measles Virus genes comprise one or More of pMV-GP of sequence ID #16, pMV-GC of sequence ID #17, pMV-GsPP of sequence ID #23, pMV-GsPC of sequence ID #25, pMV-GsPDP of sequence ID #24, pMV-GsPDC of sequence ID #26. And the helper plasmid comprises a plasmid of Seq ID 18. This invention also comprises a method of reducing the number of cancer cells, wherein the cancer cells are part of a tumour, the method comprising the steps of administering: (a) an oncolytic virus selected from the group consisting of rMV-GP, wherein an ATU comprising sequence ID #10 is inserted upstream of N protein coding region, rMV-GC, wherein an ATU comprising sequence ID #11 is inserted upstream of N protein coding region, rMV-GsPP, wherein an ATU comprising sequence ID #12 is inserted upstream of N protein coding region, rMV-GsPC, wherein an ATU comprising sequence ID #13 is inserted upstream of N protein coding region, rMV-GsPDP, wherein an ATU comprising sequence ID #14 is inserted upstream of N protein coding region or rMV-GsPDC, wherein an ATU comprising sequence ID #15 is inserted upstream of N protein coding region, or (b) a combination of the helper plasmid of Seq ID #18 and one or more of the plasmids selected from the group consisting of pMV-GP of sequence ID #16, pMV-GC of sequence ID #17, pMV-GsPP of sequence ID #23, pMV-GsPC of sequence ID #25, pMV-GsPDP of sequence ID #24, pMV-GsPDC of sequence ID #26, or (c) a defective interfering particles without the presence of contaminating replicating Measles Virus, named as Virosomes; the Virosomes comprising artificially designed Measles Virus genome like replicon RNAs that comprise exclusively of non-Measles Virus genes or a combination of non-Measles Virus and a subset of MV genes' wherein the oncolytic virus, the said one or more plasmids and the defective interfering particles comprise two or more non-viral genes inserted in the same.

This invention also includes a method wherein the cloning plasmid is derived from the plasmids pMTX-P1T (Seq ID #1), pMTX-P1T-intermediate (Seq ID #4) or pMTX-P1T-high (Seq ID #7) or pMTXP1T-NP-RE1-FH-RE2-RE3 (Seq ID #8) by inserting non-measles protein coding DNA sequences in one or both of the multiple cloning sites (MCS) provided; wherein the cloning plasmid comprises two or more non-viral genes inserted in the same.

The instant invention further comprises a method of improving the oncolytic potency of Measles Virus by incorporating one or more non-MV genes known to have anti-cancer effect.

This invention also includes Defective Interfering Particles, named as Virosome, the Defective Interfering Particles being without the presence of contaminating replicating Measles Virus; the Virosomes comprising artificially designed Measles Virus genome like replicon RNAs that comprise exclusively of non-Measles Virus genes or a combination of non-Measles Virus and a subset of MV genes; wherein the Vorosome comprises two or more non-viral genes inserted in the same.

DETAILED DESCRIPTION OF THE INVENTION

This invention comprises a oMV derivative that codes for multiple non-MV genes. Illustrative incorporation has been done of 3 different types of genes—immuno-modulating genes, genes that sensitize MV infected cells to treatment of other cancer therapies and genes which may rectify molecular lesions in cells that precipitate the cancerous phenotype or selectively kill those cells.

Cytosine deaminase and another enzyme—human prostatic acid phosphatase (PAP) are known to be useful to sensitize cancer cells to chemotherapy with prodrugs producing 5FU, BRdU and/or AraC. PAP enzyme also offers other advantage that it is only produced by prostate tissue, does not perform a physiologically critical function and can be easily assayed. Therefore, it may be useful as a marker for oMV proliferation as well as an enzyme for sensitizing oMV infected cells to chemotherapy. Therefore, Cytosine deaminase and human PAP were selected for introduction into oMV.

However, all these genes will not have a direct effect on the survival and/or proliferation of cancer cells. Discovery of defects in a number of genes such as p53, Bcl-2, HER-2/neu, PKA, TGF-alpha, EGFR, TGF-beta, IGFIR, P12, MDM2, BRCA, Bcl-2, ER, VEGF, MDR, ferritin, transferrin receptor, IRE, C-fos, HSP27, C-myc, C-raf and metallothionein genes etc [32-34] and their association with cancer and the advent of gene therapy has prompted their evaluation as potential therapeutic agents for cancer. Although most of these clinical trials have failed, genes like p53, dominant mutant of cyclin G1 (DnG1) etc have emerged as important genes which when delivered into cancer cells can help control the cancer cell growth and survival [35]. The DnG1 gene has recently emerged as a particularly useful gene for treatment of a wide range of solid tumour types. Incorporation of this gene into oncolytic MV may help increase the potency of oMV as a cancer therapeutic agent.

Therefore, it was decided to synthesize oMV derivatives which are armed with these genes for GMCSF, soluble PD-1, PAP and dominant negative cyclin G1 protein genes. Such oMV may exhibit a more potent cytotoxic effect on cancer cells and also enhance the anti-cancer immune response more effectively.

It is an embodiment of this invention that the pre-existing anti-MV immunity is circumvented by use of the DNA molecules which are useful to produce oncolytic MV derivatives. DNA will escape detection and neutralization by pre-existing anti-MV immunity and can be readily used as therapeutic agents. Previously, we have demonstrated that MV can also be produced using a simple 2 plasmid system (WO/2013/046216). In this invention, we further show that these 2 plasmids may be sufficient to induce cancer cell death by inducing the generation of oncolytic MV within the cancer cells in situ.

Reverse genetic studies have shown the feasibility of inserting upto 30% additional genetic material into MV genomic RNA and a several recombinant MV derivatives which code for and express a wide range of non-MV proteins including other viral protein genes and genes encoding human cytokines, other immunoregulatory proteins and other genes have been produced. In all these cases, the non-MV genes are introduced in the form of an artificially designed, additional transcriptional units (ATU) formed by assembling the target protein with cis-acting intergenic regions of MV genome. The ATUs can be introduced either at the start or end of viral genome or in between any two genes of MV. However, insertion of ATU at different locations seems to affect the growth kinetics of the resulting MV differently. Therefore, most reported recombinant MV derivatives only contain a single ATU coding for non-MV proteins. Consequently, inserting multiple ATUs each coding for a single gene may not be feasible.

It is well known that the oncolytic effect of MV is known to be due to the fusogenic activity of its surface glycoproteins H & F [8, 34, 35] and that expression of these fusogenic proteins alone, is sufficient to cause cancer cell death. Obviously therefore, other MV genes may NOT be essential. Elimination of these genes from the oncolytic MV derivatives may eliminate any prospects of pathogenic reversal of MV. Like all other RNA viruses, MV is also known to produce defective interfering (DI) particles which consist of truncated MV genomes. They use the proteins produced from the full length replicating MV genomes for their own replication and assembly and so, they can only be generated in cells infected with replicating MV. Reverse genetics studies have also shown that artificially designed MV genome like RNA molecules which code exclusively for non-MV proteins, can be packaged into such DI particles along with full length MV genomic RNA molecules. However, such DI particle preparations are always contaminated with parent MV.

If defective interfering particles can be produced in pure form without the presence of contaminating replicating MV, then it could be possible to design artificial MV derivatives which code for combination of any preferred genes and used as therapeutic agents for cancer and other diseases. Therefore, this invention also provides a method for generation of defective interfering particles containing artificially designed MV genome like replicon RNAs that comprise exclusively of non-MV genes or a combination of non-MV and a subset of MV genes. Such DI particles are designated/named for the purpose of this invention as non-replicating viruses or Virosomes. Since these Virosomes are formed from MV proteins, they retain the functional properties of MV and enter the cells using MV-H and MV-F proteins & express the genes coded by their genome but do not replicate to produce new progeny. They can be custom designed to contain upto 6 or more different genes of choice and help generate new more potent MV derivatives for treatment of cancer and other diseases by gene therapy. This property of Virosomes has been demonstrated by development of Oncolytic Measles Virosome derivatives by combining the expression fusogenic proteins with one or more of the above mentioned therapeutically useful genes. Such synthetic Measles Virosomes will help eliminate the complications that can potentially emerge from treatment with extremely high doses of live & replicating MV.

Moreover, Virosomes coding for non-MV surface glycoproteins such as CDV glycoproteins similar to Miest et al (2011) or Dengue virus E proteins may also be produced and used either for therapy or as novel vaccine agents for prevention of a wide range of diseases. Indeed, a number of researchers have reported the development of new vaccines against a wide range of diseases including HIV [36], SARS [37], Mumps & SIV [38], West nile fever [39] Chikengunya [40], dengue [41] and other diseases [42]. However, the problem of pre-existing anti-MV immunity has also prevented the translation of these reports into clinical use which limitation can be circumvented by the Virosomes of this invention.

Virosomes that contain a genome coding for other viral proteins and also display these proteins may provide a more useful alternative as vaccine agents. Importantly, chimeric Virosomes which display non-MV antigens alone without displaying MV surface glycoproteins (H and F) may be more potent vaccinating agents and also overcome the problem of anti-MV immunity altogether. This is shown in the present invention by producing Chimeric Dengue Virosomes which induce anti-Dengue immunity and Measles virosomes which induce anti MV immunity. This invention first demonstrates the utility of a simple two plasmid system described previously (WO/2013/046216) for producing replicating derivatives of the of MV that code for 2 to 4 additional genes as part of a single multi-cistronic additional transcriptional unit (ATU) and then goes on the describe reagents & a method for producing non-replicating MV derivatives (MV virosomes) which comprises of a genome coding either exclusively non-MV genes or a combination of a subset of MV genes and non-MV genes. This invention further shows that such "Non-replicating Measles Viruses" can mediate the gene transfer into mammalian cells effectively and will be useful as potent therapeutic agents for cancer and other diseases. The "Non-replicating Measles Viruses" are named, for the purpose of this specification as "Virosomes".

Abbreviations

MV: Measles virus. oMV: oncolytic measles virus. CPE: Cytopathic effect. N or MV-N: N protein of Measles virus. P or MV-P: P protein of Measles virus. L or MV-L: L protein of Measles virus. CytD: Cytosine deaminase. DnG1: dominant negative mutant of cyclin G1. GMCSF: human granulocyte macrophage colony stimulating factor. PAP: human prostatic acid phosphatise. ATU: additional transcriptional unit. RdRP: RNA dependent RNA polymerase. IRES: internal ribosomal entry site. Virosome: name used to describe non-replicating MV derivatives. prM: prM protein of Dengue virus. E: Envelope (E) protein of Dengue virus. GFP: green fluorescent protein. sPD-1: human soluble programmed cell death-1 (PD-1). PD-L1 or PD-L2: human programmed cell death ligand 1 or 2

BRIEF DESCRIPTION OF FIGURES AND LEGENDS

FIG. 1: Schematic representation of multicistronic ATU (additional transcriptional unit) produced for incorporation of 2 to 4 non-MV genes into replicating MV derivatives. Bi-, Tri- and Tetra-cistronic genes were assembled in silico and the resulting sequences inserted in between ntd #107 and ntd #108 of Sac II digestible fragment of MV genomic sequence. Resulting ATU was then appended to the a linker containing Afe I site on 5' end followed by Hammerhead ribozyme or RNA polymerase I sequence and the resulting fragment synthesized by gene synthesis technology. Sequences corresponding to the ATU were then digested by Afe I and Sac II enzymes and cloned into cloned into similarly digested pMV (Seq ID#28 or Seq ID#9).

Figure 2:
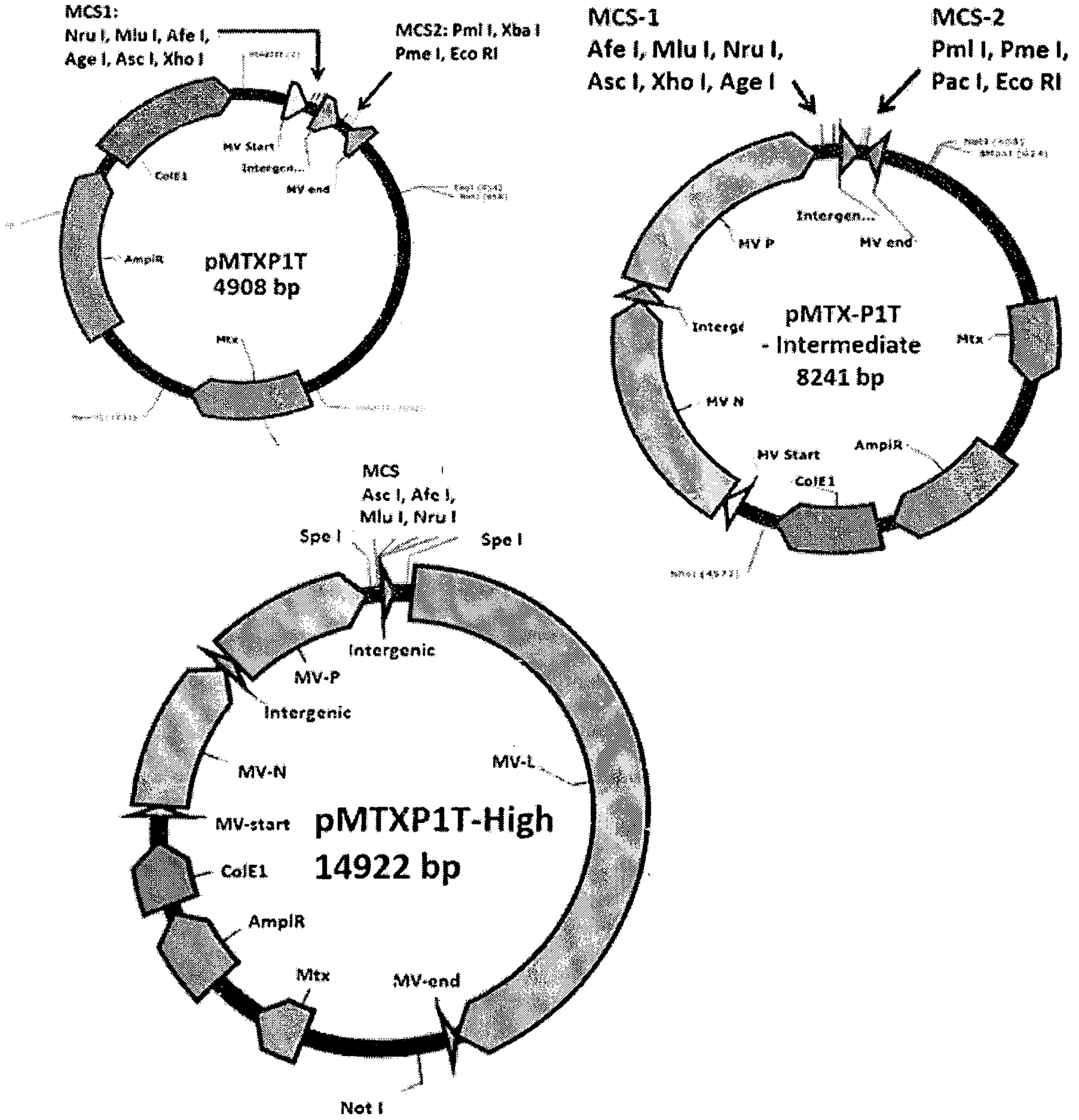

FIG. 2: Schematic representation of plasmids (1) pMTX-P1T, (2) pMTX-P1T-Intermediate, (3) pMTX-P1T-highly useful as cloning plasmids for synthesis of non-replicating MV derivatives. All the plasmids code for a MV genome like replicon RNA containing 2 multiple cloning sites (MCS) for insertion of non-measles genes.

Figure 3:
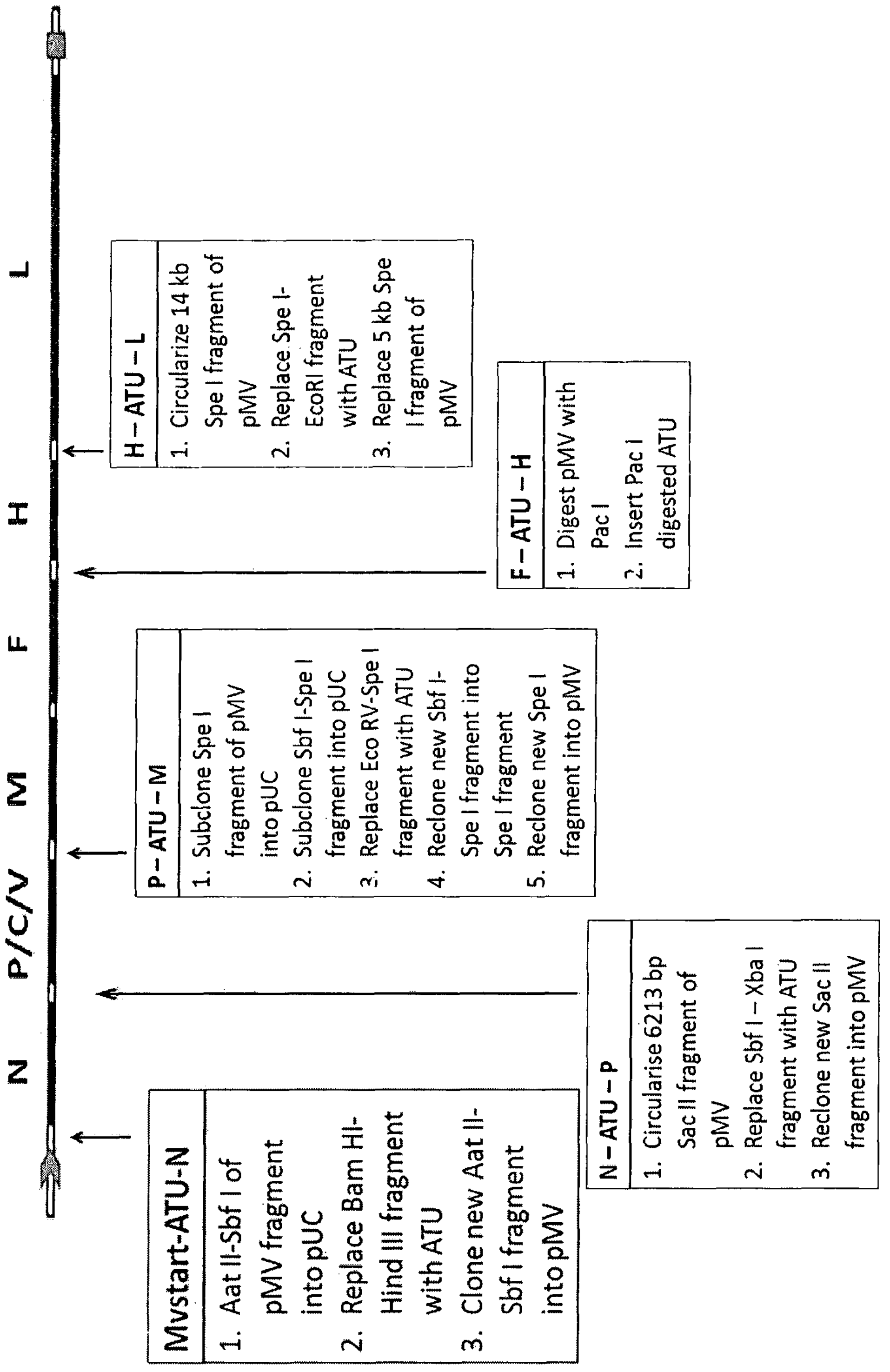

FIG. 3: Schematic representation of strategies used for inserting ATU at different locations in MV genome.

Figure 4:
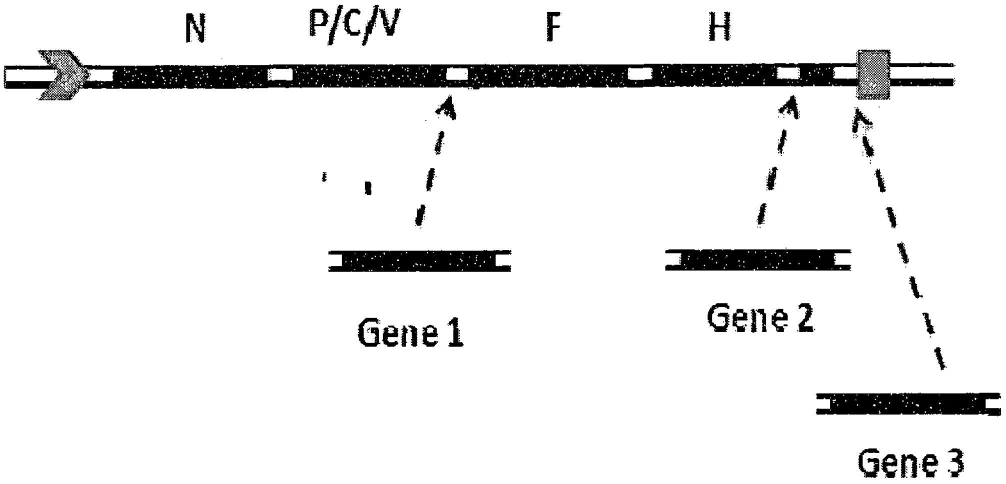

FIG. 4: Schematic representation of the plasmid pN-RE1-FH-RE2-RE3

Figure 5:
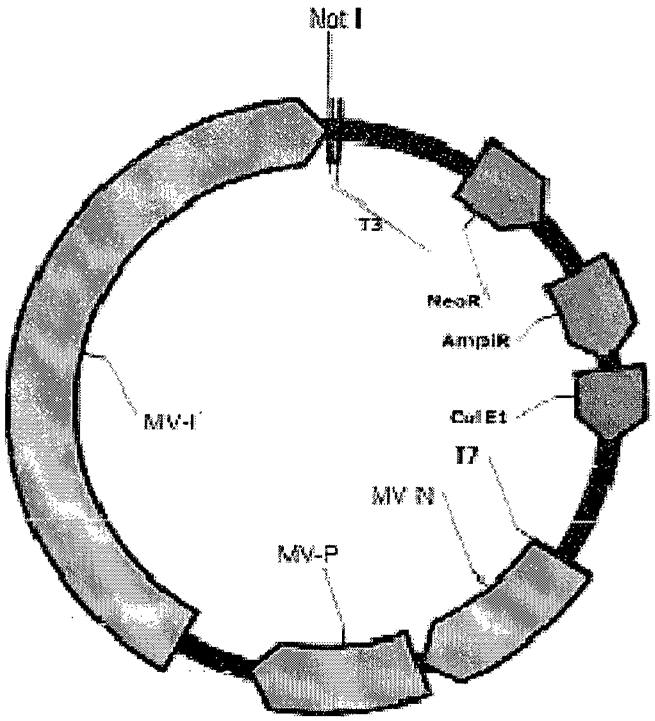

FIG. 5: Schematic representation of the Helper plasmid that codes for MV-N, MV-P and MV-L proteins.

Figure 6:
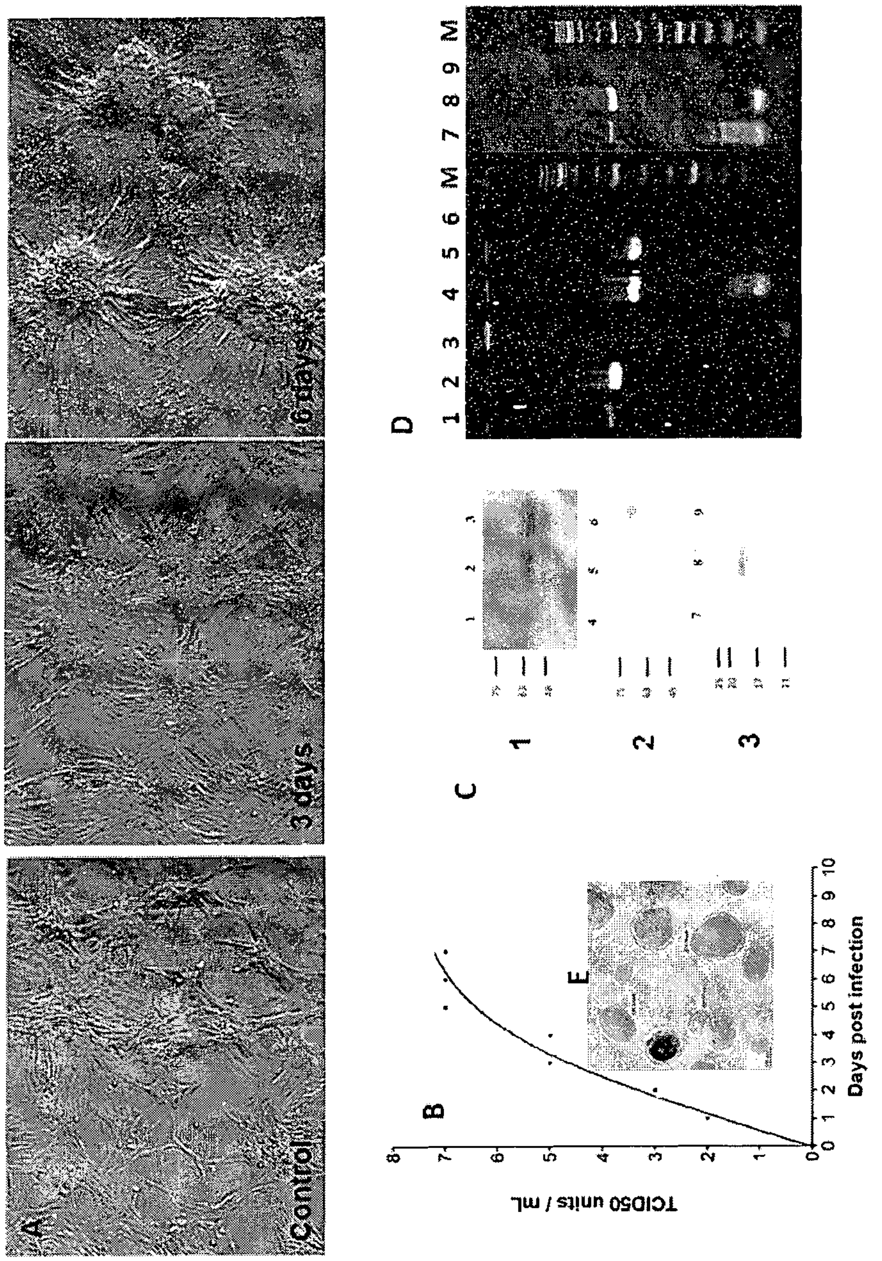

FIG. 6: Characterization of replicating MV derivatives (rMV-GP) (A) Emerging MV cytopathic effect in Vero cells co-transfected with pMV-GP and Helper plasmid. (B) Growth curve of rMV-GP (Increasing levels of rMV-GP released into culture medium of Vero cells infected with rMV-GP): Freshly plated, actively growing Vero cells were infected with culture supernatant containing rMV-GP and incubated. Culture supernatant was harvested every 24 hours and the amount of rMV-GP produced titrated using TCID50 method. (C) Analysis of proteins expressed in Vero cells infected with rMV-GP: Freshly growing, actively plated Vero cells were infected with rMV-GP and extracts prepared 72 hrs after infection. They were subjected to SDS polyacrylamide gel electrophoresis followed by western blot analysis using antibodies specific to the (1) N protein of MV, (2) P protein of MV; (kind gfits from Prof. M. S. Shaila, DMCB, llSc, Bangalore), and (3) human GMCSF (RnD systems, USA): Lane 1—uninfected cells, 2—Cells infected with rMV-GP infected cells, and Lane 3—Cells infected with unmodified MV. (D) Detection of RNA corresponding to cloned and native MV genes: Vero cells were infected with rMV-GP or unmodified MV and total cellular RNA prepared after 72 hrs post infection. This was subjected to RT-PCR analysis using primers specific to (1) GMCSF (lanes 1, 2 & 3), (2) M protein of MV (Lanes 4 & 5) and (3) N protein of MV (Lanes 6, 7 & 8). Lanes 1, 4 & 7—RNA from cells infected with rMV-GP; Lanes 2, 5 & 8: plasmids coding for corresponding proteins used as positive controls; Lanes 3, 6 & 9: RNA from cells infected with unmodified MV.

Figure 7:
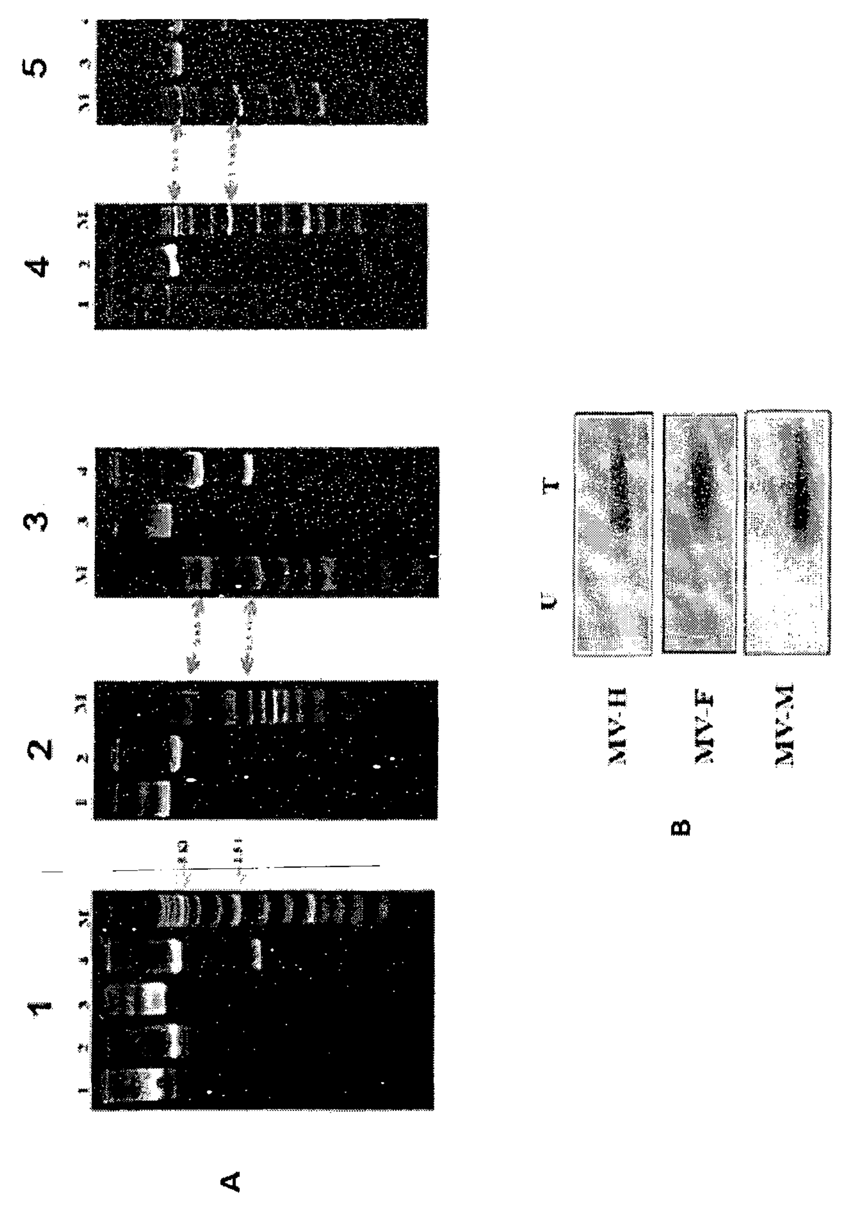

FIG. 7: Production of Vero MFH cell line: (A) Cloning of MV-M, MV-F and MV-H genes into pCDNA3.1(-): (Invitrogen, USA): (1) H gene clone: 1—pCDNA undigested, 2—pCDNA digested with Bam HI and Xho I, 3-pCDNA-H undigested, 4—pCDNA-H digested with Bam HI and Xho I; (2) F gene clone: 1—pCDNA undigested, 2—pcDNA digested with Bam HI and Nhe I, 3—pCDNA-F undigested, 4—pCDNA-F digested with Bam HI and Nhe I; (3) M gene clone: 1—pCDNA undigested, 2—pCDNA digested with Bam HI and Xho 1, 3—pCDNA-M undigested, 4—pCDNA-M digested with Bam HI and Xho I; (B) Expression of MV-M, MV-F and MV-H in vero cells: Freshly plated and actively growing Vero cells were co-transfected with pCDNA-M, pCDNA-F and pCDNA-H plasmids and incubated for 48 hrs. Cell extracts were prepared and analysed for the expression of M, F and H proteins using western blot analysis. U—untransfected vero cells, T—cells co-transfected with M, F & H plasmids.

Figure 8:
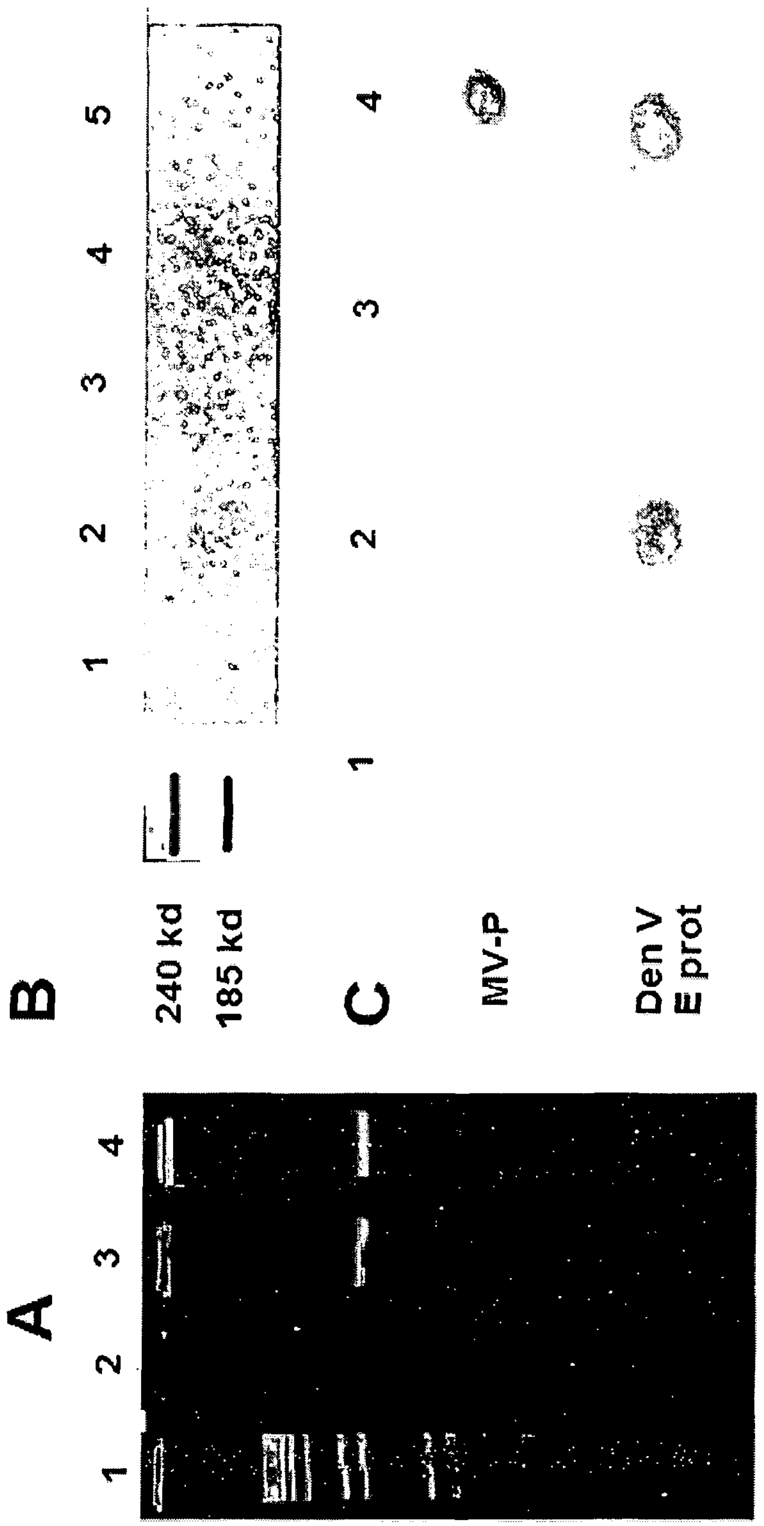

FIG. 8: Production of non-replicating MV (Virosomes): (A) RNA purified from virosomes pelleted from Dengue virosome containing culture supernatants and subjected to RT-PCR using primers specific for MV-start and MV-end regions 1-1 kb ladder, 2-negative control, 3-RNA purified from Virosomes, 4-plasmid encoding Virosome RNA (positive control) (B) SDS polyacrylamide gel electrophoresis followed by western blot analysis with antibodies specific to Rinderpest virus P protein (known to cross react with MV-P protein & a kind gift by Prof. M. S. Shaila, DMCB, IISC, Bangalore, INDIA) and Dengue virus E protein (Santacruz, USA). (C) dot immune-blot analysis: GFP virosomes & Dengue Virosomes. 1-negative control, 2-Dengue Virus like particles, GFP virosomes, Dengue virosomes FIG. 9: Virus induced oncolytic effect: Active growing PC-3 cells or Vero cells were plated in 24 well plates at 80000 cells/well and infected with (1) UV irradiated virus, (2) rMV-GP, (3) rMV-GC, (4) rNPFH-GCG at different multiplicity of infections and incubated. At the end of 5 days, number of viable cells were determined using MTT assay and percent toxicity caused by each virus calculated. Representative toxicity observed of rMV-GP against alone is shown as all viruses were found to be non-toxic to Vero cells.

Figure 10:
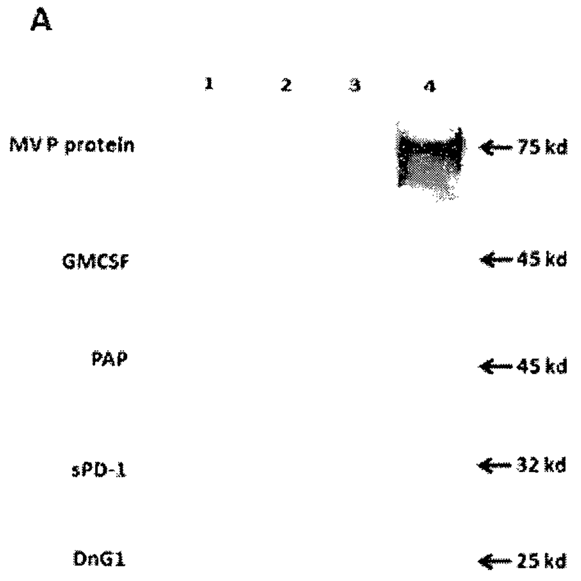
Figure 10:
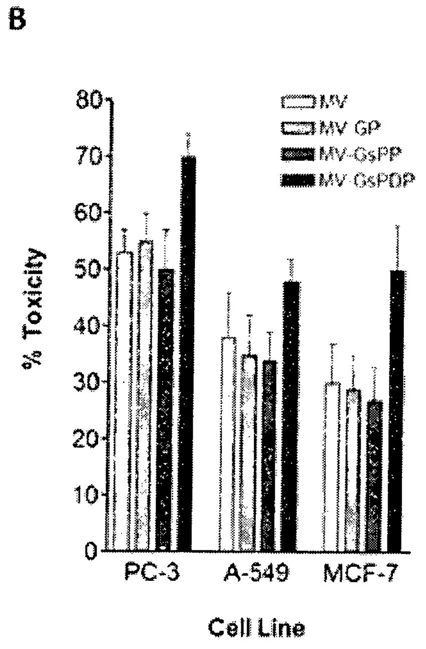

FIG. 10: Enhancement of virus induced oncolytic effect by insertion of DnG1 coding sequence: Replicating MV derivatives coding for 2 (GMCSF and PAP-rMV-GP rMV-GP), 3 (GMCSF, PAP and sPD-1-rMV-GsPP) and 4 (GMCSF, sPD-1, PAP and DnG1-rMV-GsPDP) non-MV genes were synthesized. Cell extracts produced from Vero cells infected with these viruses were tested for the presence of cloned genes by western blot analysis; (B) The effect of rMV-GP, and rMV-GsPP on the viability of PC-3, A-549 and MCF-7 cells was tested as described. It showed that both viruses were equally effective as oncolytic agents (C) Similarly, the effect of rMV-GP and rMV-GsPDP was tested against MCF-7 cells. As shown, the inhibitory effect of rMV-GPP on cancer cells was increased by incorporation of DnG1 gene in rMV-GsPDP.

Figure 11:
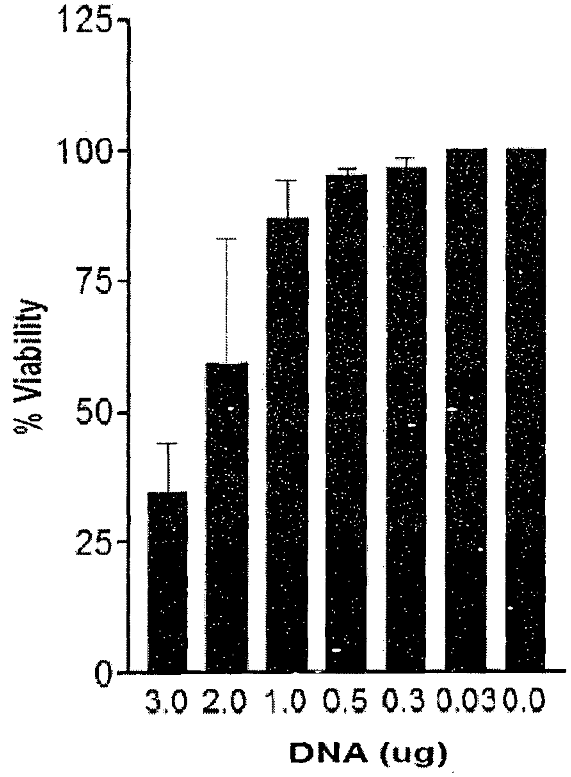

FIG. 11: Plasmid induced cancer cell death: Freshly plated actively growing PC-3 cells were co-transfected with different quantities of pMV-GP (Seq ID #16) and Helper plasmid (Seq ID #18) and incubated for 5 days. The number of viable cells were then determined using MIT assay percent viability calculated.

Figure 12:
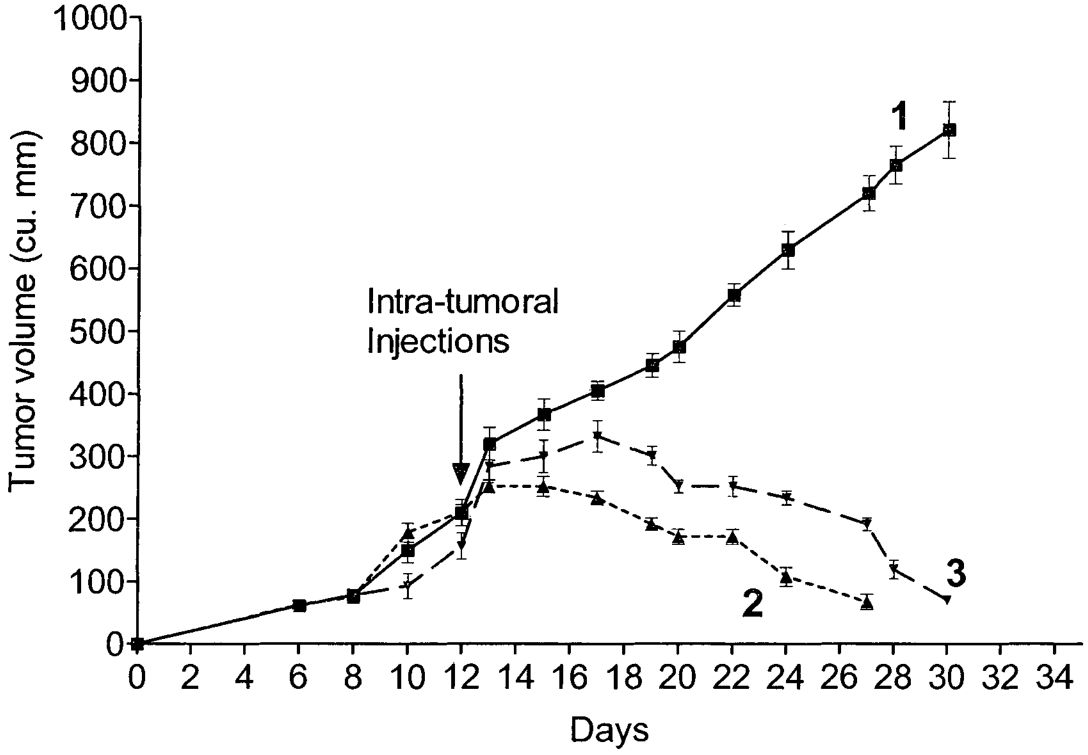

FIG. 12: In vivo Oncolytic efficacy: PC-3 tumors were established in SCID mice and treated with (1) Saline, (2) $10^6$ TCID50 units of rMV-GP or (3) 10 ug of a mixture of pMV-GP and Helper plasmids (1:1.3) intratumorally every $4^{th}$ day and the effect on tumor volumes (length×breadth×breadth/2) was determined.

Figure 13:
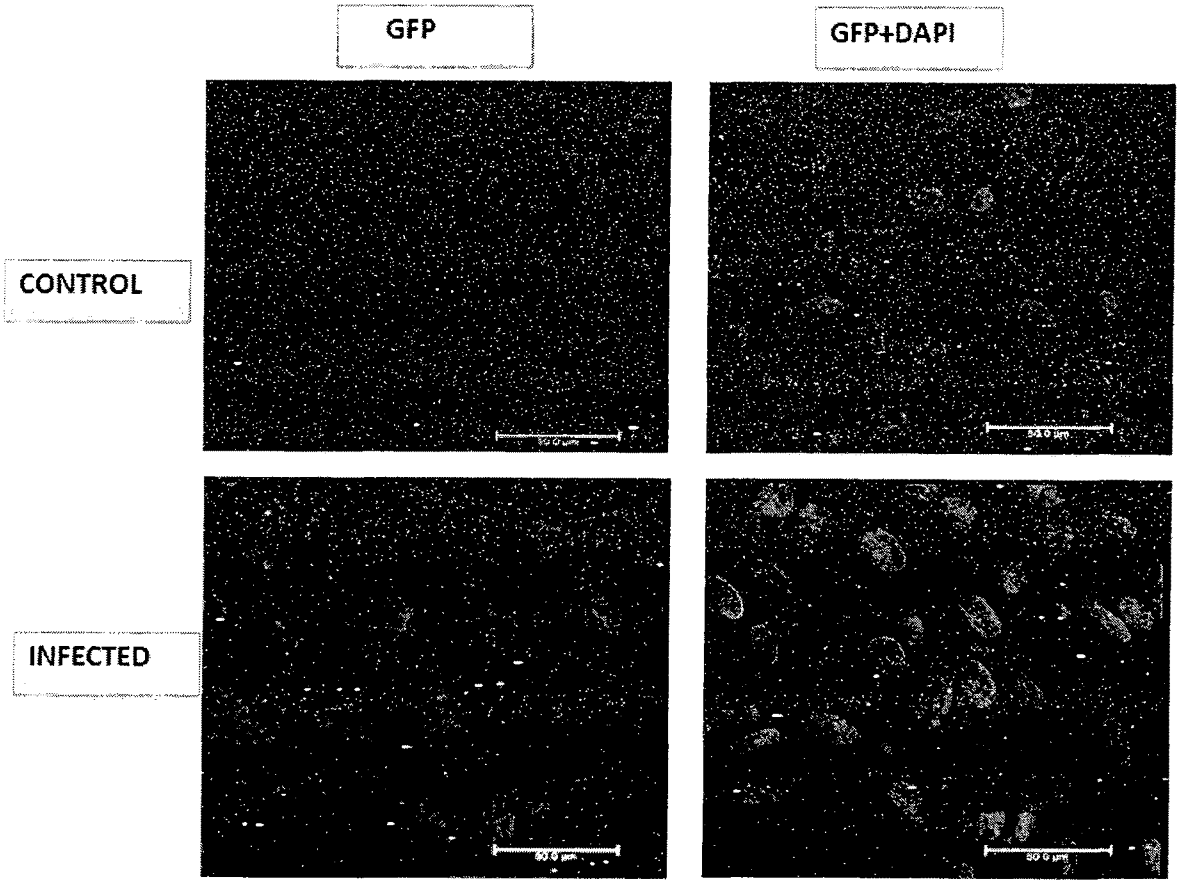

FIG. 13: Virosome mediated gene transfer: Vero cells were infected with Virosomes and their ability to transfer expression of green fluorescence protein (GFP) to vero cells determined by staining nuclei with DANI and monitoring for expression of GFP using confocal microscopy.

Figure 14:
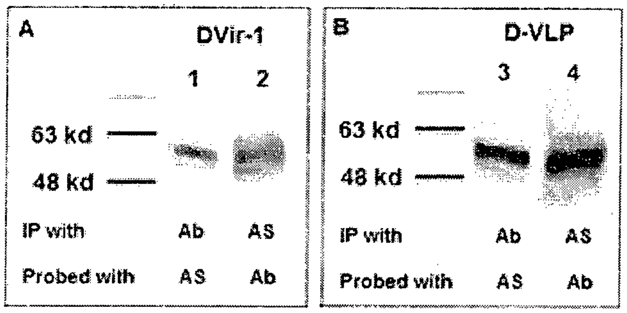
Figure 14:
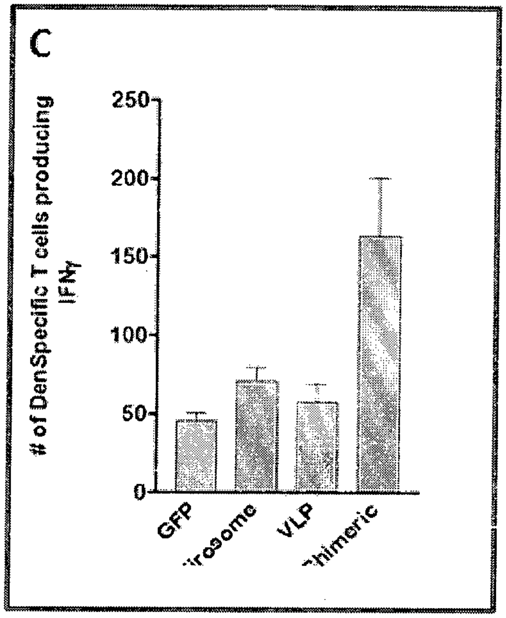

FIG. 14: Dengue virosomes induce humoral and cellular anti-Dengue immune response: (A & B) Serum from mice immunized with Dengue virosomes and a standard anti-Dengue virus E protein antibody recognize the same protein. (A) Dengue virus E protein was immunoprecipitated with serum from mice immunized with Dengue virosomes or Dengue virus like particles and subjected to SDS polyacrylamide gel electrophoresis followed by western blotting using anti-Dengue virus E protein antibody (Santacruz, USA) and vice versa. Lane 1: E protein immunoprecipitated from Dengue virosomes with standard antibody followed by detection with serum from mice immunized with Dengue virosomes; Lane 2: E protein immunoprecipitated from Dengue virosomes with serum from mice immunized with Dengue virosomes followed by detection with standard antibody; Lane 3: E protein immunoprecipitated from Dengue virus like particles (VLP) with standard antibody followed by detection with serum from mice immunized with Dengue VLP; Lane 4: E protein immunoprecipitated from Dengue VLP with serum from mice immunized with Dengue virosomes followed by detection with standard antibody. (C) Spleenocytes of mice immunized with Measles virosomes, Dengue virosomes, Chimeric Dengue virosomes and Dengue virus like particles were harvested and tested for the presence of Dengue reactive cells producing IFNgamma by ELISPOT assay.

Figure 15:
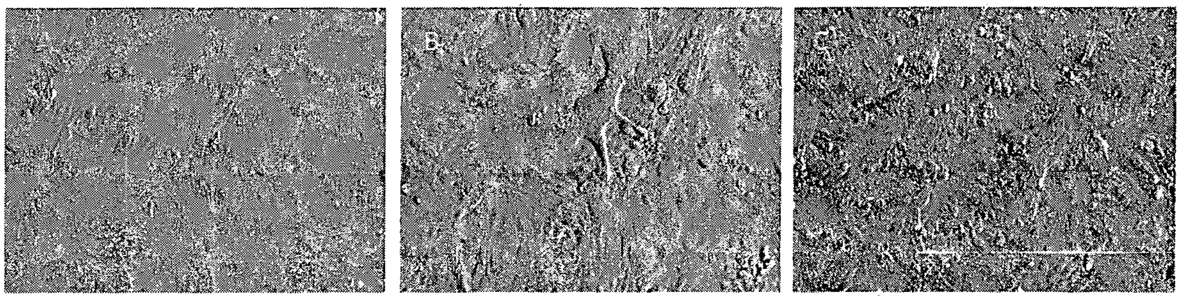

FIG. 15: Protective effect of serum from mice immunized with Measles Virosomes: Freshly plated, actively growing Vero cells were infected with PBS (A), MV (B) or MV treated with serum from mice immunized with Measles virosomes (C) and incubated for 7 days. Cells infected with untreated MV but NOT the MV treated with anti-serum showed the appearance of typical cytopathic effect indicating that the anti-Measles-virosome serum protected cells from MV infection.

DNA SEQUENCES

Seq ID 1: Plasmid pMTX-P1T. Seq ID 2: Modified Pst I fragment. Seq. ID 3: Age-MVuptoSpe-Age fragment. Seq ID 4: Plasmid pMTX-P1T-Intermediate. Seq ID 5: Pml-L2 -Eco RI fragment. Seq ID 6: Pml-L1-Pml I fragment. Seq ID 7: Plasmid pMTX-P1T-High Seq ID 8: Plasmid pMTX-NP-RE1-FH-RE2-RE3. Seq ID 9: Plasmid pMV. Seq ID 10: GMCSF-ires-PAP. Seq ID 11: GMCSF-ires-CytD. Seq ID 12: GMCSF-ires-sPD1-2A-PAP. Seq ID 13: GMCSF-ires-sPD1-2A-CytD. Seq ID 14: GMCSF-ires-sPD1-2A-DnG1-ires-PAP. Seq. ID 15: GMCSF-ires-sPD1-2A-DNG1-ires-CytD. Seq ID 16: Plasmid pMV-GP. Seq ID 17: pMV-GC Seq ID 18: Helper plasmid. Seq ID 19: Modified Afe I-Not I fragment. Seq ID 20: pMV-NPFH-GCG. Seq ID 21: pMTX-P1T-D2G. Seq ID 22: Sequence that was deleted from the pMTX-P1T-D2G. Seq ID 23: pMV-GsPP. Seq ID 24: pMV-GsPDP. Seq ID 25: pMV-GsPC Seq ID 26: pMV-GsPDC. Seq ID 27: ires-sPD1-2A-DnG1-ires. Seq ID 28: ires-sPD1-2A-DnG1-ires.

This invention describes the use of a recently described two plasmid system described in WO2013046216 that harnesses the RNA Dependent RNA Polymerase (RdRP) of non-segmented negative strand RNA viruses for expression of recombinant proteins and production of measles virus derivatives. The investion comprises (a) one cloning plasmid coding for suitably modified MV genome or a MV genome like replicon RNA that codes for desired non-MV genes cloned at conveniently provided restriction enzyme sites, and (b) one helper plasmid coding for and expressing N, P, L proteins respectively.

This invention comprises replicating and non-replicating derivatives of a virus that is attenuated. In one aspect of this invention, the said attenuated virus comprises attenuated MV (Measles Virus). Although this invention has been illustrated by using MV genome, any other virus with similar requirements for rescuing viruses from cDNA, equivalent attenuation and safety for a human being may be used in place of MV. The requirements for rescuing the above referred “any other virus” from cDNA comprise use of viral N, P and L proteins expressed from three distinct helper plasmids and use of a plasmid coding a viral anti-genomic RNA modified by insertion of a single additional transcriptional unit.

The MV derivatives of this invention comprise recombinant replicating and non-replicating derivatives of MV. The replicating MV derivatives of this invention are considered more effective as therapeutic agents for cancer than other currently used oncolytic MV derivatives due to multiple features. Firstly, the replicating MV described in this invention code for 2 to 4 non-MV genes from a single ATU, these non-MV genes have the potential to cause cancer cell death and also induce anti-tumour immunity. Secondly, these viruses are armed to deliver other/additional genes that either sensitize them to death by prodrug activating enzymes like cytosine deaminase or kill cancer cells or inhibit their growth through other mechanisms. Secondly, the non-replicating Measles virus derivatives (named as “Virosomes”) described in this invention offer a greater versatility at combining therapeutically useful genes into MV, increased safety provide an opportunity to overcome the problem of pre-existing anti-MV immunity and also expand the application of therapeutic MV to other disease conditions This invention has been illustrated by disclosing an Oncolytic Measles Virosome that combines the oncolytic effect of MV with the therapeutic effect of a dominant negative mutant of Cyclin G1, sensitizing effect of Cytosine deaminase and immunopotentiating effect of GMCSF and/or PD-1 blockade. Such Virosomes will also help eliminate the potential risk factors associated with using live MV for therapy.

The MV derivatives described in this invention can be produced using just 2 plasmid DNA molecules which can be directly used as therapeutic agents thus eliminating the high costs & difficulties involved in manufacturing the currently used massive doses of MV for cancer therapy. Such oMV producing plasmid DNA molecules can will not be recognized by anti-MV immunity and so will help overcoming the problem of pre-existing anti-MV immunity.

This invention also comprises means for designing the said replicating and non-replicating viruses. In one aspect of this invention, the said means comprise DNA molecules. The said DNA molecules comprise plasmids.

In a further aspect, this invention comprises recombinant Measles virus genome cloned with two or more therapeutically effective genes.

In a further aspect, this invention comprises plasmids useful for producing non-replicating measles viruses which contain non-viral genes including therapeutically useful genes along with a variable number of MV-genes to ensure a pre-determined level of expression.

This invention illustrates synthesis of replicating MV derivatives comprising recombinant MV derivatives that also code for 2 to 4 non-MV genes like human granulocyte macrophage colony stimulating factor (GMCSF) which is known to induce anti-tumour immune responses, prostate specific acid phosphatase (PAP) which will help enhance the specificity of induced immune response, serve as a marker to determine the replicative capacity of rMV-GP as a function of phosphatase enzyme activity, exhibit an enhanced potency of anti-cancer effect due to incorporation of cytocidal genes like Cytosine deaminase and the dominant negative mutant of Cyclin G1.

This invention also comprises synthesis of non-replicating MV derivatives, designated/named for the purpose of this specification as "Virosomes". Depending on the composition of their genome, the virosomes comprise three different types (1) those coding exclusively non-MV genes, (2) those coding for MV-N and MV-P genes along with non-MV genes and (3) those coding for MV-N, MV-P and MV-L genes along with the non-MV genes. These three virosomes are useful for expressing non-MV genes in infected cells at low, intermediate and high levels respectively.

The concept of Virosomes is illustrated by producing GFP virosomes. Ability of different types of Virosomes to express non-MV genes at different levels is illustrated by producing Dengue Virosomes which code for Dengue virus pr-M and E proteins either exclusively or in combination with MV-N, MV-P and MV-L proteins.

One virosome comprises of a genome that codes for dengue virus prM and E proteins and green fluorescent protein but NO measles virus gene.

The second synthesized Virosome contains a genome that codes for MV-N, MV-P and MV-L proteins along with Dengue virus preM and E proteins and the Green fluorescent protein.

The third synthesized Virosome contains a genome that codes for a truncated prM and E proteins of Dengue virus and the Green fluorescent protein. These Dengue virosomes have been shown to be capable of inducing in animals, an anti-Dengue immunity (FIG. 14) that protects cells from infection with Dengue virus.

In a further aspect of this invention an Oncolytic Virosome (nr-MV-HF-GCG) has also been synthesized a. This virosome comprises of a genome that codes for MV-N, MV-P, MV-H and MV-F proteins along with other non-MV genes which have therapeutically beneficial effects. Such virosomes will offer new more effective and safer MV derivatives for cancer therapy.

It is an embodiment of this invention that replicating MV derivatives like rMV-GP, rMV-GC, rMV-GsPP, rMV-GsPC, rMV-GsPDP and rMV-GsPDC induce the death of cancer cell lines like T47D, A549 or PC-3 but do not adversely affect non-cancerous cells as illustrated with cells like Vero cells.

This invention also embodies the demonstration that plasmid DNA molecules which are useful to produce replicating MV derivatives like rMV-GP and the Helper plasmid (Seq ID#18) together, are sufficient to induce cell death in PC-3 cells in a manner similar to oncolytic MV and may be, useful to circumvent the problem of pre-existing anti-MV immunity that hinders MV virotherapy.

In a further aspect this invention comprises pharmaceutical compositions comprising viruses or DNA molecules. This invention also comprises use of viruses or DNA molecules as therapeutic agents for diseases. The diseases include cancer and Dengue. Thus, this invention discloses replicating derivative of MV that induces cancer cell death and Virosomes effective against Dengue.

This invention also discloses non-replicating derivative of MV that mediates transfer of different therapeutically useful genes into cancerous and other human cells and will be useful either as therapeutic agents or agents capable of inducing desired immune responses.

This invention also embodies a reagent kit for producing the said non-replicating MV derivatives.

In another aspect this invention comprises a method of treating cancer by administering an oncolytic measles virus or DNA molecules producing the said oncolytic measles virus to a patient so as to reduce the number of cancer cells wherein the said cancer cells are part of a tumour.

In yet another aspect this invention comprises a method of reducing the number of cancer cells, wherein the cancer cells are part of a tumour, by administering an oncolytic virus or DNA molecules producing the said oncolytic measles virus to the patient.

This invention also comprises a method of producing recombinant replicating derivatives of measles virus using a single Helper plasmid and a Cloning plasmid.

This invention discloses a method of producing a non-replicating derivatives of measles virus using a single Helper plasmid and a Cloning plasmid and a packaging cell line.

This invention also embodies a cell line derived from Vero cells that expresses the M, F and H proteins of Measles virus stably and is useful as a packaging cell line for the production of non-replicating derivatives of measles virus described in non-replicating derivatives of measles virus. This invention also embodies a cell line derived from Vero cells that expresses the M protein of MV stably and is useful as a packaging cell line for the production of non-replicating MV derivatives which do not contain the H and F proteins of MV.

This invention embodies a method of producing recombinant replicating derivatives of measles virus using a single Helper plasmid and a Cloning plasmid wherein the helper plasmid expresses the N, P and L proteins of measles virus and is identical to Seq ID #18.

This invention also discloses a method of producing recombinant derivatives of measles virus wherein the cloning plasmids codes for the entire genome of measles virus modified suitably to include additional transcription unit that codes for a non-measles virus gene at a location immediately upstream of the N protein gene.

This invention embodies a method of producing recombinant derivatives of measles virus wherein the cloning plasmid codes for the entire genome of measles virus modified suitably to include non-measles virus genes as part of the different genes of measles virus.

This invention also comprises a method where in the Cloning plasmid is derived from the plasmids pMTX-P1T (Seq ID #1), pMTX-P1T-intermediate (Seq ID #4) or pMTX-P1T-high (Seq ID #7) by inserting non-measles protein coding DNA sequences in one or both of the multiple cloning sites (MCS) provided.

This invention further comprises a method where in the Cloning plasmids for producing recombinant derivatives of measles virus may code for a genome comprising exclusively of non-measles genes expressed while being a part of a measles virus genome-like replicon. This cloning plasmid may be derived from plasmid pMTX-P1T (Seq ID #1) by cloning non-MV genes in to one or both of the 2 multiple cloning sites (MCS) provided in this plasmid.

This invention also discloses a method wherein the Cloning plasmid codes for a genome comprising of the N, P, F and H protein genes of Measles virus and upto 3 additional genes coding for non-measles proteins in the form of a measles virus genome-like replicon. This plasmid may be derived from Seq ID #8) OR a non-replicating derivative of MV that contains a genome coding for the fusogenic glycoproteins like MV-H & MV-F proteins and a combination of other genes such as suicide genes, pro-drug activating enzyme coding genes, or genes that code for cytokines & proteins which induce anti-tumour immunity.

This invention comprises one or more DNA molecules useful for producing variants of non-replicating derivatives of MV termed as Virosomes—Cloning plasmids—Seq ID #1, Seq ID #4, Seq ID #7, Seq ID #20, This invention further comprises a method of producing non-replicating derivatives of measles virus using a single Helper plasmid and a Cloning plasmid and a packaging cell line where in the cloning plasmid codes for a genome comprising of non-measles virus genes and the N, P and/or L proteins of measles virus in the form of a measles virus genome-like replicon and the said cloning plasmid is derived from the plasmid pMTX-P1T-Intermediate (Seq ID #4) or pMTX-P1T-high (Seq ID #7) by inserting non-measles genes in to one or both of the multiple cloning sites (MCS) provided in these plasmids.

This invention discloses a method of producing recombinant derivatives of measles virus where in the helper plasmid codes for the N, P and L proteins of Measles virus and is identical to Sequence ID #18.

This invention comprises a replicating derivative of MV that codes for 2 or more non-MV genes which may either enhance the potential of the virus for inducing anti-cancer immunity or its cancer therapeutic effect. Such genes may include but not be limited to a cytokine and immunoregulatory cell surface molecule like sPD-1 or CTLA4, a tumour associated antigen, and genes that affects the cancer phenotype or induces cancer cell death (e.g. dominant negative mutant of Cyclin G1). Thus, MV derivatives encoding 2, 3 or 4 different non-MV genes are described.

This invention also embodies a replicating derivative of MV wherein the cytokine consists of one or more of GMCSF and other cytokines.

This invention discloses a replicating derivative of MV wherein the tumour associated antigen is prostatic acid phosphatase (PAP) or any other tumor associated antigen.

This invention discloses a replicating derivative of MV wherein the immuno-regulatory cell surface molecule is soluble PD-1, molecule.

This invention discloses a replicating derivative of MV wherein the cytocidal gene is cytosine deaminase.

This invention comprise a replicating derivative of MV wherein the cytokine is human GMCSF and the tumour associated antigen is human prostatic acid phosphatase (PAP).

This invention also comprises a method of treating cancer by administering replicating derivative of MV wherein the cytokine is human GMCSF and the tumour associated antigen is human prostatic acid phosphatase (PAP).

This invention further comprises a method of treating cancer by administering recombinant measles virus made by a method wherein the Cloning plasmid codes for a genome comprising of the N, P, F and H protein genes of Measles virus and upto 3 additional genes coding for non-measles proteins in the form of a measles virus genome like replicon further wherein the plasmid may be derived from Seq ID #8 and more specifically from Seq ID #20.

This invention discloses a pharmaceutical composition of a non-replicating virus and method to use it for treatment of one or more diseases; the pharmaceutical composition comprising, at least, the non-replicated virus and a sodium chloride or a balanced salt solution in a buffered base.

This invention also discloses a pharmaceutical composition of a replicating virus & method to use it for treatment of one or more diseases further comprising a cancer; the pharmaceutical composition comprising, at least, sodium chloride or balanced salt solution in a buffered base.

This invention embodies a pharmaceutical composition comprising one or more of DNA molecules useful for producing replicating and/or non-replicating derivatives of measles virus for therapeutic benefit, the said pharmaceutical composition comprising of water containing EDTA, salt and an agent promoting entry of DNA into animal cells.

This invention also embodies a method of using DNA molecules useful for producing the said replicating and/or non-replicating derivatives of measles virus for therapeutic benefit. The method comprising of administering a pharmaceutical composition comprising the DNA molecules useful for producing the said replicating and/or non-replicating derivatives of measles virus, water containing EDTA, salt and an agent promoting entry of DNA into animal cells.

This invention also comprises a method of treating disease by transfer genes that code for therapeutically useful proteins and/or RNA molecules into human cells by administering the recombinant non-replicating measles viruses produced by a method that comprises use of a single Helper plasmid and a Cloning plasmid and a MV packaging cell line where in (a) the Cloning plasmid is derived from the plasmids pMTX-P1T (Seq ID # 1), pMTX-P1T-intermediate (Seq ID #4) or pMTX-P1T-high (Seq ID #7) by inserting non-measles protein coding DNA sequences in one or both of the multiple cloning sites (MCS) provided, or (b) where in the cloning plasmid may code for a genome comprising exclusively of non-measles genes expressed in the form of a measles virus genome like replicon, further wherein the cloning plasmid may be derived from plasmid pMTX-P1T (Seq ID #1) by cloning non-MV genes in to one or both of the 2 multiple cloning sites (MCS) provided in this plasmid; or (c) wherein the Cloning plasmid codes for a genome comprising of the N, P, F and H protein genes of Measles virus and upto 3 additional genes coding for non-measles proteins in the form of a measles virus genome like replicon further wherein the said plasmid may be derived from Seq ID #8.

This Invention embodies non-replicating virus coding for Dengue virus subviral particles comprised of preM and E genes and a method for using this as a vaccinating agent for prevention of Dengue.

Below are given examples which are only illustrative of working of this invention and are not be construed as limiting the scope of the disclosure of this invention or the means/reagents used for the examples or conditions used for the examples. Any variation that is an obvious variation and equivalents are considered to be included within the scope of the disclosure of this invention.

EXAMPLES

1. Cells and Viruses

Vero (African green monkey kidney) cells were procured from the National Center for Cell Sciences (NCCS), Pune and grown as monolayers in Dulbecco's modified Eagle's Medium (DMEM) supplemented with 10% fetal calf serum (FCS). MVAC (Measles Virus Live I. P.) manufactured by Serum Institute of India was purchased off the counter from Emke Medicals by Applicant. To prepare a seed stock, Vero or MRC5 cells (IMCCS, Pune) were seeded in 25 sq. cm flasks at 105 cells/flask and incubated overnight at 37C in 5% C02. Cells were washed with HBSS and seeded with MV-E at a multiplicity of infection (MOI) of 0. 1 and incubated for 7 days. Culture supernatant was removed at every 24 hrs and replaced with DMEM containing 2% FCS. Virus from the harvested supernatants was pooled together, quantitated by TCID50 method. Culture supernatants containing the maximum virus titre were pooled together and used as seed stock.

2. Plasmids

The method described in this invention essentially envisages co-transfecting a Cloning plasmid and a Helper plasmid into different cell lines like vero cells which are conducive to measles virus propagation and producing the desired type of measles virus. The various Cloning plasmids which may be used for this purpose are described in details below.

Cloning Plasmids

The two plasmid expression system used here was earlier described in WO/2013/046216 and comprises of a helper plasmid that expresses the N, P and L proteins of Measles virus and a Cloning plasmid that is useful to express an artificial replicon in which upto 2 proteins can be cloned. The cloning plasmid pUC-P1P-Rep-P1T which was earlier described in WO/2013/046216 as sequence ID #6 was modified using standard molecular biology techniques as follows:

2.1 Cloning Plasmid Vectors—for Producing Non-Replicating MV Derivatives (Virosomes)

2.1.1 pMTX-P1T:

Commercially available pIRES (Clonetech Takara) was digested with Bgl II and Hpa I and processed to create blunt end. The 4172 bp fragment corresponding to the nucleotide numbers 1930 to 6102 was isolated and processed with klenow fragment of *E coli* DNA polymerase I to generate blunt ends. This was then ligated with T4 DNA ligase to the 969 base pair fragment corresponding to the sequence ID no. 3 (WO/2013/046216) which was removed from the sequence ID no 6 (WO/2013/046216) by digesting with Sac I and Hind III and processed with Klenow fragment of *E coli* DNA polymerase I to produce blunt ends. The resulting plasmid was called pNeo_P1T. The plasmid pNeo_P1T was then digested with Bst BI and Stu I and the larger fragment was purified. This was then manipulated in silico so that the Neomycin resistance gene open reading frame was replaced by protein coding region for mouse Dihydrofolate reductase (DHFR) enzyme (NP-034179.1,Genbank) and the resultant sequence (termed DHFR cassette) synthesized using the gene synthesis method (Genscript Inc, USA). and digested with Bst BI and Stu I. This Bst BI and Stu I digested DHFR cassette then was ligated into the larger fragment of Bst BI and Stu I digested pNeo_P1T to generate pMTX_P1T. The resulting pMTX_P1T plasmid contains the replicon coding gene under the control of RNA polymerase I promoter and DHFR as a selection marker (FIG. 2) and depicted by the Seq. Id. No 1.

2.1.2 pMTX-P1T-Intermediate:

This pMTX-P1T plasmid was modified further. This pMTX-P1T plasmid was digested with Pst I and the smaller fragment corresponding to the MVstart to MCS2 was discarded. A DNA corresponding to the Sequence ID no 2 was synthesized using the gene synthesis technology (Genscript Inc, USA), digested with Pst I and ligated into the larger fragment of Pst I digested pMTX-P1T to generate the plasmid pMTX-P1T-MVstart-Age-MCS1-N/P-MCS2. This pMTX-P1T-MVstart-Age-MCS1-N/P-MCS2 plasmid was digested with Age I. The region corresponding to sequence ID no. 3 was amplified by polymerase chain reaction (PCR) and extended by adding the nucleotides "TCTCGACGCGTACATGTAGCGCTCGCACCGGT" (SEQ ID NO. 29). This resulting PCR amplified DNA was digested with Age I and cloned into Age I digested P1T-MVstart-Age-MCS1-N/P-MCS2 to generate "pMTX-P1T-Intermediate" plasmid (Seq ID no. 4).

2.1.3 pMTX-P1T-High:

The plasmid pMTX-P1T-Intermediate was digested with Pml I and Eco. RI and the larger fragment was purified. A DNA corresponding to a sequence starting from the Pml I site in L protein coding region of MV (AY486084) upto the end of MV genome was PCR amplified using primers specific to the Pml I site containing region of L protein and the 3' end of MV genomic sequence extended to contain Eco RI site to obtain a Pml-L2-EcoRI fragment. This was digested with Pml I and Eco RI and cloned into the larger fragment of Pml I & Eco RI digested pMTX-P1T. The Eco RI site immediately downstream of the L2 fragment was then removed by in vitro mutagenesis to generate a pMTX-P1T-Intermediate-L2 plasmid. A DNA corresponding to H/L intergenic region followed by the 5' part of L coding region upto Pml I enzyme site (sequence ID no. 6) was then PCR amplified from plasmid encoding MV genomic RNA (WO/2013/046216) and digested with Pml I enzyme. This was then ligated into Pml I digested pMTX-P1T-Intermediate-L2 plasmid to produce "pMTX-P1T-High" (Seq ID No. 7).

2.1.4 pMTX-P1T-NP-RE1_FH_RE2_RE3:

Plasmid pMV was used to produce this plasmid. The L protein coding region from pMV was replaced by an oligonucleotide coding for restriction enzyme sites Mlu I and Afe I by in vitro mutagenesis to produce pMV-del-L. Sequence corresponding to MV-M protein was replaced by oligonucleotide linker for Eco RI and Nru I to produce pMV-del-LM. Plasmid pMV-del-LM was then digested with Afe I and Not I and the smaller fragment discarded. This was then replaced with a Modified "Afe I to Not I fragment" that introduces an additional ATU region containing the sites for restriction enzyme sites for Mlu I and Xho I into the MV backbone. This a plasmid that expresses a MV replicon that codes for N, P, F and H proteins of MV along with 3 additional transcriptional units which can be modified by insertion of upto 3 non-MV proteins (Seq ID 8).

2.1.5 Cloning Plasmids to be Used for Producing Specific Virosomes 2.1.5.1 Dengue Virosome Cloning plasmids:

The sequence coding for the Dengue virus like particles containing the preM and Envelope (E) proteins of Dengue virus serotype 2 along with a signal peptide (as described by Wang and co-workers (2009) [43] flanked by Asc I enzyme site was synthesized using Gene synthesis technology (Genscript Inc, USA) and cloned in between the Asc I & Xho I sites of pMTX-P1T to produce pMTX-P1T-D2. An orientation that showed that 5' end of D2 gene was towards the 5' end of the replicon coded by pMTX-P1T was selected.

Similarly, a nucleotide sequence corresponding to the eGFP protein was PCR amplified from the pUC-P1T plasmid (WO/2013/046216) using gene specific primers with Pac I enzyme site. The resulting GFP coding segment was then cloned into the Pac I site present in the MCS2 of pMTX-P1T to produce pMTX-P1T-D2G plasmid. An orientation that showed that 5' end of GFP gene was immediately downstream of D2 protein gene was selected. (Seq ID #21)

The same cloning strategy was used to clone D2 and GFP coding genes into pMTX-P1T-intermediate and pMTX-P1T-high to produce "pMTX-P1T-intermediate-D2G" and "pMTX-P1T-high-D2G" plasmids.

2.1.5.2 Chimeric Dengue Virosome Coding Plasmid

The coding region for the Dengue virus prM region of Dengue virus was identified from the plasmid pMTX-P1T-D2G and 273 bases corresponding to the pr region (Seq ID #21) were deleted using in vitro mutagenesis to generate pMTX-P1T-D2Gdelpr plasmid. 2.1.5.2. GFP Virosome coding plasmid: Plasmid pUC-P1T (WO/2013/046216) was digested with Asc I enzyme and the sequence corresponding to the eGFP protein cloned into the MCS1 of pMTX-P1T at Asc I site to produce pMTX-P1T-G plasmid.

2.1.5.3 Oncolytic Virosomes:

Sequence corresponding to Cytosine deaminase (CytD) reported by Erbs et al, (2000) [44] appended with sequences for Mlu I site at both ends was assembled in the order 5'-Mlu I-CytD-Afe I-Mlu I-3'. Sequence corresponding to the cytotoxic dominant negative Cyclin G1 (dnG1) protein was derived from the Cyclin G1 sequence reported by Gordon et al (2000) [45] and appended at 5' and 3' ends with suitable restriction enzyme sites in the order 5'-Eco RI-dnG1-Nru I-Eco RI-3'. The resultant Cyt D and dnG1 sequences were synthesized using gene synthesis technology (Genscript Inc, USA). On the other hand, GMCSF coding sequence was PCR amplified from the GMCSF-ires-PAP coding DNA using a forward gene specific primer containing Xho I site and a reverse gene specific primer containing the sites for Xho I and Pml I enzyme at the 5' ends.

PCR amplified GMCSF coding region was digested with Xho I and Pml I and ligated into similarly digested pMTX-P1T-NP-RE1-FH-RE2-RE3 to produce pNPFH_GMCSF. Sequence corresponding to Cyt D protein was digested with Mlu I and Afe I and ligated into similarly digested pNPFH-GMCSF to produce pNPFH-GMCSF-CytD. Finally plasmid pNPFH-GMCSF-CytD was the digested with Eco RI and Nru I and ligated to similarly digested dnG1 coding fragment to produce pNPFH_GCdnG1 to produce pNPFH_GCdnG. Plasmid pNPFH_GCdnG (or pNPFH-GCG) (Seq ID 20) codes for a MV replicon that codes for the N, P, F and H proteins of MV and GMCSF, Cytosine Deaminase and cytotoxic mutant of Cyclin G1.

2.2 Cloning Plasmids—Useful for Producing Replicating Measles Virus Coding Derivatives 2.2.1 pMV—Measles Virus Coding Plasmid:

A plasmid encoding the entire cDNA of MV genomic RNA (AY486084) was described in WO/2013/046216. This plasmid was digested with Spe I enzyme and the smaller 5802 bp Spe I fragment consisting of the nucleotide nos 3373 to 9175 from the MV genome (AY486084.1, Genbank) was isolated. Similarly the plasmid pMTX-P1T-High was then digested with Spe I and the larger 14564 bp fragment was purified. These two fragments were then ligated with T4 DNA ligase and the orientation with correct sequence orientation w.r.t. MV genomic RNA was selected to obtain the pMTX-P1T-MV plasmid. This plasmid was used to introduce additional genes and/or protein coding regions at various locations within the MV genomic sequence (Seq ID No 9). Additionally, cDNA coding for MV antigenomic RNA containing a cis-acting hammerhead ribozyme (HH) at the 5' end and the hepatitis delta virus ribozyme (HDV) at the 3' end and containing Afe I and Pme I enzyme sites at its 5' and 3' end in the order 5'-AfeI-PmeI-HH-MV antigenomic cDNA-HDV-PmeI-3' was synthesized by gene synthesized technology and cloned at the Eco RV site of pUC57 and an orientation wherein the Hind III site from the multiple cloning site of pUC57 was located upstream of the N protein coding gene was selected. This plasmid was also called as pMV and is represented by Seq ID #28.

2.2.2 Additional Transcriptional Unit (ATU) Coding DNA Fragments:

The nucleotide sequences corresponding to the protein coding regions of human GMCSF (NM000758.3; Genbank), prostatic acid phosphatase (PAP) (BC016344.1; Genbank), the GTX homeodomain IRES element described by Chappell et al, (2000) [46], Cytosine deaminase (AF 312392, Genbank), soluble human programmed cell death 1 (L27440, Genbank) and the porcine Tischovirus 2A peptide described by Szymczak et. al (2004)[47] were then assembled into bi-cistronic (1) bi-cistronic (e.g. GMCSF-ires-PAP (Seq ID 10) and GMCSF-ires-CytD (Seq ID 11), (2) tri-cistronic (e.g. GMCSF-ires-sPD1-2a-PAP (Seq ID 12), GMCSF-ires-sPD1-2a-CytD (Seq ID 13)), and tetra-cistronic (e.g. GMCSF-ires-sPD1-2aDnG1-ires-PAP, Seq ID 14, GMCSF-ires-sPD1-2aDnG1-ires-CytD, Seq ID 15) constructs in silico as shown in FIG. 1.

These were then assembled into additional transcriptional units by appending selected regions from the MV genomic RNA (AY486084) as described in Table 2 to produce ATU coding DNA fragments. Resultant fragments were synthesized by gene synthesis technology (Genscript Inc, USA).

| ATU No | Regions selected from the MV genomic RNA | Order of assembly of the fragments with multicistronic constructs |
|---|---|---|
| ATU-1 | (1) MV start (ntd # 1 to 107), (2) N/P intergenic region (ntd # 1686-1807), (3) Part of the N protein open reading frame upto Bam HI (ntd # 108 to 174) | 5'-HindIII-Mvstart-MGC-N/P-N upto Bam-3' |
| ATU-2 | (1) N/P intergenic region (ntd # 1686 to 1806), (2) N-P intergenic region along with a part of MV-P gene (ntd # 1686 to 1957 | 5'-N/P intergenic-MGC-N/P intergenic with part of P-3' |
| ATU-3 | (1) Porf end (ntd # 3265 to 3330), (2) N/P intergenic region (ntd # 1686 to 1806), (3) P/M intergenic region (ntd # 3331 to 3440), | 5'-Porf end-N/P intergenic-MGC-P/M intergenic-3' |
| ATU-4 | (1) F/H intergenic region (ntd 7111 to 7247), and (2) F/H intergenic region (ntd 7111 to 7247) | 5'-F/H intergenic-GMCSF-ires-PAP-F/H Intergenic-3' |
| ATU-5 | (1) H/L intergenic region (ntd # 9175 to 9733), (2) N/P intergenic region (ntd # 1686 to 1806), (3) part of the L protein coding region (ntd # 9234 to 9577) | 5'-H/L intergenic-GMCSF-ires-PAP-N/P intergenic-Lorf-3' |

The resulting sequences were cloned into the plasmid coding for MV genomic RNA as described to produce plasmids coding for MV containing additional genes at different locations of the MV genome.

2.2.3 Modified pUC57 Plasmids:

First the Aat II site present in the pUC57 vector was removed replacing the A present at position 2642 with G residue by site directed mutagenesis. The resulting plasmid was called pUC-delAat. Plasmid pUC57-delAat was then digested with Eco RI and Hind III to remove the multiple cloning site (MCS) and treated with the klenow fragment of *E coli* DNA polymerase I to produce blunt ended pUC57. This was then ligated with each one of the following oligonucleotide linkers to produce different modified pUC57 plasmids

| Sr No | Oligonucleotide sequence | Plasmid name |
|---|---|---|
| 2 | Spe I linker | pUC-Spe |
| 3 | 5'-GACGTCATGCCCTGCAGG-3' (SEQ ID NO. 30) | pUC-AS |
| 4 | 5'-CCTGCAGGATGCACTAGT-3' (SEQ ID NO. 31) | pUC-SS |

2.2.4 Plasmids Coding for MV Genomic RNA Containing ATU at Different Locations:

Plasmids encoding the MV genomic RNA containing an additional ATU coding for 2 or more non-MV genes inserted at different locations of the MV genome were synthesized from pMV, pATU-GP and pUC57 using standard molecular biology techniques as shown in FIG. 3 and described below:

2.2.4.1 Inserting ATU Upstream of N Gene (pMV-GP):

A plasmid encoding the entire MV genomic RNA including an additional ATU coding for bi-cistronic gene coding for GMCSF and PAP proteins was synthesized from pMV (Seq ID #9), pATU-GP (Seq ID 10) and pUC57 using standard molecular biology techniques.

The plasmid pMV was then digested with Aat II and Sbf I and the smaller 3989 bp fragment that codes for part of the RNA pol I promoter and the MV-N was removed and re-circularised by ligating it with an oligonucleotide linker for Aat II and Sbf I (5'-GACGTCATGCCCTGCAGG-3') (SEQ ID NO. 30) to produce pMV-AS. The plasmid pMV-AS was then digested with Bam HI and Hin dIII and the larger 3613 bp fragment was selected.

Similarly, the ATU-GP DNA was then digested with Bam HI and Hind III and the ATU coding 2151 bp fragment was then cloned into the Bam HI & Hin DIII digested pMV-AS plasmid to generate pUC-with-ATU plasmid. This ATU coding region from pUC-with-ATU plasmid was then removed by digestion with Aat II and Sbf I and cloned into Aat II and Sbf I digested pMV plasmid to generate pMV-GP plasmid. The resulting pMV-GP contains an additional transcription unit coding for GMCSF & PAP proteins immediately upstream of MV-N protein coding region (Seq ID #16). The same strategy was used to synthesize a plasmid encoding the genome of MV containing GMCSF and Cytosine deaminase genes (pMV-GC, (Seq ID no 17). The plasmids encoding tri- (Seq ID 23 and Seq ID 25) and tetra-cistronic (Seq ID 24, Seq ID 26) genes upstream of the N gene of MV were produced using similar strategy from Seq ID 12, Seq ID 13, Seq ID 14 and Seq ID 15 respectively.

2.2.4.2 Insertion of ATU Upstream of P Gene (pMV-GP-ATU2):

Plasmid pMV was digested with Sac II, the resulting 6213 bp fragment was purified and circularized by re-ligation with T4 DNA polymerase to produce pSacII-of-MV. This plasmid was digested with Sbf I and Xba I and the larger fragment purified. This was ligated to ATU2 DNA (described in 2.2.2.2 above) digested with Sbf I and Xba I to produce pN-ATU2-P. Plasmid pN-ATU2-P was digested with Sac II and the smaller ATU coding fragment was ligated into the larger 14153 bp fragment of pMV digested with Sac II to produce pMV-GP-ATU2. This plasmid contains ATU inserted upstream of P gene of MV.

2.2.4.3 Insertion of ATU Upstream of M Gene (pMV-GP-ATU3):

Plasmid pMV was digested with Spe I and the larger 14 kb fragment was circularized by re-ligation with T4 DNA polymerase to produce pNPL. Plasmid pNPL was digested with Sbf I and Spe I and the resulting 1415 bp fragment was purified cloned into pUC-SS digested with Spe I and Sbf I to produce pUC_PL. Plasmid pUC_PL was then digested with Eco RV and Spe I and the larger fragment purified. This was then ligated to ATU3 DNA digested with Eco RV and Spe I to produce pP-ATU3-L. Plasmid pP-ATU-L was digested with Sbf I and Spe I and the ATU coding region cloned into pNPL to produce pNP-ATU-L. Plasmid pNP-ATU-L was the digested with Spe I and ATU coding fragment was ligated to the 5802 bp fragment Produced by digesting pMV with Spe I to produce pMV-GP-ATU3. This plasmid contains ATU inserted upstream of M gene of MV.

2.2.4.4 Insertion of ATU Upstream of H Gene (pMV-GP-ATU4):

Plasmid pMV was digested with Pac I. Similarly, ATU4 DNA (described in 2.2.2.4 above) was digested Pac I and ligated with Pac I digested pMV to produce pMV-GP-ATU4. This plasmid contains ATU inserted upstream of H gene of MV.

2.2.4.5 Insertion of ATU Upstream of L Gene (pMV-GP-ATU5):

ATU5 DNA (described in 2.2.2.5 above) was digested with Spe I and Eco RI and ligated into the larger fragment produced by digesting pNLP (described 2.3.3.3 above) to produce pNP-ATU-L. The 5802 bp fragment produced by digesting pMV with Spe I was then ligated to pNP-ATU-L digested with Spe I to produce pMV-GP-ATU5. This plasmid contains ATU inserted upstream of L gene of MV.

2.2 Helper Plasmid:

RNA was prepared from the purified MVAC (Measles Virus Live I.P.) as manufactured by Serum Institute of India, which was purchased off the counter from Emke Medicals by Applicant, using the GeneJet RNA purification kit (Fermentas) according to the manufacturer's protocol. 1 g RNA was reverse transcribed using random hexamers and amplified using primers specific for the N (F: 5'-GCTAGCATGGCCACACTTTAAGG-3'

N protein sequence was then amplified and sub-cloned in between the Nhe I and Xho I sites to obtain pIRES_N. P protein sequence was then amplified from pIRES_P and cloned into the Eco RI and Mlu I sites to create pIRES_NP. Finally, the L sequence was amplified from pIRES_L and cloned into pIRES_NP between the Sal I and Not I sites to obtain pIRES_NPL. In this form, this plasmid will express N and L proteins but not P. Therefore an oligonucleotide corresponding to the mammalian HTX homeobox internal ribosomal entry site reported by Chappell et al (2000) [46] was inserted in between the MV-N and MV-P protein coding regions by site directed mutagenesis. Resulting plasmid pNiPL expresses MV-N, MV-P and MV-L in transfected cells (FIG. 4) (Seq ID #18).

3. Generation of a Packaging Cell Line for Non-Replicating Viruses

The DNAs corresponding to the coding regions of MV-M, MV-F and MV-H proteins were PCR amplified using gene specific primers using Pfu polymerase (Invitrogen) according to manufacturer's protocol. These amplified genes were then cloned into suitably digested pCDNA3.1(-) (Invitrogen, USA) plasmid vector. Clones encoding MV-M, MV-F and MV-H proteins were identified by digestion with specified restriction enzymes and confirmed by single pass sequence determination (data not shown) (FIG. 7A).

$Vero_{MFH}$ Cell Line:

Plasmids encoding MV-M, MV-F and MV-H genes were linearised by digestion with Not 1 enzyme and mixed in equal quantities and used to transfect Vero cells (3 ug in each well of Vero cells plated in 6 well plates) in Lipofectamine 2000 (Invitrogen). Transfection was allowed for 4 hrs and culture medium changed to DMEM containing 10% FCS. Cells were incubated for 24 hrs at 37 C in 5% CO2. At the end of 24 hrs, culture medium was removed and replaced by DMEM containing 10% FCS and 500 uM Geneticin. The incubation was continued at 37 C in 5% CO2 with frequent changing to fresh Geneticin containing medium for next 3 weeks. At the end of 3 weeks, colonies of Geneticin resistant cells were trypsinized and cultured as cells expressing MV-M, MV-F and MV-H proteins. These cells were diluted and plated in 96 well plate at 1 cell per plate and allowed to grow in DMEM containing 10% FCS and 500 uM Geneticin. The ability of these cells to express MV-M, MV-F and MV-H proteins was ascertained by SDS-polyacrylamide gel electrophoresis of the cell lysate followed by western blot with antibodies reactive to corresponding proteins (FIG. 7B) These were tested for their ability to support production of Virosomes (MV like particles) and selected for use as a packaging cell line. The resulting cell line was called $Vero_{MFH}$ and used as a packaging cell line for producing non-replicating MV derivatives containing H and F proteins of MV.

$Vero_M$ Cell Line:

Plasmid encoding MV-M gene was linearised by digestion with Not I enzyme transfected into Vero cells (3 ug in each well of Vero cells plated in 6 well plates). Transfection was allowed for 4 hrs and culture medium changed to DMEM containing 10% FCS. Cells were incubated for 24 hrs at 37 C in 5% CO2. At the end of 24 hrs, culture medium was removed and replaced by DMEM containing 10% FCS and 500 uM Geneticin. The incubation was continued at 37 C in 5% CO2 with frequent changing to fresh medium for next 3 weeks. At the end of 3 weeks, colonies of Geneticin resistant cells were trypsinized and cultured as cells expressing MV-M protein. These cells were diluted and plated in 96 well plate at 1 cell per plate and allowed to grow in DMEM containing 10% FCS and 500 uM Geneticin. The ability of these cells to express MV-M proteins was ascertained by SDS-polyacrylamide gel electrophoresis of the cell lysate followed by western blot with antibodies reactive to MV-M protein. These were tested for their ability to support production of Virosomes (MV like particles) and selected for use as a packaging cell line to produce non-replicating MV derivatives lacking the H and F proteins of MV. The resulting cell line was called $Vero_M$ 4. Production of Replicating Measles Viruses Actively growing Vero cells were trypsinized and plated into 6 well plates in DMEM containing 10% FCS. After incubating at 37 C in 5% CO2 for 24 hrs, culture medium was removed and cells washed with HBSS. Cells were then co-transfected with 3 ug of Virus coding plasmid (any one of the MV coding plasmids from pMV (Seq ID 9), pMV-GP (Seq ID 16), pMV-GC (Seq ID 17) or pMV GsPP (Seq ID 23), pMV-GsPDP (Seq ID 24), pMV-GsPC (Seq ID 25), pMV-GsPDP (Seq ID 26), or pMV-GP-ATU2 to pMV-GP-ATU5 plasmids) and Helper plasmid (pINPL) (1:1.5) in Lipofectamine 2000 according to manufacturer's protocol. Transfection was allowed to occur for 4 hrs and culture medium replaced with DMEM containing 10% FCS. Twenty four hours after transfection, culture medium was replaced with DMEM containing 2% FCS and incubation continued. The cells were observed daily for the appearance of cytopathic effect typical of MV. At the end of 7 days, cells showing the appearance of large syncytia were trypsinized and mixed with fresh Vero cells and re-plated in 6 well plates. Incubation was continued at 37 C in 5% CO2 with daily observation for the appearance of the typical cytopathic effect (CPE) characteristic of MV (FIG. 6A). Culture medium was collected after more than 75% of the plated cells showed MV cytopathic effect and used to infect fresh Vero cells. The appearance of CPE in these cultures was considered as an evidence of formation of the recombinant virus. Culture supernatant was collected and used as a seed stock for further propogation of the recombinant virus. The resultant viruses were named according to the Cloning plasmids used. Thus, virus produced from pMV-GP was called rMV-GP, that produced from pMV-GC was called rMV-GC and rMV-GP-ATU 2 to 5 when produced from plasmids pMV-GP to pMV-GC respectively. The growth curve of rMV-GP the studied by infecting freshly plated and actively growing Vero cells and harvesting culture supernatants every 24 hrs and determining the levels of pMV-GP using the TCID50 method (FIG. 6B). Culture supernatants containing the recombinant MV were concentrated by ultracentrifugation at 100,000×g and used to (1) prepare total viral RNA using Qiagen RNA kit (FIG. 6D) & analysed for the presence of RNA molecules coding for MV-N and MV-M and GMCSF genes and (2) negatively stained with 2% ammonium molybdate and observed under transcription electron microscope (FIG. 6E). Additionally, extracts prepared from vero cells infected with rMV-GP were also analysed for the presence of MV-N, MV-P and GMCSF proteins by westernblot analysis using antibodies specific to rinderpest virus N and P proteins (which are known to cross react with MV-N and MV-P proteins and were kindly supplied by Prof. M. S. Shaila, Department of Microbiology & Cell Biology, Indian Institute of Science, Bangalore, INDIA) and human GMCSF (R&D systems, USA) (FIG. 5C). Results of the analysis for rMV-GP that codes includes a GMCSF coding additional transcriptional unit upstream of MV-N gene is shown in FIG. 6 for illustration.

Replicating MV derivatives containing tri-cistronic ATU (virus coding plasmid corresponding to Seq ID #23 and Seq ID #25) and tetra-cistronic ATU (virus coding plasmids corresponding to Seq ID #24 and Seq ID #26) inserted upstream of the N protein coding region of MV were produced using the same method.

5. Production of Non-Replicating Derivatives of Measles Virus (Virosomes)

5.1 Measles Virosomes:

The VeroMFH cell line was maintained in DMEM supplemented with 10% FCS and 500 uM Geneticine. Actively growing VeroMFH cells were trypsinized and plated into 6 well plate at a density of 80000 cells/well and incubated for 24 hrs at 37 C in 5% CO2. They were then co-transfected with a Cloning plasmid that codes for MV replicon RNA (pMTX-P1T-GH) that expresses a MV replicon coding for GFP and Helper plasmid (pINPL) in Lipofectamine 2000 according to manufacturer's protocol. (3 ug DNA per well @ 2 ug pMTX-P1T-G+1 ug Helper plasmid). Transfection was allowed to occur for 2 hrs and culture medium replaced with DMEM supplemented with 10% FCS and cells were allowed to recover for 24 hrs. Culture medium was then removed and replaced with fresh DMEM containing 10% FCS and 750 uM Geneticine and incubated further. Culture medium was replaced every 48 hours.

Non-replicating measles viruses (Virosomes) were released into culture medium from day 4 onwards and the titres (as determined by the transfer of GFP expression into fresh Vero cells) was observed from day 5 and peaked after day 7. The presence of Virosomes was confirmed by (1) the ability of culture supernatant to infect fresh Vero cells and induce GFP expression by microscopy (FIG. 13), (2) analysis of the RNA contained in the culture supernatant by RT-PCR analysis (FIG. 8A) and (3) dot blot analysis with an antibody specific to the P protein of measles virus (kind gift from Prof. M. S. Shaila, Dept of Microbiology & Cell Biology, Indian Institute of Science, Bangalore, INDIA) and known to cross react with MV-P protein (FIG. 7B).

5.2 Dengue Virosomes:

Similarly, virosomes coding for the Dengue virus subviral particles were also produced using the cloning plasmids—(1) D2 Virosomes—produced using pMTX-P1T-D2G; (3) D2-intermediate-Virosomes—produced using pMTX-P1T-Intermediate-D2G; (4) D2-High-Virosomes—produced using pMTX-P1T-High-D2G. Dot blot analysis of virosomes showed that both Dengue & GFP virosomes contained the MV proteins (e.g. MV-P). On the other hand, Dengue virosomes contained Dengue virus E protein but not the GFP virosomes (FIG. 7C).

5.3 Measles Virosomes

Similarly, Measles virosomes were also prepared by co-transfecting $Vero_{MFH}$ cells with pMTXP1T-NP-RE1-FH-RE2-RE3 (Seq ID 8) and the Helper plasmid (Seq ID 18). They were concentrated by ultra-centrifugation at 100,000×g and washed with PBS and used to immunize Balb/C mice. Serum isolated from these mice was found to protect Vero cells from infection with MV (FIG. 15).

5.3 Chimeric Dengue Virosomes

Chimeric Dengue virosomes that display Dengue virus E protein, but not the H and F glycoproteins and also contain a genome coding for Dengue virus prM and E proteins were produced using pMTX-P1T-D2Gdelpr Plasmid as the cloning plasmid. Briefly, freshly seeded and active growing $Vero_{M}$ cells were co-transfected with pMTX-P1T-D2Gdelpr and the Helper plasmid and incubated for 7 days in DMEM containing 10% fetal calf serum. Culture supernatants containing chimeric Dengue virosomes were collected. Chimeric Dengue Virosomes were concentrated by ultracentrifugation at 100,000×g and used to immunize mice. The presence of Dengue virus E protein in these virosomes was determined by first immuoprecipitating it with anti-Dengue virus E protein antibody followed by DS-polyacrylamide electrophoresis and detection with western blot analysis using the serum from mice immunized or vice versa (FIGS. 14 A & B). That these Dengue virosomes also induced anti-Dengue cell mediated immune responses was confirmed by preparing spleenocytes from mice immunized with Dengue virosomes and enumerating the dengue virus reactive IFNg producing cells using ELISPOT assay (FIG. 14 C). Finally, the serum from mice immunized mice was tested for its ability to neutralize Dengue virus by PRNT test according to the method described by Liu et al (2014) [48].

5.3 Non-Replicating Oncolytic Virosomes:

On the other hand, non-replicating oncolytic virosomes that coded for MV-H and MV-F proteins and also the human GMCSF and PAP proteins were produced using the pNPFH_GCdnG/pNPFH-GCG plasmid.

6. rMV-GP Kills Cancer Cells Like PC-3 Cells Selectively but has No Toxic Effect on Non-Cancerous Cells The oncolytic effect of rMV-GP was tested using the prostate cancer cell lines—PC-3 and LnCAP. PC-3 and LnCAP cell lines were procured from the National Center for Cell Sciences, Pune, INDIA and maintained respectively in Ham's F12K medium and RPMI1640 supplemented with glutamine and 10% fetal bovine serum.

Figure 9:
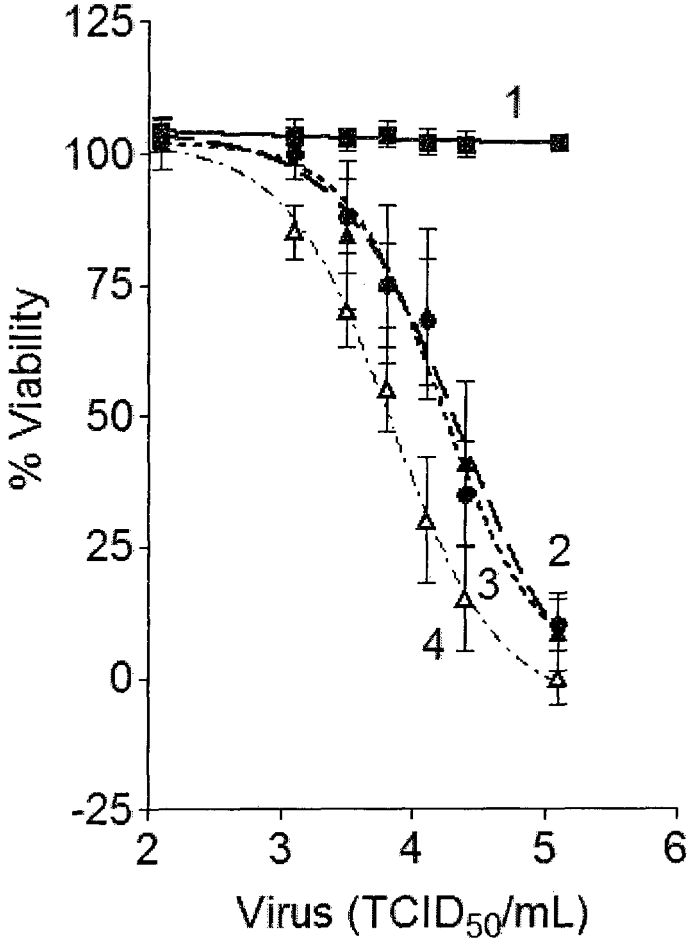

Actively growing cells were plated in 24 well plates at a density of 40000 cells/well and incubated overnight at 37° C. in 5% CO2. After the cells settled well, cells were washed with HBSS and infected with different concentrations of SBPL-0100 diluted in OptiMEM for 2 hr. Virus was then replaced with complete respective culture medium with 2% FBS and incubated at 37 C in 5% CO2 until a typical MV cytopathic effect (CPE) and/or cell death was observed. At the end of incubation, culture medium was replaced with fresh culture medium containing MTT dye (0.5 mg/mL) and incubated further for 4 hrs. Culture supernatant was then removed and replaced with DMSO to solubilize the reduced MTT formazan crystals. Plates were read of optical density at 570 nm and cytotoxicity caused by the virus was determined. As shown in FIG. 9, rMV-GP kills PC-3 cells belonging to prostate cancer in a dose dependent manner, in contrast, it has no toxic effect on non-cancerous cells like Vero cells.

6.1 Incorporation of Genes Producing Anti-Cancer Effect is Essential to Increase the Oncolytic Potency of Oncolytic MV Replicating MV derivatives expressing 3 (rMV-GsPP coding for GMCSF, sPD-1 and PAP) and 4 (rMV-GsPPD coding for GMCSF, sPD-1, PAP and DnG1) were also synthesized as mentioned earlier. Freshly plated, actively growing Vero cells were infected with MV derivatives encoding 0 (MV), 2(rMV-GP), 3(rMV-GsPP) and 4 (rMV-GsPDP) non-MV genes and incubated for 72 hrs. At the end of this period, cell extracts were prepared, proteins separated by SDS-electrophoresis and subjected to western blot analysis for detecting proteins corresponding to human GMCSF, sPD-1, PAP and DnG1 using antibodies specific to human GMCSF (MAB215-SP, R&D Systems, USA), PD-1 (AF1086-SP, R&D Systems, USA), PAP (MAB6240-SP, R&D Systems, USA) and Cyclin G1 (SC-7865, Santacruz, USA) proteins.

As expected, extracts from rMV-GsPDP infected Vero cells showed the presence of all 4 proteins; extracts from rMV-GsPP infected Vero cells showed the presence of GMCSF, sPD-1 and PAP; extracts from rMV-GP infected cells showed the presence of GMCSF and PAP and extracts from MV infected cells did not express any of the proteins GMCSF, PAP, sPD-1 and DnG1. On the other hand, all four infected cell extracts exhibited the presence of MV-H protein (FIG. 10A).

The oncolytic activity of these viruses was then tested on different cancer cell lines according to the method described above. FIG. 10B shows that rMV-GP and rMV-GsPP which are armed with GMCSF and/or sPD-1 which code for immune-regulatory genes exhibit no differences in their cytotoxicity towards PC-3, A549 and MCF-7 cell lines in contrast, inclusion of DNG1 in rMV-GsPDP increased the cytotoxic activity against cancer cells (FIG. 10C). Clearly therefore, arming MV with other genes known to have anti-cancer therapeutic effect can help increase its cancer therapeutic activity.

8. DNA Induced Oncolytic Effect

The rMV-GP produced using the 2 plasmids can induce selective oncolytic effect in cancer cell lines. The ability of DNA molecules which are useful for production of rMV-GP were then tested for their ability to induce a similar cytotoxic effect.

Actively growing PC-3 cells were trypsinized and split into 24 well plates at a density of 40000 cells/well and incubated at 37° C. in 5% CO2 overnight. After 24 hrs, cells were transfected with different quantities (3 ug/well to 0.03 ug/well) of plasmid mixture (pIN2PL+pSB-043R) in Xfect according to manufacturer's instructions. Four hours after transfection, culture medium was replaced with DMEM containing glutamine and 10% FCS and incubated over night. Twenty four hours after transfection, the culture medium was replaced by fresh culture medium containing 2% FCS and incubation continued. Every 24 hrs, cells were observed microscopically for the appearance of typical MV cytopathic effect and/or cell death. At the end of 6 days post transfection, Culture medium was replaced with fresh culture medium containing 0.5 mg/mL MTT and incubated for 4 hrs. At the end of the incubation, culture medium was removed and replaced with DMSO to solubilize the reduced MTT formazan crystals. Culture plates were then measured for optical density at 570 nm and cytotoxicity caused by the DNA molecules determined. FIG. 11 shows that co-transfection of PC-3 cells with different quantities of MV coding plasmid (rMV-GP) and the Helper plasmids induces a dose dependent toxicity in a manner similar to oncolytic MV.

9. Virosome Mediated Gene Transfer

The rMV-GP produced using the 2 plasmids can induce selective oncolytic effect in cancer cell lines. The ability of DNA molecules which are useful for production of rMV-GP were then tested for their ability to induce a similar cytotoxic effect.

Actively growing vero cells were trypsinized and seeded into chamber slides (4 chambers/slide) at a density of 40000 cells/chamber and incubated over night at 37 C in 5% CO2. Culture medium was then removed and washed with HBSS. Cells were layered with 0.5 mL of Virosomes (derived from pMTX-P1T-D2 plasmid) containing culture supernatant and incubated for 2 hrs at 37 C in 5% CO2. At the end of incubation, culture medium was replaced with fresh DMEM containing 5% fetal calfserum and incubation continued for 72 hrs. At the end of 72 hours, slides were stained with DAPI and observed under fluorescent microscope for presence of GFP. Simultaneously, culture supernatants from virosome infected vero cells was collected and centrifuged at 100,000×g. Pellet obtained from this supernatant was analysed for the presence of Dengue virus like particles using dot blot analysis.

GFP expression in virosome infected cells indicated successful transfer of GFP expression by Virosomes into vero cells. Similarly, a positive immunoblot with anti-Dengue virus E protein indicated that virosomes transferred Dengue VLP coding gene into vero cells and this Dengue VLP was expressed into culture medium as expected. It was further observed that virosomes derived from the different cloning plasmids (pMTX-P1T-D2 or pMTX-P1T-high-D2 expressed different levels of DVLP in culture supernatants. As expected, pMTX-P1T-D2 derived virosomes produced lower levels of DVLP than pMTX-P1t-high-D2 derived virosomes.

10: Cancer Therapeutic Effect of rMV-GP in Mice

The in vivo oncolytic effect of rMV-GP was tested in SCID mice according to the protocol described in Grote et al, (2003) [49]. Briefly, four-week-old CB17 SCID mice (procured from Vivolabs, Hyderabad, INDIA) were housed in individual ventilated cages (IVC) at INTOX Pvt. Ltd., Pune, INDIA and provided with food and water ad libidum. Mice received s.c. injections in the flank region with $10^7$ viable PC-3 tumour cells. After the tumours had grown upto a volume of approximately 100 cubic mm, they were injected with $10^6$ TCID50 rMV-GP in a total volume of 100 μl every $3^{rd}$ day for 5 weeks. As controls, tumours were injected daily with the same volume of UV-inactivated virus. Tumour measurements were made every alternate day in two diameters, and the tumour volume was calculated according to the formula $V=a^2b/2$ where a is the shortest and b the longest diameter. Mice whose tumours reached a volume of 2.5 cm3 or had begun to invade surrounding tissues were euthanized. The experimental protocol was approved by the Institutional Animal Ethics Committee of INTOX Pvt. Ltd. FIG. 12 (Data marked as #2) shows that rMV-GP can induce regression of xenotransplanted tumors in SCID mice. In contrast, treatment of tumors with PBS were not affected.

11: Immunopotentiating Effect of rMV-GP

The biological activity of GMCSF expressed from rMV-GP was determined using the TF-1 cell bioassay of Kitamura et al (1989). Briefly, actively growing TF-1 erythroleukemia cell line was plated at $5\times10^4$ cells/well in 24 well plate and incubated at 37 C in 5% CO2. Lysates of tumour cells infected with rMV-GP were then prepared in RIPA buffer and added to wells containing TF-1 cells (50 uL of cell extract). Cells were incubated at 37 C in 5% CO2 for 48 hrs and growth measured using MTT assay. Quantity of bioactive GMCSF produced by rMV-GP infected cells was estimated by mapping the results on a standard curve obtained by exposing TF-1 cells to standard GMCSF. Culture supernatants obtained from vero cells infected with rMV-GsPP and GsPPD were also found to contain GMCSF as detected by TF-1 cell bioassay (Data not shown).

12: Plasmid Induced Cancer Therapeutic Effect in Mice

The in vivo oncolytic effect of rMV-GP was tested in SCID mice according to the protocol described in Grote et al, (2003) [49]. Briefly, four-week-old CB17 SCID mice (procured from Vivolabs, Hyderabad, INDIA) were housed in individual ventilated cages (IVC) at INTOX Pvt. Ltd., Pune, INDIA and provided with food and water ad libidum. Mice received s.c. injections in the flank region with $10^7$ viable PC-3 tumour cells. After the tumours had grown upto a volume of approximately 100 cubic mm, they were injected with 10 ug of a mixture of the Helper plasmid and pMV-GP (1.3:1) in 100 μl saline every $3^{rd}$ day for 5 weeks. As controls, tumours were injected daily with the same volume of saline containing 10 ug pUC plasmid was used. Tumour measurements were made every alternate day in two diameters, and the tumour volume was calculated according to the formula $V=a^2b/2$ where a is the shortest and b the longest diameter. Mice whose tumours reached a volume of 2.5 cm3 or had begun to invade surrounding tissues were euthanized. The experimental protocol was approved by the Institutional Animal Ethics Committee of INTOX Pvt. Ltd. FIG. 12 (data marked as #3) shows that tumors injected with plasmids which can produce rMV-GP also induced regression of tumors albeit at a slower rate and rMV-GP virus injected cells. This shows that DNA molecules producing oncolytic MV may also be useful for inducing anti-cancer effect.

REFERENCES

1. Bluming, A. Z. and J. L. Ziegler, *Regression of Burkitt's lymphoma in association with measles infection*. Lancet, 1971. 2 (7715): p. 105-6.
2. Gross, S., *Measles and leukaemia*. Lancet, 1971. 1 (7695): p. 397-8.
3. Pasquinucci, G., *Possible effect of measles on leukaemia*. Lancet, 1971. 1 (7690): p. 136.
4. Zygiert, Z., *Hodgkin's disease: remissions after measles*. Lancet, 1971. 1 (7699): p. 593.
5. McDonald, C. J., et al., *A measles virus vaccine strain derivative as a novel oncolytic agent against breast cancer*. Breast Cancer Res Treat, 2006. 99 (2): p. 177-84.
6. Heinzerling, L., et al., *Oncolytic measles virus in cutaneous T-cell lymphomas mounts antitumor immune responses in vivo and targets interferon-resistant tumor cells*. Blood, 2005. 106 (7): p. 2287-94.
7. Kunzi, V., et al., *Recombinant measles virus induces cytolysis of cutaneous T-cell lymphoma in vitro and in vivo*. J Invest Dermatol, 2006. 126 (11): p. 2525-32.

8. Lin, E. H., et al., *Fusogenic membrane glycoproteins induce syncytia formation and death in vitro and in vivo: a potential therapy agent for lung cancer*. Cancer Gene Ther, 2010. 17 (4): p. 256-65.

9. Peng, K. W., et al., *Systemic therapy of myeloma xenografts by an attenuated measles virus*. Blood, 2001. 98 (7): p. 2002-7.

10. Galanis, E., et al., *Phase I trial of intraperitoneal administration of an oncolytic measles virus strain engineered to express carcinoembryonic antigen for recurrent ovarian cancer*. Cancer Res, 2010. 70 (3): p. 875-82.

11. Msaouel, P., A. Dispenzieri, and E. Galanis, *Clinical testing of engineered oncolytic measles virus strains in the treatment of cancer: an overview*. Curr Opin Mol Ther, 2009. 11 (1): p. 43-53.

12. Russell, S. J., et al., *Remission of disseminated cancer after systemic oncolytic virotherapy*. Mayo Clin Proc, 2014. 89 (7): p. 926-33.

13. Blechacz, B. and S. J. Russell, *Measles virus as an oncolytic vector platform*. Curr Gene Ther, 2008. 8 (3): p. 162-75.

14. Radecke, F., et al., *Rescue of measles viruses from cloned DNA*. EMBO J, 1995. 14 (23): p. 5773-84.

15. Parks, C. L., et al., *Comparison of predicted amino acid sequences of measles virus strains in the Edmonston vaccine lineage*. J Virol, 2001. 75 (2): p. 910-20.

16. Parks, C. L., et al., *Analysis of the noncoding regions of measles virus strains in the Edmonston vaccine lineage*. J Virol, 2001. 75 (2): p. 921-33.

17. Dorig, R. E., et al., *The human CD*46 *molecule is a receptor for measles virus* (*Edmonston strain*). Cell, 1993. 75 (2): p. 295-305.

18. Hsu, E. C., et al., *CDw*150 (*SLAM*) *is a receptor for a lymphotropic strain of measles virus and may account for the immunosuppressive properties of this virus*. Virology, 2001. 279 (1): p. 9-21.

19. Anderson, B. D., et al., *High CD*46 *receptor density determines preferential killing of tumor cells by oncolytic measles virus*. Cancer Res, 2004. 64 (14): p. 4919-26.

20. Rama, A., et al., *On advances in cancer suicide genes therapy*. SOJ Genet Sc, 2014. 1 (1): p. 1-6.

21. Liu, T. J., et al., *Growth suppression of human head and neck cancer cells by the introduction of a wild-type p*53 *gene via a recombinant adenovirus*. Cancer Res, 1994. 54 (14): p. 3662-7.

22. Gibson, S. A., et al., *Induction of apoptosis in oral cancer cells by an anti-bcl-*2 *ribozyme delivered by an adenovirus vector*. Clin Cancer Res, 2000. 6 (1): p. 213-22.

23. Martin, L. A. and M. Dowsett, *BCL-*2*: a new therapeutic target in estrogen receptor-positive breast cancer*? Cancer Cell, 2013. 24 (1): p. 7-9.

24. Wong, R. J., et al., *Oncolytic herpesvirus effectively treats murine squamous cell carcinoma and spreads by natural lymphatics to treat sites of lymphatic metastases*. Hum Gene Ther, 2002. 13 (10): p. 1213-23.

25. Dingli, D., et al., *Image-guided radiovirotherapy for multiple myeloma using a recombinant measles virus expressing the thyroidal sodium iodide symporter*. Blood, 2004. 103 (5): p. 1641-6.

26. Bossow, S., et al., *Armed and targeted measles virus for chemovirotherapy of pancreatic cancer*. Cancer Gene Ther, 2011. 18 (8): p. 598-608.

27. Hartkopf, A. D., et al., *Enhanced killing of ovarian carcinoma using oncolytic measles vaccine virus armed with a yeast cytosine deaminase and uracil phosphoribosyltransferase*. Gynecol Oncol, 2013. 130 (2): p. 362-8.

28. Kaufmann, J. K., et al., *Chemovirotherapy of malignant melanoma with a targeted and armed oncolytic measles virus*. J Invest Dermatol, 2013. 133 (4): p. 1034-42.

29. Grossardt, C., et al., *Granulocyte-macrophage colony-stimulating factor-armed oncolytic measles virus is an effective therapeutic cancer vaccine*. Hum Gene Ther, 2013. 24 (7): p. 644-54.

30. Engeland, C. E., et al., *CTLA*-4 *and PD-L*1 *checkpoint blockade enhances oncolytic measles virus therapy*. Mol Ther, 2014. 22 (11): p. 1949-59.

31. Rushmere, N. K., et al., *Analysis of the level of mRNA expression of the membrane regulators of complement, CD*59*, CD*55 *and CD*46*, in breast cancer*. Int J Cancer, 2004. 108 (6): p. 930-6.

32. Iankov, I.D., et al., *Infected cell carriers: a new strategy for systemic delivery of oncolytic measles viruses in cancer virotherapy*. Mol Ther, 2007, 15 (1): p. 114-22.

33. Miest, T. S., et al., *Envelope-chimeric entry-targeted measles virus escapes neutralization and achieves oncolysis*. Mol Ther, 2011. 19 (10): p. 1813-20.

34. Bateman, A., et al., *Fusogenic membrane glycoproteins as a novel class of genes for the local and immune-mediated control of tumor growth*. Cancer Res, 2000. 60 (6): p. 1492-7.

35. Higuchi, H., et al., *Viral fusogenic membrane glycoprotein expression causes syncytia formation with bioenergetic cell death: implications for gene therapy*. Cancer Res, 2000. 60 (22): p. 6396-402.

36. Liniger, M., et al., *Recombinant measles viruses expressing single or multiple antigens of human immunodeficiency virus* (*HIV*-1) *induce cellular and humoral immune responses. Vaccine,* 2009. 27 (25-26): p. 3299-305.

37. Liniger, M., et al., *Induction of neutralising antibodies and cellular immune responses against SARS coronavirus by recombinant measles viruses*. Vaccine, 2008. 26 (17): p. 2164-74.

38. Wang, Z., et al., *Recombinant measles viruses expressing heterologous antigens of mumps and simian immunodeficiency viruses*. Vaccine, 2001. 19 (17-19): p. 2329-36.

39. Brandler, S., et al., *Measles vaccine expressing the secreted form of West Nile virus envelope glycoprotein induces protective immunity in squirrel monkeys, a new model of West Nile virus infection*. J Infect Dis, 2012.206 (2): p. 212-9.

40. Brandler, S., et al., *A recombinant measles vaccine expressing chikungunya virus-like particles is strongly immunogenic and protects mice from lethal challenge with chikungunya virus. Vaccine,* 2013. 31 (36): p. 3718-25.

41. Brandler, S., et al., *Pediatric measles vaccine expressing a dengue antigen induces durable serotype-specific neutralizing antibodies to dengue virus*. PLoS Negl Trop Dis, 2007. 1 (3): p. e96.

42. Billeter, M. A., H. Y. Naim, and S. A. Udem, *Reverse genetics of measles virus and resulting multivalent recombinant vaccines: applications of recombinant measles viruses*. Curr Top Microbiol Immunol, 2009. 329: p. 129-62.

43. Wang, P. G., et al., *Efficient assembly and secretion of recombinant subviral particles of the four dengue serotypes using native prM and E proteins*. PLoS One, 2009. 4 (12): p. e8325.

44. Erbs, P., et al., *In vivo cancer gene therapy by adenovirus-mediated transfer of a bifunctional yeast cytosine deaminase/uracil phosphoribosyltransferase fusion gene*. Cancer Res, 2000. 60 (14): p. 3813-22.
45. Gordon, E. M., et al., *Inhibition of metastatic tumor growth in nude mice by portal vein infusions of matrix-targeted retroviral vectors bearing a cytocidal cyclin G1 construct*. Cancer Res, 2000. 60 (13): p. 3343-7.
46. Chappell, S. A., G. M. Edelman, and V. P. Mauro, *A 9-nt segment of a cellular mRNA can function as an internal ribosome entry site (IRES) and when present in linked multiple copies greatly enhances IRES activity*. Proc Natl Acad Sci USA, 2000. 97 (4): p. 1536-41.
47. Szymczak, A. L., et al., *Correction of multi-gene deficiency in vivo using a single 'self-cleaving' 2A peptide-based retroviral vector*. Nat Biotechnol, 2004. 22 (5): p. 589-94.
48. Liu, Y., et al., *Tetravalent recombinant dengue virus-like particles as potential vaccine candidates: immunological properties*. BMC Microbiol, 2014. 14 (1): p. 233.
49. Grote, D., R. Cattaneo, and A. K. Fielding, *Neutrophils contribute to the measles virus-induced antitumor effect: enhancement by granulocyte macrophage colony-stimulating factor expression*. Cancer Res, 2003. 63 (19): p. 6463-8.

The invention claimed is:

1. A method for producing a non-replicating derivative of a Measles Virus (MV), the non-replicating derivatives being named as a virosome and the method comprising the following steps:

a) co-transfecting a MV Packaging cell line with (i) a Cloning Plasmid and (ii) a Helper plasmid to obtain co-transfected cells, wherein the cloning plasmid comprises a MV genome-like replicon RNA coding for one or more non-MV genes and, optionally a subset of MV genes, and the helper plasmid codes for the N, P and L proteins of MV;

wherein the MV packaging cell line may or may not be modified to express M or F or H proteins of MV stably, but not requiring the help of an exogenous vaccinia virus or an exogenous T7 RNA polymerase; and b) incubating the co-transfected cells at a temperature between 35° C. to 38° C. for 3 to 10 days in a culture medium to obtain non-replicating derivatives released into the culture medium, said non-replicating derivatives referred to as virosomes; wherein the non-replicating derivatives comprise a genome selected from the group consisting of: (a) coding exclusively non-MV genes; (b) coding for MV-N and MV-P genes along with non-MV genes; and (c) coding for MV-N, MV-P, and MV-L genes along with non-MV genes, wherein the non-replicating derivatives do not code for M, H, and F genes of Measles Virus.

2. The method of claim 1, wherein the Helper plasmid has Seq ID NO:18.

3. The method of claim 1, wherein the Cloning Plasmid is selected from the group consisting of pMTX-P1T (SEQ ID NO:1), pMTX-P1T-Intermediate (SEQ ID NO:4), and pMTX-P1T-High (SEQ ID NO:7).

4. The method of claim 1, wherein the MV packaging cell comprises $Vero_{MFH}$.

5. The method of claim 1, wherein the MV packaging cell line expressing the M protein of MV stably.

6. The method of claim 1, wherein the MV packaging cell line comprises $Vero_{M}$.

* * * * *